(12) United States Patent
Yusibov et al.

(10) Patent No.: US 8,784,819 B2
(45) Date of Patent: Jul. 22, 2014

(54) INFLUENZA HEMAGGLUTININ ANTIBODIES, COMPOSITIONS AND RELATED METHODS

(75) Inventors: Vidadi Yusibov, Havertown, PA (US); Vadim Mett, Newark, DE (US); Jessica Chichester, Glen Mills, PA (US); Lauren Goldschmidt, Drexel Hill, PA (US)

(73) Assignee: iBio Inc., Newark, DE (US)

( * ) Notice: Subject to any disclaimer, the term of this patent is extended or adjusted under 35 U.S.C. 154(b) by 0 days.

(21) Appl. No.: 13/498,946

(22) PCT Filed: Sep. 29, 2010

(86) PCT No.: PCT/US2010/050693
§ 371 (c)(1),
(2), (4) Date: Aug. 30, 2012

(87) PCT Pub. No.: WO2011/041391
PCT Pub. Date: Apr. 7, 2011

(65) Prior Publication Data
US 2012/0315323 A1    Dec. 13, 2012

Related U.S. Application Data

(60) Provisional application No. 61/246,958, filed on Sep. 29, 2009.

(51) Int. Cl.
*A61K 39/42* (2006.01)
*A61K 51/00* (2006.01)
*A61K 36/14* (2006.01)

(52) U.S. Cl.
USPC .................... 424/147.1; 424/159.1; 424/1.49

(58) Field of Classification Search
None
See application file for complete search history.

(56) References Cited

U.S. PATENT DOCUMENTS

| | | | |
|---|---|---|---|
| 4,196,265 | A | 4/1980 | Koprowski et al. |
| 4,270,537 | A | 6/1981 | Romaine |
| 4,596,556 | A | 6/1986 | Morrow et al. |
| 4,653,728 | A | 3/1987 | Mochizuki et al. |
| 4,790,824 | A | 12/1988 | Morrow et al. |
| 4,816,567 | A | 3/1989 | Cabilly et al. |
| 4,886,499 | A | 12/1989 | Cirelli et al. |
| 4,935,496 | A | 6/1990 | Kudo et al. |
| 4,940,460 | A | 7/1990 | Casey et al. |
| 4,941,880 | A | 7/1990 | Burns |
| 5,015,235 | A | 5/1991 | Crossman |

(Continued)

FOREIGN PATENT DOCUMENTS

| | | |
|---|---|---|
| CZ | 20 031 859 | 2/2005 |
| EP | 404097 | 6/1990 |

(Continued)

OTHER PUBLICATIONS

Rudikoff et al., "Single amino acid substitution altering antigen-binding specificity," PNAS, vol. 79: pp. 1979-1983 (1982).*

(Continued)

*Primary Examiner* — Michelle S Horning
*Assistant Examiner* — M. Franco Salvoza
(74) *Attorney, Agent, or Firm* — Fish & Richardson P.C.

(57) ABSTRACT

Antibodies against influenza hemagglutinin, compositions containing the antibodies, and methods of using the antibodies are provided herein.

23 Claims, 12 Drawing Sheets

(56) References Cited

U.S. PATENT DOCUMENTS

| | | |
|---|---|---|
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brennerman |
| 5,480,381 A | 1/1996 | Weston |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,681,722 A | 10/1997 | Newman et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,698,426 A | 12/1997 | Huse et al. |
| 5,702,892 A | 12/1997 | Mulligan-Kehoe |
| 5,704,911 A | 1/1998 | Parsons |
| 5,705,154 A | 1/1998 | Dalie et al. |
| 5,733,743 A | 3/1998 | Johnson et al. |
| 5,750,078 A | 5/1998 | Shitara et al. |
| 5,759,817 A | 6/1998 | Barbas |
| 5,770,403 A | 6/1998 | Dalie et al. |
| 5,770,429 A | 6/1998 | Lonberg et al. |
| 5,855,866 A | 1/1999 | Thorpe et al. |
| 5,877,289 A | 3/1999 | Thorpe et al. |
| 5,888,789 A | 3/1999 | Rodriguez et al. |
| 5,893,397 A | 4/1999 | Peterson et al. |
| 5,965,132 A | 10/1999 | Thorpe et al. |
| 5,993,412 A | 11/1999 | Deily et al. |
| 6,004,555 A | 12/1999 | Thorpe et al. |
| 6,042,832 A | 3/2000 | Koprowski et al. |
| 6,093,399 A | 7/2000 | Thorpe et al. |
| 6,103,511 A | 8/2000 | Li et al. |
| 6,261,535 B1 | 7/2001 | Thorpe et al. |
| 6,524,825 B1 | 2/2003 | Mizzen et al. |
| 6,649,172 B2 | 11/2003 | Johnson |
| 6,734,173 B1 | 5/2004 | Wu et al. |
| 6,740,740 B2 | 5/2004 | Garger et al. |
| 6,797,491 B2 | 9/2004 | Neefe, Jr. et al. |
| 6,841,659 B2 | 1/2005 | Turpen et al. |
| 7,888,135 B2 | 2/2011 | Tarleton et al. |
| 2004/0093643 A1 | 5/2004 | Ensley |
| 2004/0170606 A1 | 9/2004 | Palmer et al. |
| 2004/0268442 A1 | 12/2004 | Miller et al. |
| 2005/0026291 A1 | 2/2005 | Fedorkin et al. |
| 2005/0042229 A1 | 2/2005 | Yang et al. |
| 2005/0048074 A1 | 3/2005 | Cardineau et al. |
| 2005/0054820 A1 | 3/2005 | Wu et al. |
| 2005/0186621 A1 | 8/2005 | Galarza et al. |
| 2006/0008473 A1 | 1/2006 | Yang et al. |
| 2006/0265787 A1 | 11/2006 | Piruzian et al. |
| 2007/0275014 A1 | 11/2007 | Yusibov et al. |
| 2008/0124272 A1 | 5/2008 | Yusibov et al. |
| 2008/0279877 A1 | 11/2008 | Yusibov et al. |
| 2009/0324634 A1 | 12/2009 | Knapp et al. |
| 2010/0227373 A1 | 9/2010 | Yusibov et al. |
| 2010/0239594 A1 | 9/2010 | Yusibov et al. |
| 2011/0027304 A1 | 2/2011 | Yusibov et al. |
| 2011/0059130 A1 | 3/2011 | Yusibov |

FOREIGN PATENT DOCUMENTS

| | | |
|---|---|---|
| WO | WO9311161 | 6/1993 |
| WO | WO9602555 | 2/1996 |
| WO | WO9612028 | 4/1996 |
| WO | WO9713537 | 4/1997 |
| WO | WO9737705 | 10/1997 |
| WO | WO9814595 | 4/1998 |
| WO | WO9845331 | 10/1998 |
| WO | WO9907860 | 2/1999 |
| WO | WO9934850 | 7/1999 |
| WO | WO0020612 | 4/2000 |
| WO | WO0025574 | 5/2000 |
| WO | WO0046350 | 8/2000 |
| WO | WO0200892 | 1/2002 |
| WO | WO03040179 | 5/2003 |
| WO | WO03057834 | 7/2003 |
| WO | WO03076568 | 9/2003 |
| WO | WO2004043886 | 5/2004 |
| WO | WO2004058797 | 7/2004 |
| WO | WO2005023177 | 3/2005 |
| WO | WO2005026375 | 3/2005 |
| WO | WO2005049839 | 6/2005 |
| WO | WO2005056052 | 6/2005 |
| WO | WO2005067620 | 7/2005 |
| WO | WO2005081905 | 9/2005 |
| WO | WO2005120567 | 12/2005 |
| WO | WO2006003018 | 1/2006 |
| WO | WO2006124712 | 11/2006 |
| WO | WO2007089753 | 8/2007 |
| WO | WO2007095304 | 8/2007 |
| WO | WO2007095318 | 8/2007 |
| WO | WO2007149715 | 12/2007 |
| WO | WO2008021959 | 2/2008 |
| WO | WO2008033105 | 3/2008 |
| WO | WO2008033159 | 3/2008 |
| WO | WO2008048945 | 4/2008 |
| WO | WO2008110937 | 9/2008 |
| WO | WO 2008110937 A2 * | 9/2008 |
| WO | WO2008134643 | 11/2008 |
| WO | WO2009009759 | 1/2009 |
| WO | WO2009026397 | 2/2009 |
| WO | WO2009054708 | 4/2009 |
| WO | WO2009058355 | 5/2009 |
| WO | WO2010036970 | 4/2010 |
| WO | WO2010037046 | 4/2010 |

OTHER PUBLICATIONS

Accession CAA4959, Apr. 18, 2005.

Ahlquist et al., "Gene expression vectors derived from plant RNA viruses," *Current Communications in Molecular Biology—Viral Vectors*, pp. 183-189, 1988.

Air, "Mechanism of antigenic variation in an individual epitope on influenza virus N9 neurammidase," *J. Virology*, 64(12):5797-5803, 1990.

Akol and Murray, "*Trypanosoma congolense*: Susceptibility of cattle to cyclical challenge," *Exp. Parasitol.*, 55:386-393, 1983.

Alignment of 11706573-6 to SEQ ID No. 6 in U.S. Appl. No. 10/558,109 on Feb. 24, 2009.

Alignment of 11706573-30 to SEQ ID No. 6 in U.S. Appl. No. 10/558,109 on Feb. 24, 2009.

Alignment of 11706576-12 to SEQ ID No. 6 in U.S. Appl. No. 10/558,109 on Feb. 24, 2009.

Alignment of 12110877-30 to SEQ ID No. 6 in U.S. Appl. No. 10/558,109 on Feb. 24, 2009.

(56) References Cited

OTHER PUBLICATIONS

Alvarez et al., "Plant-made subunit vaccine against pneumonic and bubonic plague is orally immunogenic in mice," *Vaccine*, 24(14):2477-2490, 2006.

Anderson et al., "Recombinant V antigen protects mice against pneumonic and bubonic plague caused by F1-capsule-positive and -negative strains of *Yersinia pestis*," *Infect. Immun.*, 64(11):4580-5, 1996.

Andrews et al., "Fraction 1 capsular antigen (F1) purification from *Yersinia pestis* CO92 and from an *Escherichia coli* recombinant strain and efficacy against lethal plague challenge," *Infect. Immun.*, 64(6):2180-7, 1996.

Ay et al., "Crystal structures and properties of de novo circularly permuted 1,3-1,4-beta-glucanases," *Proteins*, 30(2):155-67, 1998.

Aymard et al., "Role of antineuraminidase antibodies in protection against influenza," *Bulletin de l'Academie nationale de medicine*, 182(8):1723-1736, 1998 (English abstract).

Aymard et al., "Neuraminidase assays," *Developments in Biologicals*, 115:75-83, 2003.

Baldwin et al., "Vaccinia-expressed human papillomavirus 16 and 18 E6 and E7 as a therapeutic vaccination for vulval and vaginal intraepithelial neoplasia," *Clin. Cancer Res.*, 9(12):5205-5213, 2003.

Barbas et al., "Assembly of combinatorial antibody libraries on phage surfaces: The gene III site," *Proc. Natl. Acad. Sci. USA*, 88:7978, 1991.

Barbas et al., "Semisynthetic combinatorial antibody libraries: A chemical solution to the diversity problem," *Proc. Natl. Acad. Sci. USA*, 89:4457, 1992.

Barfield et al., "Gene transfer in plants of *Brassica juncea* using *Agrobacterium tumefaciens*-mediated transformation," *Plant Cell Reports*, 10(6/7):308-14, 1991.

Bates, "Genetic transformation of plants by protoplast electroporation," *Molecular Biotechnol.*, 2(2):135-145, 1994.

Beachy et al., "A genetic map for the cowpea strain of TMV," *Virology*, 73:498-507, 1976.

Bedell et al., "The E6-E7 region of human papillomavirus type 18 is sufficient for transformation of NIH 3T3 and rat-1 cells," *J. Virol.*, 61:3635-40, 1987.

Berger et al., "Therapeutic applications of monoclonal antibodies," *Am. J. Med. Sci.*, 324(1):14-30, 2002.

Bisaro et al., "Genetic analysis of tomato golden mosaic virus," *Current Communications in Molecular Biology: Viral Vectors*, pp. 172-189, 1988.

Bol et al., "A functional equivalence of top component a RNA and coat protein in the initiation of infection by alfalfa mosaic virus," *Virology*, 46:73-85, 1971.

Bol et al., "Alfalfa mosaic virus and ilarviruses: Involvement of coat protein in multiple steps of the replication cycle," *J. Gen. Virol.* 80:1089-1102, 1999.

Boyd and Beeson, "Animal models for evaluation of compounds against influenza viruses," *Journal of Antimicrobial Chemotherapy*, 1:43-47, 1975.

Brett et al., "Immunization against influenza A virus: Comparison of conventional inactivated, live-attenuated and recombinant baculovirus produced purified hemagglutinin and neuraminidase vaccines in a murine model system," *Virology*, 339(2):273-280 2005.

Brodzik et al., "Advances in alfalfa mosaic virus-mediated expression of anthrax antigen in planta," *Biochem. Biophys. Res. Commun.*, 338( 2):717-722, 2005.

Broothaerts et al., "Gene transfer to plants by diverse species of bacteria," *Nature*, 433:629-33, 2005.
Bruening et al., "In vitro and in vivo translation of the ribonucleic acids of a cowpea strain of *tobacco mosaic virus," Virology*, 71:498-517, 1976.
Burke et al., "Cloning of large segments of exogenous DNA into yeast by means of artificial chromosome vectors," *Science*, 236:806, 1987.
Buscaglia et al., "Tandem amino acid repeats from *Trypanosoma cruzi* shed antigens increase the half-life of proteins in blood," *Blood*, 93(6):2025-2032, 1999.
Calandrelli et al., "Purification and characterization of thermostable eylanase and beta-xylosidase by the termophilic bacterium *Bacillus termantarcticus," Res. Microbiol.*, 155(4):283-9, 2004.
Canizares et al., "Use of viral vectors for vaccine production in plants," *Immunol. Cell Biol.*, 83:263-270, 2005.
Chain et al., "Complete genome sequence of *Yersinia pestis* strains Antigua and Nepal516: Evidence of gene reduction in an emerging pathogen," *J. Bacteriol.*, 188(12):4453-63, 2006.
Chen et al., "Complete sequence of the binary vector pB1121 and its application in cloning T-DNA insertion from transgenic plants," *Mol. Breed.*, 11:287-293, 2003.
Chen et al., "Induction and relief of nasal congestion in ferrets infected with influenza virus," *Int. J. Exp. Path.*, 76:55-64, 1995.
Chica et al., "Semi-rational approaches to engineering enzyme activity: Combining the benefits of directed evolution and rational design," *Current Opinion in Biotechnology*, 16:378-384, 2005.
Chichester et al., "Different response requirements for IFNγ production in ELISPOT assays by CD4+ T cells from mice early and late after submission," *J. Immunol. Methods*, 309:99-107, 2006.
Chichester et al., "Immunogenicity of a subunit vaccine against *Bacillus anthracis," Vaccine*, 25:3111-3114, 2007.
Corbel, M. J., "Reasons for instability of bacterial vaccines," *Developments in Biological Standardization*, 87:113-124, 1996.
Costa et al., "Conformational stability and antibody response to the 18kDa heat-shock protein formulated into different vehicles," *Applied Biochemistry and Biotechnology*, 73(1):19-28, 1998.
Crossway et al., "Integration of foreign DNA following microinjection of tobacco mesophyll protoplasts," *Mol. Gen. Genet.*, 202:179-185, 1986.
Curtis and Nam, "Transgenic radish (*Raphanus sativus* L. *longipinnatus* Bailey) by floral-dip method—plant development and surfactant are important in optimizing transformation efficiency," *Transgenic Research*, 10(4):363-371, 2001.
Davies et al., "Affinity improvement of single antibody VH domains: Residues in all three hypervariable regions affect antigen binding," *Immunotechnology*, 2(3):169-179, 1996.
Dawson et al., "cDNA cloning of the complete genome of tobacco mosaic virus and production of infectious transcripts," *Proc. Natl. Acad. Sci., USA*, 83:1832, 1986.
DeGraff et al., "In vitro evidence that the coat protein of alfalfa mosaic virus plays a direct role in the regulation of plus and minus RNA synthesis implications for the life cycle of alfalfa mosaic virus," *Virology*, 208:583-589, 1995.
Deng et al., "Genome sequence of 2002 *Yersinia pestis* KIM," *J. Bacteriol.*, 184(16):4601-11, 2002.
Desfeux et al., "Female reproductive tissues are the primary target of *Agrobacterium*-mediated transformation by the arabidopsis floral-dip method," *Plant Physiology*, 123(3):895-904, 2000.
Dréau et al., "Human papilloma virus in melanoma biopsy specimens and its relation to melanoma progression," *Annals of Surgery*, 231:664-671, 2000.
Fenton et al., "Immunity to influenza in ferrets. XIV: Comparative immunity following infection or immunization with live or inactivated vaccine," *Br. J. Exp. Path.*, 62:297, 1981.
Fernando et al., "Expression, purification and immunological characterization of the transforming protein E7, from cervical cancer-associated human papillomavirus type 16," *Clin. Exp. Immunol.*, 115:397-403, 1999.
Flick-Smith et al., "A recombinant carboxy-terminal domain of the protective antigen of *Bacillus anthracis* protects mice against anthrax infection," *Infect. Immun.*, 70:1653-1656, 2002.
Floss et al., "Production of vaccines and therapeutic antibodies for veterinary applications in transgenic plants: An overview," *Transgenic Research*, 16(3):315-332, 2007.
Fraley et al., "Expression of bacterial genes in plant cells," *Proc. Natl. Acad. Sci. USA*, 80: 4803-4807, 1983.
Fraley et al., "Liposome-mediated delivery of Tobacco mosaic virus RNA into tobacco protoplasts: A sensitive assay for monitoring liposome-protoplast interactions," *Proc. Natl. Acad. Sci. USA*, 79:1859-1863, 1982.
Franconi et al., "Plant-derived human papillomavirus 16 E7 oncoprotein induces immune response and specific tumor production," *Cancer Res.*, 62:3654, 2002.

(56) References Cited

OTHER PUBLICATIONS

Fromm et al., "Expression of genes transferred into monocot and dicot plant cells by electroporation," *Proc. Natl. Acad. Sci. USA*, 82:5824, 1985.

Fütterer et al., "Use of DNA plant viruses and plant viral expression signals for gene expression in plants and plant protoplasts," *Current Communications in Molecular Biology—Viral Vectors*, pp. 178-182, 1988.

Gelvin, "*Agrobacterium*-mediated plant transformation: The biology behind the 'gene-jockeying' tool," *Microbiol. Mol. Biol. Rev.*, 67(1):16-37, 2003.

Giri and Narasu, "Transgenic hairy roots: recent trends and applications," *Biotechnol. Adv.*, 18:1-22, 2000.

Gleba et al., "Magnifection—a new platform for expressing recombinant vaccines in plants," *Vaccine*, 23:2042-2048, 2005.

Goldenkova et al., "A thermostable *Clostridium thermocellum* lichenase-based reporter system for studying the gene expression regulation in prokaryotic and eukaryotic cells," *Mol. Biol.*, 36:698-704, 2002.

Green et al., "Transient protein expression in three *Pisum sativum* (green pea) varieties," *Biotechnology Journal*, 4(2):230-237, 2009.

Grierson et al., "Plant viruses," *Plant Molecular Biology*, pp. 126-146, 1984.

Gu et al., "Protection against anthrax toxin by vaccination with a DNA plasmid encoding anthrax protective antigen," *Vaccine*, 17:340, 1999.

Hahn et al., "Native-like in-vivo folding of a circularly permuted jellyroll protein shown by crystal structure analysis," *Proc. Natl. Acad. Sci., USA*, 91(22):10417-10421, 1994.

Heath et al., "Protection against experimental bubonic and pneumonic plague by a recombinant capsular F1-V antigen fusion protein vaccine," *Vaccine*, 16(11/12):1131-7, 1998.

Hellens et al., "pGreen: a versatile and flexible binary Ti vector for *Agrobacterium*-mediated plant transformation," *Plant Molecular Biology*, 42: 819-832, 2000.

Herbert and Lumsden, "*Trypanosoma brucei*: A rapid 'matching' method for estimating the host's parasitemia," *Exp. Parasitol.*, 40:427, 1976.

Hobson et al., "The role of serum haemagglutination-inhibiting antibody in protection against challenge infection with influenza A2 and B viruses," *J. Hyg.*, 70:767, 1972.

Holt et al., "Domain antibodies: proteins for therapy," *Trends in Biotechnology*, 21(11):484-490, 2003.

Huang et al., "Plant-derived measles virus hemagglutinin protein induces neutralizing antibodies in mice," *Vaccine*, 19(15/16):2163-2171, 2001.

Huber et al., "Distinct contributions of vaccine-induced immunoglobulin G1 (IgG1) and IgG2a antibodies to protective immunity against influenza," *Clin. Vaccine Immunol.*, 13:981-90, 2006.

Hull et al., "Human-derived, plant-produced monoclonal antibody for the treatment of anthrax," *Vaccine*, 23:2082-2086, 2005.

Hunter et al., "Messenger RNA for the coat protein of Tobacco mosaic virus," *Nature*, 260:759-760, 1976.

Huse et al., "Generation of a large combinatorial library of the immunoglobulin repertoire in phage lambda," *Science*, 246:1275, 1989.

Ishikawa et al., "In vitro mutagenesis of the putative replicase genes of tobacco mosaic virus," *Nucleic Acids Res.*, 14:8291-8308, 1986.

Jaspars et al., "Plant viruses with a multipartite genome," *Adv. Virus Res.*, 19:37-149, 1974.

Jirholt et al., "Exploiting sequence space: Shuffling in vivo formed complementarity determining regions into a master framework," *Gene*, 215:471, 1998.

Johnson et al., Respiratory syncytial virus (RSV) G glycoprotein is not necessary for vaccine-enhanced disease induced by immunization with formalin-inactivated RSV, *J. Virol.*, 78(11):6024-32, 2004.

Jones et al., "Replacing the complementarity—determining regions in a human antibody with those from a mouse," *Nature*, 321:522, 1986.

de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," *Vaccine*, 20(29-30):3456-3464, 2002.

Kang et al., "Linkage of recognition and replication functions by assembling combinatorial antibody Fab libraries along phage surfaces," *Proc. Natl. RAcad. Sci USA*, 88:4363, 1991.

Kao et al., "A method for high-frequency intergeneric fusion of plant protoplasts," *Planta*, 115:355, 1974.

Kapila et al., "An *Agrobacterium*-mediated transient gene expression system for intact leaves," *Plant Sci.*, 122:101-108, 1997.

Kapusta et al., "A plant-derived edible vaccine against hepatitis B virus," *FASEB J.*, 13:1796-1799, 1999.

Katayama and Mine, "*Quillaja* saponin can modulate ovalbumin-induced IgE allergic responses through regulation of Th1/Th2 balance in a murine model," *J. Agric. Food Chem.*, 54:3271-6, 2006.

Kikkert et al., "Biological projectiles (phage, yeast, bacteria) for genetic transformation of plants," *In Vitro Cell. Dev. Bio.—Plant*, 35(1):43-50, 1999.

Klein et al., "High-velocity microprojectiles for delivering nucleic acids into living cells," *Nature*, 327:70-73, 1987.

Knapp et al., "Conundrum of the lack of defective RNAs (dRNAs) associated with *Tobamovirus* infections: dRNAs that can move are not replicated by the wild-type Virus; dRNAs that are replicated by the wild-type virus do not move," *J. Virol.*, 75:5518, 2001.

Knudsen and Muller, "Transformation of the developing barley endosperm by particle bombardment," *Planta*, 185:330-336, 1991.

Konieczny et al., "The combination of IgM subunits and proteolytic IgG fragments by controlled formation of interchain disulphides," *Haematologia (Budap.)*, 14:95, 1981.

Krebber et al., "Reliable cloning of functional antibody variable domains from hybridomas and spleen cell repertoires employing a reengineered phage display system," *J. Immunol. Methods*, 201:35-55, 1997.

Krens et al., "In vitro transformation of plant protoplasts with Ti-plasmid DNA," *Nature*, 296:72-74, 1982.

Kubler-Kielb et al., "Long-lasting and transmission-blocking activity of antibodies to *Plasmodium falciparum* elicited in mice by protein conjugates of Pfs25," *Proceedings of the National Academy of Sciences of USA*, 104(1):293-298, 2007.

Kumagai et al., "Rapid, high-level expression of glycosylated rice α-amylase in transfected plants by an RNA viral vector," *Gene*, 245:169-174, 2000.

Lambkin et al., "Strong local and systemic protective immunity induced in the ferret model by an intranasal virosome-formulated influenza subunit vaccine," *Vaccine*, 22:4390, 2004.

Lawton et al., "Expression of a soybean β-conclycinin gene under Cauliflower Mosaic Virus 35S and 19S promoters in transformed petunia tissues," *Plant Mol. Biol*, 9:315-324, 1987.

Lee and Air, "Contacts between influenza virus N9 neuraminidase and monoclonal antibody NC10," *Virology*, 300(2): 255-268, 2002.

Leite et al., "Expression of correctly processed human growth hormone in seeds of transgenic tobacco plants," *Molecular Breeding*, 6:47-53, 2000.

Lensen et al., "Measurement by membrane feeding of reduction in *Plasmodium falciparum* transmission induced by endemic sera," *Trans. Royal Soc. Trop. Med. Hyg.*, 90(1):20-2, 1996.

Lewandowski and Dawson, "Deletion of internal sequences results in tobacco mosaic virus defective RNAs that accumulate to high levels without interfering with replication of the helper virus," *Virology*, 251:427-437, 1998.

Li et al., "Immunization with recombinant beta-tubulin from *Trypanosoma evansi* induced protection against *T. evansi, T. equiperdum* and *T. b. brucei* infection in mice," *Parasite Immunology*, 29:191-199, 2007.

Lim et al., "An anthrax lethal factor-neutralizing monoclonal antibody protects rats before and after challenge with anthrax toxin," *Infection and Immunity*, 73:6547, 2005.

Lin et al., "Treatment of established tumors with a novel vaccine that enhances major histocompatibility Class II presentation of tumor antigen," *Cancer Research*, 56:21, 1996.

Little et al., "Of mice and men: hybridoma and recombinant antibodies," *Immunology Today*, 21(8):364-370, 2000.

(56) References Cited

OTHER PUBLICATIONS

Little et al., "Passive protection by polyclonal antibodies against *Bacillus anthracis* infection in guinea pigs," *Infect. Immun.*, 65:5171-5175, 1997.

Loesch-Fries, et al., "Expression of Alfalfa Mosaic Virus RNA 4 cDNA Transcripts in vitro and in vivo," *Virology*, 146:177-187, 1985.

Lorence and Verpoorte, "Gene transfer and expression in plants," *Methods Mol. Biol.*, 267:329-350, 2004.

Lubega et al., "Immunization with a tubulin-rich preparation from *Trypanosoma brucei* confers broad protection against African trypanosomosis," *Exp. Parasitol.*, 102:9-22, 2002.

Lubega et al., "*Trypanosoma brucei*: anti-tubulin antibodies specifically inhibit trypanosome growth in culture," *Exp. Parasitol.*, 102:134-142, 2002.

Maassab et al., "Evaluation of a cold-recombinant influenza virus vaccine in ferrets," *The Journal of Infectious Diseases*, 146(6):780-790, 1982.

Maliga et al., "Transient cycloheximide resistance in a tobacco cell line," *Mol. Gen. Genet.*, 149:267-271, 1976.

Marillonnet et al., "Systemic *Agrobacterium tumefaciens*—mediated transfection of viral replicons for efficient transient expression in plants," *Nature Biotechnology*, 23(6):718-723, 2005.

Mathew, Plant Viruses Online—Cassava Indian mosaic bigeminvirus (http://image.fs.uidaho.edu/vide/descr173.htm), downloaded on Feb. 21, 2006, 5 pgs.

Mbawuike et al., "Humoral and cell-mediated immune responses of humans to inactivated influenza vaccine with or without QS21 adjuvant," *Vaccine*, 25:3263-9, 2007.

McCormick et al., "Rapid production of specific vaccines for lymphoma by expression of the tumor-derived single-chain Fv epitopes in tobacco plants," *Proc. Natl. Acad. Sci. USA*, 96:703-708, 1999.

McHugh et al., "Improved stability of a protein vaccine through elimination of a partially unfolded state," *Protein Science*, 13:2736-2743, 2004.

Mellin et al., "Human papillomavirus (HPV) DNA in tonsillar cancer: Clinical correlates, rise of relapse, and survival," *International Journal of Cancer*, 89:300-304, 2000.

Menczel et al. "Streptomycin resistant and sensitive somatic hybrids of *Nicotiana tabacum* + *Nicotiana knightiana*: Correlation of resistance to *N. tabacum* Plastids," *Theor. Appl. Genet.*, 59:191-195, 1981.

Meshi et al., "Function of the 30 kd protein of tobacco mosaic virus: involvement in cell-to-cell movement and dispensability for replication," *EMBO J.*, 6:2557-63, 1987.

Mett et al., Plants as biofactories, *Biologicals: Journal of the International Association of Biological Standardization*, 36(6):354-358, 2008.

Mett et al., "A plant-produced plague vaccine candidate confers protection to monkeys," *Vaccine*, 25(16):3014-3017, 2007.

Mett et al., "A plant-produced influenza subunit vaccine protects ferrets against virus challenge," *Influenza and Other Respiratory Viruses*, 2(1):33-40, 2008.

Moayeri and Leppla, "The roles of anthrax toxin in pathogenesis," *Curr. Opin. Michrobiol*, 7(1):19-24, 2004.

Modelska et al., "Immunization against rabies with plant-derived antigen," *Proc. Nat. Acad. Sci., USA*, 95:2481-2485, 1998.

Moreira et al., "A thermostable maltose-tolerant α-amylase from *Asperillgus tamarii*," *J. Basic Microbiology*, 44:29-35, 2004.

Morrison et al., "Chimeric human antibody molecules: Mouse antigen-binding domains with human constant region domains," *Proc. Natl. Acad. Sci USA*, 81:6851, 1984.

Morrison et al., "Production of novel immunoglobulin molecules by gene transfection," *Mt. Sinai J. Med.*, 53:175, 1986.

Murashige et al., "A revised medium for rapid growth and bio assays with tobacco tissue cultures," *Physiologia Plantarum*, 15:473, 1962.

Musiychuk et al., "A launch vector for the production of vaccine antigens in plants," *Influenza and Other Respiratory Viruses*, 1:19-25, 2007.

Musiychuk et al., "Preparation and properties of *Clostridium thermocellum* lichenase deletion variants and their use for construction of bifunctional hybrid proteins," *Biochemistry(MOSC)*, 65(12):1397-1402, 2000.

Nagy et al., "Thermal stability of chemically denatured green fluorescent protein (GFP)—A preliminary study," *Thermochimica Acta.*, 410(1), abstract, 2004.

Nass, "Anthrax vaccine—model of a response to the biologic warfare threat," *Infect. Dis. Clin. North Am.*, 13:187-208, 1999.

NCBI GenBank Accession No. ABP96852, "Influenza A virus" (A/Egypt/2616-NAMRU3/2007(H5N1)) hemagglutinin (HA) gene, complete CDS, Apr. 30, 2007.

NCBI GenBank Accession No. AAS93885, "Influenza A virus" (A/Cheju/274/2002(H3N2)) neuraminidase (NA) gene, complete CDS, Apr. 25, 2004.

Neeleman et al., "Role of alfalfa mosaic virus coat protein gene in symptom formation," *Virology*, 181:687-693, 1991.

Neeleman et al., "Infection of tobacco with alfalfa mosaic virus cDNAs sheds light on the early function of the coat protein," *Virology*, 196:883-887, 1993.

Noah et al., "Qualification of the hemagglutination inhibition assay in support of pandemic influenza vaccine licensure," *Clin. Vaccine Immunol.*, 16(4):558-566, 2009.

Park et al., "Molecular biology of cervical cancer and its precursors," *Cancer*, 76:1902-1913, 1995.

Parkhill et al., "Genome sequence of *Yersinia pestis*, the causative agent of plague," *Nature*, 413:523-7, 2001.

Peres et al., "Shoot regeneration capacity from roots and transgenic hairy roots of tomato cultivars and wild related species," *Plant Cell, Tissue, and Organ Culture*, 65:37-44, 2001.

Petosa et al., "Crystal structure of the anthrax toxin protective antigen," *Nature*, 385:833-838, 1997.

Pfitzner et al., "Isolation and characterization of cDNA clones encoding pathogenesis-related proteins from tobacco mosaic virus infected tobacco plants," *Nucleic Acids Research*, 15(11):4449-4465, 1987.

Pilon-Smits et al., "Overexpression of ATP sulfurylase in Indian mustard leads to increased selenate uptake, reduction, and tolerance," *Plant Physiol.*, 119(1):123-132, 1999.

Piruzian et al., "A reporter system for prokaryotic and eukaryotic cells based on the thermostable lichenase from *Clostridium thermocellum*," *Mol. Genet. Genomics*, 266(5):778-86, 2002.

Piruzian et al., "The use of a thermostable B-glucanase gene from *Clostridium thermocellum* as a reporter gene in plants," *Mol. Gen. Genet.*, 257(50):561-7, 1998.

Pokorna et al., "Combined immunization with fusion genes of mutated E7 gene of human papillomavirus type 16 did not enhance antitumor effect," *The Journal of Gene Medicine*, 7(6): 696-707, 2005.

Potter et al., "Immunity to influenza in ferrets II. Influence of adjuvants on immunization," *Br. J. Exp. Pathol.*, 53:168, 1972.

Potter et al., "Immunity to influenza in ferrets VI. Immunization with adjuvanted vaccines," *Arch. Gesamte Virusforsch.*, 42:285, 1973.

Potter et al., "Immunity to influenza in ferrets V. Immunization with inactivated virus in adjuvant 65," *J. Hyq., Camb.*, 71:97, 1973.

Pruett et al., "Critical interactions in binding antibody NC41 to influenza N9 neuraminidase: Amino acid contacts on the antibody heavy chain," *Biochemistry*, 37:10660-10670, 1998.

Qian et al., "Conjugating recombinant proteins to *Pseudomonas aeruginosa* ExoProtein A: A strategy for enhancing immunogenicity of malaria vaccine candidate," *Vaccine*, 25(20): 3923-3933, 2007.

Qing et al., "Transformation of Pakchoi (*Brassica rapa* L. ssp. *chinensis*) by *Agrobacterium* infiltration," *Molecular Breeding*, 1:67-72, 2000.

Rao and Ravishankar, "Plant cell cultures: Chemical factories of secondary metabolites," *Biotechnol. Adv.*, 20:101-153, 2002.

Rasooly and Balaban, "Trypanosome microtubule-associated protein p15 as a vaccine for the prevention of African sleeping sickness," *Vaccine*, 22(8):1007-1015, 2004.

Reinstein et al., "Degradation of the E7 human papillomavirus oncoprotein by the ubiquitin-proteasome system: targeting via ubiquitination of the N-terminal residue," *Oncogene*, 19:5944-5950, 2000.

(56) References Cited

OTHER PUBLICATIONS

Riechmann et al., "Reshaping human antibodies for therapy," *Nature*, 332:323, 1988.
Riva et al., "*Agrobacterium tumefaciens*: a natural tool for plant transformation," *EJB Electronic J. Biotech.*, 1(3):118-133, 1998.
Rowe et al., "Detection of antibody to avian influenza A (H5N1) virus in human serum by using a combination of serologic assays," *J. Clin. Microbiol.*, 37:937-43, 1999.
Sabbatini et al., "Pilot study of a heptavalent vaccine-keyhole limpet hemocyanin conjugate plus QS21 in patients with epithelial ovarian, fallopian tube, or peritoneal cancer," *Clin. Cancer Res.*, 13:4170-7, 2007.
Saito et al., "Long-distance movement and viral assembly of tobacco mosaic virus mutants," *Virology*, 176:329-336, 1990.
Santi et al., "Protection conferred by recombinant *Yersinia pestis* antigens produced by a rapid and highly scalable plant expression system," *Proc. Natl. Acad. Sci. USA*, 103(4): 861-866, 2006.
Saravolac et al "Immunoprophylactic strategies against respiratory influenza virus infection," *Vaccine*, 19:2227-2232, 2001.
Scheiblauer et al., "Pathogenicity of influenza A/Seal/Mass/1/80 virus mutants for mammalian species," *Arch. Virol.*, 140:341-384, 1995.
Schell, J., "Transgenic plants as tools to study the molecular organization of plant genes," *Science*, 237:1176-1183, 1987.
Schild et al., "A single-radial-immunodiffusion technique for the assay of influenza haemagglutinin antigen—Proposals for an assay method for the haemagglutinin content of influenza vaccines," *Bull. World Health Org.*, 52:223-31, 1975.
Seedorf et al., "Human papillomavirus type 16 DNA sequence," *Virology*, 145:181, 1985.
Sen et al., "Developments in directed evolution for improving enzyme functions," *Appl. Biochem. Biotechnol.*, 143(3):212-23, 2007.
Shima et al., "Hyperthermaphilic and salt-dependent formyltransferase from *Methanopyrus kanleri," Biochem. Soc. Trans.*, 32:269-72, 2004.
Shimasaki et al., "Rapid diagnostics: the detection of neuraminidase activity as a technology for high-specificity targets," *Philosophical Transactions of the Royal Society of London. Series B, Biological Sciences*, 356(1416):1925-1931, 2001.
Shivprasad et al., "Heterologous sequences greatly affect foreign gene expression in tobacco mosaic virus-based vectors," *Virology*, 255(2):312-23, 1999.
Shoji et al., "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 27(25/26):3467-3470, 2009.
Shoji et al., "Plant-expressed HA as a seasonal influenza vaccine candidate," *Vaccine*, 26(23):2930-2934, 2008.
Singh et al., "Gln277 and Phe544 residues are involved in thermal inactivation of protective antigen of *Bacillus anthracis," Biochemical and Biophysical Research Communications*, 296:1058-1062, 2002.
Singh et al., "Study of immunization against anthrax with the purified recombinant protective antigen of *Bacillus anthracis," Infect. Immun.*, 66:3447-3448, 1998.
Singh et al., "Thermal inactivation of protective antigen of *Bacillus anthracis* and its prevention by polyol osmolytes," *Biochemical and Biophysical Research Communications*, 322:1029-1037, 2004.
Smahel et al., "Modified HPV16 E7 genes as DNA vaccine against E7-containing oncogenic cells," *Virology*, 281:231-238, 2001.
Smahel et al , "Enhancement of immunogenicity of HPV16 E7 oncogene by fusion with *E. coli* β-glucuronidase," *The Journal of Gene Medicine*, 6(10):1092-1101, 2004.
Snow et al., "The global distribution of clinical episodes of *Plasmodium falciparum* malaria," *Nature*, 434:214-217, 2005.
Soderlind et al., "Complementarity-determining region (CDR) implantation: a theme of recombination," *Immunotechnol.*, 4:279, 1999.
Soderlind et al., "Recombining germline-derived CDR sequences for creating diverse single-framework antibody libraries," *Nature Biotechnol.*, 18:852, 2000.
Soini et al., "Presence of human papillomavirus DNA and abnormal p53 protein accumulation in lung carcinoma," *Thorax*, 51:887-893, 1996.
Spilliaert et al., "Cloning and sequencing of a *Rhodothermus marinus* gene, *bglA*, coding for a thermostable β-glucanase and its expression in *Escherichia coli*," *Eur. J. Biochem.*, 224(3):923-930, 1994.
Stewart et al., "Mutant barley (1→3,1→4)-β-glucan endohydrolases with enhanced thermostability," *Protein Engineering*, 14(4):245-253, 2001.
Sweet and Smith, "Pathogenicity of influenza virus," *Microbiological Reviews*, 44(2):303-330, 1980.
Tacket et al., "Human immune responses to a novel Norwalk virus vaccine delivered in transgenic potatoes," *J. Infect. Dis.*, 182:302-305, 2000.
Thanavala et al., "Immunogenicity in humans of an edible vaccine for hepatitis B," *Proc. Natl. Acad. Sci., USA*, 102:3378-3382, 2005.
Thomas et al., "HPV-18 E6 mediated inhibition of p53 DNA binding activity is independent of E6 induced degradation," *Oncogene*, 10:261-8, 1995.
Throsby et al., "Heterosubtypic neutralizing monoclonal antibodies cross-protective against H5NI and H1N1 recovered from human IgM$^+$memory B cells," *Plos One*, LNKD-PUBMED:1907604, 3(12):E3942, 2008.
Toms et al., "Behaviour in ferrets of swine influenza virus isolated from man," *The Lancet.*, 68-71, 1977.
Tsai et al., "Crystal structure of a natural circularly permuted jellyroll protein: 1,3-1,4-β-D-glucanase from *Fibrobacter succinogenes," J. Mol. Biol.*, 330(3):607-20, 2003.
Turpen et al., "Transfection of whole plants from wounds inoculated with *Agrobacterium tumefaciens* containing cDNA of tobacco mosaic virus," *J. Virol, Methods*, 42:227, 1993.
UniProt Database accession No. P04107, Nov. 1, 1986.
UniProt Database [Online] EBI Accession No. Q0PDN1, "SubName: Full=Hemagglutinin," Sep. 5, 2006.
UniProt Database [Online] EBI Accession No. A9X0E7, "SubName: Full=Hemagglutinin; Flags: Precursor," Feb. 5, 2008.
Van der Kolk et al., "Evaluation of the standard membrane feeding assay (SMFA) for the determination of malaria transmission-reducing activity using empirical data," *Parasitology*, 130(Pt. 1):13-22, 2005 (with Erratum in: *Parasitology* 131(Pt 4):578, 2005).
Van Der Kuyl et al., "Complementation and recombination between alfalfa mosaic virus RNA3 mutants in tobacco plants," *Virology*, 183:731-738, 1991.
Van Der Kuyl et al., "Role of alfalfa mosaic virus coat protein in regulation of the balance between viral plus and minus strand RNA synthesis," *Virology*, 185:496-499, 1991.
Van Der Vossen, et al., "Early and late functions of alfalfa mosaic virus coat protein can be mutated separately," *Virology*, 202:891-903, 1994.
Verch et al., "Expression and assembly of a full-length monoclonal antibody in plants using a plant virus vector," *J. Immunol Methods*, 220:69-75, 1998.
Voinnet et al., "An enhanced transient expression system in plants based on suppression of gene silencing by the p19 protein of tomato bushy stunt virus," *Plant J.*, 33:949-956, 2003.
Volten-Doting, Plant Viruses Online (http://image.fs.uidaho.edu/vide/descr009.htm) (downloaded May 18, 2002) (11 pgs.).
Wagner et al., "Plant virus expression systems for transient production of recombinant allergens in *Nicotiana benthamiana," Methods: A Companion to Methods in Enzymology*, 32(3):228-232, 2004.
Wang et al., "Immunogenicity of *Plasmodium yoelii* merozoite surface protein 4/5 produced in transgenic plants," *International Journal of Parasitology*, 38(1):103-110, 2007.
Wang et al., "Structural basis for thermostability of β-glycosidase from the thermophilic eubacterium *Thermus nonproteolyticus* HG102," *J. Bacteriology*, 185:4248-55, 2003.
Webster et al., "Measles virus hemagglutinin protein expressed in transgenic lettuce induces neutralizing antibodies in mice following mucosal vaccination," *Vaccine*, 24(17):3538-3544, 2006.

(56) References Cited

OTHER PUBLICATIONS

Webster et al., "Protection of ferrets against influenza challenge with a DNA vaccine to the haemagglutinin," *Vaccine*, 12(16):1495-1498, 1994.
Webster et al., "Antigenic structure and variation in an influenza virus N9 neuraminidase," *J. Virology*, 61:2910-2916, 1987.
Wiesmuller et al., "Peptide vaccines and peptide libraries," *Biol. Chem.*, 382(4):571-9, 2001.
Williamson et al., "Human immune response to a plague vaccine comprising recombinant F1 and V antigens," *Infect. Immun.*, 73(6):3598-608, 2005.
Williamson et al., "A single dose sub-unit vaccine protects against pneumonic plague," *Vaccine*, 19:566-71, 2000.
Williamson et al., "A new improved sub-unit vaccine for plague: the basis of protection," *FEMS Immunol. Med. Microbiol.*, 12:223-30, 1995.
Wilson et al., "Structure of the haemagglutinin membrane glycoprotein of influenza virus at 3 Å resolution," *Nature*, 289:366, 1981.
Winter and Milstein, "Man-made antibodies," *Nature*, 349:293, 1991.
Woo, P. T. K. "The haematocrit centrifuge technique for the diagnosis of African trypanosomiasis," *Acta, Tropica.*, 27:384, 1970.
The World Health Organization Global Influenza Program Surveillance Network, Evolution of H5N1 avian influenza viruses in Asia, *Emerging Infectious Diseases*, 11(10):1515-1521, 2005.
Yang et al., "Production and diagnostic application of monoclonal antibodies against influenza virus H5," *Journal of Virological Methods*, 162(1-2):194-202, 2009.
Yusibov et al., "Antigens produced in plants by infection with chimeric plant viruses immunize against rabies virus and HIV-1," *Proc. Natl. Acad. Sci. USA*, 94:5784-5788, 1997.
Yusibov et al., "N-terminal basic amino acids of alfalfa mosaic virus coat protein involved in the initiation of infection," *Virology*, 208:405-407, 1995.
Yusibov and Loesch-Fries, "Functional significance of three basic N-terminal amino acids of alfalfa mosaic virus coat protein," *Virology*, 242:1-5, 1998.
Yusibov et al., "Purification, characterization, assembly and crystallization of assembled alfalfa mosaic virus coat protein expressed in *Escherichia coli*," *J. Gen. Virol.*, 77:567-573, 1996.
Yusibov et al., "Expression in plants and immunogenicity of plant virus-based experimental rabies vaccine," *Vaccine*, 20:3155-3164, 2002.
Yusibov et al., "An influenza N1 neuraminidase-specific monoclonal antibody with broad inactivating activity against H5N1 viruses," *Human Antibodies*, 16(1-2):33, 2007.
Yusibov et al., "An influenza N1 neuraminidase-specific monoclonal antibody protects animal against live challenge with homologous H5N1 virus," *Human Antibodies*, 17(1-2):15, 2008.
Yusibov et al., "Novel approaches to the development of vaccines: progress on anthrax". Joint meeting, Sep. 27-30, 2005, Bergen, Norway. Sep. 1, 2005, p. 13. Retrieved from the Internet: URL:http://www.sgm.ac.uk/meetings/pdfabstractsjbergen2005abs.pdf [retrieved on Jun. 13, 2012], 44 pgs.
Yusibov et al., "The potential of plant virus vectors for vaccine production," *Drugs in R & D*, 7(4):203-217, 2006.
Zapata et al., "Engineering linear F(ab')$_2$ fragments for efficient production in *Escherichia coli* and enhanced antiproliferative activity," *Prot. Eng.*, 8:1057, 1995.
Zumbach et al., "Antibodies against oncoproteins E6 and E7 of human papillomavirus types 16 and 18 in patients with head-and-neck squamous-cell carcinoma," *International Journal of Cancer*, 85:815-818, 2000.
Advisory Action Ali Reza Salimi dated Jan. 15, 2010 for U.S. Appl. No. 11/706,568 (3 pgs.).
Communication dated Sep. 23, 2009 for European Appln. No. 04776107.7 (3 pgs.).
Communication dated Apr. 21, 2010 for European Appln. No. 04776107.7 (4 pgs.).
Communication dated May 20, 2010 for European Appln. No. 04776107.7 (5 pgs.).
Communication dated May 19, 2009 for European Appln. No. 06850507.2 (3 pgs.).
Communication dated Feb. 18, 2010 for European Appln. No. 07750905.7 (2 pgs.).
Examiner's First Report dated Aug. 24, 2011 for Australian Appln. No. 2007215082 (3 pgs).
International Preliminary Report on Patentability dated Apr. 23, 2008 for Int'l. Appln. No. PCT/US06/030545 (9 pgs.).
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003969 (6 pgs.).
International Preliminary Report on Patentability dated Aug. 19, 2008 for Int'l. Appln. No. PCT/US07/003973 (6 pgs.).
International Preliminary Report on Patentability dated Mar. 17, 2009 for Int'l. Appln. No. PCT/US07/004103 (4 pgs.).
International Preliminary Report on Patentability dated Nov. 3, 2009 for Int'l. Appln. No. PCT/US08/061782 (7 pgs.).
International Preliminary Report on Patentability dated Jan. 12, 2010 for Int'l. Appln. No. PCT/US08/069860 (5 pgs.).
International Preliminary Report on Patentability dated Mar. 4, 2010 for Int'l. Appln. No. PCT/US08/073776 (6 pgs.).
International Preliminary Report on Patentability dated Mar. 29, 2011 for Int'l. Appln. No. PCT/US09/058640 (7 pgs.).
International Preliminary Report on Patentability dated Mar. 29, 2011 for Int'l. Appln. No. PCT/US09/058669 (12 pgs.).
International Search Report dated Dec. 23, 2005 for Int'l. Appln. No. PCT/US04/16452 (2 pgs.).
International Search Report and Written Opinion dated Jun. 18, 2008 for Int'l. Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Aug. 3, 2007 for Int'l. Appln. No. PCT/US07/003973 (9 pgs.).
International Search Report and Written Opinion dated Aug. 7, 2007 for Int'l. Appln. No. PCT/US07/004103 (9 pgs.).
International Search Report and Written Opinion dated Oct. 21, 2008 for Int'l. Appln. No. PCT/US08/061782 (10 pgs.).
International Search Report and Written Opinion dated May 29, 2009 for Int'l. Appln. No. PCT/US08/069860 (8 pgs.).
International Search Report and Written Opinion dated Apr. 24, 2009 for Int'l. Appln. No. PCT/US08/073776 (11 pgs.).
International Search Report and Written Opinion dated May 11, 2010 for Int'l. Appln. No. PCT/US09/058488 (20 pgs.).
International Search Report and Written Opinion dated Feb. 2, 2010 for Int'l. Appln. No. PCT/US09/058640 (13 pgs.).
International Search Report and Written Opinion dated May 19, 2010 for Int'l. Appln. No. PCT/US09/058669 (21 pgs.).
International Search Report and Written Opinion dated Jan. 27, 2011 for Int'l. Appln. No. PCT/US10/050693 (16 pgs.).
International Search Report and Written Opinion dated Apr. 4, 2008 for Int'l. Appln. No. PCT/US06/030545 (11 pgs.).
Notification of Defects in Patent Application dated Sep. 16, 2010 for Israel Patent Appln. No. 193391 (3 pgs.).
Office Action (non-final) dated Nov. 4, 2008 for U.S. Appl. No. 11/706,568 (7 pgs.).
Office Action (non-final) dated Jan. 6, 2009 for U.S. Appl. No. 11/706,568 (8 pgs.).
Office Action (final) dated Jul. 15, 2009 for U.S. Appl. No. 11/706,568 (7 pgs.).
Office Action (restriction requirement) dated Nov. 28, 2007 for U.S. Appl. No. 11/706,573 (8 pgs.).
Office Action (non-final) dated Apr. 16, 2008 for U.S. Appl. No. 11/706,573 (11 pgs.).
Office Action (non-final) dated Jan. 21, 2009 for U.S. Appl. No. 11/706,573 (10 pgs.).
Office Action (non-final) dated Feb. 22, 2010 for U.S. Appl. No. 11/706,573 (11 pgs.).

(56) References Cited

OTHER PUBLICATIONS

Office Action (non-final) dated Nov. 24, 2010 for U.S. Appl. No. 11/706,573 (11 pgs.).
Supplementary European Search Report dated Dec. 5, 2006 for European Appln. No. 04776107.7 (2 pgs.).
Supplementary European Search Report dated May 5, 2010 for European Appln. No. 07750784 (8 pgs.).
Supplementary European Search Report dated Oct. 8, 2009 for European Appln. No. 07750950 (4 pgs.).
Supplementary European Search Report dated Jun. 9, 2010 for European Appln. No. 08780572 (4 pgs.).
Supplementary European Search Report dated Jun. 19, 2012 for European Appln. No. 07750787 (6 pgs.).
Supplementary European Search Report dated Jan. 25, 2013 for European Appln. No. 08826237 (10 pgs.).

* cited by examiner

Figure 1

Plant Viral Vector pGRD4-H5 HA

LB — 35S promoter — Replicase — MP — CP sub-genomic promoter — H5 HA — Ribozyme — Nos terminator — RB

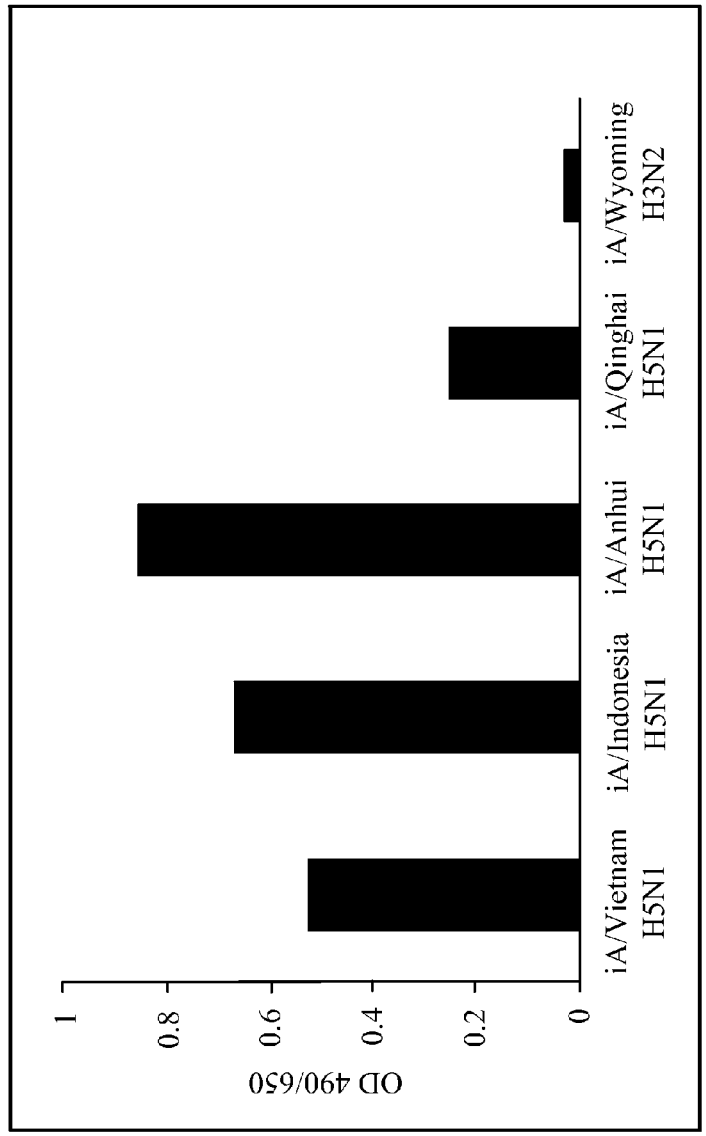

Figure 2A: Specificity of mAbs mAb 4F5 (A/Anhui/1/05)

The specificity of each monoclonal antibody to homologous and heterologous viruses was analyzed by ELISA. Plates were coated with inactivated H5N1 or H3N2 virus. Data are shown as OD 490/650 absorbance values with each monoclonal antibody concentration at 125ng/ml. These antibodies were characterized to be of subclass $IgG_1$, k

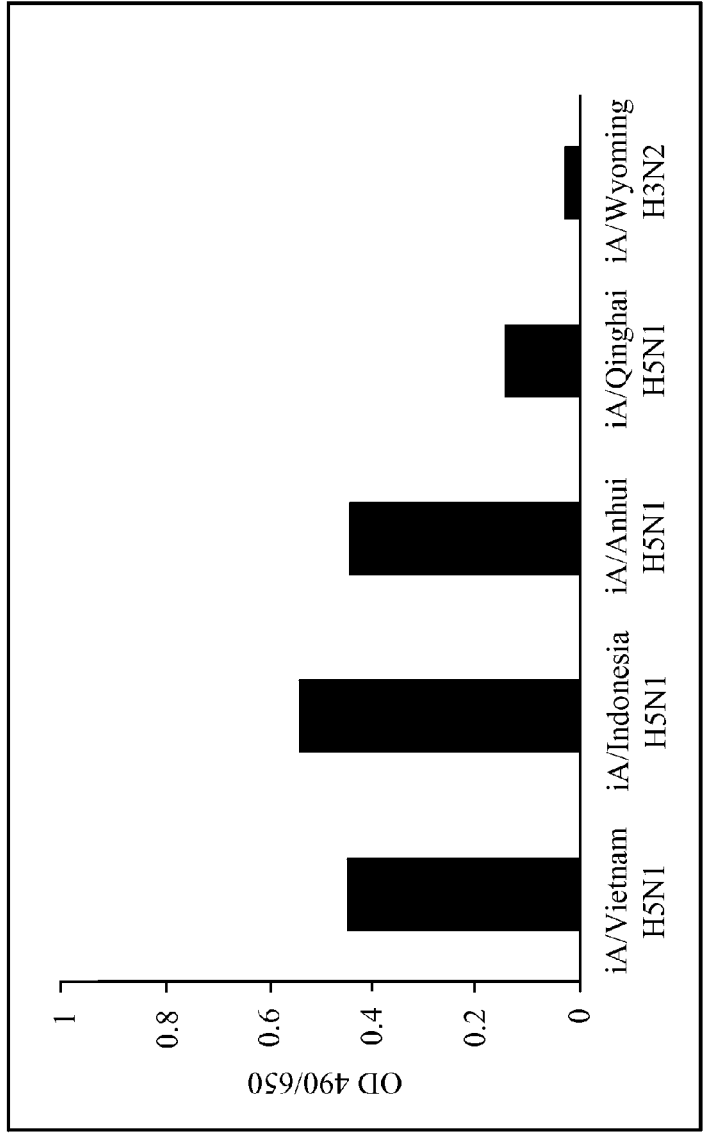

Figure 2B: Specificity of mAbs mAb 5F5 (A/Bar-headed goose/Qinghai/1A/05)

The specificity of each monoclonal antibody to homologous and heterologous viruses was analyzed by ELISA. Plates were coated with inactivated H5N1 or H3N2 virus. Data are shown as OD 490/650 absorbance values with each monoclonal antibody concentration at 125ng/ml. These antibodies were characterized to be of subclass $IgG_1$, k

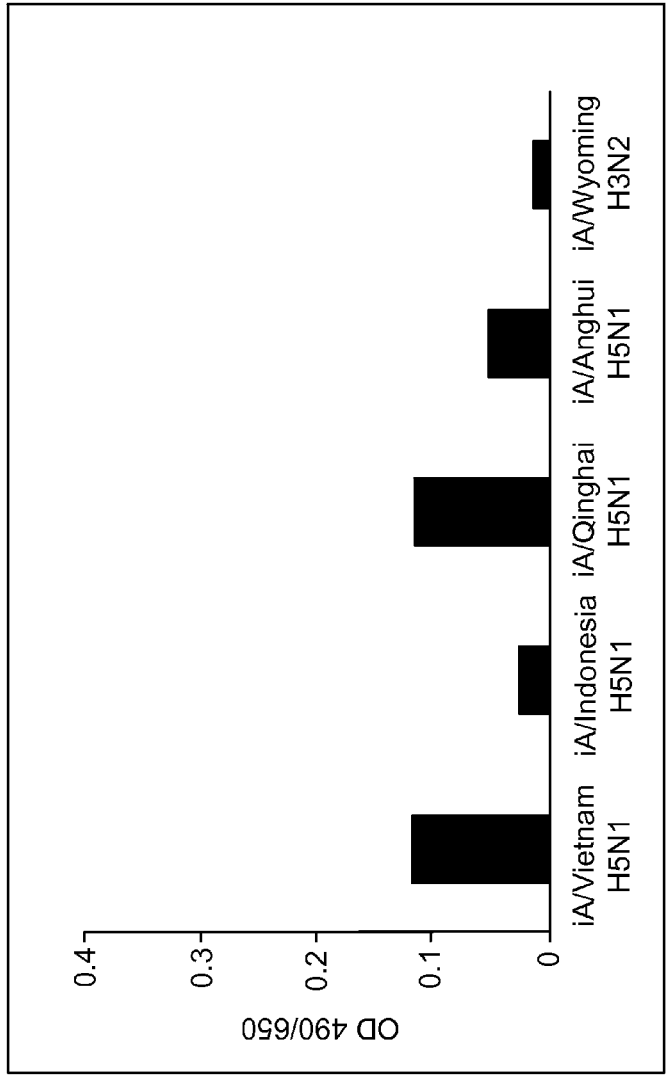
Figure 2C: Specificity of mAbs
mAb 1E11 (A/Bar-headed goose/Qinghai/1A/05)
The specificity of each monoclonal antibody to homologous and heterologous viruses was analyzed by ELISA. Plates were coated with inactivated H5N1 or H3N2 virus. Data are shown as OD 490/650 absorbance values with each

Figure 3
Hemaggluntination Inhibition of mAbs

Cross-clade HI titers

| mAb | Antigen | A/Vietnam/ 1194/04 Clade 1 | A/Indonesia/ 05/05 Clade 2.1 | A/B-H Goose Qinghai/1A/05 Clade 2.2 | A/turkey/ Turkey/1/05 Clade 2.2 | A/Anhui/1/05 Clade 2.3 |
|---|---|---|---|---|---|---|
| 1 E 11 | HAQ1 | 20.3 ± 4.7 | 81.25 ± 18.75 | < 1.56 | < 1.56 | 10.15 ± 2.35 |
| 5 F 5 | HAQ1 | 187.5 ± 62.5 | > 1000 | > 1000 | 375 ± 125 | 375 ± 125 |
| 4 F 5 | HAA1 | > 1000 | > 1000 | > 1000 | > 1000 | 23.4 ± 7.8 |
| Sheep anti-A/Vietnam/1194/04 | | 1280 | 320 | 640 | 640 | 640 |

Data are shown at the lowest antibody concentration (μg/ml) with standard deviations that inhibit hemagglutination activity (8HAU/50μl) of each strain.
For the reference serum, data are shown as endpoint titers that inhibit hemagglutination activity (8HAU/50μl) of each strain.

Figure 4

Influenza Hybridoma ELISA Data

ND=not done  pp=plant-produced

| Immuni-zation | Clone | Isotype | iA/ NIBRG-14 | iA/ Anhui | iA/ Indonesia | iA/ Qinghai | iA/ Wyoming | iA/ Hiroshima | iA/ Brisbane (H3) | iA/ Brisbane (H1) |
|---|---|---|---|---|---|---|---|---|---|---|
| HAA1 | 13B8 | IgG2a | 1.953 | 1.953 | 1.953 | ND | — | — | — | — |
|  | 4F4 | IgG1 | 7.813 | 11.719 | 3.906 | ND | — | — | — | — |
| HAQ1 | 5F5 | IgG1 | 156.25 | 156.25 | 7.813 | ND | — | — | — | — |
|  | 1E11 | IgG1 | 125 | 250 | >1ug/ml | 156 | — | — | — | — |
| HAI | 1E5 | IgG1 | >1ug/ml | 250 | 98 | >1ug/ml | — | — | — | — |
| HAWY1 | 2C7 | IgG1 | — | — | — | — | Yes | Yes | — | — |

Endpoint titers expressed in ng/ml iA = inactive virus

| | Clone | Isotype | ppHAV1 | ppHAA1 | ppHAI1 | ppHAQ1 | ppHAWY1 | Baculovirus produced HAI | Baculovirus produced HAV | Baculovirus produced HAWY |
|---|---|---|---|---|---|---|---|---|---|---|
| HAA1 | 13B8 | IgG2a | ND | 1.953 | 1.953 | 1.953 | — | 19.5 | 19.5 | — |
|  | 4F4 | IgG1 | ND | 1.953 | 1.953 | 1.953 | — | 19.5 | 19.5 | — |
| HAQ1 | 5F5 | IgG1 | ND | 1.953 | 1.953 | 1.953 | — | 19.5 | 19.5 | — |
|  | 1E11 | IgG1 | 62.5 | 125 | — | <156 | — | Yes | Yes | — |
| HAI | 1E5 | IgG1 | 15.6 | 62.5 | 0.24 | 3.906 | — | Yes | Yes | — |
| HAWY1 | 2C7 | IgG1 | — | — | — | — | <156 | — | — | Yes |

These monoclonal antibodies were produced by hybridoma cells lines generated from mice immunized with purified recombinant plant-produced hemagglutinin proteins from different strains of influenza, both pandemic as well as seasonal. Ascites produced and purified antibodies were tested for their ability to bind homologous as well as heterologous recombinant hemagglutinin proteins or inactivated influenza viruses by ELISA. A "Yes" in the charts above indicates a positive signal over background in the ELISA assay. A number indicates the endpoint titer of antibody that can bind the coating material in the assay. Unless otherwise noted the titers are expressed in ng/ml.

HI activities of anti-H5 HA mAbs

| mAb | Antigen | Viruses | | | | |
|---|---|---|---|---|---|---|
| | | A/Anhui/1/05 | A/B-H Goose Qinghai/1A/05 | A/Indonesia/ 05/05 | A/turkey/ Turkey/1/05 | A/Vietnam /1194/04 |
| 1E11 | HAQ1 | 10.15±2.35 | <1.56 | 81.25±18.75 | <1.56 | 20.3±4.7 |
| 1E5 | HAI1 | >1000 | >1000 | >1000 | >1000 | >1000 |
| 5F5 | HAQ1 | 375±125 | >1000 | >1000 | 375±125 | 187.5±62.5 |
| 4F5 | HAA1 | 23.4±7.8 | >1000 | >1000 | >1000 | >1000 |
| 13B8 | HAA1 | >1000 | >1000 | >1000 | >1000 | >1000 |
| Sheep anti-A/Vietnam/1194/04 | | 640 | 640 | 320 | 640 | 1280 |

Data are shown as the lowest antibody concentration (mg/ml) that inhibit hemagglutination activity (8 HAU/50 ml) of each strain.

For reference serum, data are shown as endpoint titers that inhibit hemagglutination activity (8HAU/50 ml) of each strain.

HI activities of anti-H3 HA mAb

| mAb | Antigen | Viruses | | | | | |
|---|---|---|---|---|---|---|---|
| | | A/Brisbane/ 10/07 | A/California/ 07/04 | A/New York/ 55/04 | A/Sydney/ 5/97 | A/Wisconsi n/67/05 | A/Wyoming 03/03 |
| 2 C 7 | HAWY1 | 3.2±0.7 | 15.6±0 | 3.2±0.7 | 500±0 | 3.2±0.7 | 3.2±0.7 |
| Reference (sheep anti-Wyoming) | | 1280 | 1280 | 640 | 640 | 1280 | 1280 |

Data are shown as the lowest antibody concentration (μg/ml) that inhibit hemagglutination activity (8 HAU/50 μl) of each strain.

For reference serum, data are shown as endpoint titers that inhibit hemagglutination activity (8HAU/50 μl) of each strain.

Figure 9

1E11 heavy chain (full length sequence):

*MEWSWIFLFLLSGTAGVHS*EVQLQQSGPELVKPGASVKMSCKASGYTFTSYVMHWVKQKPG
QGLEWIGYINPYNDGTRYNEKFRVKATLTSDKSSSTAYMELSSLTSEDSAVYYC**ARRGLITTPT
LDYW**GQGTTLTVSSAKTTPPSVYPLAPGSAAQTNSMVTLGCLVKGYFPEPVTVTWNSGSLSS
GVHTFPAVLQSDLYTLSSSVTVPSSTWPSETVTCNVAHPASSTKVDKKIVPRDCGCKPCICTVP
EVSSVFIFPPKPKDVLTITLTPKVTCVVVDISKDDPEVQFSWFVDDVEVHTAQTQPREEQFNSTF
RSVSELPIMHQDWLNGKEFKCRVNSAAFPAPIEKTISKTKGRPKAPQVYTIPPPKEQMAKDKVS
LTCMITDFFPEDITVEWQWNGQPAENYKNTQPIMDTDGSYFVYSKLNVQKSNWEAGNTFTCS
VLHEGLHNHHTEKSLSHSPGK (SEQ ID NO:74)

1E11 light chain (full length sequence):

*MMSSAQFLGLLLLCFQGTRC*DIQMTQTSSSLSASLGDRVTISCRASQDIRNYLNWYQQKPDG
TVKLLIYYTSRLHSGVPSRFSDSGSGTDYSLTISNLEQEDLATYFCQQTYTLPWTFGGGTKLEIK
RADAAPTVSIFPPSSEQLTSGGASVVCFLNNFYPKDINVKWKIDGSERQNGVLNSWTDQDSKD
STYSMSSTLTLTKDEYERHNSYTCEATHKTSTSPIVKSFNRNEC (SEQ ID NO:75)

---

4F5 heavy chain (full length sequence):

*MKLWLNWIFLVTLLNDIQC*EVKLVESGGGLVQPGGSLRLSCATSGFTFSDYYMSWVRQSPGK
ALEWLGFTRSRVLGYTTDYSASVKGRFTISRDNSQSILYLQMNSLRGEDSATYYCARDRPMDY
WGQGTSVTVSSAKTTPPSVYPLAPGSAAQTNSMVTLGCLVKGYFPEPVTVTWNSGSLSSGVH
TFPAVLQSDLYTLSSSVTVPSSTWPSETVTCNVAHPASSTKVDKKIVPRDCGCKPCICTVPEVS
SVFIFPPKPKDVLTITLTPKVTCVVVDISKDDPEVQFSWFVDDVEVHTAQTQPREEQFNSTFRS
VSELPIMHQDWLNGKEFKCRVNSAAFPAPIEKTISKTKGRPKAPQVYTIPPPKEQMAKDKVSLT
CMITDFFPEDITVEWQWNGQPAENYKNTQPIMDTDGSYFVYSKLNVQKSNWEAGNTFTCSVL
HEGLHNHHTEKSLSHSPGK (SEQ ID NO:76)

4F5 light chain (full length sequence):

*MRPSIQFLGLLLFWLHGGQC*DIQMTQSPSSLSASLGGNVTITCKASQDINKYIAWYQHKPGKG
PRLVIHYTSTLQPGIPSRFSGSGSGTDYSFSISNLEPEDIATYYCLQYDILYTFGGGTKLEIKRAD
AAPTVSIFPPSSEQLTSGGASVVCFLNNFYPKDINVKWKIDGSERQNGVLNSWTDQDSKDSTY
SMSSTLTLTKDEYERHNSYTCEATHKTSTSPIVKSFNRNEC (SEQ ID NO:77)

---

Italics, bold – signal peptide; bold – complementarity-determining regions; underlined – variable regions; other – constant region

Figure 10

1E11 heavy chain (full length sequence):

EVQLQQSGPELVKPGASVKMSCKASGYTFTSYVMHWVKQKPGQGLEWIGYINPYNDGTRYN
EKFRVKATLTSDKSSSTAYMELSSLTSEDSAVYYCARRGLITTPTLDYWGQGTTLTVSSAKTTP
PSVYPLAPGSAAQTNSMVTLGCLVKGYFPEPVTVTWNSGSLSSGVHTFPAVLQSDLYTLSSSV
TVPSSTWPSETVTCNVAHPASSTKVDKKIVPRDCGCKPCICTVPEVSSVFIFPPKPKDVLTITLT
PKVTCVVVDISKDDPEVQFSWFVDDVEVHTAQTQPREEQFNSTFRSVSELPIMHQDWLNGKE
FKCRVNSAAFPAPIEKTISKTKGRPKAPQVYTIPPPKEQMAKDKVSLTCMITDFFPEDITVEWQW
NGQPAENYKNTQPIMDTDGSYFVYSKLNVQKSNWEAGNTFTCSVLHEGLHNHHTEKSLSHSP
GK (SEQ ID NO:78)

1E11 light chain (full length sequence):

DIQMTQTSSSLSASLGDRVTISCRASQDIRNYLNWYQQKPDGTVKLLIYYTSRLHSGVPSRFSD
SGSGTDYSLTISNLEQEDLATYFCQQTYTLPWTFGGGTKLEIKRADAAPTVSIFPPSSEQLTSG
GASVVCFLNNFYPKDINVKWKIDGSERQNGVLNSWTDQDSKDSTYSMSSTLTLTKDEYERHN
SYTCEATHKTSTSPIVKSFNRNEC (SEQ ID NO:79)

---

4F5 heavy chain (full length sequence):

EVKLVESGGGLVQPGGSLRLSCATSGFTFSDYYMSWVRQSPGKALEWLGFTRSRVLGYTTDY
SASVKGRFTISRDNSQSILYLQMNSLRGEDSATYYCARDRPMDYWGQGTSVTVSSAKTTPPS
VYPLAPGSAAQTNSMVTLGCLVKGYFPEPVTVTWNSGSLSSGVHTFPAVLQSDLYTLSSSVTV
PSSTWPSETVTCNVAHPASSTKVDKKIVPRDCGCKPCICTVPEVSSVFIFPPKPKDVLTITLTPK
VTCVVVDISKDDPEVQFSWFVDDVEVHTAQTQPREEQFNSTFRSVSELPIMHQDWLNGKEFK
CRVNSAAFPAPIEKTISKTKGRPKAPQVYTIPPPKEQMAKDKVSLTCMITDFFPEDITVEWQWN
GQPAENYKNTQPIMDTDGSYFVYSKLNVQKSNWEAGNTFTCSVLHEGLHNHHTEKSLSHSPG
K (SEQ ID NO:80)

4F5 light chain (full length sequence):

DIQMTQSPSSLSASLGGNVTITCKASQDINKYIAWYQHKPGKGPRLVIHYTSTLQPGIPSRFSGS
GSGTDYSFSISNLEPEDIATYYCLQYDILYTFGGGTKLEIKRADAAPTVSIFPPSSEQLTSGGASV
VCFLNNFYPKDINVKWKIDGSERQNGVLNSWTDQDSKDSTYSMSSTLTLTKDEYERHNSYTCE
ATHKTSTSPIVKSFNRNEC (SEQ ID NO:81)

---

Bold – complementarity-determining regions; underlined – variable regions; other – constant region

US 8,784,819 B2

INFLUENZA HEMAGGLUTININ ANTIBODIES, COMPOSITIONS AND RELATED METHODS

CROSS-REFERENCE TO RELATED APPLICATIONS

This application is a National Stage application under 35 U.S.C. 371 of International Application No. PCT/US2010/050693 having an International Filing Date of Sep. 29, 2010, which claims benefit of priority from U.S. Provisional Application Ser. No. 61/246,958, filed on Sep. 29, 2009.

TECHNICAL FIELD

This invention relates to influenza hemagglutinin antibodies, and to materials and methods for making and using influenza hemagglutinin antibodies.

BACKGROUND

Influenza has a long history characterized by waves of pandemics, epidemics, resurgences and outbreaks. Influenza is a highly contagious disease that could be equally devastating both in developing and developed countries. The influenza virus presents one of the major threats to the human population. In spite of annual vaccination efforts, influenza infections result in substantial morbidity and mortality. Although flu epidemics occur nearly every year, fortunately pandemics do not occur very often. However, recent flu strains have emerged such that we are again faced with the potential of an influenza pandemic. Avian influenza virus of the type H5N1, currently causing an epidemic in poultry in Asia as well as regions of Eastern Europe, has persistently spread throughout the globe. The rapid spread of infection, as well as cross species transmission from birds to human subjects, increases the potential for outbreaks in human populations and the risk of a pandemic. The virus is highly pathogenic, resulting in a mortality rate of over fifty percent in birds as well as the few human cases which have been identified. If the virus were to achieve human to human transmission, it would have the potential to result in rapid, widespread illness and mortality.

Subtypes of the influenza virus are designated by different HA and NA resulting from antigenic shift. Furthermore, new strains of the same subtype result from antigenic drift, or mutations in the HA or NA molecules which generate new and different epitopes. While technological advances have improved the ability to produce improved influenza antigens vaccine compositions, there remains a need to provide additional sources of protection against to address emerging subtypes and strains of influenza.

SUMMARY

This document relates to antibody compositions and methods for producing antibody compositions, including production in plant systems. This document further relates to vectors encoding antibodies or antigen binding fragments thereof, as well as fusion proteins, plant cells, plants, compositions, and kits comprising antibodies or antigen binding fragments thereof, and therapeutic and diagnostic uses in association with influenza infection in a subject.

This document is based in part on the identification of anti-H5N1 hemagglutinin monoclonal antibodies (mAbs) that specifically inhibit hemagglutination of highly pathogenic avian influenza (HPAI). The protective efficacy of one of these antibodies has been demonstrated in animal challenge models (e.g., mouse models) using homologous virus. The specific and effective inhibition of these antibodies makes them useful as therapeutic tool in the treatment and/or prevention of human infection. In addition, the mAbs can be a useful diagnostic tool for typing suspected H5N1 human isolates in conjunction with other diagnostic approaches. Thus, this document provides antibodies against influenza hemagglutinin antigens, as well as antibody components produced in plants. The antibodies can inhibit hemagglutination. Also provided are antibody compositions that are reactive against influenza hemagglutinin antigen. In addition, methods for production and use of the antibodies and compositions are provided herein.

Thus, in a first aspect, this document features an isolated monoclonal antibody that binds hemagglutinin, wherein the antibody has the ability to inhibit hemagglutination, and wherein the antibody is selected from the group consisting of an antibody comprising a light chain variable region amino acid sequence at least 85% identical to the amino acid sequence as set forth in amino acids 1-97 of SEQ ID NO:79 and a heavy chain variable region amino acid sequence at least 85% identical to the amino acid sequence as set forth in amino acids 1-115 of SEQ ID NO:78; and an antibody comprising a light chain variable region amino acid sequence at least 85% identical to the amino acid sequence as set forth in amino acids 1-96 of SEQ ID NO:81 and a heavy chain variable region amino acid sequence at least 85% identical to the amino acid sequence as set forth in amino acids 1-112 of SEQ ID NO:80.

The antibody can have a light chain variable region amino acid sequence at least 90% identical to the amino acid sequence as set forth in amino acids 1-97 of SEQ ID NO:79, and a heavy chain variable region amino acid sequence at least 90% identical to the amino acid sequence as set forth in amino acids 1-115 of SEQ ID NO:78. The antibody can have a light chain variable region amino acid sequence at least 95% identical to the amino acid sequence as set forth in amino acids 1-97 of SEQ ID NO:79, and a heavy chain variable region amino acid sequence at least 95% identical to the amino acid sequence as set forth in amino acids 1-115 of SEQ ID NO:78. The antibody can have a light chain variable region amino acid sequence at least 98% identical to the amino acid sequence as set forth in amino acids 1-97 of SEQ ID NO:79, and a heavy chain variable region amino acid sequence at least 98% identical to the amino acid sequence as set forth in amino acids 1-115 of SEQ ID NO:78. The antibody can have a light chain variable region amino acid sequence at least 99% identical to the amino acid sequence as set forth in amino acids 1-97 of SEQ ID NO:79, and a heavy chain variable region amino acid sequence at least 99% identical to the amino acid sequence as set forth in amino acids 1-115 of SEQ ID NO:78. The antibody can have a light chain variable region amino as set forth in amino acids 1-97 of SEQ ID NO:79, and a heavy chain variable region amino acid sequence as set forth in amino acids 1-115 of SEQ ID NO:78.

The antibody can have a light chain variable region amino acid sequence at least 90% identical to the amino acid sequence as set forth in amino acids 1-96 of SEQ ID NO:81, and a heavy chain variable region amino acid sequence at least 90% identical to the amino acid sequence as set forth in amino acids 1-112 of SEQ ID NO:80. The antibody can have a light chain variable region amino acid sequence at least 95% identical to the amino acid sequence as set forth in amino acids 1-96 of SEQ ID NO:81, and a heavy chain variable region amino acid sequence at least 95% identical to the amino acid sequence as set forth in amino acids 1-112 of SEQ ID NO:80. The antibody can have a light chain variable region amino acid sequence at least 98% identical to the amino acid sequence as set forth in amino acids 1-96 of SEQ ID NO:81, and a heavy chain variable region amino acid sequence at least 98% identical to the amino acid sequence as set forth in amino acids 1-112 of SEQ ID NO:80. The antibody can have a light chain variable region amino acid sequence at least 99% identical to the amino acid sequence as set forth in amino acids 1-96 of SEQ ID NO:81, and a heavy chain variable region amino acid sequence at least 99% identical to the amino acid sequence as set forth in amino acids 1-112 of SEQ ID NO:80. The antibody can have a light chain variable region amino as set forth in amino acids 1-96 of SEQ ID NO:81, and a heavy chain variable region amino acid sequence as set forth in amino acids 1-112 of SEQ ID NO:80.

In another aspect, this document features an antibody that binds hemagglutinin, wherein the antibody has the ability to inhibit hemagglutination, and wherein the antibody is selected from the group consisting of an antibody comprising a light chain amino acid sequence at least 85 percent identical to the amino acid sequence set forth in SEQ ID NO:79 and a heavy chain amino acid sequence at least 85 percent identical to the amino acid sequence set forth in SEQ ID NO:78; and an antibody comprising a light chain amino acid sequence at least 85 percent identical to the amino acid sequence set forth in SEQ ID NO:81 and a heavy chain amino acid sequence at least 85 percent identical to the amino acid sequence set forth in SEQ ID NO:80.

The antibody can have a light chain amino acid sequence at least 90% identical to the amino acid sequence set forth in SEQ ID NO:79 and a heavy chain amino acid sequence at least 90% identical to the amino acid sequence set forth in SEQ ID NO:78. The antibody can have a light chain amino acid sequence at least 95% identical to the amino acid sequence set forth in SEQ ID NO:79, and a heavy chain amino acid sequence at least 95% identical to the amino acid sequence set forth in SEQ ID NO:78. The antibody can have a light chain amino acid sequence at least 98% identical to the amino acid sequence set forth in SEQ ID NO:79 and a heavy chain amino acid sequence at least 98% identical to the amino acid sequence set forth in SEQ ID NO:78. The antibody can have a light chain amino acid sequence at least 99% identical to the amino acid sequence set forth in SEQ ID NO:79 and a heavy chain amino acid sequence at least 99% identical to the amino acid sequence set forth in SEQ ID NO:78. The antibody can have a light chain amino acid sequence as set forth in SEQ ID NO:79 and a heavy chain amino acid sequence as set forth in SEQ ID NO:78.

The antibody can have a light chain amino acid sequence at least 90% identical to the amino acid sequence set forth in SEQ ID NO:81 and a heavy chain amino acid sequence at least 90% identical to the amino acid sequence set forth in SEQ ID NO:80. The antibody can have a light chain amino acid sequence at least 95% identical to the amino acid sequence set forth in SEQ ID NO:81 and a heavy chain amino acid sequence at least 95% identical to the amino acid sequence set forth in SEQ ID NO:80. The antibody can have a light chain amino acid sequence at least 98% identical to the amino acid sequence set forth in SEQ ID NO:81 and a heavy chain amino acid sequence at least 98% identical to the amino acid sequence set forth in SEQ ID NO:80. The antibody can have a light chain amino acid sequence at least 99% identical to the amino acid sequence set forth in SEQ ID NO:81 and a heavy chain amino acid sequence at least 99% identical to the amino acid sequence set forth in SEQ ID NO:80. The antibody can have a light chain amino acid sequence as set forth in SEQ ID NO:81 and a heavy chain amino acid sequence as set forth in SEQ ID NO:80.

Any of the antibodies featured herein can be an scFv, Fv, Fab', Fab, diabody, linear antibody or F(ab')2 antigen-binding fragment of an antibody; a CDR, univalent fragment, or a single domain antibody; a human, humanized or part-human antibody or antigen-binding fragment thereof, or a recombinant antibody. The antibody can be produced in a plant.

Any of the antibodies featured herein can be operatively attached to a biological agent or a diagnostic agent. For example, an antibody can be operatively attached to an agent that cleaves a substantially inactive prodrug to release a substantially active drug. The drug can be an anti-influenza agent. An antibody can be operatively attached to an anti-viral agent (e.g., an anti-influenza agent). An antibody can be operatively attached to a biological agent as a fusion protein prepared by expressing a recombinant vector that comprises, in the same reading frame, a DNA segment encoding the antibody operatively linked to a DNA segment encoding the biological agent. An antibody can be operatively attached to a biological agent via a biologically releasable bond or selectively cleavable linker.

An antibody can be operatively attached to a diagnostic, imaging or detectable agent. For example, an antibody can be operatively attached to an X-ray detectable compound, a radioactive ion or a nuclear magnetic spin-resonance isotope. An antibody can be operatively attached to (a) the X-ray detectable compound bismuth (III), gold (III), lanthanum (III) or lead (II); (b) the detectable radioactive ion copper67, gallium67, gallium68, indium111, indium113, iodine123, iodine125, iodine131, mercury197, mercury203, rhenium186, rhenium188, rubidium97, rubidium103, technetium99m or yttrium90; or (c) the detectable nuclear magnetic spin-resonance isotope cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III). An antibody can be operatively attached to biotin, avidin or to an enzyme that generates a colored product upon contact with a chromogenic substrate.

In another aspect, this document features a nucleic acid comprising a nucleotide sequence encoding an antibody light chain or an antibody heavy chain as provided herein. An expression vector containing the nucleic acid also is provided. The expression vector can further include a nucleotide sequence encoding a leader sequence.

This document also features a host cell containing an expression vector as provided herein. The host cell can be a plant cell.

In addition, this document features a plant comprising a plant cell as provided herein. The plant can be from a genus selected from the group consisting of *Brassica, Nicotiana, Petunia, Lycopersicon, Solanum, Capsium, Daucus, Apium, Lactuca, Sinapis*, or *Arabidopsis*. The plant can be from a species selected from the group consisting of *Nicotiana benthamiana, Brassica carinata, Brassica juncea, Brassica napus, Brassica nigra, Brassica oleraceae, Brassica tournifortii, Sinapis alba*, and *Raphanus sativus*. The plant can be selected from the group consisting of alfalfa, radish, mustard, mung bean, broccoli, watercress, soybean, wheat, sunflower, cabbage, clover, petunia, tomato, potato, tobacco, spinach, and lentil. The plant can be a sprouted seedling.

In another aspect, this document features a recombinant, plant-produced monoclonal antibody that binds hemagglutinin, wherein the antibody has the ability to inhibit hemagglutination, and wherein the antibody is selected from the group consisting of an antibody comprising a light chain amino acid sequence at least 85 percent identical to the amino acid sequence set forth in SEQ ID NO:79 and a heavy chain amino acid sequence at least 85 percent identical to the amino acid sequence set forth in SEQ ID NO:78; and an antibody comprising a light chain amino acid sequence at least 85 percent identical to the amino acid sequence set forth in SEQ ID NO:81 and a heavy chain amino acid sequence at least 85 percent identical to the amino acid sequence set forth in SEQ ID NO:80.

The recombinant, plant-produced monoclonal antibody can have a light chain amino acid sequence at least 95% identical to the amino acid sequence set forth in SEQ ID NO:79, and a heavy chain amino acid sequence at least 95% identical to the amino acid sequence set forth in SEQ ID NO:78. The recombinant, plant-produced monoclonal antibody can have a light chain amino acid sequence at least 98% identical to the amino acid sequence set forth in SEQ ID NO:79 and a heavy chain amino acid sequence at least 98% identical to the amino acid sequence set forth in SEQ ID NO:78. The recombinant, plant-produced monoclonal antibody can have a light chain amino acid sequence at least 99% identical to the amino acid sequence set forth in SEQ ID NO:79 and a heavy chain amino acid sequence at least 99% identical to the amino acid sequence set forth in SEQ ID NO:78. The recombinant, plant-produced monoclonal antibody can have a light chain amino acid sequence as set forth in SEQ ID NO:79 and a heavy chain amino acid sequence as set forth in SEQ ID NO:78.

The recombinant, plant-produced monoclonal antibody can have a light chain amino acid sequence at least 90% identical to the amino acid sequence set forth in SEQ ID NO:81 and a heavy chain amino acid sequence at least 90% identical to the amino acid sequence set forth in SEQ ID NO:80. The recombinant, plant-produced monoclonal antibody can have a light chain amino acid sequence at least 95% identical to the amino acid sequence set forth in SEQ ID NO:81 and a heavy chain amino acid sequence at least 95% identical to the amino acid sequence set forth in SEQ ID NO:80. The recombinant, plant-produced monoclonal antibody can have a light chain amino acid sequence at least 98% identical to the amino acid sequence set forth in SEQ ID NO:81 and a heavy chain amino acid sequence at least 98% identical to the amino acid sequence set forth in SEQ ID NO:80. The recombinant, plant-produced monoclonal antibody can have a light chain amino acid sequence at least 99% identical to the amino acid sequence set forth in SEQ ID NO:81 and a heavy chain amino acid sequence at least 99% identical to the amino acid sequence set forth in SEQ ID NO:80. The recombinant, plant-produced monoclonal antibody can have a light chain amino acid sequence as set forth in SEQ ID NO:81 and a heavy chain amino acid sequence as set forth in SEQ ID NO:80.

In still another aspect, this document features a pharmaceutical composition comprising an antibody as provided herein, and a pharmaceutically acceptable carrier. The composition can be formulated for parenteral or topical administration. The antibody can be a recombinant, plant-produced antibody. The pharmaceutically acceptable composition can be an encapsulated or liposomal formulation. The composition can further comprise a second therapeutic agent.

This document also features use of a composition as provided herein for treating an influenza infection in a subject in need thereof, as well as use of a composition as provided herein in the manufacture of a medicament for treating an influenza infection.

In another aspect, this document features a method for determining whether a subject is at risk for influenza virus infection. The method can include contacting a biological sample from the subject with an antibody as provided herein. The subject can be a human.

In yet another aspect, this document features a method for typing an influenza virus, comprising contacting the influenza virus with an antibody as provided herein, and if binding of the antibody to the influenza virus is detected, typing the influenza virus as an H5 virus.

This document also features a method for treating a subject in need thereof, comprising contacting a biological sample from the subject with an antibody as provided herein and, if the antibody shows detectable binding to the biological sample, administering an antibody as provided herein to the subject. The subject can be a human. The subject can be diagnosed as having influenza.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 depicts the plant viral vector pGRD4-H5 HA.

FIG. 2A is a graph depicting the activity of mAb 4F5 against homologous and heterologous strains of influenza viruses. FIG. 2B is a graph depicting the activity of mAb 5F5 against homologous and heterologous strains of influenza viruses. FIG. 2C is a graph depicting the activity of mAb 1E11 against homologous and heterologous strains of influenza viruses.

FIG. 3 is a table summarizing hemagglutinin inhibition activity of anti-HA mAbs.

FIG. 4 is a table summarizing binding activity of anti-HA mAbs.

FIG. 5 is a table summarizing hemagglutination inhibition activity of anti-H5 HA mAbs.

FIG. 6 is a table summarizing hemagglutination inhibition activity of anti-H3 HA mAbs.

FIG. 9 depicts the amino acid sequences, including signal peptide sequences, of heavy and light chains for mAbs 1E11 and 4F5.

FIG. 10 depicts the amino acid sequences, without signal peptide sequences, of heavy and light chains for mAbs 1E11 and 4F5.

DETAILED DESCRIPTION

Figure 7:
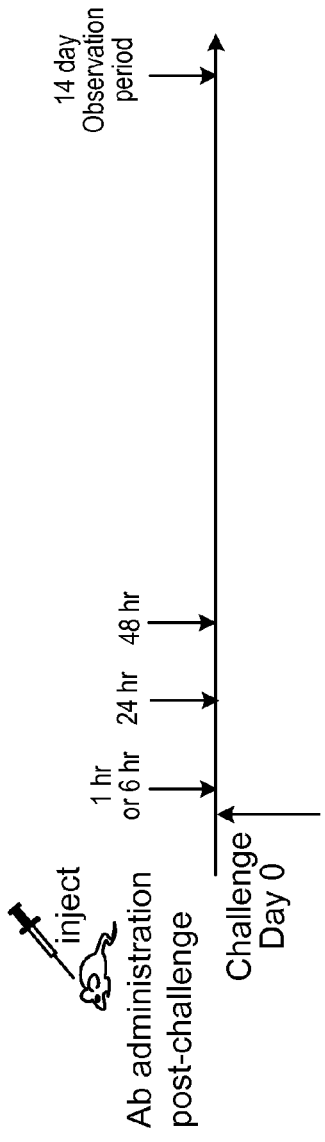
FIG. 7 depicts the experimental design used to evaluate the protective efficacy of mAbs in mice.

This document relates to influenza antibodies that can be useful to prevent, delay onset of, treat, ameliorate symptoms of, reduce occurrence of, and/or diagnose influenza infection. This document also relates to antibody compositions, and methods of production of provided antibody compositions, including but not limited to, production in plant systems. Further, this document relates to vectors, fusion proteins, plant cells, plants and compositions comprising antibodies or antigen binding fragments thereof. Still further provided are kits as well as therapeutic and diagnostic uses in association with influenza infection in a subject.

Influenza Antigens

In general, influenza antigens can include any immunogenic polypeptide that elicits an immune response against influenza virus. Immunogenic polypeptides of interest can be provided as independent polypeptides, as fusion proteins, as modified polypeptides [e.g., containing additional pendant groups such as carbohydrate groups, alkyl groups (such as methyl groups, ethyl groups, or propyl groups), phosphate groups, lipid groups, amide groups, formyl groups, biotinyl groups, heme groups, hydroxyl groups, iodo groups, isoprenyl groups, myristoyl groups, flavin groups, palmitoyl groups, sulfate groups, or polyethylene glycol]. In some embodiments, influenza antigen polypeptides for use in accordance with this disclosure have an amino acid sequence that is or includes a sequence identical to that of an influenza polypeptide found in nature; in some embodiments influenza antigen polypeptides have an amino acid sequence that is or includes a sequence identical to a characteristic portion (e.g., an immunogenic portion) of an influenza polypeptide found in nature.

In certain embodiments, full length proteins are utilized as influenza antigen polypeptides in vaccine compositions in accordance with this disclosure. In some embodiments, one or more immunogenic portions of influenza polypeptides are used. In certain embodiments, two or three or more immunogenic portions are utilized, as one or more separate polypeptides or linked together in one or more fusion polypeptides.

Influenza antigen polypeptides can include, for example, full-length influenza polypeptides, fusions thereof, and/or immunogenic portions thereof. Where portions of influenza proteins are utilized, whether alone or in fusion proteins, such portions retain immunological activity (e.g., cross-reactivity with anti-influenza antibodies). Based on their capacity to induce immunoprotective response against viral infection, hemagglutinin is an antigen of interest in generating vaccines.

In certain embodiments, full length hemagglutinin (HA) is utilized to generate HA antibodies as provided herein. In some embodiments one or more domains of HA can be used. In certain embodiments, two or three or more domains are utilized, as one or more separate polypeptides or linked together in one or more fusion polypeptides. Sequences of exemplary HA polypeptides are presented in Table 1.

TABLE 1

Exemplary HA Sequences

| GenBank Accession | Strain | HA Sequence |
|---|---|---|
| ABY51347 | A/environment/ New York/3181-1/2006 (H7N2) | 5'MNIQILAFIACVLTGAKGDKICLGHHAVANGTKVNTLTEKGI EVVNATETVETADVKKICTQGKRATDLGRCGLLGTLIGPPQCD QFLEFSSDLIIERREGTDVCYPGRFTNEESLRQILRRSGGIGKES MGFTYSGIRTNGAASACTRSGSSFYAEMKWLLSNSDNSAFPQ MTKAYRNPRNKPALIIWGVHHSESASEQTKLYGSGNKLITVRS SKYQQSFTPSPGTRRIDFHWLLLDPNDTVTFTFNGAFIAPDRAS FFRGESLGVQSDAPLDSSCRGDCFHSGGTIVSSLPFQNINSRTV GRCPRYVKQKSLLLATGMRNVPEKPKPRGLFGAIAGFIENGW EGLINGWYGFRHQNAQGEGTAADYKSTQSAIDQITGKLNRLIG KTNQQFELIDNEFNEIEQQIGNVINWTRDAMTEIWSYNAELLV AMENQHTIDLADSEMSKLYERVKKQLRENAEEDGTGCFEIFH KCDDQCMESIRNNTYDHTQYRTESLQNRIQIDPVKLSSGYKDII LWFSFGASCFILLAIAMGLVFICIKNGNMQCTICI 3' (SEQ ID NO: 1) |
| ACC61810 | A/environment/ New York/3185-1/2006 (H7N2) | 5'MNTQILAFIACVLTGVKGDKICLGHHAVANGTKVNTLTEKG IEVVNATETVETADVKKICTQGKRATDLGRCGLLGTLIGPPQC DQFLEFSSDLIIERREGTDVCYPGRFTNEESLRQILRRSGGIGKE SMGFTYSGIRTNGATSACTRSGSSFYAEMKWLLSNSDNSAFPQ MTKAYRNPRNKPALIIWGVHHSESVSEQTKLYGSGNKLITVRS SKYQQSFTPSPGARRIDFHWLLLDPNDTVTFTFNGAFIAPDRAS FFRGESLGVQSDVPLDSSCRGDCFHSGGTIVSSLPFQNINSRTV GKCPRYVKQKSLLLATGMRNVPEKPKPRGLFGAIAGFIENGW EGLINGWYGFRHQNAQGEGTAADYKSTQSAIDQITGKLNRLIG KTNQQFELIDNEFNEIEQQIGNVINWTRDAMTEIWSYNAELLV AMENQHTIDLADSEMSKLYERVKKQLRENAEEDGTGCFEIFH KCDDQCMESIRNNTYDHTQYRTESLQNRIQIDPVKLSSGYKDII LWFSFGASCFLLLAIAMGLVFICIKNGNMQCTICI 3' (SEQ ID NO: 2) |
| ABI26075 | A/guineafowl/ NY/4649-18/2006 (H7N2) | 5'MNIQILAFIACVLTGAKGDKICLGHHAVANGTKVNTLTEKGI EVVNATETVETANIKKICTQGKRPTDLGQCGLLGTLIGPPQCD QFLEFSSDLIIERREGTDVCYPGKFTNEESLRQILRRSGGIGKES MGFTYSGIRTNGATSACTRSGSSFYAEMKWLLSNSDNAAFPQ MTKSYRNPRNKPALIIWGVHHSESVSEQTKLYGSGNKLIKVRS SKYQQSFTPNPGARRIDFHWLLLDPNDTVTFTFNGAFIAPDRA SFFRGESIGVQSDAPLDSSCGGNCFHNGGTIVSSLPFQNINPRTV GKCPRYVKQKSLLLATGMRNVPEKPKKRGLFGAIAGFIENGW EGLINGWYGFRHQNAQGEGTAADYKSTQSAIDQITGKLNRLIG KTNQQFELINNEFNEVEQQIGNVINWTQDAMTEVWSYNAELL |

TABLE 1-continued

Exemplary HA Sequences

| GenBank Accession | Strain | HA Sequence |
|---|---|---|
| | | VAMENQHTIDLTDSEMSKLYERVRKQLRENAEEDGTGCFEIF HKCDDHCMESIRNNTYDHTQYRTESLQNRIQIDPVKLSGGYK DIILWFSFGASCFLLLAIAMGLVFICIKNGNMQCTICI 3' (SEQ ID NO: 3) |
| ABR37506 | A/environment/ Maryland/267/ 2006(H7N3) | 5'MNTQILALIAYMLIGAKGDKICLGHHAVANGTKVNTLTERG IEVVNATETVETVNIKKICTQGKRPTDLGQCGLLGTLIGPPQCD QFLEFDADLIIERREGTDVCYPGKFTNEESLRQILRGSGGIDKES MGFTYSGIRTNGVTSACRRSGSSFYAEMKWLLSNSDNAAFPQ MTKSYRNPRNKPALIIWGVHHSGSATEQTKLYGSGNKLITVGS SKYQQSFTPSPGARPQVNGQSGRIDFHWLLLDPNDTVTFTFNG AFIAPDRASFFRGESLGVQSDVPLDSGCEGDCFHSRGTIVSSLP FQNINPRTVGKCPRYVKQTSLLLATGMRNVPENPKTRGLFGAI AGFIENGWEGLIDGWYGFRHQNAQGEGTAADYKSTQSAIDQI TGKLNRLIDKTNQQFELIDNEFSEIEQQIGNVINWTRDSMTEV WSYNAELLVAMENQHTIDLADSEMNKLYERVRKQLRENAEE DGTGCFEIFHKCDDQCMESIRNNTYDHTQYRTESLQNRIQIDP VKLSSGYKDIILWFSFGASCFLLLAIAMGLVFICIKNGNMRCTI CI 3' (SEQ ID NO: 4) |
| ACF47475 | A/mallard/ California/ HKWF 1971/2007 (H7N7) | 5'MNTQILALIACMLIGAKGDKICLGHHAVANGTKVNTLTERG IEVVNATETVETANIKKICTQGKRPTDLGQCGLLGTLIGPPQCD QFLEFDADLIIERREGTDVCYPGKFTNEESLRQILRGSGGIDKES MGFTYSGIRTNGATSACRRSGSSFYAEMKWLLSNSDNAAFPQ MTKSYRNPRNKPALIIWGVHHSGSATEQTKLYGSGNKLITVGS SKYQQSFTPSPGARPQVNGQSGRIDFHWLLLDPNDTVTFTFNG AFIAPDRASFFRGGSLGVQSDVPLDSGCEGDCFHSGGTIVSSLP FQNINPRTVGKCPRYVKQTSLLLATGMRNVPENPKTRGLFGAI AGFIENGWEGLIDGWYGFRHQNAQGEGTAADYKSTQSAIDQI TGKLNRLIDKTNQQFELIDNEFNEIEQQIGNVINWTRDSMTEV WSYNAELLVAMENQHTIDLADSEMNKLYERVRKQLRENAEE DGTGCFEIFHKCDDQCMESIRNNTYDHTQYRTESLQNRIQINP VKLSSGYKDIILWFSFGASCFLLLAIAMGLVFICIKNGNMRCTI CI 3' (SEQ ID NO: 5) |
| ABP96852 | A/Egypt/2616- NAMRU3/2007 (H5N1) | 5'MEKIVLLLAIVSLVKSDQICIGYHANNSTEQVDTIMEKNVTV THAQDILEKTHNGKLCDLDGVKPLILRDCSVAGWLLGNPMCD EFLNVPEWSYIVEKINPANDLCYPGDFNDYEELKHLLSRINHFE KIQIIPKSSWSDYEASSGVSSACPYQGRSSFFRNVVWLIKKNNA YPTIKRSYNNTNQEDLLVLWGIHHPNDAAEQIRLYQNPTTYISI GTSTLNQRLVPKIATRSKVNGQSGRMEFFWTILKSNDAINFES NGNFIAPEYAYKIVKKGDSTIMKSELEYGNCNTKCQTPIGAINS SMPFHNIHPLTIGECPKYVKSNRLVLATGLRNSPQGERRRRKR GLFGAIAGFIEGGWQGMVDGWYGYHHSNEQGSGYAADKEST QKAIDGVTNKVNSIINKMNTQFEAVGREFNNLERRIENLNKK MEDGFLDVWTYNAELLVLMENERTLDFHDSNVKNLYDKVRL QLRDNAKELGNGCFEFYHRCDNECMESVRNGTYDYPQYSEE ARLKREEISGVKLESMGIYQILSIYSTVASSLALAIMVAGLFLW MCSNGSLQCRICI 3' (SEQ ID NO: 6) |
| ABV23934 | A/Nigeria/6e/ 07(H5N1) | 5'DQICIGYHANNSTEQVDTIMEKNVTVTHAQNILEKTHNGKL CDLDGVKPLILRDCSVAGWLLGNPMCDEFLNVPEWSYIVEKI NPANDLCYPGNFNDYEELKHLLSRINHFEKIQIIPKSSWSDHEA SSGVSSACPYQGRSSFFRNVVWLIKKDNAYPTIKRSYNNTNQE DLLVLWGIHHPNDAAEQTRLYQNPTTYISVGTSTLNQRLVPKI ATRSKVNGQSGRMEFFWTILKPNDAINFESNGNFIAPENAYKI VKKGDSTIMKSELEYGNCNTKCQTPIGAINSSMPFHNIHPLTIG ECPKYVKSNKLVLATGLRNSPQGERRRKKRGLFGAIAGFIEGG WQGMVDGWYGYHHSNEQGSGYAADKESTQKAIDGVTNKVN SIIDKMNTQFEAVGREFNNLERRIENLNKKMEDGFLDVWTYN AELLVLMENERTLDFHDSNVKNLYDKIRLQLRDNAKELGNGC FEFYHRCDNECMESVRNGTYDYPQYSEEARLKREEISGVKLES IGTYQILSIYSTVASSLTLAIMVAGLSLWMCSNGSLQCRICI 3' (SEQ ID NO: 7) |
| ABI16504 | A/China/GD01/ 2006 (H5N1) | 5'MEKIVLLLAIVSLVKSDQICIGYHANNSTEQVDTIMEKNVTV THAQDILEKTHNGKLCDLDGVKPLILRDCSVAGWLLGNPMCD EFINVPEWSYIVEKANPANDLCYPGNFNDYEELKHLLSRINHF EKIQIISKSSWSDHEASSGVSSACPYQGTPSFFRNVVWLIKKNN TYPTIKRSYNNTNQEDLLILWGIHHSNNAAEQTKLYQNPTTYIS VGTSTLNLRLVPKIATRSKVNGQSGRMDFFWTILKPNDAINFE SNGNFIAPEYAYKIVKKGDSAIMKSEVEYGNCNTKCQTPIGAI NSSMPFHNIHPLTIGECPKYVKSNKLVLATGLRNSPLRERRRK RGLFGAIAGFIEGGWQGMVDGWYGYHHSNEQGSGYAADKES TQKAIDGVTNKVNSIIDKMNTQFEAVGREFNNLERRIENLNKK |

TABLE 1-continued

Exemplary HA Sequences

| GenBank Accession | Strain | HA Sequence |
|---|---|---|
| | | MEDGFLDVWTYNAELLVLMENERTLDFHDSNVKNLYDKVRL<br>QLRDNAKELGNGCFEFYHKCDNECMESVRNGTYDYPQYSEE<br>ARLKREEISGVKLESIGTYQILSIYSTVASSLALAIMVAGLSLW<br>MCSNGSLQCRICI 3' (SEQ ID NO: 8) |
| ABY27653 | A/India/m777/ 2007 (H5N1) | 5'MEKIVLLFAIVSLVKSDQICIGYHANNSTEQVDTIMEKNVTV<br>THAQDILEKKHNGKLCDLDGVKPLILRDCSVAGWLLGNPMCD<br>EFINVPEWSYIVEKANPVNDLCYPGDFNDYEELKHLLSRINHF<br>EKIQIIPKSSWSSHEASLGVSSACPYQGKTSFFRNVVWLIKKNS<br>TYPTIKRSYNNTNQEDLLVLWGIHHPNDAAEQTKLYQNPTTYI<br>SVGTSTLNQRLVPRIATRSKVNGQSGRMEFFWTILKPNDAINF<br>ESNGNFIAPEYAYKIVKKGDSTIMKSELEYGNCNTKCQTPMGA<br>INSSMPFHNIHPLTIGECPKYVKSNRLVLATGLRNSPQRETRGL<br>FGAIAGFIEGGWQGMVDGWYGYHHSNEQGSGYAADKESTQK<br>AIDGVTNKVNSIIDKMNTQFEAVGREFNNLERRIENLNKKMED<br>GFLDVWTYNAELLVLMENERTLDFHDSNVKNLYDKVRLQLR<br>DNAKELGNGCFEFYHKCDNECMESVRNGTYDYPQYSEEARL<br>KREEISGVKLESIGIYQILSIYSTVASSLALAIMVAGLSLWMCSN<br>GSLQCRIC 3' (SEQ ID NO: 9) |
| AB136046 | A/Indonesia/ CDC326N/2006 (H5N1) | 5'DQICIGYHANNSTEQVDTIMEKNVTVTHAQDILEKTHNGKL<br>CDLDGVKPLILRDCSVAGWLLGNPMCDEFINVPEWSYIVEKA<br>NPTNDLCYPGSFNDYEELKHLLSRINHFEKIQIIPKSSWSDHEAS<br>SGVSSACPYLGSPSFFRNVVWLIKKNSTYPTIKKSYNNTNQED<br>LLVLWGIHHPNDAAEQTRLYQNPTTYISIGTSTLNQRLVPKIAT<br>RSKVNGQSGRMEFFWTILNPNDAINFESNGNFIAPEYAYKIVK<br>KGDSAIMKSELEYGNCNTKCQTPMGAINSSMPFHNIHPLTIGE<br>CPKYVKSNRLVLATGLRNSPQRESRRKKRGLFGAIAGFIEGGW<br>QGMVDGWYGYHHSNEQGSGYAADKESTQKAIDGVTNKVNSI<br>IDKMNTQFEAVGREFNNLERRIENLNKKMEDGFLDVWTYNAE<br>LLVLMENERTLDFHDSNVKNLYDKVRLQLRDNAKELGNGCF<br>EFYHKCDNECMESIRNGTYNYPQYSEEARLKREEISGVKLESI<br>GTYQILSIYSTVASSLALAIMMAGLSLWMCSNGSLQCRICI 3'<br>(SEQ ID NO: 10) |
| ACD85624 | A/Mississippi/ 05/2008 (H3N2) | 5'MKTIIALSYILCLVSAQKFPGNDNSTATLCLGHHAVPNGTIV<br>KTITNDQIEVTNATELVQSSSTGEICDSPHQILDGENCTLIDALL<br>GDPQCDGFQNKKWDLFVERSKAYSNCYPYDVPDYASLRSLV<br>ASSGTLEFNNESFNWTGVTQNGTSSACIRRSNNSFFSRLNWLT<br>HLKFKYPALNVTMPNNEEFDKLYIWGVHHPGTDNDQIFLYAQ<br>ASGRITVSTKRSQQTVIPNIRSRPRVRNIPSRISIYWTIVKPGDIL<br>LINSTGNLIAPRGYFKIRSGKSSIMRSDAPIGKCNSECITPNGSIP<br>NDKPFQNVNRITYGACPRYVKQNTLKLATGMRNVPEKQTRGI<br>FGAIAGFIENGWEGMVDGWYGFRHQNSEGIGQAADLKSTQA<br>AIDQINGKLNRLIGKTNEKFHQIEKEFSEVEGRIQDLEKYVEDT<br>KIDLWSYNAELLVALENQHTIDLTDSEMNKLFEKTKKQLREN<br>AEDMGNGCFKIYHKCDNACIGSIRNGTYDHDVYRDEALNNRF<br>QIKGVELKSGYKDWILWISFAISCFLLCVALLGFIMWACQKGN<br>IRCNICI 3' (SEQ ID NO: 11) |
| ACF10321 | A/New York/06/2008 (H3N2) | 5'MKTIIALSYILCLVFAQKLPGNDNSTATLCLGHHAVPNGTIV<br>KTITNDQIEVTNATELVQSSSTGEICDSPHQILDGENCTLIDALL<br>GDPQCDGFQNKKWDLFVERSKAYSNCYPYDVPDYASLRSLV<br>ASSGTLEFKNESFNWTGVTQNGTSSACIRRSNNSFFSRLNWLT<br>HLKFKYPALNVTMPNKEKFDKLYIWGVHHPGTDNDQIFLYAQ<br>ASGRITVSTKRSQQTVIPNIGSRLRVRDIPSRISIYWTIVKPGDIL<br>LINSTGNLIAPRGYFKIRSGKSSIMRSDAPIGKCNSECITPNGSIP<br>NDKPFQNVNRITYGACPRYVKQNTLKLATGMRNVPEKQTRGI<br>FGAIAGFIENGWEGMVDGWYGFRHQNSEGTGQAADLKSTQA<br>AIDQINGKLNRLIGKTNEKFHQIEKEFSEVEGRIQDLEKYVEDT<br>KIDLWSYNAELLVALENQHTIDLTDSEMNKLFEKTKKQLREN<br>AEDMGNGCFKIYHKCDNACIGSIRNGTYDHDVYRDEALNNRF<br>QIKGVELKSGYKDWILWISFAISCFLLCVALLGFIMWACQKGN<br>IRCNICI 3' (SEQ ID NO: 12) |
| ACD85628 | A/Idaho/03/ 2008 (H3N2) | 5'MKTIIALSYILCLVFAQKLPGNDNSTATLCLGHHAVPNGTIV<br>KTITNDQIEVTNATELVQSSSTGEICDSPHQILDGENCTLIDALL<br>GDPQCDGFQNKKWDLFVERSKAYSKCYPYDVPDYASLRSLV<br>ASSGTLEFNNESFNWTGVTQNGTSSACIRRSNNSFFSRLNWLT<br>HLKFKYPALNVTMPNNEKFDKLYIWGVHHPGTDNDQIFLYAQ<br>ASGRITVSTKRSQQTVIPNIGSRPRVRDIPSRISIYWTIVKPGDIL<br>LINSTGNLIAPRGYFKIRSGKSSIMRSDAPIGKCNSECITPNGSIP<br>NDKPFQNVNRITYGACPRYVKQNTLKLATGMRNVPEKQTRGI<br>FGAIAGFIENGWEGMVDGWYGFRHQNSEGIGQAADLKSTQA<br>AIDQINGKLNRLIGKTNEKFHQIEKEFSEVEGRIQDLEKYVEDT |

TABLE 1-continued

Exemplary HA Sequences

| GenBank Accession | Strain | HA Sequence |
|---|---|---|
| | | KIDLWSYNAELLVALENQHTIDLTDSEMNKLFEKTKKQLREN<br>AEDMGNGCFKIYHKCDNACIGSIRNGTYDHDVYRDEALNNRF<br>QIKGVELKSGYKDWILWISFAISCFLLCVALLGFIMWACQKGN<br>IRCNICI 3' (SEQ ID NO: 13) |
| ACF40065 | A/Louisiana/<br>06/2008<br>(H3N2) | 5'MKTIIALSYILCLVFAQKLPGNDNSTATLCLGHHAVPNGTIV<br>KTITNDQIEVTNATELVQSSSTGEICDSPHQILDGENCTLIDALL<br>GDPQCDGFQNKKWDLFVERSKAYSNCYPYDVPDYASLRSLV<br>ASSGTLEFNNESFNWTGVTQNGTSSACIRRSNNSFFSRLNWLT<br>HLKFKYPALNVTMPNNEKFDKLYIWGVHHPGTDNDQIFLYAQ<br>ASGRITVSTKRSQQTVIPNIGSRPRVRNIPSRISIYWTIVKPGDIL<br>LINSTGNLIAPRGYFKIRSGKSSIMRSDAPIGKCNSECITPNGSIP<br>NDKPFQNVNRITYGACPRYVKQNTLKLATGMRNVPEKQTRGI<br>FGAIAGFIENGWEGMVDGWYGFRHQNSEGIGQAADLKSTQA<br>AIDQINGKLNRLIGKTNEKFHQIEKEFSEVEGRIQDLEKYVEDT<br>KIDLWSYNAELLVALENQHTIDLTDSEMNKLFEKTKKQLREN<br>AEDMGNGCFKIYHKCDNACIGSIRNGTYDHDVYRDEALNNRF<br>QIKGVELKSGYKDWILWISFAISCFLLCVALLGFIMWACQKGN<br>IRCNICI 3' (SEQ ID NO: 14) |
| ACB11768 | A/Indiana/01/<br>2008 (H1N1) | 5'MKVKLLVLLCTFTATYADTICIGYHANNSTDTVDTVLEKNV<br>TVTHSVNLLENSHNGKLCLLKGIAPLQLGNCSVAGWILGNPEC<br>ELLISKESWSYIVEKPNPENGTCYPGHFADYEELREQLSSVSSF<br>ERFEIFPKESSWPNHTVTGVSASCSHNGESSFYRNLLWLTGKN<br>GLYPNLSKSYANNKEKEVLVLWGVHHPPNIGDQKALYHTEN<br>AYVSVVSSHYSRKFTPEIAKRPKVRDQEGRINYHWTLLEPGDT<br>IIFEANGNLIAPRYAFTLSRGFGSGIINSNAPMDKCDAKCQTPQ<br>GAINSSLPFQNVHPVTIGECPKYVRSAKLRMVTGLRNIPSIQSR<br>GLFGAIAGFIEGGWTGMVDGWYGYHHQNEQGSGYAADQKST<br>QNAINGITNKVNSVIEKMNTQFTAVGKEFNKLERRMENLNKK<br>VDDGFIDIWTYNAELLVLLENERTLDFHDSNVKNLYEKVKSQ<br>LKNNAKEIGNGCFEFYHKCNDECMESVKNGTYDYPKYSEESK<br>LNREKIDGVKLESMGVYQILAIYSTVASSLVLLVSLGAISFWM<br>CSNGSLQCRICI 3' (SEQ ID NO: 15) |
| ACB11769 | A/Pennsylvania/<br>02/2008<br>(H1N1) | 5'MKVKLLVLLCTFTATYADTICIGYHANNSTDTVDTVLEKNV<br>TVTHSVNLLENSHNGKLCLLKGIAPLQLGNCSVAGWILGNPEC<br>ELLISKESWSYIVEKPNPENGTCYPGHFADYEELREQLSSVSSF<br>ERFEIFPKESSWPNHTVTGVSASCSHNGESSFYRNLLWLTGKN<br>GLYPNLSKSYANNKEKEVLVLWGVHHPPNIGDQKTLYHTENA<br>YVSVVSSHYSRKFTPEIAKRPKVRDQEGRINYYWTLLEPGDTII<br>FEANGNLIAPRYAFALSRGFGSGIINSNAPMDKCDAKCQTPQG<br>AINSSLPFQNVHPVTIGECPKYVRSAKLRMVTGLRNIPSIQSRG<br>LFGAIAGFIEGGWTGMVDGWYGYHHQNEQGSGYAADQKSTQ<br>NAINGITNKVNSVIEKMNTQFTAVGKEFNKLERRMENLNKKV<br>DDGFIDIWTYNAELLVLLENERTLDFHDSNVKNLYEKVKSQL<br>KNNAKEIGNGCFEFYHKCNDECMESVKNGTYDYPKYSEESKL<br>NREKIDGVKLESMGVYQILAIYSTVASSLVLLVSLGAISFWMC<br>SNGSLQCRICI 3' (SEQ ID NO: 16) |
| ACD47238 | A/Alaska/02/<br>2008 (H1N1) | 5'MKVKLLVLLCTFTATYADTICIGYHANNSTDTVDTVLEKNV<br>TVTHSVNLLENSHNGKLCLLKGIAPLQLGNCSVAGWILGNPEC<br>ELLISKESWSYIVEKPNPENGTCYPGHFADYEELREQLSSVSSF<br>ERFEIFPKESAWPNHTVTGVSASCSHNGEXSFYRNLLWLTXKN<br>GLYPNLSKSYANNKEKEVLVLWGVHHPPNIGDQKALYHTEN<br>AYVSVVSSHYSRKFTPEIAKRPKVRXQEGRINYYWTLLEPGDT<br>IIFEANGNLIAPRYAFALSRGFGSGIINSNAPMDKCDAKCQTPQ<br>GAINSSLPFQNVHPVTIGECPKYVRSAKLRMVTGLRNIPSIQSR<br>GLFGAIAGFIEGGWTGMVDGWYGYHHQNEQGSGYAADQKST<br>QNAINGITNKVNSVIEKMNTQFTAVGKEFNKLERRMENLNKK<br>VDDGFIDIWTYNAELLVLLENERTLDFHDSNXKNLYEKVKSQ<br>LKNNAKEIGNGCFEFYHKCNDECMESVKNGTXDYPKYSEESK<br>LNREKIDGVKLESMGVYQILAIYSTVASSLVLLVSLGAISFWM<br>CSNGSLQCRICI 3' (SEQ ID NO: 17) |
| ACD85766 | A/Indiana/04/<br>2008 (H1N1) | 5'MKVKLLVLLCTFTATYADTICIGYHANNSTDTVDTVLEKNV<br>TVTHSVNLLENNHNGKLCLLKGIAPLQLGNCSVAGWILGNPE<br>CELLISKESWSYIVEKPNPENGTCYPGHFADYEELREQLSSVSS<br>FERFEMFPKEGSWPNHTVTGVSASCSHNGESSFYRNLLWLTG<br>KNGLYPNLXKSYANNKEKEVLVLWGVHHPPNIGDQKALYHT<br>ENAYVSVVSSHYSRKFTPEIAKRPKVRDQEGRINYYWTLLEPG<br>DTIIFEANGNLIAPRYAFALSRGFGSGIINSNAPMDNCDAKCQT<br>PQGAINSSLPFQNVHPVTIGECPKYVRSAKLRMVTGLRNIPSIQ<br>SRGLFGAIAGFIEGGWTGMVDGWYGYHHQNEQGSGYAADQ<br>KSTQNAINGITNKVNSVIEKMNTQFTAVXKEFNKLERRMENL |

TABLE 1-continued

Exemplary HA Sequences

| GenBank Accession | Strain | HA Sequence |
| --- | --- | --- |
| | | NKKVDDGFIDIWTYNAELLVLLENERTLDFHDSNVKNLYEKV<br>KSQLKNNAKEIGNGCFEFYHKCNDECMESVKNGTYDYPKYSE<br>ESKLNREKIDGVKLESMGVYQILAIYSTVASSLVLLVSLGAISF<br>WMCSNGSLQCRICI 3' (SEQ ID NO: 18) |
| ACF40125 | A/Wisconsin/<br>01/2008<br>(H1N1) | 5'MKVKLLVLLCTFTATYADTICIGYHANNSTDTVDTVLEKNV<br>TVTHSVNLLENSHNGKLCLLKGIAPLQLGNCSVAGWILGNPEC<br>ELLISKESWSYIVEKPNPENGTCYPGHFADYEELREQLSSVSSF<br>ERFEIFPKESSWPNHTVTGVSASCSHNGESSFYRNLLWLTGKN<br>GLYPNLSKSYANNKEKEVLVLWGVHHPPDIGDQKTLYHTENA<br>YVSVVSSHYSRKFTPEIAKRPKVRDQEGRINYYWTLLEPGDTII<br>FEANGNLIAPRYAFALSRGFGSGIINSNAPMDKCDAKCQTPQG<br>AINSSLPFQNVHPVTIGECPKYVRSAKLRMVTGLRNIPSIQSRG<br>LFGAIAGFIEGGWTGMVDGWYGYHHQNEQGSGYAADQKSTQ<br>NAINGITNKVNSVIEKMNTQFTAVGKEFNKLERRMENLNKKV<br>DDGFIDIWTYNAELLVLLENERTLDFHDSNVKNLYEKVKSQL<br>KNNAKEIGNGCFEFYHKCNDECMESVKNGTYDYPKYSEESKL<br>NREKIDGVKLESMGVYQILAIYSTVASSLVLLVSLGAISFWMC<br>SNGSLQCRICI 3' (SEQ ID NO: 19) |
| | Vietnam<br>H5N1 | 5'AKAGVQSVKMEKIVLLFAIVSLVKSDQICIGYHANNSTEQVD<br>TIMEKNVTVTHAQDILEKTHNGKLCDLDGVKPLILRDCSVAG<br>WLLGNPMCDEFINVPEWSYIVEKANPVNDLCYPGDFNDYEEL<br>KHLLSRINHFEKIQIIPKSSWSSHEASLGVSSACPYQGKSSFFRN<br>VVWLIKKNSTYPTIKRSYNNTNQEDLLVLWGIHHPNDAAEQT<br>KLYQNPTTYISVGTSTLNQRLVPRIATRSKVNGQSGRMEFFWT<br>ILKPNDAINFESNGNFIAPEYAYKIVKKGDSTIMKSELEYGNCN<br>TKCQTPMGAINSSMPFHNIHPLTIGECPKYVKSNRLVLATGLR<br>NSPQRERRRKKRGLFGAIAGFIEGGWQGMVDGWYGYHHSNE<br>QGSGYAADKESTQKAIDGVTNKVNSIIDKMNTQFEAVGREFN<br>NLERRIENLNKKMEDGFLDVWTYNAELLVLMENERTLDFHDS<br>NVKNLYDKVRLQLRDNAKELGNGCFEFYHKCDNECMESVRN<br>GTYDYPQYSEEARLKREEISGVKLESIGIYQILSIYSTVASSLAL<br>ALMVAGLSLWMCSNGSLQCRICI 3' (SEQ ID NO: 20) |
| | Wyoming<br>H3N2 | 5'MKTIIALSYILCLVFSQKLPGNDNSTATLCLGHHAVPNGTIV<br>KTITNDQIEVTNATELVQSSSTGGICDSPHQILDGENCTLIDALL<br>GDPQCDGFQNKKWDLFVERSKAYSNCYPYDVPDYASLRSLV<br>ASSGTLEFNNESFNWAGVTQNGTSSACKRRSNKSFFSRLNWL<br>THLKYKYPALNVTMPNNEKFDKLYIWGVHHPVTDSDQISLYA<br>QASGRITVSTKRSQQTVIPNIGYRPRVRDISSRISIYWTIVKPGDI<br>LLINSTGNLIAPRGYFKIRSGKSSIMRSDAPIGKCNSECITPNGSI<br>PNDKPFQNVNRITYGACPRYVKQNTLKLATGMRNVPEKQTRG<br>IFGAIAGFIENGWEGMVDGWYGFRHQNSEGTGQAADLKSTQA<br>AINQINGKLNRLIGKTNEKFHQIEKEFSEVEGRIQDLEKYVEDT<br>KIDLWSYNAELLVALENQHTIDLTDSEMNKLFERTKKQLREN<br>AEDMGNGCFKIYHKCDNACIESIRNGTYDHDVYRDEALNNRF<br>QIKGVELKSGYKDWILWISFAISCFLLCVALLGFIMWACQKGN<br>IRCNICI 3' (SEQ ID NO: 21) |
| DQ371928 | A/Anhui/1/2005<br>(H5N1) | 5'MEKIVLLLAIVSLVKSDQICIGYHANNSTEQVDTIMEKNVTV<br>THAQDILEKTHNGKLCDLDGVKPLILRDCSVAGWLLGNPMCD<br>EFINVPEWSYIVEKANPANDLCYPGNFNDYEELKHLLSRINHF<br>EKIQIIPKSSWSDHEASSGVSSACPYQGTPSFFRNVVWLIKKNN<br>TYPTIKRSYNNTNQEDLLILWGIHHSNDAAEQTKLYQNPTTYIS<br>VGTSTLNQRLVPKIATRSKVNGQSGRMDFFWTILKPNDAINFE<br>SNGNFIAPEYAYKIVKKGDSAIVKSEVEYGNCNTKCQTPIGAIN<br>SSMPFHNIHPLTIGECPKYVKSNKLVLATGLRNSPLRERRRKR<br>GLFGAIAGFIEGGWQGMVDGWYGYHHSNEQGSGYAADKEST<br>QKAIDGVTNKVNSIIDKMNTQFEAVGREFNNLERRIENLNKK<br>MEDGFLDVWTYNAELLVLMENERTLDFHDSNVKNLYDKVRL<br>QLRDNAKELGNGCFEFYHKCDNECMESVRNGTYDYPQYSEE<br>ARLKREEISGVKLESIGTYQILSIYSTVASSLALAIMVAGLSLW<br>MCSNGSLQCRICI 3' (SEQ ID NO: 22) |
| ISDN125873 | A/Indonesia/5/<br>05 | 5'MEKIVLLLAIVSLVKSDQICIGYHANNSTEQVDTIMEKNVTV<br>THAQDILEKTHNGKLCDLDGVKPLILRDCSVAGWLLGNPMCD<br>EFINVPEWSYIVEKANPTNDLCYPGSFNDYEELKHLLSRINHFE<br>KIQIIPKSSWSDHEASSGVSSACPYLGSPSFFRNVVWLIKKNST<br>YPTIKKSYNNTNQEDLLVLWGIHHPNDAAEQTRLYQNPTTYIS<br>IGTSTLNQRLVPKIATRSKVNGQSGRMEFFWTILKPNDAINFES<br>NGNFIAPEYAYKIVKKGDSAIMKSELEYGNCNTKCQTPMGAIN<br>SSMPFHNIHPLTIGECPKYVKSNRLVLATGLRNSPQRESRRKKR<br>GLFGAIAGFIEGGWQGMVDGWYGYHHSNEQGSGYAADKEST<br>QKAIDGVTNKVNSIIDKMNTQFEAVGREFNNLERRIENLNKK |

TABLE 1-continued

Exemplary HA Sequences

| GenBank Accession | Strain | HA Sequence |
|---|---|---|
| | | MEDGFLDVWTYNAELLVLMENERTLDFHDSNVKNLYDKVRL QLRDNAKELGNGCFEFYHKCDNECMESIRNGTYNYPQYSEEA RLKREEISGVKLESIGTYQILSIYSTVASSLALAIMMAGLSLWM CSNGSLQCRICI 3' (SEQ ID NO: 23) |
| DQ137873 | A/bar-headed goose/Qinghai/ 0510/05 (H5N1) | 5'MERIVLLLAIVSLVKSDQICIGYHANNSTEQVDTIMEKNVTV THAQDILEKTHNGKLCDLDGVKPLILRDCSVAGWLLGNPMCD EFLNVPEWSYIVEKINPANDLCYPGNFNDYEELKHLLSRINHFE RIQIIPKSSWSDHEASSGVSSACPYQGRSSFFRNVVWLIKKNNA YPTIKRSYNNTNQEDLLVLWGIHHPNDAAEQTRLYQNPTTYIS VGTSTLNQRLVPKIATRSKVNGQSGRMEFFWTILKPNDAINFE SNGNFIAPENAYKNCQKGDSTIMKSELEYGNCNTKCQTPIGAI NSSMPFHNIHPLTIGECPKYVKSNRLVLATGLRNSPQGERRRK KRGLFGAIAGFIEGGWQGMVDGWYGYHHSNEQGSGYAADK ESTQKAIDGVTNKVNSIIDKMNTQFEAVGREFNNLERRIENLN KKMEDGFLDVWTYNAELLVLMENERTLDFHDSNVKNLYDK VRLQLRDNAKELGNGCFEFYHRCDNECMESVRNGTYDYPQY SEEEARLKREEISGVKLESIGTYQILSIYSTVASSLALAIMVAGLS LWMCSNG 3' (SEQ ID NO: 24) |
| | A/VietNam/ 1194/04 | 5'MEKIVLLFAIVSLVKSDQICIGYHANNSTEQVDTIMEKNVTV THAQDILEKTHNGKLCDLDGVKPLILRDCSVAGWLLGNPMCD EFINVPEWSYIVEKANPVNDLCYPGDFNDYEELKHLLSRINHF EKIQIIPKSSWSSHEASLGVSSACPYQGKSSFFRNVVWLIKKNS TYPTIKRSYNNTNQEDLLVLWGIHHPNDAAEQTKLYQNPTTYI SVGTSTLNQRLVPRIATRSKVNGQSGRMEFFWTILKPNDAINF ESNGNFIAPEYAYKIVKKGDSTIMKSELEYGNCNTKCQTPMGA INSSMPFHNIHPLTIGECPKYVKSNRLVLATGLRNSPQRERRRK KRGLFGAIAGFIEGGWQGMVDGWYGYHHSNEQGSGYAADK ESTQKAIDGVTNKVNSIIDKMNTQFEAVGREFNNLERRIENLN KKMEDGFLDVWTYNAELLVLMENERTLDFHDSNVKNLYDK VRLQLRDNAKELGNGCFEFYHKCDNECMESVRNGTYDYPQY SEEEARLKREEISGVKLESIGIYQILSIYSTVASSLALAIMVAGLSL WMCSNGSLQCRICI 3' (SEQ ID NO: 25) |
| | B/Brisbane/3/ 07 | 5'MKAIIVLLMVVTSNADRICTGITSSNSPHVVKTATQGEVNVT GVIPLTTTPTKSYFANLKGTKTRGKLCPDCLNCTDLDVALGRP MCVGTTPSAKASILHEVRPVTSGCFPIMHDRTKIRQLANLLRG YENIRLSTQNVIDAEKAPGGPYRLGTSGSCPNATSKSGFFATM AWAVPKDNNKNATNPLTVEVPYICTEGEDQITVWGFHSDDKT QMKNLYGDSNPQKFTSSANGVTTHYVSQIGGFPDQTEDGGLP QSGRIVVDYMMQKPGKTGTIVYQRGVLLPQKVWCASGRSKVI KGSLPLIGEADCLHEKYGGLNKSKPYYTGEHAKAIGNCPIWV KTPLKLANGTKYRPPAKLLKERGFFGAIAGFLEGGWEGMIAG WHGYTSHGAHGVAVAADLKSTQEAINKITKNLNSLSELEVKN LQRLSGAMDELHNEILELDEKVDDLRADTISSQIELAVLLSNEG IINSEDEHLLALERKLKKMLGPSAVDIGNGCFETKHKCNQTCL DRIAAGTFNAGEFSLPTFDSLNITAASLNDDGLDNHTILLYYST AASSLAVTLMLAIFIVYMVSRDNVSCSICL 3' (SEQ ID NO: 26) |
| ACA28844 | A/Brisbane/59/ 2007 (H1N1) | 5'MKVKLLVLLCTFTATYADTICIGYHANNSTDTVDTVLEKNV TVTHSVNLLENSHNGKLCLLKGIAPLQLGNCSVAGWILGNPEC ELLISKESWSYIVEKPNPENGTCYPGHFADYEELREQLSSVSSF ERFEIFPKESSWPNHTVTGVSASCSHNGESSFYRNLLWLTGKN GLYPNLSKSYANNKEKEVLVLWGVHHPPNIGDQKALYHTEN AYVSVVSSHYSRKFTPEIAKRPKVRDQEGRINYYWTLLEPGDT IIFEANGNLIAPRYAFALSRGFGSGIINSNAPMDKCDAKCQTPQ GAINSSLPFQNVHPVTIGECPKYVRSAKLRMVTGLRNIPSIQSR GLFGAIAGFIEGGWTGMVDGWYGYHHQNEQGSGYAADQKST QNAINGITNKVNSVIEKMNTQFTAVGKEFNKLERRMENLNKK VDDGFIDIWTYNAELLVLLENERTLDFHDSNVKNLYEKVKSQ LKNNAKEIGNGCFEFYHKCNDECMESVKNGTYDYPKYSEESK LNREKIDGVKLESMGVYQILAIYSTVASSLVLLVSLGAISFWM CSNGSLQCRICI 3' (SEQ ID NO: 27) |
| | A/Brisbane/10/ 2007 (H3N2) | 5'QKLPGNDNSTATLCLGHHAVPNGTIVKTITNDQIEVTNATEL VQSSSTGEICDSPHQILDGENCTLIDALLGDPQCDGFQNKKWD LFVERSKAYSNCYPYDVPDYASLRSLVASSGTLEFNNESFNWT GVTQNGTSSACIRRSNNSFFSRLNWLTHLKFKYPALNVTMPN NEKFDKLYIWGVHHPGTDNDQIFPYAQASGRITVSTKRSQQTV IPNIGSRPRVRNIPSRISIYWTIVKPGDILLINSTGNLIAPRGYFKI RSGKSSIMRSDAPIGKCNSECITPNGSIPNDKPFQNVNRITYGAC PRYVKQNTLKLATGMRNVPEKQTRGIFGAIAGFIENGWEGMV DGWYGFRHQNSEGIGQAADLKSTQAAIDQINGKLNRLIGKTN EKFHQIEKEFSEVEGRIQDLEKYVEDTKIDLWSYNAELLVALE |

TABLE 1-continued

Exemplary HA Sequences

| GenBank Accession | Strain | HA Sequence |
|---|---|---|
| | | NQHTIDLTDSEMNKLFEKTKKQLRENAEDMGNGCFKIYHKCD<br>NACIGSIRNGTYDHDVYRDEALNNRFQIKGVELKSGYKDWIL<br>WISFAISCFLLCVALLGFIMWACQKGNIRCNI 3' (SEQ ID NO: 28) |
| ACA33493 | B/Florida/4/2006 | 5'MKAIIVLLMVVTSNADRICTGITSSNSPHVVKTATQGEVNVT<br>GVIPLTTTPTKSYFANLKGTRTRGKLCPDCLNCTDLDVALGRP<br>MCVGTTPSAKASILHEVKPVTSGCFPIMHDRTKIRQLPNLLRG<br>YENIRLSTQNVIDAEKAPGGPYRLGTSGSCPNATSKSGFFATM<br>AWAVPKDNNKNATNPLTVEVPYICTEGEDQITVWGFHSDDKT<br>QMKNLYGDSNPQKFTSSANGVTTHYVSQIGSFPDQTEDGGLP<br>QSGRIVVDYMMQKPGKTGTIVYQRGVLLPQKVWCASGRSKVI<br>KGSLPLIGEADCLHEKYGGLNKSKPYYTGEHAKAIGNCPIWV<br>KTPLKLANGTKYRPPAKLLKERGFFGAIAGFLEGGWEGMIAG<br>WHGYTSHGAHGVAVAADLKSTQEAINKITKNLNSLSELEVKN<br>LQRLSGAMDELHNEILELDEKVDDLRADTISSQIELAVLLSNEG<br>IINSEDEHLLALERKLKKMLGPSAVEIGNGCFETKHKCNQTCL<br>DRIAAGTFNAGEFSLPTFDSLNITAASLNDDGLDNHTILLYYST<br>AASSLAVTLMLAIFIVYMVSRDNVSCSICL 3' (SEQ ID NO: 29) |
| | B/Malaysia/2506/2004-like | 5'MKAIIVLLMVVTSNADRIICTGITSSNSPHVVKTATQGEVNV<br>TGVIPLTTTPTKSHFANLKGTETRGKLCPKCLNCTDLDVALGR<br>PKCTGNIPSARVSILHEVRPVTSGCFPIMHDRTKIRQLPNLLRG<br>YEHIRLSTHNVINAENAPGGPYKIGTSGSCPNVTNGNGFFATM<br>AWAVPKDNNKTATNSLTIEVPYICTEGEDQITVWGFHSDNET<br>QMAKLYGDSKPQKFTSSANGVTTHYVSQIGGFPNQTEDGGLP<br>QSGRIVVDYMVQKSGKTGTITYQRGILLPQKVWCASGRSKVI<br>KGSLPLIGEADCLHEKYGGLNKSKPYYTGEHAKAIGNCPIWV<br>KTPLKLANGTKYRPPAKLLKERGFFGAIAGFLEGGWEGMIAG<br>WHGYTSHGAHGVAVAADLKSTQEAINKITKNLNSLSELEVKN<br>LQRLSGAMDELHNEILELDEKVDDLRADTISSQIELAVLLSNEG<br>IINSEDEHLLALERKLKKMLGPSAVEIGNGCFETKHKCNQTCL<br>DRIAAGTFDAGEFSLPTFDSLNITAASLNDDGLDNHTILLYYST<br>AASSLAVTLMIAIFVVYMVSRDNVSCSICL 3' (SEQ ID NO: 30) |
| AAP34324 | A/New Caledonia/20/99 (H1N1) | 5'MKAKLLVLLCTFTATYADTICIGYHANNSTDTVDTVLEKNV<br>TVTHSVNLLEDSHNGKLCLLKGIAPLQLGNCSVAGWILGNPEC<br>ELLISKESWSYIVETPNPENGTCYPGYFADYEELREQLSSVSSF<br>ERFEIFPKESSWPNHTVTGVSASCSHNGKSSFYRNLLWLTGKN<br>GLYPNLSKSYVNNKEKEVLVLWGVHHPPNIGNQRALYHTEN<br>AYVSVVSSHYSRRFTPEIAKRPKVRDQEGRINYYWTLLEPGDT<br>IIFEANGNLIAPWYAFALSRGFGSGIITSNAPMDECDAKCQTPQ<br>GAINSSLPFQNVHPVTIGECPKYVRSAKLRMVTGLRNIPSIQSR<br>GLFGAIAGFIEGGWTGMVDGWYGYHHQNEQGSGYAADQKST<br>QNAINGITNKVNSVIEKMNTQFTAVGKEFNKLERRMENLNKK<br>VDDGFLDIWTYNAELLVLLENERTLDFHDSNVKNLYEKVKSQ<br>LKNNAKEIGNGCFEFYHKCNNECMESVKNGTYDYPKYSEESK<br>LNREKIDGVKLESMGVYQILAIYSTVASSLVLLVSLGAISFWM<br>CSNGSLQCRICI 3' (SEQ ID NO: 31) |
| ABU99109 | A/Solomon Islands/3/2006 (H1N1) | 5'MKVKLLVLLCTFTATYADTICIGYHANNSTDTVDTVLEKNV<br>TVTHSVNLLEDSHNGKLCLLKGIAPLQLGNCSVAGWILGNPEC<br>ELLISRESWSYIVEKPNPENGTCYPGHFADYEELREQLSSVSSF<br>ERFEIFPKESSWPNHTTTGVSASCSHNGESSFYKNLLWLTGKN<br>GLYPNLSKSYANNKEKEVLVLWGVHHPPNIGDQRALYHKEN<br>AYVSVVSSHYSRKFTPEIAKRPKVRDQEGRINYYWTLLEPGDT<br>IIFEANGNLIAPRYAFALSRGFGSGIINSNAPMDECDAKCQTPQ<br>GAINSSLPFQNVHPVTIGECPKYVRSAKLRMVTGLRNIPSIQSR<br>GLFGAIAGFIEGGWTGMVDGWYGYHHQNEQGSGYAADQKST<br>QNAINGITNKVNSVIEKMNTQFTAVGKEFNKLERRMENLNKK<br>VDDGFIDIWTYNAELLVLLENERTLDFHDSNVKNLYEKVKSQ<br>LKNNAKEIGNGCFEFYHKCNDECMESVKNGTYDYPKYSEESK<br>LNREKIDGVKLESMGVYQILAIYSTVASSLVLLVSLGAISFWM<br>CSNGSLQCRICI 3' (SEQ ID NO: 32) |
| | A/Wisconsin/67/2005 (H3N2) | 5'MKTIIALSYILCLVFAQKLPGNDNSTATLCLGHHAVPNGTIV<br>KTITNDQIEVTNATELVQSSSTGGICDSPHQILDGENCTLIDALL<br>GDPQCDGFQNKKWDLFVERSKAYSNCYPYDVPDYASLRSLV<br>ASSGTLEFNDESFNWTGVTQNGTSSSCKRRSNNSFFSRLNWLT<br>HLKFKYPALNVTMPNNEKFDKLYIWGVHHPVTDNDQIFLYAQ<br>ASGRITVSTKRSQQTVIPNIGSRPRIRNIPSRISIYWTIVKPGDILL<br>INSTGNLIAPRGYFKIRSGKSSIMRSDAPIGKCNSECITPNGSIPN<br>DKPFQNVNRITYGACPRYVKQNTLKLATGMRNVPEKQTRGIF<br>GAIAGFIENGWEGMVDGWYGFRHQNSEGIGQAADLKSTQAAI<br>NQINGKLNRLIGKTNEKFHQIEKEFSEVEGRIQDLEKYVEDTKI |

TABLE 1-continued

Exemplary HA Sequences

| GenBank Accession | Strain | HA Sequence |
|---|---|---|
| | | DLWSYNAELLVALENQHTIDLTDSEMNKLFERTKKQLRENAE DMGNGCFKIYHKCDNACIGSIRNGTYDHDVYRDEALNNRFQI KGVELKSGYKDWILWISFAISCFLLCVALLGFIMWACQKGNIR CNICI 3' (SEQ ID NO: 33) |
| AAT08000 | A/Wyoming/3/ 03(H3N2) | 5'MKTIIALSYILCLVFSQKLPGNDNSTATLCLGHHAVPNGTIV KTITNDQIEVTNATELVQSSSTGGICDSPHQILDGENCTLIDALL GDPQCDGFQNKKWDLFVERSKAYSNCYPYDVPDYASLRSLV ASSGTLEFNNESFNWAGVTQNGTSSACKRRSNKSFFSRLNWL THLKYKYPALNVTMPNNEKFDKLYIWGVHHPVTDSDQISLYA QASGRITVSTKRSQQTVIPNIGYRPRVRDISSRISIYWTIVKPGDI LLINSTGNLIAPRGYFKIRSGKSSIMRSDAPIGKCNSECITPNGSI PNDKPFQNVRITYGACPRYVKQNTLKLATGMRNVPEKQTRG IFGAIAGFIENGWEGMVDGWYGFRHQNSEGTGQAADLKSTQA AINQINGKLNRLIGKTNEKFHQIEKEFSEVEGRIQDLEKYVEDT KIDLWSYNAELLVALENQHTIDLTDSEMNKLFERTKKQLREN AEDMGNGCFKIYHKCDNACIESIRNGTYDHDVYRDEALNNRF QIKGVELKSGYKDWILWISFAISCFLLCVALLGFIMWACQKGN IRCNICI 3' (SEQ ID NO: 34) |
| AAR02640 | A/Netherlands/ 219/03 (H7N7) | 5'SKSRGYKMNTQILVFALVASIPTNADKICLGHHAVSNGTKV NTLTERGVEVVNATETVERTNVPRICSKGKRTVDLGQCGLLG TITGPPQCDQFLEFSADLIIERREGSDVCYPGKFVNEEALRQILR ESGGIDKETMGFTYSGIRTNGTTSACRRSGSSFYAEMKWLLSN TDNAAFPQMTKSYKNTRKDPALIIWGIHHSGSTTEQTKLYGSG NKLITVGSSNYQQSFVPSPGARPQVNGQSGRIDFHWLILNPND TVTFSFNGAFIAPDRASFLRGKSMGIQSEVQVDANCEGDCYHS GGTIISNLPFQNINSRAVGKCPRYVKQESLLLATGMKNVPEIPK RRRRGLFGAIAGFIENGWEGLIDGWYGFRHQNAQGEGTAADY KSTQSAIDQITGKLNRLIEKTNQQFELIDNEFTEVERQIGNVIN WTRDSMTEVWSYNAELLVAMENQHTIDLADSEMNKLYERVK RQLRENAEEDGTGCFEIFHKCDDDCMASIRNNTYDHSKYREE AIQNRIQIDPVKLSSGYKDVILWFSFGASCFILLAIAMGLVFICV KNGNMRCTICI 3' (SEQ ID NO: 35) |

While sequences of exemplary influenza antigen polypeptides are provided herein, it will be appreciated that any sequence having immunogenic characteristics of HA may be employed. In some embodiments, an influenza antigen polypeptide can have an amino acid sequence that is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a sequence selected from the group consisting of SEQ ID NOS:1-35. In some embodiments, such an influenza antigen polypeptide retains immunogenic activity.

In some embodiments, an influenza antigen polypeptide can have an amino acid sequence that comprises about 100 contiguous amino acids of a sequence selected from the group consisting of SEQ ID NOS:1-35. In some embodiments, an influenza antigen polypeptide has an amino acid sequence which is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of a sequence selected from the group consisting of SEQ ID NOS:1-35.

In some embodiments, an influenza antigen polypeptide can have an amino acid sequence that comprises about 150, about 200, about 250, about 300, about 350, about 400, about 450, about 500, about 550, or more contiguous amino acids of a sequence selected from the group consisting of SEQ ID NOS:1-35. In some embodiments, an influenza antigen polypeptide has an amino acid sequence which is about 60% identical, about 70% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 150, 200, 250, 300, 350, or more amino acids of a sequence selected from the group consisting of SEQ ID NOS:1-35.

For example, sequences having sufficient identity to influenza antigen polypeptide(s) which retain immunogenic characteristics are capable of binding with antibodies which react with one or more antigens provided herein. Immunogenic characteristics often include three dimensional presentation of relevant amino acids or side groups. One skilled in the art can readily identify sequences with modest differences in sequence (e.g., with difference in boundaries and/or some sequence alternatives, that, nonetheless preserve immunogenic characteristics).

In some embodiments, particular portions and/or domains of any of the exemplary sequences set forth in SEQ ID NOS: 1-35 may be omitted from an influenza polypeptide. For example, HA polypeptides typically contain a transmembrane anchor sequence. HA polypeptides in which the transmembrane anchor sequence has been omitted are contemplated herein.

As exemplary antigens, we have utilized sequences from hemagglutinin of particular subtypes as described in detail herein. Various subtypes of influenza virus exist and continue to be identified as new subtypes emerge. It will be understood by one skilled in the art that the methods and compositions provided herein may be adapted to utilize sequences of additional subtypes. Such variation is contemplated and encompassed within the methods and compositions provided herein.

Hemagglutinin Polypeptide Fusions with Thermostable Proteins

In certain aspects, provided are HA polypeptide(s) comprising fusion polypeptides which comprise a HA polypeptide (or a portion or variant thereof) operably linked to a thermostable protein. Fusion polypeptides can be produced in any available expression system known in the art. In certain embodiments, f TABLE 2-continued Thermostable Glycosidase Proteins

| Accession | Strain | Thermostable Protein Sequence |
|---|---|---|
| | | TADANGSIGIPLPKIDGGAPIAKELGNFVYQININGQWVDLS<br>NSSSQSKFAYSANGYNNMSDANQWGYWADYIYGLWFQPIQ<br>ENMQIRIGYPLNGQAGGNIGNNFVNYTFIGNPNAPRPDVSD<br>QEDISIGTPTDPAIAGMNLIWQDEFNGTTLDTSKWNYETGY<br>YLNNDPATWGWGNAELQHYTNSTQNVYVQDGKLNIKAMN<br>DSKSFPQDPNRYAQYSSGKINTKDKLSLKYGRVDFRAKLPT<br>GDGVWPALWMLPKDSVYGTWAASGEIDVMEARGRLPGSV<br>SGTIHFGGQWPVNQSSGGDYHFPEGQTFANDYHVYSVVWE<br>EDNIKWYVDGKFFYKVTNQQWYSTAAPNNPNAPFDEPFYLI<br>MNLAVGGNFDGGRTPNASDIPATMQVDYVRVYKEQ 3'<br>(SEQ ID NO: 40) |
| P27051 | Beta-<br>glucanase<br>Bacillus<br>licheni-<br>formis | 5'MSYRVKRMLMLLVTGLFLSLSTFAASASAQTGGSFYEPFN<br>NYNTGLWQKADGYSNGNMFNCTWRANNVSMTSLGEMRL<br>SLTSPSYNKFDCGENRSVQTYGYGLYEVNMKPAKNVGIVSS<br>FFTYTGPTDGTPWDEIDIEFLGKDTTKVQFNYYTNGVGNHE<br>KIVNLGFDAANSYHTYAFDWQPNSIKWYVDGQLKHTATTQ<br>IPQTPGKIMMNLWNGAGVDEWLGSYNGVTPLSRSLHWVRY<br>TKR 3' (SEQ ID NO: 41) |
| P45797 | Beta-<br>glucanase<br>Paeni-<br>bacillus<br>polymyxa<br>Bacillus<br>polymyxa | 5'MMKKKSWFTLMITGVISLFFSVSAFAGNVFWEPLSYFNSS<br>TWQKADGYSNGQMFNCTWRANNVNFTNDGKLKLSLTSPA<br>NNKFDCGEYRSTNNYGYGLYEVSMKPAKNTGIVSSFFTYTG<br>PSHGTQWDEIDIEFLGKDTTKVQFNYYTNGVGGHEKIINLGF<br>DASTSFHTYAFDWQPGYIKWYVDGVLKHTATTNIPSTPGKI<br>MMNLWNGTGVDSWLGSYNGANPLYAEYDWVKYTSN 3'<br>(SEQ ID NO: 42) |
| P45798 | Beta-<br>glucanase<br>Rhodo-<br>thermus<br>marinus | 5'MCTMPLMKLKKMMRRTAFLLSVLIGCSMLGSDRSDKAPH<br>WELVWSDEFDYSGLPDPEKWDYDVGGHGWGNQELQYYTR<br>ARIENARVGGGVLIIEARHEPYEGREYTSARLVTRGKASWT<br>YGRFEIRARLPSGRGTWPAIWMLPDRQTYGSAYWPDNGEID<br>IMEHVGFNPDVVHGTVHTKAYNHLLGTQRGGSIRVPTARTD<br>FHVYAIEWTPEEIRWFVDDSLYYRFPNERLTDPEADWRHWP<br>FDQPFHLIMNIAVGGAWGGQQGVDPEAFPAQLVVDYVRVY<br>RWVE 3' (SEQ ID NO: 43) |
| P38645 | Beta-<br>glucosidase<br>Thermobis-<br>pora<br>bispora | 5'MTESAMTSRAGRGRGADLVAAVVQGHAAASDAAGDLSF<br>PDGFIWGAATAAYQIEGAWREDGRGLWDVFSHTPGKVASG<br>HTGDIACDHYHRYADDVRLMAGLGDRVYRFSVAWPRIVPD<br>GSGPVNPAGLDFYDRLVDELLGHGITPYPTLYHWDLPQTLE<br>DRGGWAARDTAYRFAEYALAVHRRLGDRVRCWITLNEPW<br>VAAFLATHRGAPGAADVPRFRAVHHLLLGHGLGLRLRSAG<br>AGQLGLTLSLSPVIEARPGVRGGGRRVDALANRQFLDPALR<br>GRYPEEVLKIMAGHARLGHPGRDLETIHQPVDLLGVNYYSH<br>VRLAAEGEPANRLPGSEGIRFERPTAVTAWPGDRPDGLRTL<br>LLRLSRDYPGVGLIITENGAAFDDRADGDRVHDPERIRYLTA<br>TLRAVHDAIMAGADLRGYFVWSVLDNFEWAYGYHKRGIV<br>YVDYTTMRRIPRESALWYRDVVRRNGLRNGE 3' (SEQ ID<br>NO: 44) |
| P40942 | Celloxyla-<br>nase<br>Clostridium<br>sterco-<br>rarium | 5'MNKFLNKKWSLILTMGGIFLMATLSLIFATGKKAFNDQTS<br>AEDIPSLAEAFRDYFPIGAAIEPGYTTGQIAELYKKHVNMLV<br>AENAMKPASLQPTEGNFQWADADRIVQFAKENGMELRFHT<br>LVWHNQTPTGFSLDKEGKPMVEETDPQKREENRKLLLQRL<br>ENYIRAVVLRYKDDIKSWDVVNEVIEPNDPGGMRNSPWYQI<br>TGTEYIEVAFRATREAGGSDIKLYINDYNTDDPVKRDILYEL<br>VKNLLEKGVPIDGVGHQTHIDIYNPPVERIIESIKKFAGLGLD<br>NIITELDMSIYSWNDRSDYGDSIPDYILTLQAKRYQELFDAL<br>KENKDIVSAVVFWGISDKYSWLNGFPVKRTNAPLLFDRNFM<br>PKPAFWAIVDPSRLRE 3' (SEQ ID NO: 45) |
| P14002 | Beta-<br>glucosidase<br>Clostridium<br>thermo-<br>cellum | 5'MAVDIKKIIKQMTLEEKAGLCSGLDFWHTKPVERLGIPSIM<br>MTDGPHGLRKQREDAEIADINNSVPATCFPSAAGLACSWDR<br>ELVERVGAALGEECQAENVSILLGPGANIKRSPLCGRNFEYF<br>SEDPYLSSELAASHIKGVQSQGVGACLKHFAANNQEHRRMT<br>VDTIVDERTLREIYFASFENAVKKARPWVVMCAYNKLNGE<br>YCSENRYLLTEVLKNEWMHDGFVVSDWGAVNDRVSGLDA<br>GLDLEMPTSHGITDKKIVEAVKSGKLSENILNRAVERILKVIF<br>MALENKKENAQYDKDAHHRLARQAAAESMVLLKNEDDVL<br>PLKKSGTIALIGAFVKKPRYQGSGSSHITPTRLDDIYEEIKKA<br>GGDKVNLVYSEGYRLENDGIDEELINEAKKAASSSDVAVVF<br>AGLPDEYESEGFDRTHMSIPENQNRLIEAVAEVQSNIVVVLL<br>NGSPVEMPWIDKVKSVLEAYLGGQALGGALADVLFGEVNP<br>SGKLAETFPVKLSHNPSYLNFPGEDDRVEYKEGLFVGYRYY<br>DTKGIEPLFPFGHGLSYTKFEYSDISVDKKDVSDNSIINVSVK |

TABLE 2-continued

Thermostable Glycosidase Proteins

| Accession | Strain | Thermostable Protein Sequence |
|---|---|---|
| | | VKNVGKMAGKEIVQLYVKDVKSSVRRPEKELKGFEKVFLN<br>PGEEKTVTFTLDKRAFAYYNTQIKDWHVESGEFLILIGRSSR<br>DIVLKESVRVNSTVKIRKRFTVNSAVEDVMSDSSAAAVLGP<br>VLKEITDALQIDMDNAHDMMAANIKNMPLRSLVGYSQGRL<br>SEEMLEELVDKINNVE 3' (SEQ ID NO: 46) |
| O33830 | Alpha-<br>glucosidase<br>*Thermotoga<br>maritima* | 5'MPSVKIGIIGAGSAVFSLRLVSDLCKTPGLSGSTVTLMDID<br>EERLDAILTIAKKYVEEVGADLKFEKTMNLDDVIIDADPVIN<br>TAMVGGHTYLEKVRQIGEKYGYYRGIDAQEFNMVSDYYTF<br>SNYNQLKYFVDIARKIEKLSPKAWYLQAANPIFEGTTLVTRT<br>VPIKAVGFCHGHYGVMEIVEKLGLEEEKVDWQVAGVNHGI<br>WLNRFRYNGGNAYPLLDKWIEEKSKDWKPENPFNDQLSPA<br>AIDMYRFYGVMPIGDTVRNSSWRYHRDLETKKKWYGEPW<br>GGADSEIGWKWYQDTLGKVTEITKKVAKFIKENPSVRLSDL<br>GSVLGKDLSEKQFVLEVEKILDPERKSGEQHIPPFIDALLNDN<br>KARFVVNIPNKGIIHGIDDDVVVEVPALVDKNGIHPEKIEPPL<br>PDRVVKYYLRPRIMRMEMALEAFLTGDIRIIKELLYRDPRTK<br>SDEQVEKVIEEILALPENEEMRKHYLKR 3' (SEQ ID NO: 47) |
| O43097 | Xylanase<br>*Thermo-<br>myces<br>lanuginosus* | 5'MVGFTPVALAALAATGALAFPAGNATELEKRQTTPNSEG<br>WHDGYYYSWWSDGGAQATYTNLEGGTYEISWGDGGNLV<br>GGKGWNPGLNARAIHFEGVYQPNGNSYLAVYGWTRNPLV<br>EYYIVENFGTYDPSSGATDLGTVECDGSIYRLGKTTRVNAPS<br>IDGTQTFDQYWSVRQDKRTSGTVQTGCHFDAWARAGLNV<br>NGDHYYQIVATEGYFSSGYARITVADVG 3' (SEQ ID NO: 48) |
| P54583 | Endo-<br>glucanase<br>E1 *Acido-<br>thermus<br>cellulo-<br>lyticus* | 5'MPRALRRVPGSRVMLRVGVVVAVLALVAALANLAVPRP<br>ARAAGGGYWHTSGREILDANNVPVRIAGINWFGPETCNYV<br>VHGLWSRDYRSMLDQIKSLGYNTIRLPYSDDILKPGTMPNSI<br>NFYQMNQDLQGLTSLQVMDKIVAYAGQIGLRIILDRHRPDC<br>SGQSALWYTSSVSEATWISDLQALAQRYKGNPTVVGFDLH<br>NEPHDPACWGCGDPSIDWRLAAERAGNAVLSVNPNLLIFVE<br>GVQSYNGDSYWWGGNLQGAGQYPVVLNVPNRLVYSAHD<br>YATSVYPQTWFSDPTFPNNMPGIWNKNWGYLFNQNIAPVW<br>LGEFGTTLQSTTDQTWLKTLVQYLRPTAQYGADSFQWTFW<br>SWNPDSGDTGGILKDDWQTVDTVKDGYLAPIKSSIFDPVGA<br>SASPSSQPSPSVSPSPSPSASRTPTPTPTPTASPTPTLTPTATP<br>TPTASPTPSPTAASGARCTASYQVNSDWGNGFTVTVAVTNS<br>GSVATKTWTVSWTFGGNQTITNSWNAAVTQNGQSVTARN<br>MSYNNVIQPGQNTTFGFQASYTGSNAAPTVACAAS 3' (SEQ ID NO: 49) |
| P14288 | β-galacto-<br>sidase<br>*Sulfolobus<br>acidocal-<br>darius* | 5'MLSFPKGFKFGWSQSGFQSEMGTPGSEDPNSDWHVWVH<br>DRENIVSQVVSGDLPENGPGYWGNYKRFHDEAEKIGLNAV<br>RINVEWSRIFPRPLPKPEMQTGTDKENSPVISVDLNESKLRE<br>MDNYANHEALSHYRQILEDLRNRGFHIVLNMYHWTLPIWL<br>HDPIRVRRGDFTGPTGWLNSRTVYEFARFSAYVAWKLDDL<br>ASEYATMNEPNVVWGAGYAFPRAGFPPNYLSFRLSEIAKW<br>NIIQAHARAYDAIKSVSKKSVGIIYANTSYYPLRPQDNEAVEI<br>AERLNRWSFFDSIIKGEITSEGQNVREDLRNRLDWIGVNYYT<br>RTVVTKAESGYLTLPGYGDRCERNSLSLANLPTSDFGWEFF<br>PEGLYDVLLKYWNRYGLPLYVMENGIADDADYQRPYYLVS<br>HIYQVHRALNEGVDVRGYLHWSLADNYEWSSGFSMRFGLL<br>KVDYLTKRLYWRPSALVYREITRSNGIPEELEHLNRVPPIKP<br>LRH 3' (SEQ ID NO: 50) |
| O52629 | β-galac-<br>tosidase<br>*Pyrococcus<br>woesei* | 5'MFPEKFLWGVAQSGFQFEMGDKLRRNIDTNTDWWHWVR<br>DKTNIEKGLVSGDLPEEGINNYELYEKDHEIARKLGLNAYRI<br>GIEWSRIFPPWPTTFIDVDYSYNESYNLIEDVKITKDTLEELDEI<br>ANKREVAYYRSVINSLRSKGFKVIVNLNHFTLPYWLHDPIEA<br>RERALTNKRNGWVNPRTVIEFAKYAAYIAYKFGDIVDMWS<br>TFNEPMVVVELGYLAPYSGFPPGVLNPEAAKLAILHMINAH<br>ALAYRQIKKFDTEKADKDSKEPAEVGIIYNNIGVAYPKDPN<br>DSKDVKAAENDNFFHSGLFFEAIHKGKLNIEFDGETFIDAPY<br>LKGNDWIGVNYYTREVVTYQEPMFPSIPLITFKGVQGYGYA<br>CRPGTLSKDDRPVSDIGWELYPEGMYDSIVEAHKYGVPVYV<br>TENGIADSKDILRPYYIASHIKMTEKAFEDGYEVKGYFHWA<br>LTDNFEWALGFRMRFGLYEVNLITKERIPREKSVSIFREIVAN<br>NGVTKKIEEELLRG 3' (SEQ ID NO: 51) |

TABLE 2-continued

Thermostable Glycosidase Proteins

| Accession | Strain | Thermostable Protein Sequence |
|---|---|---|
| P29094 | Oligo-16-glucosidase *Geobacillus thermoglucosidasius* | 5'MERVWWKEAVVYQIYPRSFYDSNGDGIGDIRGIIAKLDYL KELGVDVVWLSPVYKSPNDDNGYDISDYRDIMDEFGTMAD WKTMLEEMHKRGIKLVMDLVVNHTSDEHPWFIESRKSKDN PYRDYYIWRPGKNGKEPNNWESVFSGSAWEYDEMTGEYYL HLFSKKQPDLNWENPKVRREVYEMMKFWLDKGVDGFRMD VINMISKVPELPDGEPQSGKKYASGSRYYMNGPRVHEFLQE MNREVLSKYDIMTVGETPGVTPKEGILYTDPSRRELNMVFQ FEHMDLDSGPGGKWDIRPWSLADLKKTMTKWQKELEGKG WNSLYLNNHDQPRAVSRFGDDGKYRVESAKMLATFLHMM QGTPYIYQGEEIGMTNVRFPSIEDYRDIETLNMYKERVEEYG EDPQEVMEKIYYKGRDNARTPMQWDDSENAGFTAGTPWIP VNPNYKEINVKAALEDPNSVFHYYKKLIQLRKQHDIIVYGT YDLILEDDPYIYRYTRTLGNEQLIVITNFSEKTPVFRLPDHIIY KTKELLISNYDVDEAEELKEIRLRPWEARVYKIRLP 3' (SEQ ID NO: 52) |
| P49067 | Alpha-amylase *Pyrococcus furiosus* | 5'MGDKINFIFGIHNHQPLGNFGWVFEEAYEKCYWPFLETLE EYPNMKVAIHTSGPLIEWLQDNRPEYIDLLRSLVKRGQVEIV VAGFYEPVLASIPKEDRIEQIRLMKEWAKSIGFDARGVWLTE RVWQPELVKTLKESGIDYVIVDDYHFMSAGLSKEELYWPY YTEDGGEVIAVFPIDEKLRYLIPFRPVDKVLEYLHSLIDGDES KVAVFHDDGEKFGIWPGTYEWVYEKGWLREFFDRISSDEKI NLMLYTEYLEKYKPRGLVYLPIASYFEMSEWSLPAKQARLF VEFVNELKVKGIFEKYRVFVRGGIWKNFFYKYPESNYMHK RMLMVSKLVRNNPEARKYLLRAQCNDAYWHGLFGGVYLP HLRRAIWNNLIKANSYVSLGKVIRDIDYDGFEEVLIENDNFY AVFKPSYGGSLVEFSSKNRLVNYVDVLARRWEHYHGYVES QFDGVASIHELEKKIPDEIRKEVAYDKYRRFMLQDHVVPLG TTLEDFMFSRQQEIGEFPPRVPYSYELLDGGIRLKREHLGIEVE KTVKLVNDGFEVEYIVNNKTGNPVLFAVELNVAVQSIMESP GVLRGKEIVVDDKYAVGKFALKFEDEMEVWKYPVKTLSQS ESGWDLIQQGVSYIVPIRLEDKIRFKLKFEEASG 3' (SEQ ID NO: 53) |
| JC7532 | Cellulase *Bacillus* species | 5'MMLRKKTKQLISSILILVLLLSLFPAALAAEGNTREDNFKH LLGNDNVKRPSEAGALQLQEVDGQMTLVDQHGEKIQLRGM STHGLQWFPEILNDNAYKALSNDWDSNMIRLAMYVGENGY ATNPELIKQRVIDGIELAIENDMYVIVDWHVHAPGDPRDPV YAGAKDFFREIAALYPNNPHIIYELANEPSSNNNGGAGIPNN EEGWKAVKEYADPIVEMLRKSGNADDNIIIVGSPNWSQRPD LAADNPIDDHHTMYTVHFYTGSHAASTESYPSETPNSERGN VMSNTRYALENGVAVFATEWGTSQASGDGGPYFDEADVWI EFLNENNISWANWSLTNKNEVSGAFTPFELGKSNATNLDPG PDHVWAPEELSLSGEYVRARIKGVNYEPIDRTKYTKVLWDF NDGTKQGFGVNSDSPNKELIAVDNENNTLKVSGLDVSNDVS DGNFWANARLSANGWGKSVDILGAEKLTMDVIVDEPTTVA IAAIPQSSKSGWANPERAVRVNAEDFVQQTDGKYKAGLTIT GEDAPNLKNIAFHEEDNNMNNIILFVGTDAADVIYLDNIKVI GTEVEIPVVHDPKGEAVLPSVFEDGTRQGWDWAGESGVKT ALTIEEANGSNALSWEFGYPEVKPSDNWATAPRLDFWKSDL VRGENDYVAFDFYLDPVRATEGAMNINLVFQPPTNGYWVQ APKTYTINFDELEEANQVNGLYHYEVKINVRDITNIQDDTLL RNMMIIFADVESDFAGRVFVDNVRFEGAATTEPVEPEPVDP GEETPPVDEKEAKKEQKEAEKEEKEAVKEEKKEAKEEKKA VKNEAKKK 3' |
| Q60037 | Xylanase A *Thermotoga maritima* | 5'MQVRKRRGLLDVSTAVLVGILAGFLGVVLAASGVLSFGK EASSKGDSSLETVLALSFEGTTEGVVPFGKDVVLTASQDVA ADGEYSLKVENRTSPWDGVEIDLTGKVKSGADYLLSFQVY QSSDAPQLFNVVARTEDEKGERYDVILDKVVVSDHWKEILV PFSPTFEGTPAKYSLIIVASKNTNFNFYLDKVQVLAPKESGPK VIYETSFENGVGDWQPRGDVNIEASSEVAHSGKSSLFISNRQ KGWQGAQINLKGILKTGKTYAFEAWVYQNSGQDQTIIMTM QRKYSSDASTQYEWIKSATVPSGQWVQLSGTYTIPAGVTVE DLTLYFESQNPTLEFYVDDVKIVDTTSAEIKIEMEPEKEIPAL KEVLKDYFKVGVALPSKVFLNPKDIELITKHFNSITAENEMK PESLLAGIENGKLKFRFETADKYIQFVEENGMVIRGHTLVW HNQTPDWFFKDENGNLLSKEAMTERLKEYIHTVVGHFKGK VYAWDVVNEAVDPNQPDGLRRSTWYQIMGPDYIELAFKFA READPDAKLFYNDYNTFEPRKRDIIYNLVKDLKEKGLIDGIG MQCHISLATDIKQIEEAIKKFSTIPGIEIHITELDMSVYRDSSSN YPEAPRTALIEQAHKMMQLFEIFKKYSNVITNVTFWGLKDD YSWRATRRNDWPLIFDKDHQAKLAYWAIVAPEVLPPLPKES RISEGEAVVVGMDDSYLMSKPIEILDEEGNVKATIRAVWK DSTIYIYGEVQDKTKKPAEDGVAIFINPNNERTPYLQPDDTY AVLWTNWKTEVNREDVQVKKFVGPGFRRYSFEMSITIPGVE |

TABLE 2-continued

Thermostable Glycosidase Proteins

| Accession | Strain | Thermostable Protein Sequence |
|---|---|---|
| | | FKKDSYIGFDAAVIDDGKWYSWSDTTNSQKTNTMNYGTLK<br>LEGIMVATAKYGTPVIDGEIDEIWNTTEEIETKAVAMGSLDK<br>NATAKVRVLWDENYLYVLAIVKDPVLNKDNSNPWEQDSV<br>EIFIDENNHKTGYYEDDDAQFRVNYMNEQTFGTGGSPARFK<br>TAVKLIEGGYIVEAAIKWKTIKPTPNTVIGFNIQVNDANEKG<br>QRVGIISWSDPTNNSWRDPSKFGNLRLIK 3' (SEQ ID NO: 55) |
| P33558 | Xylanase A<br>*Clostridium stercorarium* | 5'MKRKVKKMAAMATSIIMAIMIILHSIPVLAGRITYDNETGT<br>HGGYDYELWKDYGNTIMELNDGGTFSCQWSNIGNALFRKG<br>RKFNSDKTYQELGDIVVEYGCDYNPNGNSYLCVYGWTRNP<br>LVEYYIVESWGSWRPPGATPKGTITQWMAGTYEIYETTRVN<br>QPSIDGTATFQQYWSVRTSKRTSGTISVTEHFKQWERMGMR<br>MGKMYEVALTVEGYQSSGYANVYKNEIRIGANPTPAPSQSP<br>IRRDAFSIIEAEEYNSTNSSTLQVIGTPNNGRGIGYIENGNTVT<br>YSNIDFGSGATGFSATVATEVNTSIQIRSDSPTGTLLGTLYVS<br>STGSWNTYQTVSTNISKITGVHDIVLVFSGPVNVDNFIFSRSS<br>PVPAPGDNTRDAYSIIQAEDYDSSYGPNLQIFSLPGGGSAIGY<br>IENGYSTTYKNIDFGDGATSVTARVATQNATTIQVRLGSPSG<br>TLLGTIYVGSTGSFDTYRDVSATISNTAGVKDIVLVFSGPVN<br>VDWFVFSKSGT 3' (SEQ ID NO: 56) |
| P05117 | Polygalacturonase-2 precursor<br>*Solanum lycopersicum* | 5'MVIQRNSILLLIIIFASSISTCRSNVIDDNLFKQVYDNILEQEF<br>AHDFQAYLSYLSKNIESNNNIDKVDKNGIKVINVLSFGAKG<br>DGKTYDNIAFEQAWNEACSSRTPVQFVVPKNKNYLLKQITF<br>SGPCRSSISVKIFGSLEASSKISDYKDRRLWIAFDSVQNLVVG<br>GGGTINGNGQVWWPSSCKINKSLPCRDAPTALTFWNCKNL<br>KVNNLKSKNAQQIHIKFESCTNVVASNLMINASAKSPNTDG<br>VHVSNTQYIQISDTIIGTGDDCISIVSGSQNVQATNITCGPGH<br>GISIGSLGSGNSEAYVSNVTVNEAKIIGAENGVRIKTWQGGS<br>GQASNIKFLNVEMQDVKYPIIIDQNYCDRVEPCIQQFSAVQV<br>KNVVYENIKGTSATKVAIKFDCSTNFPCEGIIMENINLVGESG<br>KPSEATCKNVHFNNAEHVTPHCTSLEISEDEALLYNY 3'<br>(SEQ ID NO: 57) |
| P04954 | Cellulase D<br>*Clostridium thermocellum* | 5'MSRMTLKSSMKKRVLSLLIAVVFLSLTGVFPSGLIETKVSA<br>AKITENYQFDSRIRLNSIGFIPNHSKKATIAANCSTFYVVKED<br>GTIVYTGTATSMFDNDTKETVYIADFSSVNEEGTYYLAVPG<br>VGKSVNFKIAMNVYEDAFKTAMLGMYLLRCGTSVSATYNG<br>IHYSHGPCHTNDAYLDYINGQHTKKDSTKGWHDAGDYNK<br>YVVNAGITVGSMFLAWEHFKDQLEPVALEIPEKNNSIPDFLD<br>ELKYEIDWILTMQYPDGSGRVAHKVSTRNFGGFIMPENEHD<br>ERFFVPWSSAATADFVAMTAMAARIFRPYDPQYAEKCINAA<br>KVSYEFLKNNPANVFANQSGFSTGEYATVSDADDRLWAAA<br>EMWETLGDEEYLRDFENRAAQFSKKIEADFDWDNVANLG<br>MFTYLLSERPGKNPALVQSIKDSLLSTADSIVRTSQNHGYGR<br>TLGTTYYWGCNGTVVRQTMILQVANKISPNNDYVNAALDA<br>ISHVFGRNYYNRSYVTGLGINPPMNPHDRRSGADGIWEPWP<br>GYLVGGGWPGPKDWVDIQDSYQTNEIAINWNAALIYALAG<br>FVNYNSPQNEVLYGDVNDDGKVNSTDLTLLKRYVLKAVST<br>LPSSKAEKNADVNRDGRVNSSDVTILSRYLIRVIEKLPI 3'<br>(SEQ ID NO: 58) |
| Q4J929 | N-glycosylase<br>*Sulfolobus acidocaldarius* | 5'MLRSLVLNEKLRARVLERAEEFLLNNKADEEVWFRELVL<br>CILTSNSSFISAYKSMNYILDKILYMDEKEISILLQESGYRFYN<br>LKAKYLYRAKNLYGKVKKTIKEIADKDQMQAREFIATHIYG<br>IGYKEASHFLRNVGYLDLAIIDRHILRFINNLGIPIKLKSKREY<br>LLAESLLRSIANNLNVQVGLLDLFIFFKQTNTIVK 3' (SEQ ID NO: 59) |
| O33833 | Beta-fructosidase<br>*Thermotoga maritima* | 5'MFKPNYHFFPITGWMNDPNGLIFWKGKYHMFYQYNPRKP<br>EWGNICWGHAVSDDLVHWRHLPVALYPDDETHGVFSGSA<br>VEKDGKMFLVYTYYRDPTHNKGEKETQCVAMSENGLDFV<br>KYDGNPVISKPPEEGTHAFRDPKVNRSNGEWRMVLGSGKD<br>EKIGRVLLYTSDDLFHWKYEGVIFEDETTKEIECPDLVRIGE<br>KDILIYSITSTNSVLFSMGELKEGKLNVEKRGLLDHGTDFYA<br>AQTFFGTDRVVVIGWLQSWLRTGLYPTKREGWNGVMSLPR<br>ELYVENNELKVKPVDELLALRKRKVFETAKSGTFLLDVKEN<br>SYEIVCEFSGEIELRMGNESEEVVITKSRDELIVDTTRSGVSG<br>GEVRKSTVEDEATNRIRAFLDSCSVEFFFNDSIAFSFRIHPEN<br>VYNILSVKSNQVKLEVFELENIWL 3' (SEQ ID NO: 60) |

TABLE 2-continued

Thermostable Glycosidase Proteins

| Accession | Strain | Thermostable Protein Sequence |
|---|---|---|
| P49425 | Endo-14-beta-mannosidase *Rhodothermus marinus* | 5'MAGPHRSRAAGPPPFAVDEHVALEMVAFRGEVFAGHGLL ADQRLIAHTGRPALNAQRITQQKQRDQCRGQRHRHHQGGR NLRKAHRTFHEHQSTQDQAHDAPHGQQAKTGHEGLGHEH AQAQHQQGQSNVVDRQDGEPVEAQHQKDGAQRAGNAPA GRVELEQQPVEAQHQQQEGDVRIGKRRQNAFAPPALDHVH GGPGRLQRHGLAVERHVPAVQQHQQRVQRGRQQIDHVLG HGLPGRQRLAFRDGPRRPVGVASPVLGQRPCPGHRIVQNLF RHGIDPCRVGRCRRSPSELHGMGCADVRARGHGRHMRGQR DEHPGRGRPCARRRHVDDDRDRTPQEKLYDVARGLDEPAR RVHFDDEADRSVFRGLAQPAPDEPEGRRRDRLVLQRQSVN HRRGRLSRHRQQHQPQQQRPHGNQAFLGKYEKRRRKPTAC LKSLRRFPDKDAPVLYFVNQLEKTKRRMTLLLVWLIFTGVA GEIRLEAEDGELLGVAVDSTLTGYSGRGYVTGFDAPEDSVR FSFEAPRGVYRVVFGVSFSSRFASYALRVDDWHQTGSLIKR GGGFFEASIGEIWLDEGAHTMAFQLMNGALDYVRLEPVSY GPPARPPAQLSDSQATASAQALFAFLLSEYGRHILAGQQQNP YRRDFDAINYVRNVTGKEPALVSFDLIDYSPTREAHGVVHY QTPEDWIAWAGRDGIVSLMWHWNAPTDLIEDPSQDCYWW YGFYTRCTTFDVAAALADTSSERYRLLLRDIDVIAAQLQKF QQADIPVLWRPLHEAAGGWFWWGAKGPEPFKQLWRLLYE RLVHHHGLHNLIWVYTHEPGAAEWYPGDAYVDIVGRDVY ADDPDALMRSDWNELQTLFGGRKLVALTETGTLPDVEVITD YGIWWSWFSIWTDPFLRDVDPDRLTRVYHSERVLTRDELPD WRSYVLHATTVQPAGDLALAVYPNPGAGRLHVEVGLPVAA PVVVEVFNLLGQRVFQYQAGMQPAGLWRRAFELALAPGV YLVQVRAGNLVARRRWVSVR 3' (SEQ ID NO: 61) |
| P06279 | Alpha-amylase *Geobacillus stearothermophilus* | 5'MLTFHRIIRKGWMFLLAFLLTALLFCPTGQPAKAAAPFNG TMMQYFEWYLPDDGTLWTKVANEANNLSSLGITALWLPPA YKGTSRSDVGYGVYDLYDLGEFNQKGAVRTKYGTKAQYL QAIQAAHAAGMQVYADVVFDHKGGADGTEWVDAVEVNP SDRNQEISGTYQIQAWTKFDFPGRGNTYSSFKWRWYHFDG VDWDESRKLSRIYKFRGIGKAWDWEVDTENGNYDYLMYA DLDMDHPEVVTELKSWGKWYVNTTNIDGFRLDAVKHIKFS FFPDWLSDVRSQTGKPLFTVGEYWSYDINKLHNYIMKTNGT MSLFDAPLHNKFYTASKSGGTFDMRTLMTNTLMKDQPTLA VTFVDNHDTEPGQALQSWVDPWFKPLAYAFILTRQEGYPC VFYGDYYGIPQYNIPSLKSKIDPLLIARRDYAYGTQHDYLDH SDIIGWTREGVTEKPGSGLAALITDGPGGSKWMYVGKQHA GKVFYDLTGNRSDTVTINSDGWGEFKVNGGSVSVWVPRKT TVSTIAWSITTRPWTDEFVRWTEPRLVAWP 3' (SEQ ID NO: 62) |
| P45702 P45703 P40943 | Xylanase *Geobacillus stearothermophilus* | 5'MPTNLFFNAHHSPVGAFASFTLGFPGKSGGLDLELARPPR QNVLIGVESLHESGLYHVLPFLETAEEDESKRYDIENPDPNP QKPNILIPFAKEEIQREFHVATDTWKAGDLTFTIYSPVKAVP NPETADEEELKLALVPAVIVEMTIDNTNGTRARRAFFGFEGT DPYTSMRRIDDTCPQLRGVGQGRILSIVSKDEGVRSALHFSM EDILTAQLEENWTFGLGKVGALIVDVPAGEKKTYQFAVCFY RGGYVTAGMDASYFYTRFFQNIEEVGLYALEQAEVLKEQSF RSNKLIEKEWLSDDQTFMMAHAIRSYYGNTQLLEHEGKPIW VVNEGEYRMMNTFDLTVDQLFFELKLNPWTVKNVLDLYVE RYSYEDRVRFPGEETEYPSGISFTHDMGVANTFSRPHYSSYE LYGISGCFSHMTHEQLVNWVLCAAVYIEQTKDWAWRDKR LAILEQCLESMVRRDHPDPEQRNGVMGLDSTRTMGGAEITT YDSLDVSLGQARNNLYLAGKCWAAYVALEKLFRDVGKEE LAALAGEQAEKCAATIVSHVTDDGYIPAIMGEGNDSKIIPAIE GLVFPYFTNCHEALDENGRFGAYIQALRNHLQYVLREGICL FPDGGWKISSTSNNSWLSKIYLCQFIARHILGWEWDEQGKR ADAAHVAWLTHPTLSIWSWSDQIIAGEITGSKYYPRGVTSIL WLEEGE 3' (SEQ ID NO: 63)<br><br>5'MCSSIPSLREVFANDFRIGAAVNPVTLEAQQSLLIRHVNSL TAENHMKFEHLQPEEGRFTFDIAIKSSTSPFSSHGVRGHTLV WHNQTPSWVFQDSQGHFVGRDVLLERMKSHISTVVQRYKG KVYCWDVINEAVADEGSEWLRSSTWRQIIGDDFIQQAFLYA HEADPEALLFYNDYNECFPEKREKIYTLVKSLRDKGIPIHGIG MQAHWSLNRPTLDEIRAAIERYASLGVILHITELDISMFEFDD HRKDLAAPTNEMVERQAERYEQIF SLFKEYRDVIQNVTFWG IADDHTWLDHFPVQGRKNWPLLFDEQHNPKPAFWRVVNI 3' (SEQ ID NO: 64) |

TABLE 2-continued

Thermostable Glycosidase Proteins

| Accession | Strain | Thermostable Protein Sequence |
|---|---|---|
| | | 5'MRNVVRKPLTIGLALTLLLPMGMTATSAKNADSYAKKPH<br>ISALNAPQLDQRYKNEFTIGAAVEPYQLQNEKDVQMLKRHF<br>NSIVAENVMKPISIQPEEGKFNFEQADRIVKFAKANGMDIRF<br>HTLVWHSQVPQWFFLDKEGKPMVNETDPVKREQNKQLLL<br>KRLETHIKTIVERYKDDIKYWDVVNEVVGDDGKLRNSPWY<br>QIAGIDYIKVAFQAARKYGGDNIKLYMNDYNTEVEPKRTAL<br>YNLVKQLKEEGVPIDGIGHQSHIQIGWPSEAEIEKTINMFAAL<br>GLDNQITELDVSMYGWPPRAYPTYDAIPKQKFLDQAARYD<br>RLFKLYEKLSDKISNVTFWGIADNHTWLDSRADVYYDANG<br>NVVVDPNAPYAKVEKGKGKDAPFVFGPDYKVKPAYWAIID<br>HK 3' (SEQ ID NO: 65) |
| P09961 | Alpha-<br>amylase 1<br>*Dictyo-<br>glomus<br>thereto-<br>philum* | 5'MTKSIYFSLGIHNHQPVGNFDFVIERAYEMSYKPLINFFFK<br>HPDFPINVHFSGFLLLWLEKNHPEYFEKLKIMAERGQIEFVS<br>GGFYEPILPIIPDKDKVQQIKKLNKYIYDKFGQTPKGMWLAE<br>RVWEPHLVKYIAEAGIEYVVVDDAHFFSVGLKEEDLFGYYL<br>MEEQGYKLAVFPISMKLRYLIPFADPEETITYLDKFASEDKS<br>KIALLFDDGEKFGLWPDTYRTVYEEGWLETFVSKIKENFLL<br>VTPVNLYTYMQRVKPKGRIYLPTASYREMMEWVLFPEAQK<br>ELEELVEKLKTENLWDKFSPYVKGGFWRNFLAKYDESNHM<br>QKKMLYVWKKVQDSPNEEVKEKAMEEVFQGQANDAYWH<br>GIFGGLYLPHLRTAIYEHLIKAENYLENSEIRFNIFDFDCDGN<br>DEIIVESPFFNLYLSPNHGGSVLEWDFKTKAFNLTNVLTRRK<br>EAYHSKLSYVTSEAQGKSIHERWTAKEEGLENILFYDNHRR<br>VSFTEKIFESEPVLEDLWKDSSRLEVDSFYENYDYEINKDEN<br>KIRVLFSGVFRGFELCKSYILYKDKSFVDVVYEIKNVSETPIS<br>LNFGWEINLNFLAPNHPDYYFLIGDQKYPLSSFGIEKVNNW<br>KIFSGIGIELECVLDVEASLYRYPIETVSLSEEGFERVYQGAL<br>IHFYKVDLPVGSTWRTTIRFWVK 3' (SEQ ID NO: 66) |
| Q60042 | Xylanase A<br>*Thermotoga<br>neapolitana* | 5'MRKKRRGFLNASTAVLVGILAGFLGVVLAATGALGFAVR<br>ESLLLKQFLFLSFEGNTDGASPFGKDVVVTASQDVAADGEY<br>SLKVENRTSVWDGVEIDLTGKVNTGTDYLLSFHVYQTSDSP<br>QLFSVLARTEDEKGERYKILADKVVVPNYWKEILVPFSPTFE<br>GTPAKFSLIITSPKKTDFVFYVDNVQVLTPKEAGPKVVYETS<br>FEKGIGDWQPRGSDVKISISPKVAHSGKKSLFVSNRQKGWH<br>GAQISLKGILKTGKTYAFEAWVYQESGQDQTIIMTMQRKYS<br>SDSSTKYEWIKAATVPSGQWVQLSGTYTIPAGVTVEDLTLY<br>FESQNPTLEFYVDDVKVVDTTSAEIKLEMNPEEEIPALKDVL<br>KDYFRVGVALPSKVFINQKDIALISKHSNSSTAENEMKPDSL<br>LAGIENGKLKFRFETADKYIEFAQQNGMVVRGHTLVWHNQ<br>TPEWFFKDENGNLLSKEEMTERLREYIHTVVGHFKGKVYA<br>WDVVNEAVDPNQPDGLRRSTWYQIMGPDYIELAFKFAREA<br>DPNAKLFYNDYNTFEPKKRDIIYNLVKSLKEKGLIDGIGMQC<br>HISLATDIRQIEEAIKKFSTIPGIEIHITELDISVYRDSTSNYSEA<br>PRTALIEQAHKMAQLFKIFKKYSNVITNVTFWGLKDDYSWR<br>ATRRNDWPLIFDKDYQAKLAYWAIVAPEVLPPLPKESKISEG<br>EAVVVGMMDDSYMMSKPIEIYDEEGNVKATIRAIWKDSTIY<br>VYGEVQDATKKPAEDGVAIFINPNNERTPYLQPDDTYVVLW<br>TNWKSEVNREDVEVKKFVGPGFRRYSFEMSITIPGVEFKKD<br>SYIGFDVAVIDDGKWYSWSDTTNSQKTNTMNYGTLKLEGV<br>MVATAKYGTPVIDGEIDDIWNTTEEIETKSVAMGSLEKNAT<br>AKVRVLWDEENLYVLAIVKDPVLNKDNSNPWEQDSVEIFID<br>ENNHKTGYYEDDDAQFRVNYMNEQSFGTGASAARFKTAV<br>KLIEGGYIVEAAIKWKTIKPSPNTVIGFNVQVNDANEKGQRV<br>GIISWSDPTNNSWRDPSKFGNLRLIK 3' (SEQ ID NO: 67) |
| AAN05438<br>AAN05439 | Beta-<br>glycosidase<br>*Thermus<br>thermo-<br>philus* | 5'MDDHAEKFLWGVATSAYQIEGATQEDGRGPSIWDAFARR<br>PGAIRDGSTGEPACDHYRRYEEDIALMQSLGVRAYRFSVAW<br>PRILPEGRGRINPKGLAFYDRLVDRLLASGITPFLTLYHWDLP<br>LALEERGGWRSRETAFAFAEYAEAVARALADRVPFFATLNE<br>PWCSAFLGHWTGEHAPGLRNLEAALRAAHHLLLGHGLAVE<br>ALRAAGARRVGIVLNFAPAYGEDPEAVDVADRYHNRYFLD<br>PILGKGYPESPFRDPPPVPILSRDLELVARPLDFLGVNYYAPV<br>RVAPGTGTLPVRYLPPEGPATAMGWEVYPEGLHHLLKRLG<br>REVPWPLYVTENGAAYPDLWTGEAVVEDPERVAYLEAHVE<br>AALRAREEGVDLRGYFVWSLMDNFEWAFGYTRRFGLYYV<br>DFPSQRRIPKRSALWYRERIARAQT 3' (SEQ ID NO: 68)<br><br>5'MTENAEKFLWGVATSAYQIEGATQEDGRGPSIWDAFAQR<br>PGAIRDGSTGEPACDHYRRYEEDIALMQSLGVRAYRFSVAW<br>PRILPEGRGRINPKGLAFYDRLVDRLLASGITPFLTLYHWDLP<br>LALEERGGWRSRETAFAFAEYAEAVARALADRVPFFATLNE<br>PWCSAFLGHWTGEHAPGLRNLEAALRAAHHLLLGHGLAVE<br>ALRAAGARRVGIVLNFAPAYGEDPEAVDVADRYHNRFFLD<br>PILGKGYPESPFRDPPPVPILSRDLELVARPLDFLGVNYYAPV |

TABLE 2-continued

Thermostable Glycosidase Proteins

| Accession | Strain | Thermostable Protein Sequence |
|---|---|---|
| | | RVAPGTGTLPVRYLPPEGPATAMGWEVYPEGLYHLLKRLG<br>REVPWPLYVTENGAAYPDLWTGEAVVEDPERVAYLEAHVE<br>AALRAREEGVDLRGYFVWSLMDNFEWAFGYTRRFGLYYV<br>DFPSQRRIPKRSALWYRERIARAQT 3' (SEQ ID NO: 69) |
| AAN05437 | Sugar permease Thermus thermo- philus | 5'MAQVGRGASPLSRARVPPLPHPLDGEHLPHDPAGGGHGK<br>ASSQDAPVGQLPGHLARPAFFHYLKNSFLVCSLTTVFALAV<br>ATFAGYALARFRFPGAELFGGSVLVTQVIPGILFLIPIYIMYIY<br>VQNWVRSALGLEVRLVGSYGGLVFTYTAFFVPLSIWILRGF<br>FASIPKELEEAAMVDGATPFQAFHRVILPLALPGLAATAVYI<br>FLTAWDELLFAQVLTTEATATVPVGIRNFVGNYQNRYDLV<br>MAAATVATLPVLVLFFFVQRQLIQGLTAGAVKG 3' (SEQ ID NO: 70) |
| AAN05440 | Beta- glycosidase Thermus filiformis | 5'MAENAEKFLWGVATSAYQIEGATQEDGRGPSIWDTFARR<br>PGAIRDGSTGEPACDHYHRYEEDIALMQSLGVGVYRFSVA<br>WPRILPEGRGRINPKGLAFYDRLVDRLLAAGITPFLTLYHWD<br>LPQALEDRGGWRSRETAFAFAEYAEAVARALADRVPFFATL<br>NEPWCSAFLGHWTGEHAPGLRNLEAALRAAHHLLLGHGLA<br>VEALRAAGAKRVGIVLNFAPVYGEDPEAVDVADRYHNRYF<br>LDPILGRGYPESPFQDPPPTPNLSRDLELVARPLDFLGVNYY<br>APVRVAPGTGPLPVRYLPPEGPVTAMGWEVYPEGLYHLLK<br>RLGREVPWPLYITENGAAYPDLWTGEAVVEDPERVAYLEA<br>HVEAALRAREEGVDLRGYFVWSLMDNFEWAFGYTRRFGL<br>YYVDFPSQRRIPKRSALWYRERIARAQL 3' (SEQ ID NO: 71) |
| AAD43138 | Beta- glycosidase Thermo- sphaera aggregans | 5'MKFPKDFMIGYSSSPFQFEAGIPGSEDPNSDWWVWVHDPE<br>NTAAGLVSGDFPENGPGYWNLNQNDHDLAEKLGVNTIRVG<br>VEWSRIFPKPTFNVKVPVERDENGSIVHVDVDDKAVERLDE<br>LANKEAVNHYVEMYKDWVERGRKLILNLYHWPLPLWLHN<br>PIMVRRMGPDRAPSGWLNEESVVEFAKYAAYIAWKMGELP<br>VMWSTMNEPNVVYEQGYMFVKGGFPPGYLSLEAADKARR<br>NMIQAHARAYDNIKRFSKKPVGLIYAFQWFELLEGPAEVFD<br>KFKSSKLYYFTDIVSKGSSIINVEYRRDLANRLDWLGVNYYS<br>RLVYKIVDDKPIILHGYGFLCTPGGISPAENPCSDFGWEVYPE<br>GLYLLLKELYNRYGVDLIVTENGVSDSRDALRPAYLVSHVY<br>SVWKAANEGIPVKGYLHWSLTDNYEWAQGFRQKFGLVMV<br>DFKTKKRYLRPSALVFREIATHNGIPDELQHLTLIQ 3' (SEQ ID NO: 72) |

While sequences of exemplary thermostable polypeptides are provided herein, it will be appreciated that any sequence exhibiting thermostability may be employed. In some embodiments, a thermostable polypeptide can have an amino acid sequence with about 60%, about 70%, about 80%, about 85%, about 90%, about 91%, about 92%, about 93%, about 94%, about 95%, about 96%, about 97%, about 98%, about 99%, or 100% sequence identity to an amino acid sequence selected from the group consisting of SEQ ID NOS:36-72. In some embodiments, such a thermostable polypeptide can retain thermostability.

In some embodiments, a thermostable polypeptide can have an amino acid sequence that comprises about 100 contiguous amino acids of a sequence selected from the group consisting of SEQ ID NOS:36-72. In some embodiments, a thermostable polypeptide can have an amino acid sequence with about 60%, about 70%, about 80%, about 85%, about 90%, about 91%, about 92%, about 93%, about 94%, about 95%, about 96%, about 97%, about 98%, about 99%, or 100% sequence identity to a contiguous stretch of about 100 amino acids from a sequence selected from the group consisting of SEQ ID NOS:36-72.

In some embodiments, a thermostable polypeptide can have an amino acid sequence comprising about 150, about 200, about 250, about 300, about 350, about 400, about 450, about 500, about 550, about 600, about 650, about 700, or more than 700 contiguous amino acids of a sequence selected from the group consisting of SEQ ID NOS:36-72. In some embodiments, a thermostable polypeptide can have an amino acid sequence with about 60%, about 70%, about 80%, about 85%, about 90%, about 91%, about 92%, about 93%, about 94%, about 95%, about 96%, about 97%, about 98%, about 99%, or 100% sequence identity to a contiguous stretch of about 150, 200, 250, 300, 350, or more than 350 amino acids from a sequence selected from the group consisting of SEQ ID NO:36-72.

When designing fusion proteins and polypeptides, it typically is desirable to preserve immunogenicity of the antigen. Still further, it is desirable in certain aspects to provide constructs which provide thermostability of a fusion protein. This feature facilitates easy, time efficient and cost effective recovery of a target antigen. In certain aspects, antigen fusion partners may be selected which provide additional advantages, including enhancement of immunogenicity, potential to incorporate multiple vaccine determinants, yet lack prior immunogenic exposure to vaccination subjects. Further beneficial qualities of fusion peptides of interest include proteins which provide ease of manipulation for incorporation of one or more antigens, as well as proteins which have potential to confer ease of production, purification, and/or formulation for vaccine preparations. One of ordinary skill in the art will appreciate that three dimensional presentation can affect each of these beneficial characteristics. Preservation of immunity or preferential qualities therefore may affect, for example, choice of fusion partner and/or choice of fusion location (e.g., N-terminus, C-terminus, internal, combinations thereof). Alternatively or additionally, preferences may affect length of segment selected for fusion, whether it be length of antigen or length of fusion partner selected.

As described herein, a variety of antigens can be fused with a thermostable protein. For example, the thermostable carrier molecule LicB, also referred to as lichenase, can be used for production of fusion proteins. LicB is 1,3-1,4-β glucanase (LicB) from *Clostridium thermocellum*, and has the following amino acid sequence (also set forth in EMBL accession: X63355 [gi:40697]):

```
                                          (SEQ ID NO: 36)
MKNRVISLLMASLLLVLSVIVAPFYKAEAATVVNTPFVAVFSNFDSSQ

WEKADWANGSVFNCVWKPSQVTFSNGKMILTLDREYGGSYPYKSGE

YRTKSFFGYGYYEVRMKAAKNVGIVSSFFTYTGPSDNNPWDEIDIEFL

GKDTTKVQFNWYKNGVGGNEYLHNLGFDASQDFHTYGFEWRPDYID

FYVDGKKVYRGTRNIPVTPGKIMMNLWPGIGVDEWLGRYDGRTPLQ

AEYEYVKYYPNGVPQDNPTPTPTIAPSTPTNPNLPLKGDVNGDGHVNS

SDYSLFKRYLLRVIDRFPVGDQSVADVNRDGRIDSTDLTMLKRYLIRAI

PSL.
```

LicB belongs to a family of globular proteins. Based on the three dimensional structure of LicB, its N- and C-termini are situated close to each other on the surface, in close proximity to the active domain. LicB also has a loop structure exposed on the surface that is located far from the active domain. We have generated constructs such that the loop structure and N- and C-termini of protein can be used as insertion sites for HA polypeptides. HA polypeptides can be expressed as N- or C-terminal fusions or as inserts into the surface loop. Importantly, LicB maintains its enzymatic activity at low pH and at high temperature (up to 75° C.). Thus, use of LicB as a carrier molecule contributes advantages, including likely enhancement of target specific immunogenicity, potential to incorporate multiple vaccine determinants, and straightforward formulation of vaccines that may be delivered nasally, orally or parenterally. Furthermore, production of LicB fusions in plants should reduce the risk of contamination with animal or human pathogens. See examples provided herein.

Fusion proteins comprising HA polypeptides can be produced in any of a variety of expression systems, including both in vitro and in vivo systems. One skilled in the art will readily appreciate that optimization of nucleic acid sequences for a particular expression system is often desirable. For example, an exemplary optimized sequence for expression of HA polypeptide-LicB fusions in plants is provided, and is shown in SEQ ID NO:73:

(SEQ ID NO: 73)

5'<u>MGFVLFSQLPSFLLVSTLLLFLVISHSCRAQN</u>GGSYPYKSGEYRTK

SFFGYGYYEVRMKAAKNVGIVSSFFTYTGPSDNNPWDEIDIEFLGKDT

TKVQFNWYKNGVGGNEYLHNLGFDASQDFHTYGFEWRPDYIDFYVD

GKKVYRGTRNIPVTPGKIMMNLWPGIGVDEWLGRYDGRTPLQAEYE

YVKYYPNGrsk1VVNTPFVAVFSNFDSSQWEKADWANGSVFNCVWKP

SQVTFSNGKMILTLDREYvd*<u>HHHHHHKDEL</u>* 3'.

In SEQ ID NO:73, the bold/underlined portion corresponds to the signal sequence, the italicized/underlined portion corresponds to the 6× His tag and endoplasmic reticulum retention sequence, and the two portions in lowercase letters correspond to restriction sites.

Thus, any relevant nucleic acid encoding a HA polypeptide(s), fusion protein(s), or immunogenic portions thereof is intended to be encompassed within nucleic acid constructs provided herein.

For production in plant systems, transgenic plants expressing HA polypeptide(s) (e.g., HA polypeptide(s), fusion(s) thereof, and/or immunogenic portion(s) thereof) may be utilized. Alternatively or additionally, transgenic plants may be produced using methods well known in the art to generate stable production crops. Additionally, plants utilizing transient expression systems may be utilized for production of HA polypeptide(s). When utilizing plant expression systems, whether transgenic or transient expression in plants is utilized, any of nuclear expression, chloroplast expression, mitochondrial expression, or viral expression may be taken advantage of according to the applicability of the system to antigen desired. Furthermore, additional expression systems for production of antigens and fusion proteins can be utilized. For example, mammalian expression systems (e.g., mammalian cell lines such as CHO cells), bacterial expression systems (e.g., *E. coli*), insect expression systems (e.g., baculovirus), yeast expression systems, and in vitro expression systems (e.g., reticulate lysates) may be used for expression of antigens and fusion proteins.

Production of Influenza Antigens

Influenza antigens (including influenza protein(s), fragments, variants, and/or fusions thereof) can be produced in any suitable system; production is not limited to plant systems. Vector constructs and expression systems are well known in the art and may be adapted to incorporate use of influenza antigens provided herein. For example, influenza antigens (including fragments, variants, and/or fusions) can be produced in known expression systems, including mammalian cell systems, transgenic animals, microbial expression systems, insect cell systems, and plant systems, including transgenic and transient plant systems. Particularly where influenza antigens are produced as fusion proteins, it may be desirable to produce such fusion proteins in plant systems.

In some embodiments, influenza antigens are produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Also, plants can economically produce very large amounts of biomass without requiring sophisticated facilities. Moreover, plants are not subject to contamination with animal pathogens. Like liposomes and microcapsules, plant cells are expected to provide protection for passage of antigen to the gastrointestinal tract.

Plants may be utilized for production of heterologous proteins via use of various production systems. One such system includes use of transgenic/genetically-modified plants where a gene encoding target product is permanently incorporated into the genome of the plant. Transgenic systems may generate crop production systems. A variety of foreign proteins, including many of mammalian origin and many vaccine candidate antigens, have been expressed in transgenic plants and shown to have functional activity (Tacket et al., 2000, *J. Infect. Dis.*, 182:302; and Thanavala et al., 2005, *Proc. Natl. Acad. Sci., USA*, 102:3378). Additionally, administration of unprocessed transgenic plants expressing hepatitis B major surface antigen to non-immunized human volunteers resulted in production of immune response (Kapusta et al., 1999, *FASEB J.*, 13:1796).

Another system for expressing polypeptides in plants utilizes plant viral vectors engineered to express foreign sequences (e.g., transient expression). This approach allows for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout the entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying desired antigenic epitopes on their surface. This approach allows for time-efficient production of antigen and/or antibody candidates, since the particulate nature of an antigen and/or antibody candidate facilitates easy and cost-effective recovery from plant tissue. Additional advantages include enhanced target-specific immunogenicity, the potential to incorporate multiple antigen determinants and/or antibody sequences, and ease of formulation into antigen and/or antibody that can be delivered nasally, orally or parenterally. As an example, spinach leaves containing recombinant plant viral particles carrying epitopes of virus fused to coat protein have generated immune response upon administration (Modelska et al., 1998, *Proc. Natl. Acad. Sci., USA*, 95:2481; and Yusibov et al., 2002, *Vaccine*, 19/20:3155).

Production of Hemagglutinin Antigens

HA antigens (including HA polypeptide(s), fusions thereof, and/or immunogenic portions thereof) may be produced in any suitable system; production is not limited to plant systems. Vector constructs and expression systems are well known in the art and may be adapted to incorporate use of HA polypeptides provided herein. For example, HA polypeptides can be produced in known expression systems, including mammalian cell systems, transgenic animals, microbial expression systems, insect cell systems, and plant systems, including transgenic and transient plant systems. Particularly where HA polypeptides are produced as fusion proteins, it may be desirable to produce such fusion proteins in plant systems.

In some embodiments, HA polypeptides are desirably produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Also, plants can economically produce very large amounts of biomass without requiring sophisticated facilities. Moreover, plants are not subject to contamination with animal pathogens. Like liposomes and microcapsules, plant cells are expected to provide protection for passage of antigen to the gastrointestinal tract.

Plants may be utilized for production of heterologous proteins via use of various production systems. One such system includes use of transgenic/genetically-modified plants where a gene encoding target product is permanently incorporated into the genome of the plant. Transgenic systems may generate crop production systems. A variety of foreign proteins, including many of mammalian origin and many vaccine candidate antigens, have been expressed in transgenic plants and shown to have functional activity. (Tacket et al., 2000, *J. Infect. Dis.*, 182:302; and Thanavala et al., 2005, *Proc. Natl. Acad. Sci., USA*, 102:3378; both of which are incorporated herein by reference). Additionally, administration of unprocessed transgenic plants expressing hepatitis B major surface antigen to non-immunized human volunteers resulted in production of immune response (Kapusta et al., 1999, *FASEB J.*, 13:1796; incorporated herein by reference).

One system for expressing polypeptides in plants utilizes plant viral vectors engineered to express foreign sequences (e.g., transient expression). This approach allows for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout the entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying desired antigenic epitopes on their surface. This approach allows for time-efficient production of vaccine candidates, since the particulate nature of a vaccine candidate facilitates easy and cost-effective recovery from plant tissue. Additional advantages include enhanced target-specific immunogenicity, the potential to incorporate multiple vaccine determinants, and ease of formulation into vaccines that can be delivered nasally, orally or parenterally. As an example, spinach leaves containing recombinant plant viral particles carrying epitopes of virus fused to coat protein have generated immune response upon administration (Modelska et al., 1998, *Proc. Natl. Acad. Sci., USA*, 95:2481; and Yusibov et al., 2002, *Vaccine*, 19/20:3155; both of which are incorporated herein by reference).

Plant Expression Systems

The teachings herein are applicable to a wide variety of different plants. In general, any plants that are amendable to expression of introduced constructs as described herein are useful in accordance with the methods disclosed herein. In some embodiments, it is desirable to use young plants in order to improve the speed of protein/polypeptide production. As indicated here, in many embodiments, sprouted seedlings are utilized. As is known in the art, most sprouts are quick growing, edible plants produced from storage seeds. However, those of ordinary skill in the art will appreciate that the term "sprouted seedling" has been used herein in a more general context, to refer to young plants whether or not of a variety typically classified as "sprouts." Any plant that is grown long enough to have sufficient green biomass to allow introduction and/or expression of an expression construct as provided for herein (recognizing that the relevant time may vary depending on the mode of delivery and/or expression of the expression construct) can be considered a "sprouted seedling" herein.

In many embodiments, edible plants are utilized (i.e., plants that are edible by—not toxic to—the subject to whom the protein or polypeptide is to be administered).

Any plant susceptible to incorporation and/or maintenance of heterologous nucleic acid and capable of producing heterologous protein can be utilized. In general, it may be desirable to utilize plants that are amenable to growth under defined conditions, for example in a greenhouse and/or in aqueous systems. It may be desirable to select plants that are not typically consumed by human beings or domesticated animals and/or are not typically part of the human food chain, so that they may be grown outside without concern that expressed polynucleotide may be undesirably ingested. In some embodiments, however, it will be desirable to employ edible plants. In particular embodiments, it will be desirable to utilize plants that accumulate expressed polypeptides in edible portions of a plant.

Often, certain desirable plant characteristics will be determined by the particular polynucleotide to be expressed. To give but a few examples, when a polynucleotide encodes a protein to be produced in high yield (as will often be the case, for example, when antigen proteins are to be expressed), it will often be desirable to select plants with relatively high biomass (e.g., tobacco, which has additional advantages that it is highly susceptible to viral infection, has a short growth period, and is not in the human food chain). Where a polynucleotide encodes antigen protein whose full activity requires (or is inhibited by) a particular post-translational modification, the ability (or inability) of certain plant species to accomplish relevant modification (e.g., a particular glycosylation) may direct selection. For example, plants are capable of accomplishing certain post-translational modifications (e.g., glycosylation), however, plants will not generate sialyation patterns which are found in mammalian post-translational modification. Thus, plant production of antigen may result in production of a different entity than the identical protein sequence produced in alternative systems.

In certain embodiments, crop plants, or crop-related plants are utilized. In certain specific embodiments, edible plants are utilized.

Plants for use in accordance with the methods provided herein include, for example, Angiosperms, Bryophytes (e.g., Hepaticae and Musci), Pteridophytes (e.g., ferns, horsetails, and lycopods), Gymnosperms (e.g., conifers, cycase, Ginko, and Gnetales), and Algae (e.g., Chlorophyceae, Phaeophyceae, Rhodophyceae, Myxophyceae, Xanthophyceae, and Euglenophyceae). Exemplary plants include members of the families Leguminosae (Fabaceae; e.g., pea, alfalfa, and soybean); Gramineae (Poaceae; e.g., corn, wheat, and rice); Solanaceae, particularly of the genus *Lycopersicon* (e.g., tomato), *Solanum* (e.g., potato and eggplant), Capsium (e.g., pepper), *Nicotiana* (e.g., tobacco); Umbelliferae, particularly of the genus *Daucus* (e.g., carrot), *Apium* (e.g., celery), or Rutaceae (e.g., oranges); Compositae, particularly of the genus *Lactuca* (e.g., lettuce); and Brassicaceae (Cruciferae), particularly of the genus *Brassica* or *Sinapis*. In certain aspects, useful plants may be species of *Brassica* or *Arabidopsis*. Some exemplary Brassicaceae family members include *Brassica campestris, B. carinata, B. juncea, B. napus, B. nigra, B. oleraceae, B. tournifortii, Sinapis alba*, and *Raphanus sativus*. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, and edible flowers such as sunflower.

A wide variety of plant species may be suitable in the practices described herein. For example, a variety of different bean and other species including, for example, adzuki bean, alfalfa, barley, broccoli, bill jump pea, buckwheat, cabbage, cauliflower, clover, collard greens, fenugreek, flax, garbanzo bean, green pea, Japanese spinach, kale, kamut, kohlrabi, marrowfat pea, mung bean, mustard greens, pinto bean, radish, red clover, soy bean, speckled pea, sunflower, turnip, yellow trapper pea, and others may be amenable to the production of heterologous proteins from viral vectors launched from an agrobacterial construct (e.g., introduced by agroinfiltration). In some embodiments, bill jump pea, green pea, marrowfat pea, speckled pea, and/or yellow trapper pea are particularly useful. In certain embodiments, therefore, this document provides production of proteins or polypeptides (e.g., antigens) in one or more of these plants using an agrobacterial vector that launches a viral construct (i.e., an RNA with characteristics of a plant virus) encoding the relevant protein or polypeptide of interest. In some embodiments, the RNA has characteristics of (and/or includes sequences of) AlMV. In some embodiments, the RNA has characteristics of (and/or includes sequences of) TMV.

It will be appreciated that, in one aspect, this document provides young plants (e.g., sprouted seedlings) that express a target protein or polypeptide of interest. In some embodiments, the young plants were grown from transgenic seeds; this document also provides seeds which can be generated and/or utilized for the methods described herein. Seeds transgenic for any gene of interest can be sprouted and optionally induced for production of a protein or polypeptide of interest. For example, seeds capable of expressing any gene of interest can be sprouted and induced through: i) virus infection, ii) agroinfiltration, or iii) bacteria that contain virus genome. Seeds capable of expressing a transgene for heavy or light chain of any monoclonal antibody can be sprouted and induced for production of full-length molecule through: i) virus infection, ii) agroinfiltration, or iii) inoculation with bacteria that contain virus genome. Seeds capable of expressing a transgene for one or more components of a complex molecule comprising multiple components such as sIgA can be sprouted and used for producing a fully functional molecule through: i) virus infection, ii) agroinfiltration, or iii) inoculation with bacteria that contain virus genome. Seeds from healthy non-transgenic plants can be sprouted and used for producing target sequences through: i) virus infection, ii) agroinfiltration, or iii) inoculation with bacteria that contain a virus genome.

In some embodiments, the young plants were grown from seeds that were not transgenic. Typically, such young plants will harbor viral sequences that direct expression of the protein or polypeptide of interest. In some embodiments, the plants may also harbor agrobacterial sequences, optionally including sequences that "launched" the viral sequences.

Introducing Vectors into Plants

In general, vectors may be delivered to plants according to known techniques. For example, vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

A wide variety of viruses are known that infect various plant species, and can be employed for polynucleotide expression (see, for example, in *The Classification and Nomenclature of Viruses*, "Sixth Report of the International Committee on Taxonomy of Viruses" (Ed. Murphy et al.), Springer Verlag: New York, 1995; Grierson et al., *Plant Molecular Biology*, Blackie, London, pp. 126-146, 1984; Gluzman et al., *Communications in Molecular Biology: Viral Vectors*, Cold Spring Harbor Laboratory, Cold Spring Harbor, N.Y., pp. 172-189, 1988; and Mathew, *Plant Viruses Online*; all of which are incorporated herein by reference). In certain embodiments, rather than delivering a single viral vector to a plant cell, multiple different vectors are delivered which, together, allow for replication (and, optionally cell-to-cell and/or long distance movement) of viral vector(s). Some or all of the proteins may be encoded by the genome of transgenic plants. In certain aspects, described in further detail herein, these systems include one or more viral vector components.

Vector systems that include components of two heterologous plant viruses in order to achieve a system that readily infects a wide range of plant types and yet poses little or no risk of infectious spread. An exemplary system has been described previously (see, e.g., PCT Publication WO 00/25574 and U.S. Patent Publication 2005/0026291, both of which are incorporated herein by reference). As noted herein, viral vectors can be applied to plants (e.g., plants, portions of plant, or sprouts), through infiltration, mechanical inoculation, or spraying, for example. Where infection is to be accomplished by direct application of a viral genome to a plant, any available technique may be used to prepare the genome. For example, many viruses that are usefully employed in accordance with the present disclosure have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, and reticulocyte lysate), and also the convenience of maintaining a DNA copy of an RNA vector, ssRNA vectors may be prepared by in vitro transcription, particularly with T7 or SP6 polymerase.

In certain embodiments, rather than introducing a single viral vector type into a plant, multiple different viral vectors are introduced. Such vectors may, for example, trans-complement each other with respect to functions such as replication, cell-to-cell movement, and/or long distance movement. Vectors may contain different polynucleotides encoding HA polypeptides as provided herein. Selection for plant(s) or portions thereof that express multiple polypeptides encoding one or more HA polypeptide(s) may be performed as described above for single polynucleotides or polypeptides.

Plant Tissue Expression Systems

As discussed herein, HA polypeptides may be produced in any desirable system. Vector constructs and expression systems are well known in the art and may be adapted to incorporate use of HA polypeptides provided herein. For example, transgenic plant production is known and generation of constructs and plant production may be adapted according to known techniques in the art. In some embodiments, transient expression systems in plants are desirable. Two of these systems include production of clonal roots and clonal plant systems, and derivatives thereof, as well as production of sprouted seedlings systems.

Clonal Plants

Clonal roots maintain RNA viral expression vectors and stably produce target protein uniformly in an entire root over extended periods of time and multiple subcultures. In contrast to plants, where a target gene is eliminated via recombination during cell-to-cell or long distance movement, in root cultures the integrity of a viral vector is maintained and levels of target protein produced over time are similar to those observed during initial screening. Clonal roots allow for ease of production of heterologous protein material for oral formulation of antigen and vaccine compositions. Methods and reagents for generating a variety of clonal entities derived from plants which are useful for production of antigen (e.g., antigen proteins as provided herein) have been described previously and are known in the art (see, for example, PCT Publication WO 05/81905; incorporated herein by reference). Clonal entities include clonal root lines, clonal root cell lines, clonal plant cell lines, and clonal plants capable of production of antigen (e.g., antigen proteins as described herein). This document further provides methods and reagents for expression of antigen polynucleotide and polypeptide products in clonal cell lines derived from various plant tissues (e.g., roots, leaves), and in whole plants derived from single cells (clonal plants). Such methods are typically based on use of plant viral vectors of various types.

For example, in one aspect, this document provides methods of obtaining a clonal root line that expresses a polynucleotide encoding a HA polypeptide, comprising the steps of: (i) introducing a viral vector that comprises a polynucleotide encoding an HA polypeptide as described herein into a plant or portion thereof; and (ii) generating one or more clonal root lines from a plant. Clonal root lines may be generated, for example, by infecting a plant or plant portion (e.g., a harvested piece of leaf) with an *Agrobacterium* (e.g., *A. rhizogenes*) that causes formation of hairy roots. Clonal root lines can be screened in various ways to identify lines that maintain virus, or lines that express a polynucleotide encoding a HA polypeptide at high levels, for example. This document further provides clonal root lines, e.g., clonal root lines produced as described herein, and further encompasses methods of expressing polynucleotides and producing polypeptide(s) encoding HA polypeptide(s) using clonal root lines.

This document further provides methods of generating a clonal root cell line that expresses a polynucleotide encoding a HA polypeptide, comprising the steps of: (i) generating a clonal root line, cells of which contain a viral vector whose genome comprises a polynucleotide encoding a HA polypeptide; (ii) releasing individual cells from a clonal root line; and (iii) maintaining cells under conditions suitable for root cell proliferation. Clonal root cell lines and methods of expressing polynucleotides and producing polypeptides using clonal root cell lines also are provided herein.

In some aspects, this document provides methods of generating a clonal plant cell line that expresses a polynucleotide encoding a HA polypeptide, comprising the steps of: (i) generating a clonal root line, cells of which contain a viral vector whose genome comprises a polynucleotide encoding a HA polypeptide; (ii) releasing individual cells from a clonal root line; and (iii) maintaining cells in culture under conditions appropriate for plant cell proliferation. Also provided herein are methods for generating a clonal plant cell line that expresses a polynucleotide encoding a HA polypeptide, comprising the steps of: (i) introducing into cells of a plant cell line maintained in culture a viral vector that comprises a polynucleotide encoding a HA polypeptide; and (ii) enriching for cells that contain viral vector. Enrichment may be performed, for example, by (i) removing a portion of cells from the culture; (ii) diluting removed cells so as to reduce cell concentration; (iii) allowing diluted cells to proliferate; and (iv) screening for cells that contain viral vector. Clonal plant cell lines may be used for production of a HA polypeptide as provided herein.

This document provides a number of methods for generating clonal plants, cells of which contain a viral vector that comprises a polynucleotide encoding a HA polypeptide as disclosed herein. For example, this document provides methods of generating a clonal plant that expresses a polynucleotide encoding a HA polypeptide, comprising the steps of: (i) generating a clonal root line, cells of which contain a viral vector whose genome comprises a polynucleotide encoding a HA polypeptide; (ii) releasing individual cells from a clonal root line; and (iii) maintaining released cells under conditions appropriate for formation of a plant. This document further provides methods for generating a clonal plant that expresses a polynucleotide encoding a HA polypeptide, comprising the steps of: (i) generating a clonal plant cell line, cells of which contain a viral vector whose genome comprises a polynucleotide encoding a HA polypeptide; and (ii) maintaining cells under conditions appropriate for formation of a plant. In general, clonal plants as provided herein can express any polynucleotide encoding a HA polypeptide in accordance with this document. Such clonal plants can be used for production of an antigen polypeptide.

As noted above, this document provides systems for expressing a polynucleotide or polynucleotide(s) encoding HA polypeptide(s) in clonal root lines, clonal root cell lines, clonal plant cell lines (e.g., cell lines derived from leaf or stem), and in clonal plants. A polynucleotide encoding a HA polypeptide can be introduced into an ancestral plant cell using a plant viral vector whose genome includes polynucleotide encoding an HA polypeptide operably linked to (i.e., under control of) a promoter. A clonal root line or clonal plant cell line can established from a cell containing virus according to any of several techniques, including those that are further described below. The plant virus vector or portions thereof can be introduced into a plant cell by infection, by inoculation with a viral transcript or infectious cDNA clone, by electroporation, or by T-DNA mediated gene transfer, for example.

The following sections describe methods for generating clonal root lines, clonal root cell lines, clonal plant cell lines, and clonal plants that express a polynucleotide encoding a HA polypeptide as provided herein. A "root line" is distinguished from a "root cell line" in that a root line produces actual rootlike structures or roots while a root cell line consists of root cells that do not form rootlike structures. Use of the term "line" is intended to indicate that cells of the line can proliferate and pass genetic information on to progeny cells. Cells of a cell line typically proliferate in culture without being part of an organized structure such as those found in an intact plant. Use of the term "root line" is intended to indicate that cells in the root structure can proliferate without being part of a complete plant. It is noted that the term "plant cell" encompasses root cells. However, to distinguish methods for generating root lines and root cell lines from those used to directly generate plant cell lines from non-root tissue (as opposed to generating clonal plant cell lines from clonal root lines or clonal plants derived from clonal root lines), the terms "plant cell" and "plant cell line" as used herein generally refer to cells and cell lines that consist of non-root plant tissue. Plant cells can be from, for example, leaf, stem, shoot, or flower part. It is noted that seeds can be derived from clonal plants generated as derived herein. Such seeds may contain viral vector as will plants obtained from such seeds. Methods for obtaining seed stocks are well known in the art (see, for example, U.S. Patent Publication 2004/093643; incorporated herein by reference).

Clonal Root Lines

This document provides systems for generating a clonal root line in which a plant viral vector is used to direct expression of a polynucleotide encoding a HA polypeptide. One or more viral expression vector(s) including a polynucleotide encoding a HA polypeptide operably linked to a promoter can be introduced into a plant or a portion thereof according to any of a variety of known methods. For example, plant leaves can be inoculated with viral transcripts. Vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

Where infection is to be accomplished by direct application of a viral genome to a plant, any available technique may be used to prepare viral genome. For example, many viruses that are usefully employed in accordance with the present disclosure have ssRNA genomes. ssRNA may be prepared by transcription of a DNA copy of the genome, or by replication of an RNA copy, either in vivo or in vitro. Given the readily available, easy-to-use in vitro transcription systems (e.g., SP6, T7, and reticulocyte lysate), and also the convenience of maintaining a DNA copy of an RNA vector, ssRNA vectors can be prepared by in vitro transcription, particularly with T7 or SP6 polymerase. Infectious cDNA clones can be used. Agrobacterially mediated gene transfer can be used to transfer viral nucleic acids such as viral vectors (either entire viral genomes or portions thereof) to plant cells using, e.g., agroinfiltration, according to methods known in the art.

A plant or plant portion may then be then maintained (e.g., cultured or grown) under conditions suitable for replication of viral transcript. In certain embodiments, virus spreads beyond the initially inoculated cell, e.g., locally from cell to cell and/or systemically from an initially inoculated leaf into additional leaves. However, in some embodiments, virus does not spread. Thus viral vector may contain genes encoding functional MP and/or CP, but may be lacking one or both of such genes. In general, viral vector is introduced into (infects) multiple cells in the plant or portion thereof.

Following introduction of viral vector into a plant, leaves are harvested. In general, leaves may be harvested at any time following introduction of a viral vector. However, it may be desirable to maintain a plant for a period of time following introduction of a viral vector into the plant, e.g., a period of time sufficient for viral replication and, optionally, spread of virus from the cells into which it was initially introduced. A clonal root culture (or multiple cultures) is prepared, e.g., by known methods further described below.

In general, any available method may be used to prepare a clonal root culture from a plant or plant tissue into which a viral vector has been introduced. One such method employs genes that exist in certain bacterial plasmids. These plasmids are found in various species of *Agrobacterium* that infect and transfer DNA to a wide variety of organisms. As a genus, *Agrobacteria* can transfer DNA to a large and diverse set of plant types including numerous dicot and monocot angiosperm species and gymnosperms (see, for example, Gelvin, 2003, *Microbiol. Mol. Biol. Rev.*, 67:16, and references therein, all of which are incorporated herein by reference). The molecular basis of genetic transformation of plant cells is transfer from bacterium and integration into plant nuclear genome of a region of a large tumor-inducing (Ti) or rhizogenic (Ri) plasmid that resides within various Agrobacterial species. This region is referred to as the T-region when present in the plasmid and as T-DNA when excised from plasmid. Generally, a single-stranded T-DNA molecule is transferred to a plant cell in naturally occurring Agrobacterial infection and is ultimately incorporated (in double-stranded form) into the genome. Systems based on Ti plasmids are widely used for introduction of foreign genetic material into plants and for production of transgenic plants.

Infection of plants with various Agrobacterial species and transfer of T-DNA has a number of effects. For example, *A. tumefaciens* causes crown gall disease while *A. rhizogenes* causes development of hairy roots at the site of infection, a condition known as "hairy root disease." Each root arises from a single genetically transformed cell. Thus root cells in roots are clonal, and each root represents a clonal population of cells. Roots produced by *A. rhizogenes* infection are characterized by a high growth rate and genetic stability (Giri et al., 2000, *Biotech. Adv.*, 18:1, and references therein, all of which are incorporated herein by reference). In addition, such roots are able to regenerate genetically stable plants (Giri 2000, supra).

In general, this document encompasses use of any strain of *Agrobacteria*, particularly any *A. rhizogenes* strain, that is capable of inducing formation of roots from plant cells. As mentioned above, a portion of the Ri plasmid (Ri T-DNA) is responsible for causing hairy root disease. While transfer of this portion of the Ri plasmid to plant cells can conveniently be accomplished by infection with *Agrobacteria* harboring the Ri plasmid, this document encompasses use of alternative methods of introducing the relevant region into a plant cell. Such methods include any available method of introducing genetic material into plant cells including, but not limited to, biolistics, electroporation, PEG-mediated DNA uptake, and Ti-based vectors. The relevant portions of Ri T-DNA can be introduced into plant cells by use of a viral vector. Ri genes can be included in the same vector that contains a polynucleotide encoding a HA polypeptide or in a different viral vector, which can be the same or a different type to that of the vector that contains a polynucleotide encoding a HA polypeptide as provided herein. It is noted that the entire Ri T-DNA may not be required for production of hairy roots, and this document encompasses use of portions of Ri T-DNA, provided that such portions contain sufficient genetic material to induce root formation, as known in the art. Additional genetic material, e.g., genes present within the Ri plasmid but not within T-DNA, may be transferred to a plant cell, particularly genes whose expression products facilitate integration of T-DNA into the plant cell DNA.

In order to prepare a clonal root line in accordance with certain embodiments, harvested leaf portions are contacted with *A. rhizogenes* under conditions suitable for infection and transformation. Leaf portions are maintained in culture to allow development of hairy roots. Each root is clonal, i.e., cells in the root are derived from a single ancestral cell into which Ri T-DNA was transferred. In some embodiments, a portion of such ancestral cells will contain a viral vector. Thus cells in a root derived from such an ancestral cell may contain viral vector since it will be replicated and will be transmitted during cell division. Thus a high proportion (e.g., at least 50%, at least 75%, at least 80%, at least 90%, at least 95%), all (100%), or substantially all (at least 98%) of cells will contain viral vector. It is noted that since viral vector is inherited by daughter cells within the clonal root, movement of viral vector within the root is not necessary to maintain viral vector throughout the root. Individual clonal hairy roots may be removed from the leaf portion and further cultured. Such roots are also referred to herein as root lines. Isolated clonal roots continue to grow following isolation.

A variety of different clonal root lines have been generated using methods as described herein. These root lines were generated using viral vectors containing polynucleotide(s) encoding a HA polypeptide as provided herein (e.g., encoding HA polypeptide(s), fusions thereof, and/or immunogenic portions thereof). Root lines were tested by Western blot. Root lines displayed a variety of different expression levels of various polypeptides. Root lines displaying high expression were selected and further cultured. These root lines were subsequently tested again and shown to maintain high levels of expression over extended periods of time, indicating stability. Expression levels were comparable to or greater than expression in intact plants infected with the same viral vector used to generate clonal root lines. In addition, stability of expression of root lines was superior to that obtained in plants infected with the same viral vector. Up to 80% of such virus-infected plants reverted to wild type after 2-3 passages. (Such passages involved inoculating plants with transcripts, allowing infection (local or systemic) to become established, taking a leaf sample, and inoculating fresh plants that are subsequently tested for expression).

Root lines may be cultured on a large scale for production of antigen polypeptides, as discussed further below. It is noted that clonal root lines (and cell lines derived from clonal root lines) can generally be maintained in medium that does not include various compounds, e.g., plant growth hormones such as auxins and cytokinins, that typically are employed in culture of root and plant cells. This feature greatly reduces expense associated with tissue culture, and it may contribute significantly to economic feasibility of protein production using plants.

Any of a variety of methods may be used to select clonal roots that express a polynucleotide encoding HA polypeptide(s) as provided herein. Western blots, ELISA assays, and other suitable techniques can be used to detect an encoded polypeptide. In the case of detectable markers such as GFP, alternative methods such as visual screens can be performed. If a viral vector that contains a polynucleotide that encodes a selectable marker is used, an appropriate selection can be imposed (e.g., leaf material and/or roots derived therefrom can be cultured in the presence of an appropriate antibiotic or nutritional condition and surviving roots identified and isolated). Certain viral vectors contain two or more polynucleotide(s) encoding HA polypeptide(s), e.g., two or more polynucleotides encoding different polypeptides. If one of these is a selectable or detectable marker, clonal roots that are selected or detected by selecting for or detecting expression of the marker will have a high probability of also expressing a second polynucleotide. Screening for root lines that contain particular polynucleotides can also be performed using PCR and other nucleic acid detection methods.

Alternatively or additionally, clonal root lines can be screened for presence of virus by inoculating host plants that will form local lesions as a result of virus infection (e.g., hypersensitive host plants). For example, 5 mg of root tissue can be homogenized in 50 μl of phosphate buffer and used to inoculate a single leaf of a tobacco plant. If virus is present in root cultures, within two to three days characteristic lesions will appear on infected leaves. This means that root line contains recombinant virus that carries a polynucleotide encoding a HA polypeptide. If no local lesions are formed, there is no virus, and the root line is rejected as negative. This method is highly time and cost efficient. After initially screening for the presence of virus, roots that contain virus may be subjected to secondary screening, e.g., by Western blot or ELISA to select high expressers. Additional screens can be applied, such as screens for rapid growth, growth in particular media, or growth under particular environmental conditions, for example. These screening methods may, in general, be applied in the development of any of clonal root lines, clonal root cell lines, clonal plant cell lines, and/or clonal plants described herein.

As will be evident to one of ordinary skill in the art, a variety of modifications may be made to the methods for generating clonal root lines that contain a viral vector, and such modifications are within the scope of this document. For example, while it is generally desirable to introduce viral vector into an intact plant or portion thereof prior to introduction of Ri T-DNA genes, in certain embodiments, the Ri-DNA is introduced prior to introducing viral vector. In addition, it is possible to contact intact plants with *A. rhizogenes* rather than harvesting leaf portions and then exposing them to bacterium.

Other methods of generating clonal root lines from single cells of a plant or portion thereof that harbor a viral vector can be used (i.e., methods not using *A. rhizogenes* or genetic material from the Ri plasmid). For example, treatment with certain plant hormones or combinations of plant hormones is known to result in generation of roots from plant tissue.

Clonal Cell Lines Derived from Clonal Root Lines

As described above, this document provides methods for generating clonal root lines, wherein cells in root lines contain a viral vector. As is well known in the art, a variety of different cell lines can be generated from roots. For example, root cell lines can be generated from individual root cells obtained from a root using a variety of known methods. Such root cell lines may be obtained from various different root cell types within the root. In general, root material is harvested and dissociated (e.g., physically and/or enzymatically digested) to release individual root cells, which are then further cultured. Complete protoplast formation is generally not necessary. If desired, root cells can be plated at very dilute cell concentrations, so as to obtain root cell lines from single root cells. Root cell lines derived in this manner are clonal root cell lines containing viral vector. Such root cell lines therefore exhibit stable expression of a polynucleotide encoding a HA polypeptide as provided herein. Clonal plant cell lines can be obtained in a similar manner from clonal roots, e.g., by culturing dissociated root cells in the presence of appropriate plant hormones. Screens and successive rounds of enrichment can be used to identify cell lines that express a polynucleotide encoding a HA polypeptide at high levels. However, if the clonal root line from which the cell line is derived already expresses at high levels, such additional screens may be unnecessary.

As in the case of the clonal root lines, cells of a clonal root cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within a clonal root cell line, movement of viral vector among cells is not necessary to maintain viral vector. Clonal root cell lines can be used for production of a polynucleotide encoding a HA polypeptide, as described below.

Clonal Plant Cell Lines

This document provides methods for generating a clonal plant cell line in which a plant viral vector is used to direct expression of a polynucleotide encoding a HA polypeptide as provided herein. According to these methods, one or more viral expression vector(s) including a polynucleotide encoding a HA polypeptide operably linked to a promoter is introduced into cells of a plant cell line that is maintained in cell culture. A number of plant cell lines from various plant types are known in the art, any of which can be used. Newly derived cell lines can be generated according to known methods for use in practicing the methods disclosed herein. A viral vector can be introduced into cells of a plant cell line according to any of a number of methods. For example, protoplasts can be made and viral transcripts then electroporated into cells. Other methods of introducing a plant viral vector into cells of a plant cell line also can be used.

A method for generating clonal plant cell lines and a viral vector suitable for introduction into plant cells (e.g., protoplasts) can be used as follows: Following introduction of viral vector, a plant cell line may be maintained in tissue culture. During this time viral vector may replicate, and polynucleotide(s) encoding a HA polypeptide(s) as provided herein may be expressed. Clonal plant cell lines are derived from culture, e.g., by a process of successive enrichment. For example, samples may be removed from culture, optionally with dilution so that the concentration of cells is low, and plated in Petri dishes in individual droplets. Droplets are then maintained to allow cell division.

It will be appreciated that droplets may contain a variable number of cells, depending on the initial density of the culture and the amount of dilution. Cells can be diluted such that most droplets contain either 0 or 1 cell if it is desired to obtain clonal cell lines expressing a polynucleotide encoding a HA polypeptide after only a single round of enrichment. However, it can be more efficient to select a concentration such that multiple cells are present in each droplet and then screen droplets to identify those that contain expressing cells. In general, any appropriate screening procedure can be employed. For example, selection or detection of a detectable marker such as GFP can be used. Western blots or ELISA assays can be used. Individual droplets (100 μl) contain more than enough cells for performance of these assays. Multiple rounds of enrichment are performed to isolate successively higher expressing cell lines. Single clonal plant cell lines (i.e., populations derived from a single ancestral cell) can be generated by further limiting dilution using standard methods for single cell cloning. However, it is not necessary to isolate individual clonal lines. A population containing multiple clonal cell lines can be used for expression of a polynucleotide encoding one or more HA polypeptide(s).

In general, certain considerations described above for generation of clonal root lines apply to the generation of clonal plant cell lines. For example, a diversity of viral vectors containing one or more polynucleotide(s) encoding a HA polypeptide(s) as provided herein can be used as can combinations of multiple different vectors. Similar screening methods can be used. As in the case of clonal root lines and clonal root cell lines, cells of a clonal plant cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within a clonal plant cell line, movement of viral vector among cells is not necessary to maintain viral vector. The clonal plant cell line can be used for production of a polypeptide encoding a HA polypeptide as described below.

Clonal Plants

Clonal plants can be generated from clonal roots, clonal root cell lines, and/or clonal plant cell lines produced according to various methods described herein. Methods for generation of plants from roots, root cell lines, and plant cell lines such as clonal root lines, clonal root cell lines, and clonal plant cell lines described herein are well known in the art (see, e.g., Peres et al., 2001, *Plant Cell, Tissue, Organ Culture*, 65:37; incorporated herein by reference; and standard reference works on plant molecular biology and biotechnology cited elsewhere herein). This document therefore provides a method of generating a clonal plant comprising steps of (i) generating a clonal root line, clonal root cell line, or clonal plant cell line according to any of the methods described herein; and (ii) generating a whole plant from a clonal root line, clonal root cell line, or clonal plant. Clonal plants may be propagated and grown according to standard methods.

As in the case of clonal root lines, clonal root cell lines, and clonal plant cell lines, cells of a clonal plant are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (100%), or substantially all (at least 98%) of cells will contain viral vector. It is noted that since viral vector is inherited by daughter cells within the clonal plant, movement of viral vector is not necessary to maintain viral vector.

Sprouts and Sprouted Seedling Plant Expression Systems

Any of a variety of different systems can be used to express proteins or polypeptides in young plants (e.g., sprouted seedlings). In some embodiments, transgenic cell lines or seeds are generated, which are then sprouted and grown for a period of time so that a protein or polypeptide included in the transgenic sequences is produced in young plant tissues (e.g., in sprouted seedlings). Typical technologies for the production of transgenic plant cells and/or seeds include *Agrobacterium tumefaciens* mediated gene transfer and microprojectile bombardment or electroporation.

Systems and reagents for generating a variety of sprouts and sprouted seedlings which are useful for production of HA polypeptide(s) as described herein have been described previously and are known in the art (see, for example, PCT Publication WO 04/43886; incorporated herein by reference). This document further provides sprouted seedlings, which may be edible, as a biomass containing a HA polypeptide. In certain aspects, biomass is provided directly for consumption of antigen containing compositions. In some aspects, biomass is processed prior to consumption, for example, by homogenizing, crushing, drying, or extracting. In certain aspects, HA polypeptides are purified from biomass and formulated into a pharmaceutical composition.

Additionally provided are methods for producing HA polypeptide(s) in sprouted seedlings that can be consumed or harvested live (e.g., sprouts, sprouted seedlings of the *Brassica* genus). In certain aspects, the methods can include growing a seed to an edible sprouted seedling in a contained, regulatable environment (e.g., indoors and/or in a container). A seed can be a genetically engineered seed that contains an expression cassette encoding a HA polypeptide, which expression is driven by an exogenously inducible promoter. A variety of exogenously inducible promoters can be used that are inducible, for example, by light, heat, phytohormones, and/or nutrients.

In some embodiments, this document provides methods of producing HA polypeptide(s) in sprouted seedlings by first generating a seed stock for a sprouted seedling by transforming plants with an expression cassette that encodes HA polypeptide using an *Agrobacterium* transformation system, wherein expression of a HA polypeptide is driven by an inducible promoter. Transgenic seeds can be obtained from a transformed plant, grown in a contained, regulatable environment, and induced to express a HA polypeptide.

In some embodiments, methods are provided that include infecting sprouted seedlings with a viral expression cassette encoding a HA polypeptide, expression of which may be driven by any of a viral promoter or an inducible promoter. Sprouted seedlings can be grown for two to fourteen days in a contained, regulatable environment or at least until sufficient levels of HA polypeptide have been obtained for consumption or harvesting.

This document further provides systems for producing HA polypeptide(s) in sprouted seedlings that include a housing unit with climate control and a sprouted seedling containing an expression cassette that encodes one or more HA polypeptides, wherein expression is driven by a constitutive or inducible promoter. Systems can provide unique advantages over the outdoor environment or greenhouse, which cannot be controlled. Thus, this document enables a grower to precisely time the induction of expression of HA polypeptide. It can greatly reduce time and cost of producing HA polypeptide(s).

In certain aspects, transiently transfected sprouts contain viral vector sequences encoding an HA polypeptide as provided herein. Seedlings can be grown for a time period so as to allow for production of viral nucleic acid in sprouts, followed by a period of growth wherein multiple copies of virus are produced, thereby resulting in production of HA polypeptide(s).

In certain aspects, genetically engineered seeds or embryos that contain a nucleic acid encoding HA polypeptide(s) are grown to sprouted seedling stage in a contained, regulatable environment. The contained, regulatable environment may be a housing unit or room in which seeds can be grown indoors. All environmental factors of a contained, regulatable environment may be controlled. Since sprouts do not require light to grow, and lighting can be expensive, genetically engineered seeds or embryos may be grown to sprouted seedling stage indoors in the absence of light.

Other environmental factors that can be regulated in a contained, regulatable environment include temperature, humidity, water, nutrients, gas (e.g., $O_2$ or $CO_2$ content or air circulation), chemicals (small molecules such as sugars and sugar derivatives, or hormones such as phytohormones, including gibberellins and abscisic acid), and the like.

According to certain methods provided herein, expression of a nucleic acid encoding a HA polypeptide may be controlled by an exogenously inducible promoter. Exogenously inducible promoters are caused to increase or decrease expression of a nucleic acid in response to an external, rather than an internal stimulus. A number of environmental factors can act as inducers for expression of nucleic acids carried by expression cassettes of genetically engineered sprouts. A promoter may be a heat-inducible promoter, such as a heat-shock promoter. For example, using as heat-shock promoter, temperature of a contained environment may simply be raised to induce expression of a nucleic acid. Other promoters include light inducible promoters. Light-inducible promoters can be maintained as constitutive promoters if light in a contained regulatable environment is always on. Alternatively or additionally, expression of a nucleic acid can be turned on at a particular time during development by simply turning on the light. A promoter may be a chemically inducible promoter is used to induce expression of a nucleic acid. According to these embodiments, a chemical could simply be misted or sprayed onto seed, embryo, or seedling to induce expression of nucleic acid. Spraying and misting can be precisely controlled and directed onto target seed, embryo, or seedling to which it is intended. The contained environment is devoid of wind or air currents, which could disperse chemical away from intended target, so that the chemical stays on the target for which it was intended.

The time at which expression is induced can be selected to maximize expression of a HA polypeptide in sprouted seedling by the time of harvest. Inducing expression in an embryo at a particular stage of growth, for example, inducing expression in an embryo at a particular number of days after germination, may result in maximum synthesis of a HA polypeptide at the time of harvest. For example, inducing expression from the promoter 4 days after germination may result in more protein synthesis than inducing expression from the promoter after 3 days or after 5 days. Those skilled in the art will appreciate that maximizing expression can be achieved by routine experimentation. In certain methods, sprouted seedlings are harvested at about 1 day, 2 days, 3 days, 4 days, 5 days, 6 days, 7 days, 8 days, 9 days, 10 days, 11 days, or 12 days after germination.

In cases where the expression vector has a constitutive promoter instead of an inducible promoter, sprouted seedling may be harvested at a certain time after transformation of sprouted seedling. For example, if a sprouted seedling were virally transformed at an early stage of development, for example, at embryo stage, sprouted seedlings may be harvested at a time when expression is at its maximum post-transformation, e.g., at about 1 day, 2 days, 3 days, 4 days, 5 days, 6 days, 7 days, 8 days, 9 days, 10 days, 11 days, 12 days, 13 days, or 14 days post-transformation. It could be that sprouts develop one, two, three or more months post-transformation, depending on germination of seed.

Generally, once expression of HA polypeptide(s) begins, seeds, embryos, or sprouted seedlings are allowed to grow until sufficient levels of HA polypeptide(s) are expressed. In certain aspects, sufficient levels are levels that would provide a therapeutic benefit to a patient if harvested biomass were eaten raw. Alternatively or additionally, sufficient levels are levels from which HA polypeptide can be concentrated or purified from biomass and formulated into a pharmaceutical composition that provides a therapeutic benefit to a patient upon administration. Typically, HA polypeptide is not a protein expressed in sprouted seedling in nature. At any rate, HA polypeptide is typically expressed at concentrations above that which would be present in the sprouted seedling in nature.

Once expression of HA polypeptide is induced, growth is allowed to continue until sprouted seedling stage, at which time sprouted seedlings are harvested. Sprouted seedlings can be harvested live. Harvesting live sprouted seedlings has several advantages including minimal effort and breakage. Sprouted seedlings may be grown hydroponically, making harvesting a simple matter of lifting a sprouted seedling from its hydroponic solution. No soil is required for growth of sprouted seedlings, but soil may be provided if deemed necessary or desirable by the skilled artisan. Because sprouts can be grown without soil, no cleansing of sprouted seedling material is required at the time of harvest. Being able to harvest the sprouted seedling directly from its hydroponic environment without washing or scrubbing minimizes breakage of harvested material. Breakage and wilting of plants induces apoptosis. During apoptosis, certain proteolytic enzymes become active, which can degrade pharmaceutical protein expressed in the sprouted seedling, resulting in decreased therapeutic activity of the protein. Apoptosis-induced proteolysis can significantly decrease yield of protein from mature plants. Using methods provided herein, apoptosis may be avoided when no harvesting takes place until the moment proteins are extracted from the plant.

For example, live sprouts may be ground, crushed, or blended to produce a slurry of sprouted seedling biomass, in a buffer containing protease inhibitors. Buffer may be maintained at about 4° C. In some aspects, sprouted seedling biomass is air-dried, spray dried, frozen, or freeze-dried. As in mature plants, some of these methods, such as air-drying, may result in a loss of activity of pharmaceutical protein. However, because sprouted seedlings are very small and have a large surface area to volume ratio, this is much less likely to occur. Those skilled in the art will appreciate that many techniques for harvesting biomass that minimize proteolysis of expressed protein are available and could be applied to the subject matter described herein.

In some embodiments, sprouted seedlings are edible. In certain embodiments, sprouted seedlings expressing sufficient levels of HA polypeptides are consumed upon harvesting (e.g., immediately after harvest, within minimal period following harvest) so that absolutely no processing occurs before sprouted seedlings are consumed. In this way, any harvest-induced proteolytic breakdown of HA polypeptide before administration of HA polypeptide to a patient in need of treatment is minimized. For example, sprouted seedlings that are ready to be consumed can be delivered directly to a patient. Alternatively or additionally, genetically engineered seeds or embryos are delivered to a patient in need of treatment and grown to sprouted seedling stage by a patient. In one aspect, a supply of genetically engineered sprouted seedlings is provided to a patient, or to a doctor who will be treating patients, so that a continual stock of sprouted seedlings expressing certain desirable HA polypeptide may be cultivated. This may be particularly valuable for populations in developing countries, where expensive pharmaceuticals are not affordable or deliverable. The ease with which sprouted seedlings can be grown can make them particularly desirable for such developing populations.

The regulatable nature of the contained environment can impart advantages over growing plants in the outdoor environment. In general, growing genetically engineered sprouted seedlings that express pharmaceutical proteins in plants provides a pharmaceutical product faster (because plants are harvested younger) and with less effort, risk, and regulatory considerations than growing genetically engineered plants. A contained, regulatable environment reduces or eliminates risk of cross-pollinating plants in nature.

For example, a heat inducible promoter likely would not be used outdoors because outdoor temperature cannot be controlled. The promoter would be turned on any time the outdoor temperature rose above a certain level. Similarly, the promoter would be turned off every time the outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as outdoors. Growth of genetically engineered plants in a greenhouse is quite costly. In contrast, in the present system, every variable can be controlled so that the maximum amount of expression can be achieved with every harvest.

In certain embodiments, sprouted seedlings as provided herein can be grown in trays that can be watered, sprayed, or misted at any time during development of sprouted seedling. For example, a tray may be fitted with one or more watering, spraying, misting, and draining apparatus that can deliver and/or remove water, nutrients, and/or chemicals at specific time and at precise quantities during development of the sprouted seedling. For example, seeds require sufficient moisture to keep them damp. Excess moisture drains through holes in trays into drains in the floor of the room. Typically, drainage water is treated as appropriate for removal of harmful chemicals before discharge back into the environment.

Another advantage of trays is that they can be contained within a very small space. Since no light is required for sprouted seedlings to grow, trays containing seeds, embryos, or sprouted seedlings may be tightly stacked vertically on top of one another, providing a large quantity of biomass per unit floor space in a housing facility constructed specifically for these purposes. In addition, stacks of trays can be arranged in horizontal rows within the housing unit. Once seedlings have grown to a stage appropriate for harvest (about two to fourteen days) individual seedling trays are moved into a processing facility, either manually or by automatic means, such as a conveyor belt.

The system provided herein is unique in that it provides a sprouted seedling biomass, which is a source of a HA polypeptide(s). Whether consumed directly or processed into the form of a pharmaceutical composition, because sprouted seedlings are grown in a contained, regulatable environment, sprouted seedling biomass and/or pharmaceutical composition derived from biomass can be provided to a consumer at low cost. In addition, the fact that the conditions for growth of sprouted seedlings can be controlled makes the quality and purity of product consistent. A contained, regulatable environment can obviate many safety regulations of the EPA that can prevent scientists from growing genetically engineered agricultural products outdoors.

Transformed Sprouts

A variety of methods can be used to transform plant cells and produce genetically engineered sprouted seedlings. Two available methods for transformation of plants that require that transgenic plant cell lines be generated in vitro, followed by regeneration of cell lines into whole plants include *Agrobacterium tumefaciens* mediated gene transfer and microprojectile bombardment or electroporation. In some embodiments, transient expression systems are utilized. Typical technologies for producing transient expression of proteins or polypeptides in plant tissues utilize plant viruses. Viral transformation provides more rapid and less costly methods of transforming embryos and sprouted seedlings that can be harvested without an experimental or generational lag prior to obtaining the desired product. For any of these techniques, the skilled artisan would appreciate how to adjust and optimize transformation protocols that have traditionally been used for plants, seeds, embryos, or spouted seedlings.

This document provides expression systems having advantages of viral expression systems (e.g., rapid expression, high levels of production) and of *Agrobacterium* transformation (e.g., controlled administration). In particular, as discussed in detail below, this document provides systems in which an agrobacterial construct (i.e., a construct that replicates in *Agrobacterium* and therefore can be delivered to plant cells by delivery of *Agrobacterium*) includes a plant promoter that, after being introduced into a plant, directs expression of viral sequences (e.g., including viral replication sequences) carrying a gene for a protein or polypeptide of interest. This system allows controlled, high level transient expression of proteins or polypeptides in plants.

A variety of different embodiments of expression systems, some of which produce transgenic plants and others of which provide for transient expression, are discussed in further detail individually below. For any of these techniques, the skilled artisan reading the present specification would appreciate how to adjust and optimize protocols for expression of proteins or polypeptides in young plant tissues (e.g., sprouted seedlings).

*Agrobacterium* Transformation

*Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines are produced by the *Agrobacterium* and catabolized by the plant. The bacterial genes responsible for expression of opines are a convenient source of control elements for chimeric expression cassettes. In some embodiments, an *Agrobacterium* transformation system may be used to generate young plants (e.g., sprouted seedlings, including edible sprouted seedlings), which are merely harvested earlier than mature plants. *Agrobacterium* transformation methods can easily be applied to regenerate sprouted seedlings expressing HA polypeptides.

In general, transforming plants with *Agrobacterium* involves transformation of plant cells grown in tissue culture by co-cultivation with an *Agrobacterium tumefaciens* carrying a plant/bacterial vector. The vector contains a gene encoding a HA polypeptide. The *Agrobacterium* transfers vector to plant host cell and is then eliminated using antibiotic treatment. Transformed plant cells expressing HA polypeptide are selected, differentiated, and finally regenerated into complete plantlets (Hellens et al., 2000, *Plant Mol. Biol.,* 42:819; Pilon-Smits et al., 1999, *Plant Physiolog.,* 119:123; Barfield et al., 1991, *Plant Cell Reports,* 10:308; and Riva et al., 1998, *J. Biotech.,* 1(3); all of which are incorporated by reference herein).

Agrobacterial expression vectors for use as described herein can include a gene (or expression cassette) encoding a HA polypeptide designed for operation in plants, with companion sequences upstream and downstream of the expression cassette. Companion sequences are generally of plasmid or viral origin and provide necessary characteristics to the vector to transfer DNA from bacteria to the desired plant host.

The basic bacterial/plant vector construct may desirably provide a broad host range prokaryote replication origin, a prokaryote selectable marker. Suitable prokaryotic selectable markers include resistance toward antibiotics such as ampicillin or tetracycline. Other DNA sequences encoding additional functions that are well known in the art may be present in the vector.

Agrobacterium T-DNA sequences are required for Agrobacterium mediated transfer of DNA to the plant chromosome. The tumor-inducing genes of T-DNA are typically removed during construction of an agrobacterial expression construct and are replaced with sequences encoding a HA polypeptide. T-DNA border sequences are retained because they initiate integration of the T-DNA region into the plant genome. If expression of HA polypeptide is not readily amenable to detection, the bacterial/plant vector construct may include a selectable marker gene suitable for determining if a plant cell has been transformed, e.g., nptII kanamycin resistance gene. On the same or different bacterial/plant vector (Ti plasmid) are Ti sequences. Ti sequences include virulence genes, which encode a set of proteins responsible for excision, transfer and integration of T-DNA into the plant genome (Schell, 1987, *Science,* 237:1176-86; incorporated herein by reference). Other sequences suitable for permitting integration of heterologous sequence into the plant genome may include transposon sequences, and the like, for homologous recombination.

On the same or different bacterial/plant vector (Ti plasmid) are Ti sequences. Ti sequences include the virulence genes, which encode a set of proteins responsible for the excision, transfer and integration of the T-DNA into the plant genome (Schell, 1987, *Science,* 237:1176-83; incorporated herein by reference). Other sequences suitable for permitting integration of the heterologous sequence into the plant genome may also include transposon sequences, and the like, for homologous recombination.

Certain constructs will include an expression cassette encoding an antigen protein. One, two, or more expression cassettes may be used in a given transformation. The recombinant expression cassette contains, in addition to a HA polypeptide encoding sequence, at least the following elements: a promoter region, plant 5' untranslated sequences, initiation codon (depending upon whether or not an expressed gene has its own), and transcription and translation termination sequences. In addition, transcription and translation terminators may be included in expression cassettes or chimeric genes. Signal secretion sequences that allow processing and translocation of a protein, as appropriate, may be included in the expression cassette.

A variety of promoters, signal sequences, and transcription and translation terminators are described, for example, in Lawton et al. (1987, *Plant Mol. Biol.,* 9:315-24; incorporated herein by reference) or in U.S. Pat. No. 5,888,789 (incorporated herein by reference). In addition, structural genes for antibiotic resistance are commonly utilized as a selection factor (Fraley et al., 1983, *Proc. Natl. Acad. Sci., USA,* 80:4803-7; incorporated herein by reference). Unique restriction enzyme sites at the 5' and 3' ends of the cassette allow for easy insertion into a pre-existing vector.

Other binary vector systems for *Agrobacterium*-mediated transformation, carrying at least one T-DNA border sequence are described in PCT Publication WO 2000/020612 (incorporated herein by reference). Further discussion of *Agrobacterium*-mediated transformation is found in Gelvin (2003, *Microbiol. Mol. Biol. Rev.,* 67:16-37; and references therein; all of which are incorporated herein by reference) and Lorence and Verpoorte (2004, *Methods Mol. Biol.,* 267:329-50; incorporated herein by reference).

In certain embodiments, bacteria other than *Agrobacteria* are used to introduce a nucleic acid sequence into a plant. See, e.g., Broothaerts et al. (2005, *Nature,* 433:629-33; incorporated herein by reference).

Seeds are prepared from plants that have been infected with *Agrobacteria* (or other bacteria) such that the desired heterologous gene encoding a protein or polypeptide of interest is introduced. Such seeds are harvested, dried, cleaned, and tested for viability and for the presence and expression of a desired gene product. Once this has been determined, seed stock is typically stored under appropriate conditions of temperature, humidity, sanitation, and security to be used when necessary. Whole plants may then be regenerated from cultured protoplasts, e.g., as described in Evans et al. (*Handbook of Plant Cell Cultures*, Vol. 1, MacMillan Publishing Co., New York, N.Y., 1983; incorporated herein by reference); and in Vasil (ed., *Cell Culture and Somatic Cell Genetics of Plants*, Acad. Press, Orlando, Fla., Vol. I, 1984, and Vol. III, 1986; incorporated herein by reference). In certain aspects, plants are regenerated only to sprouted seedling stage. In some aspects, whole plants are regenerated to produce seed stocks and sprouted seedlings are generated from seeds of the seed stock.

In certain embodiments, the plants are not regenerated into adult plants. For example, in some embodiments, plants are regenerated only to the sprouted seedling stage. In other embodiments, whole plants are regenerated to produce seed stocks and young plants (e.g., sprouted seedlings) for use in accordance with the present disclosure, and are generated from the seeds of previously produced seed stock.

All plants from which protoplasts can be isolated and cultured to give whole, regenerated plants can be transformed by *Agrobacteria* so that whole plants are recovered that contain a transferred gene. It is known that practically all plants can be regenerated from cultured cells or tissues, including, but not limited to, all major species of plants that produce edible sprouts. Some suitable plants include alfalfa, mung bean, radish, wheat, mustard, spinach, carrot, beet, onion, garlic, celery, rhubarb, leafy plants such as cabbage and lettuce, watercress or cress, herbs such as parsley, mint, and clover, cauliflower, broccoli, soybean, lentils, and edible flowers such as sunflower.

Means for regeneration of plants from transformed cells vary from one species of plants to the next. However, those skilled in the art will appreciate that generally a suspension of transformed protoplants containing copies of a heterologous gene is first provided. Callus tissue is formed and shoots may be induced from callus and subsequently rooted. Alternatively or additionally, embryo formation can be induced from a protoplast suspension. These embryos germinate as natural embryos to form plants. Steeping seed in water or spraying seed with water to increase the moisture content of the seed to between 35%-45% initiates germination. For germination to proceed, seeds are typically maintained in air saturated with water under controlled temperature and airflow conditions. The culture media will generally contain various amino acids and hormones, such as auxin and cytokinins. It is advantageous to add glutamic acid and proline to the medium, especially for such species as alfalfa. Shoots and roots normally develop simultaneously. Efficient regeneration will depend on the medium, the genotype, and the history of the culture. If these three variables are controlled, then regeneration is fully reproducible and repeatable.

Mature plants, grown from the transformed plant cells, are selfed and non-segregating, homozygous transgenic plants are identified. The inbred plant produces seeds containing antigen-encoding sequences. Such seeds can be germinated and grown to sprouted seedling stage to produce HA polypeptide(s) as provided herein.

In related embodiments, transgenic seeds (e.g., carrying the transferred gene encoding a HA polypeptide, typically integrated into the genome) may be formed into seed products and sold with instructions on how to grow young plants to the appropriate stage (e.g., sprouted seedling stage) for harvesting and/or administration or harvesting into a formulation as described herein. In some related embodiments, hybrids or novel varieties embodying desired traits may be developed from inbred plants.

Direct Integration

Direct integration of DNA fragments into the genome of plant cells by microprojectile bombardment or electroporation may also be used to introduce expression constructs encoding HA polypeptides into plant tissues (see, e.g., Kikkert, et al., 1999, *Plant: J. Tiss. Cult. Assoc.,* 35:43; and Bates, 1994, *Mol. Biotech.,* 2:135; both of which are incorporated herein by reference). More particularly, vectors that express HA polypeptide(s) can be introduced into plant cells by a variety of techniques. As described above, vectors may include selectable markers for use in plant cells. Vectors may include sequences that allow their selection and propagation in a secondary host, such as sequences containing an origin of replication and selectable marker. Typically, secondary hosts include bacteria and yeast. In some embodiments, a secondary host is bacteria (e.g., *Escherichia coli*, the origin of replication is a colE1-type origin of replication) and a selectable marker is a gene encoding ampicillin resistance. Such sequences are well known in the art and are commercially available (e.g., Clontech, Palo Alto, Calif. or Stratagene, La Jolla, Calif.).

Vectors as provided herein may be modified to intermediate plant transformation plasmids that contain a region of homology to an *Agrobacterium tumefaciens* vector, a T-DNA border region from *Agrobacterium tumefaciens*, and chimeric genes or expression cassettes described above. Further vectors may include a disarmed plant tumor inducing plasmid of *Agrobacterium tumefaciens.*

According to some embodiments, direct transformation of vectors can involve microinjecting vectors directly into plant cells by use of micropipettes to mechanically transfer recombinant DNA (see, e.g., Crossway, 1985, *Mol. Gen. Genet.,* 202:179, incorporated herein by reference). Genetic material may be transferred into a plant cell using polyethylene glycols (see, e.g., Krens et al., 1982, *Nature* 296:72; incorporated herein by reference). Another method of introducing nucleic acids into plants via high velocity ballistic penetration by small particles with a nucleic acid either within the matrix of small beads or particles, or on the surface (see, e.g., Klein et al., 1987, Nature 327:70; and Knudsen et al., *Planta,* 185: 330; both of which are incorporated herein by reference). Yet another method of introduction is fusion of protoplasts with other entities, either minicells, cells, lysosomes, or other fusible lipid-surfaced bodies (see, e.g., Fraley et al., 1982, *Proc. Natl. Acad. Sci., USA,* 79:1859; incorporated herein by reference). Vectors in accordance with this document may be introduced into plant cells by electroporation (see, e.g., Fromm et al. 1985, *Proc. Natl. Acad. Sci., USA,* 82:5824; incorporated herein by reference). According to this technique, plant protoplasts are electroporated in the presence of plasmids containing a gene construct. Electrical impulses of high field strength reversibly permeabilize biomembranes allowing introduction of plasmids. Electroporated plant protoplasts reform the cell wall divide and form plant callus, which can be regenerated to form sprouted seedlings. Those skilled in the art will appreciate how to utilize these methods to transform plants cells that can be used to generate edible sprouted seedlings.

Viral Transformation

Similar to conventional expression systems, plant viral vectors can be used to produce full-length proteins, including full length antigen. Plant virus vectors may be used to infect and produce antigen(s) in seeds, embryos, or sprouted seedlings, for example. In this regard infection includes any method of introducing a viral genome, or portion thereof, into a cell, including, but not limited to, the natural infectious process of a virus, abrasion, and inoculation. The term includes introducing a genomic RNA transcript, or a cDNA copy thereof, into a cell. The viral genome need not be a complete genome but will typically contain sufficient sequences to allow replication. The genome may encode a viral replicase and may contain any cis-acting nucleic acid elements necessary for replication. Expression of high levels of foreign genes encoding short peptides as well as large complex proteins (e.g., by tobamoviral vectors) is described (see, e.g., McCormick et al., 1999, *Proc. Natl. Acad. Sci., USA,* 96:703; Kumagai et al. 2000, *Gene,* 245:169; and Verch et al., 1998, *J. Immunol. Methods,* 220:69; all of which are incorporated herein by reference). Thus, plant viral vectors have a demonstrated ability to express short peptides as well as large complex proteins.

In certain embodiments, young plants (e.g., sprouts), which express HA polypeptide, are generated utilizing a host/virus system. Young plants produced by viral infection provide a source of transgenic protein that has already been demonstrated to be safe. For example, sprouts are free of contamination with animal pathogens. Unlike, for example, tobacco, proteins from an edible sprout could at least in theory be used in oral applications without purification, thus significantly reducing costs.

In addition, a virus/young plant (e.g., sprout) system offers a much simpler, less expensive route for scale-up and manufacturing, since the relevant genes (encoding the protein or polypeptide of interest) are introduced into the virus, which can be grown up to a commercial scale within a few days. In contrast, transgenic plants can require up to 5-7 years before sufficient seeds or plant material is available for large-scale trials or commercialization.

As described herein, plant RNA viruses can have certain advantages, which make them attractive as vectors for foreign protein expression. The molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once infectious virus material enters a susceptible host cell, it replicates to high levels and spreads rapidly throughout the entire sprouted seedling (one to ten days post inoculation, e.g., 1 day, 2 days, 3 days, 4 days, 5 days, 6 days, 7 days, 8 days, 9 days, 10 days, or more than 10 days post-inoculation). Virus particles are easily and economically recovered from infected sprouted seedling tissue. Viruses have a wide host range, enabling use of a single construct for infection of several susceptible species. These characteristics are readily transferable to sprouts.

Foreign sequences can be expressed from plant RNA viruses, typically by replacing one of the viral genes with desired sequence, by inserting foreign sequences into the virus genome at an appropriate position, or by fusing foreign peptides to structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (AlMV), and chimeras thereof.

The genome of AlMV is a representative of the Bromoviridae family of viruses and consists of three genomic RNAs (RNAs1-3) and subgenomic RNA (RNA4). Genomic RNAs1 and 2 encode virus replicase proteins P1 and 2, respectively. Genomic RNA3 encodes cell-to-cell movement protein P3 and coat protein (CP). CP is translated from subgenomic RNA4, which is synthesized from genomic RNA3, and is required to start infection. Studies have demonstrated the involvement of CP in multiple functions, including genome activation, replication, RNA stability, symptom formation, and RNA encapsidation (see e.g., Bol et al., 1971, *Virology*, 46:73; Van Der Vossen et al., 1994, *Virology* 202:891; Yusibov et al., *Virology*, 208:405; Yusibov et al., 1998, *Virology*, 242:1; Bol et al., (Review, 100 refs.), 1999, *J. Gen. Virol.*, 80:1089; De Graaff, 1995, *Virology*, 208:583; Jaspars et al., 1974, *Adv. Virus Res.*, 19:37; Loesch-Fries, 1985, *Virology*, 146:177; Neeleman et al., 1991, *Virology*, 181:687; Neeleman et al., 1993, *Virology*, 196: 883; Van Der Kuyl et al., 1991, *Virology*, 183:731; and Van Der Kuyl et al., 1991, *Virology*, 185:496; all of which are incorporated herein by reference).

Encapsidation of viral particles is typically required for long distance movement of virus from inoculated to un-inoculated parts of seed, embryo, or sprouted seedling and for systemic infection. Inoculation can occur at any stage of plant development. In embryos and sprouts, spread of inoculated virus should be very rapid. Virions of AlMV are encapsidated by a unique CP (24 kD), forming more than one type of particle. The size (30- to 60-nm in length and 18 nm in diameter) and shape (spherical, ellipsoidal, or bacilliform) of the particle depends on the size of the encapsidated RNA. Upon assembly, the N-terminus of AlMV CP is thought to be located on the surface of the virus particles and does not appear to interfere with virus assembly (Bol et al., 1971, *Virology*, 6:73; incorporated herein by reference). Additionally, ALMV CP with an additional 38-amino acid peptide at its N-terminus forms particles in vitro and retains biological activity (Yusibov et al., 1995, *J. Gen. Virol.*, 77:567; incorporated herein by reference).

AlMV has a wide host range, which includes a number of agriculturally valuable crop plants, including plant seeds, embryos, and sprouts. Together, these characteristics make ALMV CP an excellent candidate as a carrier molecule and AlMV an attractive candidate vector for expression of foreign sequences in a plant at the sprout stage of development. Moreover, upon expression from a heterologous vector such as TMV, AlMV CP encapsidates TMV genome without interfering with virus infectivity (Yusibov et al., 1997, *Proc. Natl. Acad. Sci., USA*, 94:5784; incorporated herein by reference). This allows use of TMV as a carrier virus for AlMV CP fused to foreign sequences.

TMV, the prototype of tobamoviruses, has a genome consisting of a single plus-sense RNA encapsidated with a 17.0 kD CP, which results in rod-shaped particles (300 nm in length). CP is the only structural protein of TMV and is required for encapsidation and long distance movement of virus in an infected host (Saito et al., 1990, *Virology* 176:329; incorporated herein by reference). 183 and 126 kD proteins are translated from genomic RNA and are required for virus replication (Ishikawa et al., 1986, *Nucleic Acids Res.*, 14:8291; incorporated herein by reference). 30 kD protein is the cell-to-cell movement protein of virus (Meshi et al., 1987, *EMBO J.*, 6:2557). Movement and coat proteins are translated from subgenomic mRNAs (Hunter et al., 1976, *Nature*, 260: 759; Bruening et al., 1976, *Virology*, 71:498; and Beachy et al., 1976, *Virology*, 73:498; all of which are incorporated herein by reference).

Other methods that may be utilized to introduce a gene encoding a HA polypeptide into plant cells include transforming the flower of a plant. Transformation of *Arabidopsis thaliana* can be achieved by dipping plant flowers into a solution of *Agrobacterium tumefaciens* (Curtis et al., 2001, Transgenic Res., 10:363; and Qing et al., 2000, *Molecular Breeding: New Strategies in Plant Improvement* 1:67; both of which are incorporated herein by reference). Transformed plants are formed in the population of seeds generated by "dipped" plants. At a specific point during flower development, a pore exists in the ovary wall through which *Agrobacterium tumefaciens* gains access to the interior of the ovary. Once inside the ovary, the *Agrobacterium tumefaciens* proliferates and transforms individual ovules (Desfeux et al., 2000, *Plant Physiology*, 123:895; incorporated herein by reference). Transformed ovules follow the typical pathway of seed formation within the ovary.

*Agrobacterium*-Mediated Transient Expression

As indicated herein, systems for rapid (e.g., transient) expression of proteins or polypeptides in plants can be desirable. Among other things, this document provides a powerful system for achieving such rapid expression in plants (particularly in young plants, e.g., sprouted seedlings) that utilizes an agrobacterial construct to deliver a viral expression system encoding a HA polypeptide.

Specifically, as described herein, a "launch vector" is prepared that contains agrobacterial sequences including replication sequences and also contains plant viral sequences (including self-replication sequences) that carry a gene encoding the protein or polypeptide of interest. A launch vector is introduced into plant tissue, preferably by agroinfiltration, which allows substantially systemic delivery. For transient transformation, non-integrated T-DNA copies of the launch vector remain transiently present in the nucleolus and are transcribed leading to the expression of the carrying genes (Kapila et al., 1997, *Plant Science*, 122:101-108; incorporated herein by reference). *Agrobacterium*-mediated transient expression, differently from viral vectors, cannot lead to the systemic spreading of the expression of the gene of interest. One advantage of this system is the possibility to clone genes larger than 2 kb to generate constructs that would be impossible to obtain with viral vectors (Voinnet et al., 2003, *Plant J.*, 33:949-56; incorporated herein by reference). Furthermore, using such technique, it is possible to transform the plant with more than one transgene, such that multimeric proteins (e.g., antibodies subunits of complexed proteins) can be expressed and assembled. Furthermore, the possibility of co-expression of multiple transgenes by means of co-infiltration with different *Agrobacterium* can be taken advantage of, either by separate infiltration or using mixed cultures.

In certain embodiments, a launch vector includes sequences that allow for selection (or at least detection) in *Agrobacteria* and also for selection/detection in infiltrated tissues. Furthermore, a launch vector typically includes sequences that are transcribed in the plant to yield viral RNA production, followed by generation of viral proteins. Furthermore, production of viral proteins and viral RNA yields rapid production of multiple copies of RNA encoding the pharmaceutically active protein of interest. Such production results in rapid protein production of the target of interest in a relatively short period of time. Thus, a highly efficient system for protein production can be generated.

The agroinfiltration technique utilizing viral expression vectors can be used to produce limited quantity of protein of interest in order to verify the expression levels before deciding if it is worth generating transgenic plants. Alternatively or additionally, the agroinfiltration technique utilizing viral expression vectors is useful for rapid generation of plants capable of producing huge amounts of protein as a primary production platform. Thus, this transient expression system can be used on industrial scale.

Further provided are any of a variety of different Agrobacterial plasmids, binary plasmids, or derivatives thereof such as pBIV, pBI1221, and pGreen, which can be used in these and other aspects of the present disclosure. Numerous suitable vectors are known in the art and can be directed and/or modified according to methods known in the art, or those described herein so as to utilize in the methods described provided herein.

An exemplary launch vector, pBID4, contains the 35S promoter of cauliflower mosaic virus (a DNA plant virus) that drives initial transcription of the recombinant viral genome following introduction into plants, and the nos terminator, the transcriptional terminator of *Agrobacterium* nopaline synthase. The vector further contains sequences of the tobacco mosaic virus genome including genes for virus replication (126/183K) and cell-t-cell movement (MP). The vector further contains a gene encoding a polypeptide of interest, inserted into a unique cloning site within the tobacco mosaic virus genome sequences and under the transcriptional control of the coat protein subgenomic mRNA promoter. Because this "target gene" (i.e., gene encoding a protein or polypeptide of interest) replaces coding sequences for the TMV coat protein, the resultant viral vector is naked self-replicating RNA that is less subject to recombination than CP-containing vectors, and that cannot effectively spread and survive in the environment. Left and right border sequences (LB and RB) delimit the region of the launch vector that is transferred into plant cells following infiltration of plants with recombinant *Agrobacterium* carrying the vector. Upon introduction of *agrobacteria* carrying this vector into plant tissue (typically by agroinfiltration but alternatively by injection or other means), multiple single-stranded DNA (ssDNA) copies of sequence between LB and RB are generated and released in a matter of minutes. These introduced sequences are then amplified by viral replication. Translation of the target gene results in accumulation of large amounts of target protein or polypeptide in a short period of time.

In some embodiments, *Agrobacterium*-mediated transient expression produces up to about 5 g or more of target protein per kg of plant tissue. For example, in some embodiments, up to about 4 g, about 3 g, about 2 g, about 1 g, or about 0.5 g of target protein is produced per kg of plant tissue. In some embodiments, at least about 20 mg to about 500 mg, or about 50 mg to about 500 mg of target protein, or about 50 mg to about 200 mg, or about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1500 mg, about 1750 mg, about 2000 mg, about 2500 mg, about 3000 mg or more of protein per kg of plant tissue is produced.

In some embodiments, these expression levels are achieved within about 6, about 5, about 4, about 3, or about 2 weeks from infiltration. In some embodiments, these expression levels are achieved within about 10, about 9, about 8, about 7, about 6, about 5, about 4, about 3, about 2 days, or even about 1 day, from introduction of the expression construct. Thus, the time from introduction (e.g., infiltration) to harvest is typically less than about 2 weeks, about 10 days, about 1 week or less. This allows production of protein within about 8 weeks or less from the selection of amino acid sequence (even including time for "preliminary" expression studies). Also, each batch of protein can typically be produced within about 8 weeks, about 6 weeks, about 5 weeks, or less. Those of ordinary skill in the art will appreciate that these numbers may vary somewhat depending on the type of plant used. Most sprouts, including peas, will fall within the numbers given. *Nicotiana benthamiana*, however, may be grown longer, particularly prior to infiltration, as they are slower growing (from a much smaller seed). Other expected adjustments will be clear to those of ordinary skill in the art based on biology of the particular plants utilized.

A launch vector system has been used to produce a variety of target proteins and polypeptides in a variety of different young plants. In some embodiments, certain pea varieties including for example, marrowfat pea, bill jump pea, yellow trapper pea, speckled pea, and green pea are particularly useful in the practice of methods as disclosed herein, for example.

Various *Nicotiana* plants can be particularly useful in the practice of this disclosure, including in particular *Nicotiana benthamiana*. It will be understood by those of ordinary skill in the art that *Nicotiana* plants are generally not considered to be "sprouts." Nonetheless, young *Nicotiana* plants (particularly young *Nicotiana benthamiana* plants) can be useful in the practices provided herein. In general, in some embodiments, *Nicotiana benthamiana* plants are grown for a time sufficient to allow development of an appropriate amount of biomass prior to infiltration (i.e., to delivery of *agrobacteria* containing the launch vector). Typically, the plants are grown for a period of more than about 3 weeks, more typically more than about 4 weeks, or between about 5 to about 6 weeks to accumulate biomass prior to infiltration.

It has further surprisingly been found that, although both TMV and AlMV sequences can prove effective in such launch vector constructs, in some embodiments, AlMV sequences are particularly efficient at ensuring high level production of delivered protein or polypeptides.

Thus, in some embodiments, proteins or polypeptides of interest can be produced in young pea plants or young *Nicotania* plants (e.g., *Nicotiana benthamiana*) from a launch vector that directs production of AlMV sequences carrying the gene of interest.

Expression Constructs

Many features of expression constructs useful as described herein will be specific to the particular expression system used, as discussed above. However, certain aspects that may be applicable across different expression systems are discussed in further detail here.

To give but one example, in some embodiments, it will be desirable that expression of the protein or polypeptide (or nucleic acid) of interest be inducible. In many such embodiments, production of an RNA encoding the protein or polypeptide of interest (and/or production of an antisense RNA) is under the control of an inducible (e.g. exogenously inducible) promoter. Exogenously inducible promoters are caused to increase or decrease expression of a transcript in response to an external, rather than an internal stimulus. A number of environmental factors can act as such an external stimulus. In certain embodiments, transcription is controlled by a heat-inducible promoter, such as a heat-shock promoter.

Externally inducible promoters may be particularly useful in the context of controlled, regulatable growth settings. For example, using a heat-shock promoter the temperature of a contained environment may simply be raised to induce expression of the relevant transcript. In will be appreciated, of course, that a heat inducible promoter could never be used in the outdoors because the outdoor temperature cannot be controlled. The promoter would be turned on any time the outdoor temperature rose above a certain level. Similarly, the promoter would be turned off every time the outdoor temperature dropped. Such temperature shifts could occur in a single day, for example, turning expression on in the daytime and off at night. A heat inducible promoter, such as those described herein, would likely not even be practical for use in a greenhouse, which is susceptible to climatic shifts to almost the same degree as the outdoors. Growth of genetically engineered plants in a greenhouse is quite costly. In contrast, in the present system, every variable can be controlled so that the maximum amount of expression can be achieved with every harvest.

Other externally-inducible promoters than can be utilized include light inducible promoters. Light-inducible promoters can be maintained as constitutive promoters if the light in the contained regulatable environment is always on. Alternatively, expression of the relevant transcript can be turned on at a particular time during development by simply turning on the light.

In yet other embodiments, a chemically inducible promoter is used to induce expression of the relevant transcript. According to these embodiments, the chemical could simply be misted or sprayed onto a seed, embryo, or young plant (e.g., seedling) to induce expression of the relevant transcript. Spraying and misting can be precisely controlled and directed onto a particular seed, embryo, or young plant (e.g., seedling) as desired. A contained environment is devoid of wind or air currents, which could disperse the chemical away from the intended recipient, so that the chemical stays on the recipient for which it was intended.

Production and Isolation of Antigen

In general, standard methods known in the art may be used for culturing or growing plants, plant cells, and/or plant tissues (e.g., clonal plants, clonal plant cells, clonal roots, clonal root lines, sprouts, sprouted seedlings, and plants) for production of antigen(s). A wide variety of culture media and bioreactors have been employed to culture hairy root cells, root cell lines, and plant cells (see, for example, Giri et al., 2000, *Biotechnol. Adv.*, 18:1; Rao et al., 2002, *Biotechnol. Adv.*, 20:101; and references in both of the foregoing, all of which are incorporated herein by reference). Clonal plants may be grown in any suitable manner.

In a certain embodiments, HA polypeptides as provided herein can be produced by any known method. In some embodiments, a HA polypeptide is expressed in a plant or portion thereof. Proteins are isolated and purified in accordance with conventional conditions and techniques known in the art. These include methods such as extraction, precipitation, chromatography, affinity chromatography, electrophoresis, and the like. Thus, this document provides methods that include purification and affordable scaling up of production of HA polypeptide(s) using any of a variety of plant expression systems known in the art and provided herein, including viral plant expression systems described herein.

In some embodiments, it can be desirable to isolate HA polypeptide(s) for vaccine products. Where a protein is produced from plant tissue(s) or a portion thereof, e.g., roots, root cells, plants, plant cells, that express them, methods described in further detail herein, or any applicable methods known in the art may be used for any of partial or complete isolation from plant material. Where it is desirable to isolate the expression product from some or all of plant cells or tissues that express it, any available purification techniques may be employed. Those of ordinary skill in the art are familiar with a wide range of fractionation and separation procedures (see, for example, Scopes et al., *Protein Purification: Principles and Practice,* 3$^{rd}$ Ed., Janson et al., 1993; *Protein Purification: Principles, High Resolution Methods, and Applications*, Wiley-VCH, 1998; Springer-Verlag, NY, 1993; and Roe, *Protein Purification Techniques*, Oxford University Press, 2001; each of which is incorporated herein by reference). Often, it will be desirable to render the product more than about 50%, about about 94%, about 95%, about 96%, about 97%, about 98%, or about 99% pure. See, e.g., U.S. Pat. Nos. 6,740,740 and 6,841,659 (both of which are incorporated herein by reference) for discussion of certain methods useful for purifying substances from plant tissues or fluids.

Those skilled in the art will appreciate that a method of obtaining desired HA polypeptide(s) product(s) is by extraction. Plant material (e.g., roots and/or leaves) may be extracted to remove desired products from residual biomass, thereby increasing the concentration and purity of product. Plants may be extracted in a buffered solution. For example, plant material may be transferred into an amount of ice-cold water at a ratio of one to one by weight that has been buffered with, e.g., phosphate buffer. Protease inhibitors can be added as required. The plant material can be disrupted by vigorous blending or grinding while suspended in buffer solution and extracted biomass removed by filtration or centrifugation. The product carried in solution can be further purified by additional steps or converted to a dry powder by freeze-drying or precipitation. Extraction can be carried out by pressing. Plants or roots can be extracted by pressing in a press or by being crushed as they are passed through closely spaced rollers. Fluids expressed from crushed plants or roots are collected and processed according to methods well known in the art. Extraction by pressing allows release of products in a more concentrated form. However, overall yield of product may be lower than if product were extracted in solution.

In some embodiments, produced proteins or polypeptides are not isolated from plant tissue but rather are provided in the context of live plants (e.g., sprouted seedlings). In some embodiments, where the plant is edible, plant tissue containing expressed protein or polypeptide is provided directly for consumption. Thus, this document provides edible young plant biomass (e.g., edible sprouted seedlings) containing expressed protein or polypeptide.

Where edible plants (e.g., sprouted seedlings) express sufficient levels of pharmaceutical proteins or polypeptides and are consumed live, in some embodiments absolutely no harvesting occurs before the sprouted seedlings are consumed. In this way, it is guaranteed that there is no harvest-induced proteolytic breakdown of the pharmaceutical protein before administration of the pharmaceutical protein to a patient in need of treatment. For example, young plants (e.g., sprouted seedlings) that are ready to be consumed can be delivered directly to a patient. Alternatively, genetically engineered seeds or embryos are delivered to a patient in need of treatment and grown to the sprouted seedling stage by the patient. In some embodiments, a supply of genetically engineered sprouted seedlings is provided to a patient, or to a doctor who will be treating patients, so that a continual stock of sprouted seedlings expressing certain desirable pharmaceutical proteins may be cultivated. This may be particularly valuable for populations in developing countries, where expensive pharmaceuticals are not affordable or deliverable. The ease with which the sprouted seedlings can be grown can make them particularly desirable for such developing populations.

In some embodiments, plant biomass is processed prior to consumption or formulation, for example, by homogenizing, crushing, drying, or extracting. In some embodiments, the expressed protein or polypeptide is isolated or purified from the biomass and formulated into a pharmaceutical composition.

For example, live plants (e.g., sprouts) may be ground, crushed, or blended to produce a slurry of biomass, in a buffer containing protease inhibitors. Preferably the buffer is at about 4° C. In certain embodiments, the biomass is air-dried, spray dried, frozen, or freeze-dried. As in mature plants, some of these methods, such as air-drying, may result in a loss of activity of the pharmaceutical protein or polypeptide. However, because plants (e.g., sprouted seedlings) may be very small and typically have a large surface area to volume ratio, this is much less likely to occur. Those skilled in the art will appreciate that many techniques for harvesting the biomass that minimize proteolysis of the pharmaceutical protein or polypeptide are available and could be applied to the methods provided herein.

Antibodies

This document also provides pharmaceutical antigen and antibody proteins for therapeutic use, such as influenza antigen(s) (e.g., influenza protein(s) or an immunogenic portion(s) thereof, or fusion proteins comprising influenza antibody protein(s) or an antigen binding portion(s) thereof) active as antibody for therapeutic and/or prophylactic treatment of influenza infection. Further, this document provides veterinary uses, as such influenza antigen is active in veterinary applications. In certain embodiments, influenza antigen(s) and/or antibodies may be produced by plant(s) or portion(s) thereof (e.g., root, cell, sprout, cell line, or plant) as described herein. In certain embodiments, provided influenza antigens and/or antibodies are expressed in plants, plant cells, and/or plant tissues (e.g., sprouts, sprouted seedlings, roots, root culture, clonal cells, clonal cell lines, or clonal plants), and can be used directly from plant or partially purified or purified in preparation for pharmaceutical administration to a subject.

Monoclonal Antibodies

Various methods for generating monoclonal antibodies (MAbs) are now very well known in the art. The most standard monoclonal antibody generation techniques generally begin along the same lines as those for preparing polyclonal antibodies (*Antibodies: A Laboratory Manual*, Cold Spring Harbor Laboratory, 1988, which is hereby incorporated by reference). A polyclonal antibody response is initiated by immunizing an animal with an immunogenic anionic phospholipid and/or aminophospholipid composition and, when a desired titer level is obtained, the immunized animal can be used to generate MAbs. Typically, the particular screening and selection techniques disclosed herein are used to select antibodies with the sought after properties.

MAbs may be readily prepared through use of well-known techniques, such as those exemplified in U.S. Pat. No. 4,196,265, incorporated herein by reference. Typically, the technique involves immunizing a suitable animal with a selected immunogen composition to stimulate antibody producing cells. Rodents such as mice and rats are exemplary animals, however, the use of rabbit, sheep and frog cells is possible. The use of rats may provide certain advantages (Goding, 1986, pp. 60-61; incorporated herein by reference), but mice are sometimes preferred, with the BALB/c mouse often being most preferred as this is most routinely used and generally gives a higher percentage of stable fusions.

Following immunization, somatic cells with the potential for producing the desired antibodies, specifically B lymphocytes (B cells), are selected for use in the MAb generation and fusion with cells of an immortal myeloma cell, generally one of the same species as the animal that was immunized. Myeloma cell lines suited for use in hybridoma-producing fusion procedures typically are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

This culturing provides a population of hybridomas from which specific hybridomas are selected, followed by serial dilution and cloning into individual antibody producing lines, which can be propagated indefinitely for production of antibody.

MAbs produced are generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

Antibody Fragments and Derivatives

Irrespective of the source of the original antibody against a hemagglutinin, either the intact antibody, antibody multimers, or any one of a variety of functional, antigen-binding regions of the antibody may be used. Exemplary functional regions include scFv, Fv, Fab', Fab and F(ab').sub.2 fragments of antibodies. Techniques for preparing such constructs are well known to those in the art and are further exemplified herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Antibody fragments can be obtained by proteolysis of the whole immunoglobulin by the non-specific thiolprotease, papain. Papain digestion yields two identical antigen-binding fragments, termed "Fab fragments," each with a single antigen-binding site, and a residual "Fc fragment." The various fractions are separated by protein A-Sepharose or ion exchange chromatography.

The usual procedure for preparation of F(ab').sub.2 fragments from IgG of rabbit and human origin is limited proteolysis by the enzyme pepsin. Pepsin treatment of intact antibodies yields an F(ab').sub.2 fragment that has two antigen-combining sites and is still capable of cross-linking antigen.

A Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab').sub.2 antibody fragments were originally produced as pairs of Fab' fragments that have hinge cysteines between them. Other chemical couplings of antibody fragments are known.

An "Fv" fragment is the minimum antibody fragment that contains a complete antigen-recognition and binding site. This region consists of a dimer of one heavy chain and one light chain variable domain in tight, con-covalent association. It is in this configuration that three hypervariable regions of each variable domain interact to define an antigen-binding site on the surface of the $V_H$-$V_L$ dimer. Collectively, six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments (now known as "single chains") comprise the $V_H$ and $V_L$ domains of an antibody, wherein these domains are present in a single polypeptide chain. Generally, the Fv polypeptide further comprises a polypeptide linker between $V_H$ and $V_L$ domains that enables sFv to form the desired structure for antigen binding.

The following patents are incorporated herein by reference for the purposes of even further supplementing the present teachings regarding the preparation and use of functional, antigen-binding regions of antibodies, including scFv, Fv, Fab', Fab and F(ab').sub.2 fragments of antibodies: U.S. Pat. Nos. 5,855,866; 5,877,289; 5,965,132; 6,093,399; 6,261,535; and 6,004,555. WO 98/45331 is also incorporated herein by reference for purposes including even further describing and teaching the preparation of variable, hypervariable and complementarity determining (CDR) regions of antibodies.

"Diabodies" are small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between two domains on the same chain, the domains are forced to pair with the complementary domains of another chain and create two antigen-binding sites. Diabodies are described in EP 404,097 and WO 93/11161, each specifically incorporated herein by reference. "Linear antibodies," which can be bispecific or monospecific, comprise a pair of tandem Fd segments (V.sub.H-C.sub.H1-V.sub.H-C.sub.H1) that form a pair of antigen binding regions, as described (see, for example, Zapata et al., 1995, incorporated herein by reference).

In using a Fab' or antigen binding fragment of an antibody, with the attendant benefits on tissue penetration, one may derive additional advantages from modifying the fragment to increase its half-life. A variety of techniques may be employed, such as manipulation or modification of the antibody molecule itself, and conjugation to inert carriers. Any conjugation for the sole purpose of increasing half-life, rather than to deliver an agent to a target, should be approached carefully in that Fab' and other fragments are chosen to penetrate tissues. Nonetheless, conjugation to non-protein polymers, such PEG and the like, is contemplated.

Modifications other than conjugation are therefore based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either N-terminal or C-terminal, or both, which is generally used to prolong half-life of biological molecules. By way of example only, one may wish to modify termini by acylation or amination.

Bispecific Antibodies

Bispecific antibodies in general may be employed, so long as one arm binds to an aminophospholipid or anionic phospholipid and the bispecific antibody is attached, at a site distinct from the antigen binding site, to a therapeutic agent.

In general, the preparation of bispecific antibodies is well known in the art. One method involves the separate preparation of antibodies having specificity for the aminophospholipid or anionic phospholipid, on the one hand, and a therapeutic agent on the other. Peptic F(ab')$_2$ fragments are prepared from two chosen antibodies, followed by reduction of each to provide separate Fab'$_{SH}$ fragments. SH groups on one of two partners to be coupled are then alkylated with a cross-linking reagent such as O-phenylenedimaleimide to provide free maleimide groups on one partner. This partner may then be conjugated to the other by means of a thioether linkage, to give the desired F(ab')$_2$ heteroconjugate. Other techniques are known wherein cross-linking with SPDP or protein A is carried out, or a trispecific construct is prepared.

One method for producing bispecific antibodies is by the fusion of two hybridomas to form a quadroma. As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

CDR Technologies

Antibodies are comprised of variable and constant regions. The term "variable," as used herein in reference to antibodies, means that certain portions of the variable domains differ extensively in sequence among antibodies, and are used in the binding and specificity of each particular antibody to its particular antigen. However, the variability is concentrated in three segments termed "hypervariable regions," both in the light chain and the heavy chain variable domains.

The more highly conserved portions of variable domains are called the framework region (FR). Variable domains of native heavy and light chains each comprise four FRs (FR1, FR2, FR3 and FR4, respectively), largely adopting a beta-sheet configuration connected by three hypervariable regions, which form loops connecting, and in some cases forming part of, the beta-sheet structure.

The hypervariable regions in each chain are held together in close proximity by the FRs and, with hypervariable regions from the other chain, contribute to the formation of the antigen-binding site of antibodies (Kabat et al., 1991, incorporated herein by reference). Constant domains are not involved directly in binding an antibody to an antigen, but exhibit various effector functions, such as participation of the antibody in antibody-dependent cellular toxicity.

The term "hypervariable region," as used herein, refers to amino acid residues of an antibody that are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-56 (H2) and 95-102 (H3) in the heavy chain variable domain; Kabat et al., 1991, incorporated herein by reference) and/or those residues from a "hypervariable loop" (i.e. residues 26-32 (L1), 50-52(L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

The DNA and deduced amino acid sequences of Vh and V kappa chains of the HA antibodies described in FIGS. 9 and 10 encompass CDR1-3 of variable regions of heavy and light chains of the antibody. In light of the sequence and other information provided herein, and the knowledge in the art, a range of antibodies similar to those described in FIGS. 9 and 10, and improved antibodies and antigen binding regions, can now be prepared and are thus encompassed by this disclosure. Sequences of the light and heavy chain variable regions of the HA antibodies described in FIGS. 9 and 10 can be determined using standard techniques.

In certain embodiments, this document provides at least one CDR of the antibody produced by one or more of the HA antibodies described in FIGS. 9 and 10, to be deposited. In some embodiments, this document provides a CDR, antibody, or antigen binding region thereof, which binds to at least a hemagglutinin, and which comprises at least one CDR of the antibody produced by one or more of the HA antibodies described in FIGS. 9 and 10, to be deposited.

In one embodiment, this document provides an antibody, or antigen binding region thereof, in which the framework regions of one or more of the HA antibodies described in FIGS. 9 and 10 have been changed from mouse to a human IgG, such as human IgG1 or other IgG subclass to reduce immunogenicity in humans. In some embodiments, sequences of one or more of the HA antibodies described in FIGS. 9 and 10 are examined for the presence of T-cell epitopes, as is known in the art. The underlying sequence can then be changed to remove T-cell epitopes, i.e., to "deimmunize" the antibody.

The availability of DNA and amino acid sequences of Vh and V kappa chains of one or more of the HA antibodies described in FIGS. 9 and 10 means that a range of antibodies can now be prepared using CDR technologies. In particular, random mutations are made in the CDRs and products screened to identify antibodies with higher affinities and/or higher specificities. Such mutagenesis and selection is routinely practiced in the antibody arts, and it can be particularly suitable for use in the methods provided herein, given the advantageous screening techniques disclosed herein. A convenient way for generating such substitutional variants is affinity maturation using phage display.

CDR shuffling and implantation technologies can be used with antibodies in accordance with the present disclosure, specifically one or more of the HA antibodies described in FIGS. 9 and 10. CDR shuffling inserts CDR sequences into a specific framework region (Jirholt et al., 1998, incorporated herein by reference). CDR implantation techniques permit random combination of CDR sequences into a single master framework (Soderlind et al., 1999, 2000, each incorporated herein by reference). Using such techniques, CDR sequences of one or more of the HA antibodies described in FIGS. 9 and 10, for example, are mutagenized to create a plurality of different sequences, which are incorporated into a scaffold sequence and the resultant antibody variants screened for desired characteristics, e.g., higher affinity.

Antibodies from Phagemid Libraries

Recombinant technology now allows the preparation of antibodies having a desired specificity from recombinant genes encoding a range of antibodies (Van Dijk et al., 1989; incorporated herein by reference). Certain recombinant techniques involve isolation of antibody genes by immunological screening of combinatorial immunoglobulin phage expression libraries prepared from RNA isolated from spleen of an immunized animal (Morrison et al., 1986; Winter and Milstein, 1991; Barbas et al., 1992; each incorporated herein by reference). For such methods, combinatorial immunoglobulin phagemid libraries are prepared from RNA isolated from spleen of an immunized animal, and phagemids expressing appropriate antibodies are selected by panning using cells expressing antigen and control cells. Advantage of this approach over conventional hybridoma techniques include approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. Vectors are subsequently combined randomly to form a single vector that directs co-expression of heavy and light chains to form antibody fragments. The general technique for filamentous phage display is described (U.S. Pat. No. 5,658,727, incorporated herein by reference). In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate a gene that encodes the member from the library. Additional methods for screening phagemid libraries are described (U.S. Pat. Nos. 5,580,717; 5,427,908; 5,403,484; and 5,223,409, each incorporated herein by reference).

One method for the generation and screening of large libraries of wholly or partially synthetic antibody combining sites, or paratopes, utilizes display vectors derived from filamentous phage such as M13, fl or fd (U.S. Pat. No. 5,698,426, incorporated herein by reference). Filamentous phage display vectors, referred to as "phagemids," yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991; each incorporated herein by reference). The surface expression library is screened for specific Fab fragments that bind hemagglutinin molecules by standard affinity isolation procedures. The selected Fab fragments can be characterized by sequencing the nucleic acids encoding the polypeptides after amplification of the phage population.

One method for producing diverse libraries of antibodies and screening for desirable binding specificities is described (U.S. Pat. Nos. 5,667,988 and 5,759,817, each incorporated herein by reference). The method involves the preparation of libraries of heterodimeric immunoglobulin molecules in the form of phagemid libraries using degenerate oligonucleotides and primer extension reactions to incorporate degeneracies into CDR regions of immunoglobulin variable heavy and light chain variable domains, and display of mutagenized polypeptides on the surface of the phagemid. Thereafter, the display protein is screened for the ability to bind to a preselected antigen. A further variation of this method for producing diverse libraries of antibodies and screening for desirable binding specificities is described U.S. Pat. No. 5,702,892, incorporated herein by reference). In this method, only heavy chain sequences are employed, heavy chain sequences are randomized at all nucleotide positions which encode either the CDRI or CDRIII hypervariable region, and the genetic variability in the CDRs is generated independent of any biological process.

Transgenic Mice Containing Human Antibody Libraries

Recombinant technology is available for the preparation of antibodies. In addition to the combinatorial immunoglobulin phage expression libraries disclosed above, one molecular cloning approach is to prepare antibodies from transgenic mice containing human antibody libraries. Such techniques are described (U.S. Pat. No. 5,545,807, incorporated herein by reference).

In a most general sense, these methods involve the production of a transgenic animal that has inserted into its germline genetic material that encodes for at least part of an immunoglobulin of human origin or that can rearrange to encode a repertoire of immunoglobulins. The inserted genetic material may be produced from a human source, or may be produced synthetically. The material may code for at least part of a known immunoglobulin or may be modified to code for at least part of an altered immunoglobulin.

The inserted genetic material is expressed in the transgenic animal, resulting in production of an immunoglobulin derived at least in part from the inserted human immunoglobulin genetic material. The inserted genetic material may be in the form of DNA cloned into prokaryotic vectors such as plasmids and/or cosmids. Larger DNA fragments are inserted using yeast artificial chromosome vectors (Burke et al., 1987; incorporated herein by reference), or by introduction of chromosome fragments (Richer et al., 1989; incorporated herein by reference). The inserted genetic material may be introduced to the host in conventional manner, for example by injection or other procedures into fertilized eggs or embryonic stem cells.

Once a suitable transgenic animal has been prepared, the animal is simply immunized with the desired immunogen. Depending on the nature of the inserted material, the animal may produce a chimeric immunoglobulin, e.g. of mixed mouse/human origin, where the genetic material of foreign origin encodes only part of the immunoglobulin; or the animal may produce an entirely foreign immunoglobulin, e.g. of wholly human origin, where the genetic material of foreign origin encodes an entire immunoglobulin.

Polyclonal antisera may be produced from the transgenic animal following immunization. Immunoglobulin-producing cells may be removed from the animal to produce the immunoglobulin of interest. Generally, monoclonal antibodies are produced from the transgenic animal, e.g., by fusing spleen cells from the animal with myeloma cells and screening the resulting hybridomas to select those producing the desired antibody. Suitable techniques for such processes are described herein.

In one approach, the genetic material may be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg may develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals are usually employed to produce human antibodies of a single isotype, more specifically an isotype that is essential for B cell maturation, such as IgM and possibly IgD. Another method for producing human antibodies is described in U.S. Pat. Nos. 5,545,806; 5,569, 825; 5,625,126; 5,633,425; 5,661,016; and 5,770,429; each incorporated by reference, wherein transgenic animals are described that are capable of switching from an isotype needed for B cell development to other isotypes.

In the method described in U.S. Pat. Nos. 5,545,806; 5,569, 825; 5,625,126; 5,633,425; 5,661,016; and 5,770,429, human immunoglobulin transgenes contained within a transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Humanized Antibodies

Human antibodies generally have at least three potential advantages for use in human therapy. First, because the effector portion is human, it may interact better with other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, half-life in human circulation will be similar to naturally occurring human antibodies, allowing smaller and less frequent doses to be given.

Various methods for preparing human antibodies are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" antibody are well known to those of skill in the art.

A number of methods have been described to produce humanized antibodies. Controlled rearrangement of antibody domains joined through protein disulfide bonds to form new, artificial protein molecules or "chimeric" antibodies can be utilized (Konieczny et al., 1981; incorporated herein by reference). Recombinant DNA technology can be used to construct gene fusions between DNA sequences encoding mouse antibody variable light and heavy chain domains and human antibody light and heavy chain constant domains (Morrison et al., 1984; incorporated herein by reference).

DNA sequences encoding antigen binding portions or complementarity determining regions (CDR's) of murine monoclonal antibodies can be grafted by molecular means into DNA sequences encoding frameworks of human antibody heavy and light chains (Jones et al., 1986; Riechmann et al., 1988; each incorporated herein by reference). Expressed recombinant products are called "reshaped" or humanized antibodies, and comprise the framework of a human antibody light or heavy chain and antigen recognition portions, CDR's, of a murine monoclonal antibody.

One method for producing humanized antibodies is described in U.S. Pat. No. 5,639,641, incorporated herein by reference. A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to CDR's, amino acids from the donor immunoglobulin framework that are capable of interacting with CDR's to effect binding affinity, such as one or more amino acids that are immediately adjacent to a CDR in the donor immunoglobulin or those within about 3A as predicted by molecular modeling. Heavy and light chains may each be designed by using any one, any combination, or all of various position criteria described in U.S. Pat. Nos. 5,693,762; 5,693,761; 5,585,089; and 5,530,101, each incorporated herein by reference. When combined into an intact antibody, humanized immunoglobulins are substantially non-immunogenic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries described herein. In a general sense, the method utilizes sequences from the antigen binding site of an antibody or population of antibodies directed against an antigen of interest. Thus for a single rodent antibody, sequences comprising part of the antigen binding site of the antibody may be combined with diverse repertoires of sequences of human antibodies that can, in combination, create a complete antigen binding site.

Antigen binding sites created by this process differ from those created by CDR grafting, in that only the portion of sequence of the original rodent antibody is likely to make contacts with antigen in a similar manner. Selected human sequences are likely to differ in sequence and make alternative contacts with the antigen from those of the original binding site. However, constraints imposed by binding of the portion of original sequence to antigen and shapes of the antigen and its antigen binding sites, are likely to drive new contacts of human sequences to the same region or epitope of the antigen. This process has therefore been termed "epitope imprinted selection," or "EIS."

Starting with an animal antibody, one process results in the selection of antibodies that are partly human antibodies. Such antibodies may be sufficiently similar in sequence to human antibodies to be used directly in therapy or after alteration of a few key residues. In EIS, repertoires of antibody fragments can be displayed on the surface of filamentous phase and genes encoding fragments with antigen binding activities selected by binding of the phage to antigen.

Yet additional methods for humanizing antibodies contemplated for use are described in U.S. Pat. Nos. 5,750,078; 5,502,167; 5,705,154; 5,770,403; 5,698,417; 5,693,493; 5,558,864; 4,935,496; and 4,816,567, each incorporated herein by reference.

As discussed in the above techniques, the advent of methods of molecular biology and recombinant technology, it is now possible to produce antibodies as described herein by recombinant means and thereby generate gene sequences that code for specific amino acid sequences found in the polypeptide structure of antibodies. This has permitted the ready production of antibodies having sequences characteristic of inhibitory antibodies from different species and sources, as discussed above. In accordance with the foregoing, the antibodies useful in the methods described herein are anti-hemagglutinin antibodies, specifically antibodies whose specificity is toward the same epitope of hemagglutinin as 4F5, 5F5, and 1E11 antibodies described herein, and include all therapeutically active variants and antigen binding fragments thereof whether produced by recombinant methods or by direct synthesis of the antibody polypeptides.

This document provides plants, plant cells, and plant tissues expressing antibodies that maintain pharmaceutical activity when administered to a subject in need thereof. Exemplary subjects include vertebrates (e.g., mammals, such as humans, and veterinary subjects such as bovines, ovines, canines, and felines). In certain aspects, an edible plant or portion thereof (e.g., sprout, root) can be administered orally to a subject in a therapeutically effective amount. In some aspects one or more influenza antibody is provided in a pharmaceutical preparation, as described herein.

Therapeutic, Prophylactic, and Diagnostic Compositions

In some embodiments, HA antibodies are used for diagnostic purposes. To give but one example, HA antibodies can be used to identify a subtype, clade, and/or strain of influenza with which a subject is infected. In some embodiments, HA antibodies can be used to identify patient populations that may be responsive to particular influenza treatments.

This document provides vaccine compositions comprising a least one HA antibody, fusion thereof, and/or portion(s) thereof. In some embodiments, such compositions are intended to elicit a physiological effect upon administration to a subject. A vaccine protein may have healing curative or palliative properties against a disorder or disease and can be administered to ameliorate relieve, alleviate, delay onset of, reverse or lessen symptoms or severity of a disease or disorder. A vaccine comprising an HA antibody may have prophylactic properties and can be used to prevent or delay the onset of a disease or to lessen the severity of such disease, disorder, or pathological condition when it does emerge. A physiological effect elicited by treatment of a subject with antigen as described herein can include an effective immune response such that infection by an organism is thwarted. Considerations for administration of HA antibodies to a subject in need thereof are discussed in further detail in the section below entitled "Administration."

In general, active vaccination involves the exposure of a subject's immune system to one or more agents that are recognized as unwanted, undesired, and/or foreign and elicit an endogenous immune response. Typically, such an immune response results in the activation of antigen-specific naive lymphocytes that then give rise to antibody-secreting B cells or antigen-specific effector and memory T cells or both. This approach can result in long-lived protective immunity that may be boosted from time to time by renewed exposure to the same antigenic material.

In some embodiments, a vaccine composition comprising at least one HA antibody is a subunit vaccine. In general, a subunit vaccine comprises purified antigens rather than whole organisms. Subunit vaccines are not infectious, so they can safely be given to immunosuppressed people, and they are less likely to induce unfavorable immune reactions and/or other adverse side effects. One potential disadvantage of subunit vaccines are that the antigens may not retain their native conformation, so that antibodies produced against the subunit may not recognize the same protein on the pathogen surface; and isolated protein does not stimulate the immune system as well as a whole organism vaccine. Therefore, in some situations, it may be necessary to administer subunit vaccines in higher doses than a whole-agent vaccine (e.g., live attenuated vaccines or inactivated pathogen vaccines) in order to achieve the same therapeutic effect. In contrast, whole-agent vaccines, such as vaccines that utilize live attenuated or inactivated pathogens, typically yield a vigorous immune response, but their use has limitations. For example, live vaccine strains can sometimes cause infectious pathologies, especially when administered to immune-compromised recipients. Moreover, many pathogens, particularly viruses (such as influenza), undergo continuous rapid mutations in their genome, which allow them to escape immune responses to antigenically distinct vaccine strains.

In some embodiments, subunit vaccines can comprise at least one plant-produced HA antibody. In some embodiments, about 100 µg, about 90 µg, about 80 µg, about 70 µg, about 60 µg, about 50 µg, about 40 µg, about 35 µg, about 30 µg, about 25 µg, about 20 µg, about 15 µg, about 5 µg, about 4 µg, about 3 µg, about 2 µg, or about 1 µg of plant-produced HA antibody and/or immunogenic portion thereof can be used to stimulate an immune response and/or to prevent, delay the onset of, and/or provide protection against influenza infection.

In some embodiments, this document provides subunit vaccines against influenza. In some embodiments, subunit vaccines comprise an antigen that has been at least partially purified from non-antigenic components. For example, a subunit vaccine may be an HA antibody, fusion thereof, and/or immunogenic portion thereof that is expressed in a live organism (such as a plant, virus, bacterium, yeast, mammalian cell, or egg), but is at least partially purified from the non-antigen components of the live organism. In some embodiments, a subunit vaccine is at least 30%, at least 40%, at least 50%, at least 60%, at least 70%, at least 80%, at least 90%, at least 95%, at least 98%, or at least 99% purified from the non-antigen components of the organism in which the antigen was expressed. In some embodiments, a subunit vaccine may be an HA antibody, fusion thereof, and/or immunogenic portion thereof that is chemically-synthesized.

In some embodiments, a subunit vaccine may be an HA antibody, fusion thereof, and/or immunogenic portion thereof that is expressed in a live organism (such as a plant, virus, bacterium, yeast, mammalian cell, or egg), but is not at least partially purified from the non-antigen components of the live organism. For example, a subunit vaccine may be an HA antibody, fusion thereof, and/or immunogenic portion thereof that is expressed in a live organism that is administered directly to a subject in order to elicit an immune response. In some embodiments, a subunit vaccine may be an HA antibody, fusion thereof, and/or immunogenic portion thereof that is expressed in a plant, as described herein, wherein the plant material is administered directly to a subject in order to elicit an immune response.

This document provides pharmaceutical HA antibodies, fusions thereof, and/or immunogenic portions thereof, active as subunit vaccines for therapeutic and/or prophylactic treatment of influenza infection. In certain embodiments, HA antibodies may be produced by plant(s) or portion(s) thereof (e.g., root, cell, sprout, cell line, or plant). In certain embodiments, provided HA antibodies are expressed in plants, plant cells, and/or plant tissues (e.g., sprouts, sprouted seedlings, roots, root culture, clonal cells, clonal cell lines, or clonal plants), and can be used directly from plant or partially purified or purified in preparation for pharmaceutical administration to a subject.

Also provided are plants, plant cells, and plant tissues expressing HA antibodies that maintain pharmaceutical activity when administered to a subject in need thereof. Exemplary subjects include vertebrates (e.g., mammals such as humans, as well as veterinary subjects such as bovines, ovines, canines, and felines). In certain aspects, an edible plant or portion thereof (e.g., sprout, root) can be administered orally to a subject in a therapeutically effective amount. In some aspects one or more HA antibodies are provided in a pharmaceutical preparation, as described herein.

Where it is desirable to formulate an influenza vaccine comprising plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments, it is desirable to have expressed HA antibodies in an edible plant (and, specifically in edible portions of the plant) so that the material can subsequently be eaten. For instance, where vaccine antigen is active after oral delivery (when properly formulated), it may be desirable to produce antigen protein in an edible plant portion, and to formulate expressed HA antibody for oral delivery together with some or all of the plant material with which the protein was expressed.

Vaccine compositions can comprise one or more HA antibodies. In certain embodiments, exactly one HA antibody is included in an administered vaccine composition. In certain embodiments, at least two HA antibodies are included in an administered vaccine composition. In some aspects, combination vaccines may include one thermostable fusion protein comprising an HA antibody; in some aspects, two or more thermostable fusion proteins comprising HA antibody are provided.

In some embodiments, vaccine compositions comprise exactly one HA antibody. In some embodiments, vaccine compositions comprise exactly two HA antibodies. In some embodiments, vaccine compositions comprise exactly three HA antibodies. In some embodiments, vaccine compositions comprise four or more (e.g., 4, 5, 6, 7, 8, 9, 10, 15, or more) HA antibodies.

In some embodiments, vaccine compositions comprise exactly one HA antibody and exactly one NA antibody (e.g., NA monoclonal antibody 2B9, described in co-pending application U.S. Ser. No. 11/707,257, filed Feb. 13, 2007, published as US 2008/0124272 on May 29, 2008, entitled "INFLUENZA ANTIBODIES, COMPOSITIONS, AND RELATED METHODS," incorporated herein by reference). In some embodiments, vaccine compositions comprise exactly two HA antibodies and exactly two NA antibodies. In some embodiments, vaccine compositions comprise exactly three HA antibodies and exactly three NA antibodies. In some embodiments, vaccine compositions comprise four or more (e.g., 4, 5, 6, 7, 8, 9, 10, 15, or more) HA antibodies and four or more (e.g., 4, 5, 6, 7, 8, 9, 10, 15, or more) NA antibodies. In some embodiments, vaccine compositions comprise exactly one HA antibody and two or more (e.g., 2, 3, 4, 5, 6, 7, 8, 9, 10, 15, or more) NA antibodies. In some embodiments, vaccine compositions comprise two or more (e.g., 2, 3, 4, 5, 6, 7, 8, 9, 10, 15, or more) HA antibodies and exactly one NA antibody.

In some embodiments, vaccine compositions comprise polytopes (i.e., tandem fusions of two or more amino acid sequences) of two or more HA antibodies and/or immunogenic portions thereof. For example, in some embodiments, a polytope comprises exactly one HA antibody. In some embodiments, a polytope comprises exactly two HA antibodies. In some embodiments, a polytope comprises exactly three HA antibodies. In some embodiments, a polytope comprises four or more (e.g., 4, 5, 6, 7, 8, 9, 10, 15, or more) HA antibodies.

Where combination vaccines are utilized, it will be understood that any combination of HA antibodies may be used for such combinations. Compositions may include multiple HA antibodies, including multiple antigens provided herein. Furthermore, compositions may include one or more antibodies provided herein with one or more additional antibodies and/or other therapeutic agents. Combinations of HA antibodies include HA antibodies derived from one or more various subtypes or strains such that immunization confers immune response against more than one infection type. Combinations of HA antibodies may include at least one, at least two, at least three, at least four or more antibodies that recognize HA from different influenza subtypes or strains. In some combinations, at least two or at least three antibodies that recognize HA from different influenza subtypes are combined in one vaccine composition.

Additional Vaccine Components

Vaccine compositions also can include any suitable adjuvant, which can enhance the immunogenicity of the vaccine when administered to a subject. Such adjuvant(s) include, without limitation, saponins, such as extracts of *Quillaja saponaria* (QS), including purified subfractions of food grade QS such as QUIL-A® and QS21; alum; metallic salt particles (e.g., aluminum hydroxide and aluminum phosphate); mineral oil; MF59®; Malp2; incomplete Freund's adjuvant; complete Freund's adjuvant; alhydrogel; 3 de-O-acylated monophosphoryl lipid A (3D-MPL); lipid A; *Bortadella pertussis; Mycobacterium tuberculosis*; Merck Adjuvant 65 (Merck and Company, Inc., Rahway, N.J.); squalene; virosomes; oil-in-water emulsions (e.g., SBAS2); and liposome formulations (e.g., SBAS1). Further adjuvants include immunomodulatory oligonucleotides, for example unmethylated CpG sequences as disclosed in WO 96/02555. Combinations of different adjuvants, such as those mentioned hereinabove, are contemplated as providing an adjuvant which is a preferential stimulator of TH1 cell response. For example, QS21 can be formulated together with 3D-MPL. The ratio of QS21:3 D-MPL will typically be in the order of 1:10 to 10:1; 1:5 to 5:1; and often substantially 1:1. The desired range for optimal synergy may be 2.5:1 to 1:1 3D-MPL: QS21. Doses of purified QS extracts suitable for use in a human vaccine formulation are from 0.01 mg to 10 mg per kilogram of bodyweight.

It should be noted that certain thermostable proteins (e.g., lichenase) may themselves demonstrate immunoresponse potentiating activity, such that use of such protein whether in a fusion with an HA antibody or separately may be considered use of an adjuvant. Thus, vaccine compositions may further comprise one or more adjuvants. Certain vaccine compositions may comprise two or more adjuvants. Furthermore, depending on formulation and routes of administration, certain adjuvants may be desired in particular formulations and/or combinations.

In certain situations, it may be desirable to prolong the effect of a vaccine by slowing the absorption of one or more components of the vaccine product (e.g., protein) that is subcutaneously or intramuscularly injected. This may be accomplished by use of a liquid suspension of crystalline or amorphous material with poor water solubility. The rate of absorption of product then depends upon its rate of dissolution, which in turn, may depend upon size and form. Alternatively or additionally, delayed absorption of a parenterally administered product is accomplished by dissolving or suspending the product in an oil vehicle. Injectable depot forms are made by forming microcapsule matrices of protein in biodegradable polymers such as polylactide-polyglycolide. Depending upon the ratio of product to polymer and the nature of the particular polymer employed, rate of release can be controlled. Examples of biodegradable polymers include poly(orthoesters) and poly(anhydrides). Depot injectable formulations may be prepared by entrapping product in liposomes or microemulsions, which are compatible with body tissues. Alternative polymeric delivery vehicles can be used for oral formulations. For example, biodegradable, biocompatible polymers such as ethylene vinyl acetate, polyanhydrides, polyglycolic acid, collagen, polyorthoesters, and polylactic acid can be used. Antigen(s) or an immunogenic portions thereof may be formulated as microparticles, e.g., in combination with a polymeric delivery vehicle.

Enterally administered preparations of vaccine antigens may be introduced in solid, semi-solid, suspension or emulsion form and may be compounded with any pharmaceutically acceptable carriers, such as water, suspending agents, and emulsifying agents. Antigens may be administered by means of pumps or sustained-release forms, especially when administered as a preventive measure, so as to prevent the development of disease in a subject or to ameliorate or delay an already established disease. Supplementary active compounds, e.g., compounds independently active against the disease or clinical condition to be treated, or compounds that enhance activity of a compound provided herein, can be incorporated into or administered with compositions. Flavorants and coloring agents can be used.

Vaccine products, optionally together with plant tissue, are particularly well suited for oral administration as pharmaceutical compositions. Oral liquid formulations can be used and may be of particular utility for pediatric populations. Harvested plant material may be processed in any of a variety of ways (e.g., air drying, freeze drying, and/or extraction), depending on the properties of the desired therapeutic product and its desired form. Such compositions as described above may be ingested orally alone or ingested together with food or feed or a beverage. Compositions for oral administration include plants; extractions of plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, plants may be air dried by placing them in a commercial air dryer at about 120° F. until biomass contains less than 5% moisture by weight. The dried plants may be stored for further processing as bulk solids or further processed by grinding to a desired mesh sized powder. Alternatively or additionally, freeze-drying may be used for products that are sensitive to air-drying. Products may be freeze dried by placing them into a vacuum drier and dried frozen under a vacuum until the biomass contains less than about 5% moisture by weight. Dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, or liquid dosage. Those skilled in the art will appreciate the various formulations and modalities of delivery of herbal preparations that may be applied to the present disclosure.

Pharmaceutical formulations also can comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this document.

In some embodiments, the pharmaceutically acceptable excipient is at least 95%, at least 96%, at least 97%, at least 98%, at least 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g., polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®, polyoxyethylene ethers, (e.g., polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER®188, cetrimonium bromide, cetylpyridinium chloride, benzalkonium chloride, docusate sodium, and/or combinations thereof.

Exemplary binding agents include, without limitation, starch (e.g., cornstarch and starch paste); gelatin; sugars (e.g., sucrose, glucose, dextrose, dextrin, molasses, lactose, lactitol, and mannitol); natural and synthetic gums [e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan]; alginates; polyethylene oxide; polyethylene glycol; inorganic calcium salts; silicic acid; polymethacrylates; waxes; water; alcohol; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Vaccine products, optionally together with plant tissue, are particularly well suited for oral administration as pharmaceutical compositions. Oral liquid formulations can be used and may be of particular utility for pediatric populations. Harvested plant material may be processed in any of a variety of ways (e.g., air drying, freeze drying, and/or extraction), depending on the properties of the desired therapeutic product and its desired form. Such compositions as described above may be ingested orally alone or ingested together with food or feed or a beverage. Compositions for oral administration include plants; extractions of plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, plants may be air dried by placing them in a commercial air dryer at about 120° F. until biomass contains less than 5% moisture by weight. Dried plants may be stored for further processing as bulk solids or further processed by grinding to a desired mesh sized powder. Alternatively or additionally, freeze-drying may be used for products that are sensitive to air-drying. Products may be freeze dried by placing them into a vacuum drier and dried frozen under a vacuum until the biomass contains less than about 5% moisture by weight. Dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, or liquid dosage. Those skilled in the art will appreciate the various formulations and modalities of delivery of herbal preparations that may be applied to the present disclosure.

In some methods, a plant or portion thereof expressing an HA antibody, or biomass thereof, is administered orally as medicinal food. Such edible compositions can be consumed by eating raw if in a solid form, or by drinking if in liquid form. The plant material can be directly ingested without a prior processing step or after minimal culinary preparation. In some embodiments, a vaccine antigen may be expressed in a sprout that can be eaten directly. For instance, vaccine antigens can be expressed in alfalfa sprouts, mung bean sprouts, spinach leaf sprouts, or lettuce leaf sprouts that can be eaten directly. In some embodiments, plant biomass may be processed and the material recovered after the processing step can be ingested.

Processing methods useful in accordance with the present disclosure are methods commonly used in the food or feed industry. Final products of such methods typically include a substantial amount of an expressed antigen and can be conveniently eaten or drunk. The final product may be mixed with other food or feed forms, such as salts, carriers, favor enhancers, antibiotics, and the like, and consumed in solid, semi-solid, suspension, emulsion, or liquid form. Such methods can include a conservation step, such as, e.g., pasteurization, cooking, or addition of conservation and preservation agents. Any plant may be used and processed to produce edible or drinkable plant matter. The amount of HA antibody in a plant-derived preparation may be tested by methods standard in the art, e.g., gel electrophoresis, ELISA, or western blot analysis, using a probe or antibody specific for product. This determination may be used to standardize the amount of vaccine antigen protein ingested. For example, the amount of vaccine antigen may be determined and regulated, for example, by mixing batches of product having different levels of product so that the quantity of material to be drunk or eaten to ingest a single dose can be standardized. A contained, regulatable environment should, however, minimize the need to carry out such standardization procedures.

A vaccine protein produced in a plant cell or tissue and eaten by a subject may be preferably absorbed by the digestive system. One advantage of the ingestion of plant tissue that has been only minimally processed is to provide encapsulation or sequestration of the protein in cells of the plant. Thus, product may receive at least some protection from digestion in the upper digestive tract before reaching the gut or intestine and a higher proportion of active product would be available for uptake.

Dosage forms for topical and/or transdermal administration of a compound as provided herein may include ointments, pastes, creams, lotions, gels, powders, solutions, sprays, inhalants and/or patches. Generally, the active ingredient is admixed under sterile conditions with a pharmaceutically acceptable excipient and/or any needed preservatives and/or buffers as may be required. Additionally, this disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and the active ingredient may constitute 0.1% to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface-active agent, and/or a preservative such as methylhydroxybenzoate. The droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e., by rapid inhalation through the nasal passage from a container of the powder held close to the nose.

Formulations suitable for nasal administration may, for example, comprise from about as little as 0.1% (w/w) and as much as 100% (w/w) of the active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 nm to about 200 nm, and may further comprise one or more of the additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this document.

In certain situations, it may be desirable to prolong the effect of a vaccine by slowing the absorption of one or more components of the vaccine product (e.g., protein) that is subcutaneously or intramuscularly injected. This may be accomplished by use of a liquid suspension of crystalline or amorphous material with poor water solubility. The rate of absorption of product then depends upon its rate of dissolution, which in turn, may depend upon size and form. Alternatively or additionally, delayed absorption of a parenterally administered product is accomplished by dissolving or suspending the product in an oil vehicle. Injectable depot forms are made by forming microcapsule matrices of protein in biodegradable polymers such as polylactide-polyglycolide. Depending upon the ratio of product to polymer and the nature of the particular polymer employed, rate of release can be controlled. Examples of biodegradable polymers include poly(orthoesters) and poly(anhydrides). Depot injectable formulations may be prepared by entrapping product in liposomes or microemulsions, which are compatible with body tissues. Alternative polymeric delivery vehicles can be used for oral formulations. For example, biodegradable, biocompatible polymers such as ethylene vinyl acetate, polyanhydrides, polyglycolic acid, collagen, polyorthoesters, and polylactic acid, can be used. Antigen(s) or an immunogenic portions thereof may be formulated as microparticles, e.g., in combination with a polymeric delivery vehicle.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

Among other things, this document provides subunit vaccines. In some embodiments, subunit vaccines may be administered to a subject at low doses in order to stimulate an immune response and/or confer protectivity. As used herein, the term "low-dose vaccine" generally refers to a vaccine that is immunogenic and/or protective when administered to a subject at low-doses. Administration of a low-dose vaccine can comprise administration of a subunit vaccine composition comprising less than 100 µg of an HA antibody, fusion thereof, and/or immunogenic portion thereof.

In some embodiments, administration of a low-dose subunit vaccine comprises administering a subunit vaccine comprising less than about 100 µg, less than about 90 µg, less than about 80 µg, less than about 70 µg, less than about 60 µg, less than about 50 µg, less than about 40 µg, less than about 35 µg, less than about 30 µg, less than about 25 µg, less than about 20 µg, less than about 15 µg, less than about 5 µg, less than about 4 µg, less than about 3 µg, less than about 2 µg, or less than about 1 µg of plant-produced HA antibody, fusion thereof, and/or immunogenic portion thereof to a subject in need thereof. In some embodiments, the plant-produced HA antibody, fusion thereof, and/or immunogenic portion thereof has been at least partially purified from non-antigenic components, as described herein. In some embodiments, the plant-produced HA antibody, fusion thereof, and/or immunogenic portion thereof has not been at least partially purified from non-antigenic components, as described herein. Suitable vaccine compositions for administration to a subject are described in further detail in the section above, entitled "Vaccines."

HA antibodies, fusions thereof, and/or immunogenic portions thereof, and/or pharmaceutical compositions thereof (e.g., vaccines) may be administered using any amount and any route of administration effective for treatment.

The exact amount required will vary from subject to subject, depending on the species, age, and general condition of the subject, the severity of the infection, the particular composition, its mode of administration, its mode of activity, and the like. HA antibodies are typically formulated in dosage unit form for ease of administration and uniformity of dosage. It will be understood, however, that the total daily usage of the compositions provided herein will be decided by the attending physician within the scope of sound medical judgment. The specific therapeutically effective dose level for any particular subject or organism will depend upon a variety of factors including the disorder being treated and the severity of the disorder; the activity of the specific HA antibody employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Pharmaceutical compositions (e.g., vaccines) may be administered by any route. In some embodiments, pharmaceutical compositions can be administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol; and/or through a portal vein catheter. In general, the most appropriate route of administration will depend upon a variety of factors, including the nature of the agent being administered (e.g., its stability in the environment of the gastrointestinal tract) and the condition of the subject (e.g., whether the subject is able to tolerate a particular mode of administration).

In some embodiments, vaccines are delivered by multiple routes of administration (e.g., by subcutaneous injection and by intranasal inhalation). For vaccines involving two or more doses, different doses may be administered via different routes.

In some embodiments, vaccines are delivered by subcutaneous injection. In some embodiments, vaccines are administered by intramuscular and/or intravenous injection. In some embodiments, vaccines are delivered by intranasal inhalation.

In some embodiments, vaccines as provided herein are delivered by oral and/or mucosal routes. Oral and/or mucosal delivery has the potential to prevent infection of mucosal tissues, the primary gateway of infection for many pathogens. Oral and/or mucosal delivery can prime systemic immune response. There has been considerable progress in the development of heterologous expression systems for oral administration of antigens that stimulate the mucosal-immune system and can prime systemic immunity. Previous efforts at delivery of oral vaccine however, have demonstrated a requirement for considerable quantities of antigen in achieving efficacy. Thus, economical production of large quantities of target antigens is a prerequisite for creation of effective oral vaccines. Development of plants expressing antigens, including thermostable antigens, represents a more realistic approach to such difficulties.

In certain embodiments, an HA antibody expressed in a plant or portion thereof is administered to a subject orally by direct administration of a plant to a subject. In some aspects a vaccine protein expressed in a plant or portion thereof is extracted and/or purified, and used for the preparation of a pharmaceutical composition. It may be desirable to formulate such isolated products for their intended use (e.g., as a pharmaceutical agent or vaccine composition). In some embodiments, it will be desirable to formulate products together with some or all of plant tissues that express them.

In certain embodiments, an HA antibody expressed in a plant or portion thereof is administered to a subject orally by direct administration of a plant to a subject. In some aspects a vaccine protein expressed in a plant or portion thereof is extracted and/or purified, and used for preparation of a pharmaceutical composition. It may be desirable to formulate such isolated products for their intended use (e.g., as a pharmaceutical agent or vaccine composition). In some embodiments, it will be desirable to formulate products together with some or all of plant tissues that express them.

A vaccine protein produced in a plant cell or tissue and eaten by a subject may be preferably absorbed by the digestive system. One advantage of the ingestion of plant tissue that has been only minimally processed is to provide encapsulation or sequestration of the protein in cells of the plant. Thus, product may receive at least some protection from digestion in the upper digestive tract before reaching the gut or intestine and a higher proportion of active product would be available for uptake.

Where it is desirable to formulate product together with plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments, it is desirable to have expressed HA antibody in an edible plant (and, specifically in edible portions of the plant) so that the material can subsequently be eaten. For instance, where vaccine antigen is active after oral delivery (when properly formulated), it may be desirable to produce antigen protein in an edible plant portion, and to formulate expressed HA antibody for oral delivery together with some or all of the plant material with which a protein was expressed.

In certain embodiments, HA antibodies as provided herein and/or pharmaceutical compositions thereof (e.g., vaccines) may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In certain embodiments, the desired dosage may be delivered using multiple administrations (e.g., two, three, four, five, six, seven, eight, nine, ten, eleven, twelve, thirteen, fourteen, or more administrations).

Compositions are administered in such amounts and for such time as is necessary to achieve the desired result. In certain embodiments, a "therapeutically effective amount" of a pharmaceutical composition is that amount effective for treating, attenuating, or preventing a disease in a subject. Thus, the "amount effective to treat, attenuate, or prevent disease," as used herein, refers to a nontoxic but sufficient amount of the pharmaceutical composition to treat, attenuate, or prevent disease in any subject. For example, the "therapeutically effective amount" can be an amount to treat, attenuate, or prevent infection (e.g., influenza infection)

It will be appreciated that HA antibodies and/or pharmaceutical compositions thereof can be employed in combination therapies. The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, HA antibodies useful for treating, preventing, and/or delaying the onset of influenza infection may be administered concurrently with another agent useful for treating, preventing, and/or delaying the onset of influenza infection), or they may achieve different effects (e.g., control of any adverse effects). This document encompasses the delivery of pharmaceutical compositions in combination with agents that may improve their bioavailability, reduce and/or modify their metabolism, inhibit their excretion, and/or modify their distribution within the body.

Pharmaceutical compositions in accordance with the present disclosure may be administered either alone or in combination with one or more other therapeutic agents. By "in combination with," it is not intended to imply that the agents must be administered at the same time and/or formulated for delivery together, although these methods of delivery are within the scope of this document. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In general, it is expected that agents utilized in combination with be utilized at levels that do not exceed the levels at which they are utilized individually. In some embodiments, the levels utilized in combination will be lower than those utilized individually.

In certain embodiments, vaccine compositions comprising at least one HA antibody are administered in combination with other influenza vaccines. In certain embodiments, vaccine compositions comprising at least one HA antibody are administered in combination with other influenza therapeutics. In certain embodiments, vaccine compositions comprising at least one HA antibody are administered in combination with antiviral drugs, such as neuraminidase inhibitors (e.g., oseltamivir [TAMIFLU®], zanamivir [RELENZAAND®] and/or M2 inhibitors (e.g., adamantane, adamantane derivatives, and rimantadine).

Kits

In one aspect, this document provides a pharmaceutical pack or kit including at least one HA antibody as provided herein. In certain embodiments, pharmaceutical packs or kits include live sprouted seedlings, clonal entity or plant producing an antibody or antigen binding fragment as provided herein, or preparations, extracts, or pharmaceutical compositions containing antibody in one or more containers filled with optionally one or more additional ingredients of pharmaceutical compositions as provided herein. In some embodiments, pharmaceutical packs or kits include pharmaceutical compositions comprising purified HA antibody, in one or more containers optionally filled with one or more additional ingredients of pharmaceutical compositions. In certain embodiments, the pharmaceutical pack or kit includes an additional approved therapeutic agent (e.g., influenza antibody, influenza vaccine, influenza therapeutic) for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents. As but one non-limiting example, HA antibody can be provided as oral formulations and administered as therapy. Alternatively or additionally, HA antibody can be provided in an injectable formulation for administration. In one embodiment, HA antibody can be provided in an inhalable formulation for administration. Pharmaceutical doses or instructions therefore may be provided in the kit for administration to an individual suffering from or at risk for influenza infection.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain information, exemplification and guidance, which can be adapted to the practice of this invention in its various embodiments and the equivalents thereof.

EXAMPLES

Example 1

Cloning, Expression, and Purification of Influenza HA

The HA sequences encoding hemagglutinin (HA) from A/Anhui/1/2005 (SEQ ID NO:22), A/Bar-headed goose/Qinghai/0510/05 (SEQ ID NO:24), A/Indonesia/5/05 (SEQ ID NO:23), and A/Wyoming/3/03 (H3N2) (SEQ ID NO:34) were optimized for expression in plants and synthesized by GENEART AG (Regensburg, Germany). The PR-1a signal peptide was added to the N-terminus and the endoplasmic reticulum retention signal (KDEL) and a poly-histidine affinity purification tag ($His_6$) were added to the C-terminus. The resulting sequence was inserted into the launch vector pGRD4 to obtain pGRD4-HA (illustrated in FIG. 1). The pGRD4 vector is based on Tobacco mosaic virus (TMV) and was engineered using the pGreen/pSoup system as a binary expression vector by introducing the Cauliflower mosaic virus (CaMV) 35S promoter, the nos terminator, and the hammerhead ribozyme sequence from the launch vector pBID4. pGRD4-HA and pSoup, which provides replication functions in trans, were then introduced into *Agrobacterium tumefaciens* strain GV3101. The resulting bacterial strain was grown in AB medium (18.7 mM $NH_4Cl$, 2.5 mM $MgSO_4$, 2 mM KCl, 0.07 mM $CaCl_2$, 2.7 µM $FeSO_4$, 17.2 mM $K_2HPO_4$, 6.4 mM $NaH_2PO_4$, 0.2% glucose) overnight at 28° C. The bacteria were introduced into the aerial parts of 6-week-old *Nicotiana benthamiana* plants grown hydroponically in rockwool slabs, by vacuum infiltration at a cell density of $OD_{600}$=0.5. Seven days after vacuum infiltration, leaf tissue was harvested, and homogenized using a household blender. The extracts were clarified by centrifugation (78 000×g for 30 min) and HA was purified using Ni-column chromatography (pre-packed His Trap HP Ni columns, GE Healthcare, NJ). Further purification was carried out by anion exchange chromatography (Sepharose Q columns, GE Healthcare, NJ) on a Bio-Rad Duo Flow system using Biologics software.

Example 2

Generation of Plants and Antigen Production

*Agrobacterium* Infiltration of Plants: *Agrobacterium*-mediated transient expression system achieved by *Agrobacterium* infiltration was utilized (Turpen et al. (1993) J. Virol. Methods 42:227). Healthy leaves of *Nicotiana benthamiana* were infiltrated with *A. rhizogenes* containing viral vectors engineered to express NINA.

The *A. tumefaciens* strain A4 (ATCC 43057; ATCC, Manassas, Va.) was transformed with the constructs pBI-D4-PR-NA-KDEL and pBI-D4-PR-NA-VAC. *Agrobacterium* cultures were grown and induced as described (Kapila et al. (1997) Plant Sci. 122:101). A 2 ml starter-culture (picked from a fresh colony) was grown overnight in YEB (5 g/l beef extract, 1 g/l yeast extract, 5 g/l peptone, 5 g/l sucrose, 2 mM MgSO4) with 25 µg/ml kanamycin at 28° C. The starter culture was diluted 1:500 into 500 ml of YEB with 25 µg/ml kanamycin, 10 mM 2-4(-morpholino)ethanesulfonic acid (MES) pH 5.6, 2 mM additional MgSO4 and 20 µM acetosyringone. The diluted culture was then grown overnight to an O.D.600 of ~1.7 at 28° C. The cells were centrifuged at 3,000×g for 15 minutes and re-suspended in MMA medium (MS salts, 10 mM MES pH 5.6, 20 g/l sucrose, 200 µM acetosyringone) to an O.D.600 of 2.4, kept for 1-3 hour at room temperature, and used for *Agrobacterium*-infiltration. *N. benthamiana* leaves were injected with the *Agrobacterium*-suspension using a disposable syringe without a needle. Infiltrated leaves were harvested 6 days post-infiltration. Plants were screened for the presence of target antigen expression by immunoblot analysis.

Example 3

Production of Antigen 100 mg samples of *N. benthamiana* infiltrated leaf material were harvested at 4, 5, 6 and 7 days post-infection. The fresh tissue was analyzed for protein expression right after being harvested or collected at −80° C. for the preparation of subsequent crude plants extracts or for fusion protein purification.

Fresh samples were resuspended in cold PBS 1× plus protease inhibitors (Roche) in a 1/3 w/v ratio (1 ml/0.3 g of tissue) and ground with a pestle. The homogenates were boiled for 5 minutes in SDS gel loading buffer and then clarified by centrifugation for 5 minutes at 12,000 rpm at 4° C. The supernatants were transferred to fresh tubes, and 20 µl, 1 µl, or dilutions thereof were separated by 12% SDS-PAGE and analyzed by Western analysis using anti-His6-HA mouse polyclonal antibodies.

HA expression in *N. benthamiana* plants infiltrated either with *A. tumefaciens* containing the plasmid pBID4-HA-KDEL led to a specific band corresponding to the molecular weight of NA-KDEL. Quantification of HA-KDEL expressed in crude extract was made by immunoblotting both on manually infiltrated tissues and on vacuum-infiltrated tissues.

Purification of Antigens:

Leaves from plants infiltrated with recombinant *A. tumefaciens* containing the pBID4-HA-KDEL construct were ground by homogenization. Extraction buffer with "EDTA-free" protease inhibitors (Roche) and 1% Triton X-100 was used at a ratio of 3× (w/v) and rocked for 30 minutes at 4° C. Extracts were clarified by centrifugation at 9000×g for 10 minutes at 4° C. Supernatants were sequentially filtered through Mira cloth, centrifuged at 20,000×g for 30 minutes at 4° C., and filtered through a 0.45-μm filter before chromatographic purification.

The resulting extracts were cut using ammonium sulfate precipitation. Briefly, $(NH_4)_2SO_4$ was added to 20% saturation, incubated on ice for 1 hour, and spun down at 18,000×g for 15 minutes. Pellets were discarded and $(NH_4)_2SO_4$ was added slowly to 60% saturation, incubated on ice for 1 hour, and spun down at 18,000×g for 15 minutes. Supernatants were discarded and the resulting pellets were resuspended in buffer, maintained on ice for 20 minutes, and centrifuged at 18,000×g for 30 minutes. Supernatants were dialyzed overnight against 10,000 volumes of washing buffer.

His-tagged HA-KDEL proteins were purified using Ni-NTA sepharose ("Chelating Sepharose Fast Flow Column;" Amersham) at room temperature under gravity. The purification was performed under non-denaturing conditions. Proteins were collected as 0.5 ml fractions that were unified, combined with 20 mM EDTA, dialyzed against 1×PBS overnight at 4° C., and analyzed by SDS-PAGE. Alternatively, fractions were collected, unified, combined with 20 mM EDTA, dialyzed against 10 mM NaH2PO4 overnight at 4° C., and purified by anion exchange chromatography. For HA-KDEL purification, anion exchange column Q Sepharose Fast Flow (Amersham Pharmacia Biosciences) was used. Samples of the HA-KDEL affinity or ion-exchange purified proteins were separated on 12% polyacrylamide gels followed by Coomassie staining.

After dialysis, samples were analyzed by immunoblotting using the mAb α-anti-His6. The His-tag was maintained by the expressed proteins, and the final concentration of the purified protein was determined using GeneTools software from Syngene (Frederick, Md.).

Example 4

Western Blot and ELISA Analysis of Purified ppH5HA-I

Samples of HA, purified from infiltrated *N. benthamiana* leaves, were separated on 10% SDS-polyacrylamide gels, transferred onto a polyvinylidene fluoride membrane (Millipore, Billerica, Mass.) and blocked with 0.5% I-block (Applied Biosystems, CA). The membrane was then incubated with a mouse monoclonal antibody against poly-His (Roche-Applied-Science, IN) followed by horseradish peroxidase (HRP)-conjugated goat anti-mouse antibody (Jackson ImmunoResearch Laboratory Inc., PA). Proteins reacting with the anti-His antibody were visualized using SuperSignal West Pico Chemiluminescent Substrate (Pierce, IL). The image was taken using GeneSnap software on a GeneGnome and quantified using Gene Tools software (Syngene Bioimaging, MD).

Example 5

Derivation of a Murine Hybridoma Secreting Monoclonal Antibody

Six-week-old Balb/c mice were immunized with plant-produced HA subcutaneously at 2-week intervals on days 0, 14, and 28. All immunizations included 10 μg of Quil A adjuvant (Accurate Chemical, NY). Mice were boosted intraperitoneally 3-4 days prior to spleen harvest. Spleens were teased into single cell suspensions and red blood cells were lysed ($NH_4Cl$ solution). Splenocytes were combined with P3 myeloma cells at a 1:1 ratio. A solution of 50% PEG was added and the cells were incubated at 37° C. for 2 hrs. After the incubation, the cell pellet was resuspended in media containing 1×HAT and plated in 96 well plates and incubated for two weeks. HAT containing media was replaced as needed. On day 14, the cells were feed media containing HT (not HAT) for 1 week, replacing media every-other day. At this point the hybridoma cell lines were screened by ELISA, initially on plant-produced antigen and then inactivated virus. Positive wells were put through several rounds of limiting dilution to isolate a single clone and screened again. At this point, the isotype of the antibody was determined and cell supernatants were screened for functionality by hemagglutination inhibition assays (HI) against homologous and heterologous viruses. Antibodies from selected clones were then purified from mouse ascites at Rockland Immunochemicals.

45 million spleen cells were fused with 5 million P3XAg8.653 murine myeloma cells using polyethylene glycol. The resulting 50 million fused cells were plated at $5 \times 10^5$ cells per well in 10×96 well plates. HAT (hypoxanthine, aminopterin, and thymidine) selection followed 24 hours later and continued until colonies arose. All immunoglobulin-secreting hybridomas were subcloned by three rounds of limiting dilution in the presence of HAT.

Hybridomas were screened on ELISA plates for secretion of H5 HA specific immunoglobulin. Hybridomas 1E11, 4F5, 5F5, 13B8, 1E5 and 2C7 each had a high specific signal.

Example 6

Characterization of mAb Specificity

The specificity of each mAb to homologous and heterologous influenza viruses was analyzed by ELISA. Plates were coated with inactivated H5N1 or H3N2 virus; antibody concentration was 125 ng/ml. The reactivity of mAb 4F5 (A/Anhui/1/05), mAb5F5 (A/Bar-headed goose/Qinghai/1A/05 and mAb 1E11 (A/Bar-headed goose/Qinghai/1A/05) against a panel of influenza strains (iA Vietnam (H5N1); iA/Indonesia (H5N1); A/Anhui/1/05 (H5N1); A/Bar-headed goose/Qinghai/1A/05 (H5N1); and iA/Wyoming (H3N2)) is shown in FIG. 2A, FIG. 2B and FIG. 2C, respectively.

Example 7

Hemagglutination Inhibition Activity of mAbs 1E11, 5F5 and 4F5

MAbs 1E11, 5F5 and 4F5 were assayed for hemagglutination inhibition activity. Culture supernatants of hybridoma cells were treated with receptor-destroying enzyme (RDE; Denka Seiken Co. Ltd., Tokyo, Japan) and an HI assay was carried out with 1% horse erythrocytes containing 0.1% bovine serum albumin, as described in Noah et al. (Clin Vaccine Immunol., 16(4), 558-566 2009). Briefly, two-fold serial dilution of culture supernatant or purified monoclonal antibodies were mixed with 8 HAU/50 μl of influenza virus in the V-bottom 96-well plates and incubated for 45 to 60 minutes at room temperature. Horse erythrocytes were diluted to 1% with PBS and then added to the 96-well plates containing antibody/serum mixture. After 30-45 minutes incubation, wells were observed for agglutination and the HI titer of the individual samples was determined as the reciprocal of the highest dilution which caused complete inhibition of hemagglutination. Sheep anti-A/Vietnam/1194/04 was used as a reference serum.

The results of this experiment are shown in FIG. 3. The values in the table are the lowest concentration (ug/ml) that inhibited hemagglutination activity (8HAU/50 ul) for each strain. For the reference serum, the numbers shown are end-point titers for hemagglutination activity (8HAU/50 ul) for each strain. mAbs 1E11 and 5F5 inhibited hemagglutination activity of homologous as well as heterologous viruses; mAb 4F5 demonstrated hemagglutination inhibition only against homologous virus.

Example 8

Analysis of Binding Activity of mAbs 13B8, 4F5, 5F5, 1E11, 1E5 and 2C7

Ascites produced and purified mAbs 13B8, 4F5, 5F5, 1E11, 1E5 and 2C7 were screened for binding activity against a panel of inactivated whole viruses, purified plant-produced HAs and baculovirus produced HAs. The results of this experiment are shown in FIG. 4. All anti-H5 mAbs were shown to bind multiple H5N1 virus strains from both Clade 1 and Clade 2. None of the anti-H5 mAbs bound to influenza viruses of subtypes H3N2 or H1N1.

Example 9

Hemagglutination Inhibition Activity of Anti-HA mAbs

Ascites produced and purified mAbs 13B8, 4F5, 5F5, 1E11, 1E5 and 2C7 were screened for hemagglutination inhibition activity according of the method of Example 7. The results of this analysis for the anti-H5 HA mAbs, 13B8, 4F5, 5F5, 1E11, 1E5, are shown in FIG. 5; the results of this analysis for the anti-H3 HA mAb, 2C7, is shown in FIG. 6.

Example 10

Evaluation of Anti-HA mAbs In Vivo

Figure 8:
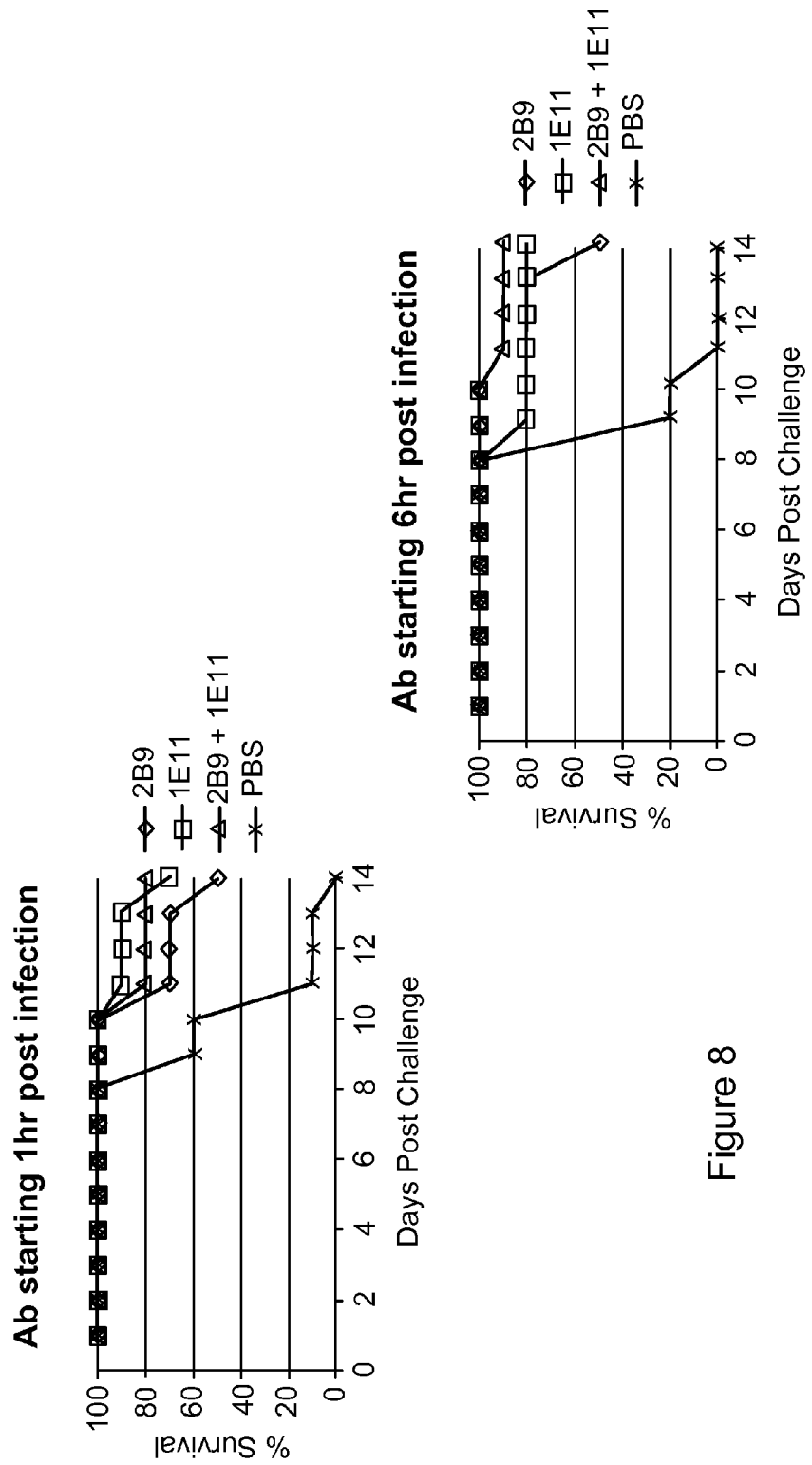
FIG. 8 depicts the results of an experiment to evaluate the protective efficacy of mAbs in mice.

The ability of the anti-H5 HA mAb, 1E11, to protect mice from challenge with influenza virus in vivo was analyzed according to the experimental design shown in FIG. 7. Female mice were challenged on Day 0 with 30 μL of $10^{6.4}$ $EID_{50}$/mL of H5N1 Avian Influenza virus. On Days 0-2, each animal was dosed with either 100 μL or 200 μL of mAb 2B9 (an anti-neuraminidase mAb), mAb 1E11, combination of mAb 2B9 and mAb 1E11, or DPBS intravenously into the tail vein. On Day 0, Groups 1, 3, 5, and 7 were dosed beginning approximately 1 hour after challenge, and Groups 2, 4, 6, and 8 were dosed beginning approximately 6 hours after challenge. Mice were assessed for clinical signs, body weight, and body temperature changes throughout the study (Day 0 to Day 14). The results of this study are shown in FIG. 8. Treatment of H5N1 challenged mice with monoclonal antibodies 2B9 and/or 1E11 at 1 (FIG. 8A) or 6 (FIG. 8B) hours after challenge provided 50%-90% protection from lethality. In general, mAb 1E11 provided a higher level of protection by 20%-30% compared to the 2B9 antibody. The timing for the administration of the mAb did not have a substantial impact on survival or body temperature. The timing for the administration of the mAb had only a modest impact on body weight for groups treated with the 2B9 antibody, with animals dosed 6 hours after challenge appearing more stable in body weight at study termination, indicating a better performance of the antibody.

Example 11

Half-Life Study of mAb1E11 in Mice

The stability of mAb 1E11 was measured in mice according to standard methods. The half-life of the antibody was 8.4 days when administered intravenously and 13.7 days when administered intramuscularly.

Example 12

Amino Acid Sequences of mAbs 1E11 and 4F5

The nucleotide sequences of the light and heavy chains of mAbs 1E11 and 4F5 were determined by standard methods. Conceptual translations of each sequence are shown in FIG. 9. The heavy chain of 1E11 has the acid sequence set forth in SEQ ID NO:74; the light chain of 1E11 has the acid sequence set forth in SEQ ID NO:75. The heavy chain of 4F5 has the acid sequence set forth in SEQ ID NO:76; the light chain of 4F5 has the acid sequence set forth in SEQ ID NO:77. Signal peptide/leader sequences are shown in italics.

Sequences of the 1E11 and 4F5 heavy and light chains without signal peptide/leader sequences are shown in FIG. 10. The heavy chain of 1E11 without the signal peptide/leader sequence has the acid sequence set forth in SEQ ID NO:78; the light chain of 1E11 without the signal peptide/leader sequence has the acid sequence set forth in SEQ ID NO:79. The heavy chain of 4F5 without the signal peptide/leader sequence has the acid sequence set forth in SEQ ID NO:80; the light chain of 4F5 without the signal peptide/leader sequence has the acid sequence set forth in SEQ ID NO:81.

What is claimed is:

1. An isolated monoclonal antibody that binds hemagglutinin, wherein the antibody has the ability to inhibit hemagglutination, and wherein the antibody is selected from the group consisting of:
an antibody comprising the light chain variable region amino acid sequence set forth in amino acids 1-97 of SEQ ID NO:79, and the heavy chain variable region amino acid sequence set forth in amino acids 1-115 of SEQ ID NO:78; and
an antibody comprising the light chain variable region amino acid sequence set forth in amino acids 1-96 of SEQ ID NO:81, and the heavy chain variable region amino acid sequence set forth in amino acids 1-112 of SEQ ID NO:80.

2. The antibody of claim 1, wherein the antibody comprises the light chain variable region amino acid sequence set forth in amino acids 1-97 of SEQ ID NO:79, and the heavy chain variable region amino acid sequence set forth in amino acids 1-115 of SEQ ID NO:78.

3. The antibody of claim 1, wherein the antibody comprises the light chain variable region amino set forth in amino acids 1-96 of SEQ ID NO:81, and the heavy chain variable region amino acid sequence set forth in amino acids 1-112 of SEQ ID NO:80.

4. An antibody that binds hemagglutinin, wherein the antibody has the ability to inhibit hemagglutination, and wherein the antibody is selected from the group consisting of:
an antibody comprising the light chain amino acid sequence set forth in SEQ ID NO:79, and the heavy chain amino acid sequence set forth in SEQ ID NO:78; and
an antibody comprising the light chain amino acid sequence set forth in SEQ ID NO:81, and the heavy chain amino acid sequence set forth in SEQ ID NO:80.

5. The antibody of claim 4, wherein the antibody comprises the light chain amino acid sequence set forth in SEQ ID NO:79 and the heavy chain amino acid sequence set forth in SEQ ID NO:78.

6. The antibody of claim 4, wherein the antibody comprises the light chain amino acid sequence set forth in SEQ ID NO:81 and the heavy chain amino acid sequence set forth in SEQ ID NO:80.

7. An antigen-binding fragment of an antibody that binds hemagglutinin and has the ability to inhibit hemagglutination, wherein the antigen-binding fragment comprises:
the light chain variable region amino acid sequence set forth in amino acids 1-97 of SEQ ID NO:79, and the heavy chain variable region amino acid sequence set forth in amino acids 1-115 of SEQ ID NO:78; or
the light chain variable region amino acid sequence set forth in amino acids 1-96 of SEQ ID NO:81, and the heavy chain variable region amino acid sequence set forth in amino acids 1-112 of SEQ ID NO:80;
wherein the antigen-binding fragment is an scFv, Fv, Fab', Fab, diabody, linear antibody, or F(ab')$_2$ antigen-binding fragment.

8. The antigen-binding fragment of claim 7, wherein the antigen-binding fragment is a univalent fragment, or a single domain antibody.

9. The antibody of claim 1, wherein the antibody is a human, humanized, or part-human antibody.

10. The antibody of claim 1, wherein the antibody is a recombinant antibody.

11. The antibody of claim 1, wherein the antibody is produced in a plant.

12. The antibody of claim 1, wherein the antibody is operatively attached to a biological agent, an imaging agent, a detectable agent, or a diagnostic agent.

13. The antibody of claim 12, wherein the antibody is operatively attached to an agent that cleaves a substantially inactive prodrug to release a substantially active drug.

14. The antibody of claim 13, wherein the drug is an anti-influenza agent.

15. The antibody of claim 12, wherein the antibody is operatively attached to an anti-viral agent.

16. The antibody of claim 12, wherein the antibody is operatively attached to the biological agent as a fusion protein prepared by expressing a recombinant vector that comprises, in the same reading frame, a DNA segment encoding the antibody operatively linked to a DNA segment encoding the biological agent.

17. The antibody of claim 12, wherein the antibody is operatively attached to the biological agent via a biologically releasable bond or selectively cleavable linker.

18. The antibody of claim 12, wherein the antibody is operatively attached to an X-ray detectable compound, a radioactive ion or a nuclear magnetic spin-resonance isotope.

19. The antibody of claim 12, wherein the antibody is operatively attached to biotin, avidin or to an enzyme that generates a colored product upon contact with a chromogenic substrate.

20. A pharmaceutical composition comprising the antibody of claim 1, and a pharmaceutically acceptable carrier.

21. The composition of claim 20, wherein the composition is formulated for parenteral or topical administration.

22. The composition of claim 20, wherein the antibody is a recombinant, plant-produced antibody.

23. The composition of claim 20, wherein the pharmaceutically acceptable composition is an encapsulated or liposomal formulation.

* * * * *

SEQUENCE LISTING

<160> NUMBER OF SEQ ID NOS: 81

<210> SEQ ID NO 1
<211> LENGTH: 552
<212> TYPE: PRT
<213> ORGANISM: Influenza virus

<400> SEQUENCE: 1

```
Met Asn Ile Gln Ile Leu Ala Phe Ile Ala Cys Val Leu Thr Gly Ala
 1               5                  10                  15

Lys Gly Asp Lys Ile Cys Leu Gly His His Ala Val Ala Asn Gly Thr
             20                  25                  30

Lys Val Asn Thr Leu Thr Glu Lys Gly Ile Glu Val Val Asn Ala Thr
             35                  40                  45

Glu Thr Val Glu Thr Ala Asp Val Lys Lys Ile Cys Thr Gln Gly Lys
         50                  55                  60

Arg Ala Thr Asp Leu Gly Arg Cys Gly Leu Leu Gly Thr Leu Ile Gly
65                  70                  75                  80

Pro Pro Gln Cys Asp Gln Phe Leu Glu Phe Ser Ser Asp Leu Ile Ile
                 85                  90                  95

Glu Arg Arg Glu Gly Thr Asp Val Cys Tyr Pro Gly Arg Phe Thr Asn
                100                 105                 110

Glu Glu Ser Leu Arg Gln Ile Leu Arg Arg Ser Gly Ile Gly Lys
            115                 120                 125

Glu Ser Met Gly Phe Thr Tyr Ser Gly Ile Arg Thr Asn Gly Ala Ala
            130                 135                 140

Ser Ala Cys Thr Arg Ser Gly Ser Ser Phe Tyr Ala Glu Met Lys Trp
145                 150                 155                 160

Leu Leu Ser Asn Ser Asp Asn Ser Ala Phe Pro Gln Met Thr Lys Ala
                165                 170                 175

Tyr Arg Asn Pro Arg Asn Lys Pro Ala Leu Ile Ile Trp Gly Val His
                180                 185                 190

His Ser Glu Ser Ala Ser Glu Gln Thr Lys Leu Tyr Gly Ser Gly Asn
            195                 200                 205

Lys Leu Ile Thr Val Arg Ser Ser Lys Tyr Gln Gln Ser Phe Thr Pro
            210                 215                 220

Ser Pro Gly Thr Arg Arg Ile Asp Phe His Trp Leu Leu Leu Asp Pro
225                 230                 235                 240

Asn Asp Thr Val Thr Phe Thr Phe Asn Gly Ala Phe Ile Ala Pro Asp
                245                 250                 255

Arg Ala Ser Phe Phe Arg Gly Glu Ser Leu Gly Val Gln Ser Asp Ala
                260                 265                 270

Pro Leu Asp Ser Ser Cys Arg Gly Asp Cys Phe His Ser Gly Gly Thr
            275                 280                 285

Ile Val Ser Ser Leu Pro Phe Gln Asn Ile Asn Ser Arg Thr Val Gly
            290                 295                 300

Arg Cys Pro Arg Tyr Val Lys Gln Lys Ser Leu Leu Leu Ala Thr Gly
305                 310                 315                 320

Met Arg Asn Val Pro Glu Lys Pro Lys Pro Arg Gly Leu Phe Gly Ala
                325                 330                 335

Ile Ala Gly Phe Ile Glu Asn Gly Trp Glu Gly Leu Ile Asn Gly Trp
            340                 345                 350

Tyr Gly Phe Arg His Gln Asn Ala Gln Gly Glu Gly Thr Ala Ala Asp
            355                 360                 365

Tyr Lys Ser Thr Gln Ser Ala Ile Asp Gln Ile Thr Gly Lys Leu Asn
            370                 375                 380

Arg Leu Ile Gly Lys Thr Asn Gln Gln Phe Glu Leu Ile Asp Asn Glu
385                 390                 395                 400

Phe Asn Glu Ile Glu Gln Gln Ile Gly Asn Val Ile Asn Trp Thr Arg
                405                 410                 415

Asp Ala Met Thr Glu Ile Trp Ser Tyr Asn Ala Glu Leu Leu Val Ala
```

```
                    420             425              430
Met Glu Asn Gln His Thr Ile Asp Leu Ala Asp Ser Glu Met Ser Lys
                435                 440                 445

Leu Tyr Glu Arg Val Lys Lys Gln Leu Arg Glu Asn Ala Glu Glu Asp
        450                 455                 460

Gly Thr Gly Cys Phe Glu Ile Phe His Lys Cys Asp Asp Gln Cys Met
465                 470                 475                 480

Glu Ser Ile Arg Asn Asn Thr Tyr Asp His Thr Gln Tyr Arg Thr Glu
                485                 490                 495

Ser Leu Gln Asn Arg Ile Gln Ile Asp Pro Val Lys Leu Ser Ser Gly
                500                 505                 510

Tyr Lys Asp Ile Ile Leu Trp Phe Ser Phe Gly Ala Ser Cys Phe Ile
                515                 520                 525

Leu Leu Ala Ile Ala Met Gly Leu Val Phe Ile Cys Ile Lys Asn Gly
                530                 535                 540

Asn Met Gln Cys Thr Ile Cys Ile
545                 550

<210> SEQ ID NO 2
<211> LENGTH: 552
<212> TYPE: PRT
<213> ORGANISM: Influenza virus

<400> SEQUENCE: 2

Met Asn Thr Gln Ile Leu Ala Phe Ile Ala Cys Val Leu Thr Gly Val
1               5                   10                  15

Lys Gly Asp Lys Ile Cys Leu Gly His His Ala Val Ala Asn Gly Thr
                20                  25                  30

Lys Val Asn Thr Leu Thr Glu Lys Gly Ile Glu Val Val Asn Ala Thr
            35                  40                  45

Glu Thr Val Glu Thr Ala Asp Val Lys Lys Ile Cys Thr Gln Gly Lys
        50                  55                  60

Arg Ala Thr Asp Leu Gly Arg Cys Gly Leu Leu Gly Thr Leu Ile Gly
65                  70                  75                  80

Pro Pro Gln Cys Asp Gln Phe Leu Glu Phe Ser Ser Asp Leu Ile Ile
                85                  90                  95

Glu Arg Arg Glu Gly Thr Asp Val Cys Tyr Pro Gly Arg Phe Thr Asn
                100                 105                 110

Glu Glu Ser Leu Arg Gln Ile Leu Arg Arg Ser Gly Ile Gly Lys
                115                 120                 125

Glu Ser Met Gly Phe Thr Tyr Ser Gly Ile Arg Thr Asn Gly Ala Thr
            130                 135                 140

Ser Ala Cys Thr Arg Ser Gly Ser Ser Phe Tyr Ala Glu Met Lys Trp
145                 150                 155                 160

Leu Leu Ser Asn Ser Asp Asn Ser Ala Phe Pro Gln Met Thr Lys Ala
                165                 170                 175

Tyr Arg Asn Pro Arg Asn Lys Pro Ala Leu Ile Ile Trp Gly Val His
                180                 185                 190

His Ser Glu Ser Val Ser Glu Gln Thr Lys Leu Tyr Gly Ser Gly Asn
            195                 200                 205

Lys Leu Ile Thr Val Arg Ser Ser Lys Tyr Gln Gln Ser Phe Thr Pro
            210                 215                 220

Ser Pro Gly Ala Arg Arg Ile Asp Phe His Trp Leu Leu Leu Asp Pro
225                 230                 235                 240
```

-continued

```
Asn Asp Thr Val Thr Phe Thr Phe Asn Gly Ala Phe Ile Ala Pro Asp
                245                 250                 255

Arg Ala Ser Phe Phe Arg Gly Glu Ser Leu Gly Val Gln Ser Asp Val
            260                 265                 270

Pro Leu Asp Ser Ser Cys Arg Gly Asp Cys Phe His Ser Gly Gly Thr
        275                 280                 285

Ile Val Ser Ser Leu Pro Phe Gln Asn Ile Asn Ser Arg Thr Val Gly
    290                 295                 300

Lys Cys Pro Arg Tyr Val Lys Gln Lys Ser Leu Leu Leu Ala Thr Gly
305                 310                 315                 320

Met Arg Asn Val Pro Glu Lys Pro Lys Pro Arg Gly Leu Phe Gly Ala
                325                 330                 335

Ile Ala Gly Phe Ile Glu Asn Gly Trp Glu Gly Leu Ile Asn Gly Trp
            340                 345                 350

Tyr Gly Phe Arg His Gln Asn Ala Gln Gly Glu Gly Thr Ala Ala Asp
        355                 360                 365

Tyr Lys Ser Thr Gln Ser Ala Ile Asp Gln Ile Thr Gly Lys Leu Asn
    370                 375                 380

Arg Leu Ile Gly Lys Thr Asn Gln Gln Phe Glu Leu Ile Asp Asn Glu
385                 390                 395                 400

Phe Asn Glu Ile Glu Gln Gln Ile Gly Asn Val Ile Asn Trp Thr Arg
                405                 410                 415

Asp Ala Met Thr Glu Ile Trp Ser Tyr Asn Ala Glu Leu Leu Val Ala
            420                 425                 430

Met Glu Asn Gln His Thr Ile Asp Leu Ala Asp Ser Glu Met Ser Lys
        435                 440                 445

Leu Tyr Glu Arg Val Lys Lys Gln Leu Arg Glu Asn Ala Glu Glu Asp
    450                 455                 460

Gly Thr Gly Cys Phe Glu Ile Phe His Lys Cys Asp Asp Gln Cys Met
465                 470                 475                 480

Glu Ser Ile Arg Asn Asn Thr Tyr Asp His Thr Gln Tyr Arg Thr Glu
                485                 490                 495

Ser Leu Gln Asn Arg Ile Gln Ile Asp Pro Val Lys Leu Ser Ser Gly
            500                 505                 510

Tyr Lys Asp Ile Ile Leu Trp Phe Ser Phe Gly Ala Ser Cys Phe Leu
        515                 520                 525

Leu Leu Ala Ile Ala Met Gly Leu Val Phe Ile Cys Ile Lys Asn Gly
    530                 535                 540

Asn Met Gln Cys Thr Ile Cys Ile
545                 550

<210> SEQ ID NO 3
<211> LENGTH: 552
<212> TYPE: PRT
<213> ORGANISM: Influenza virus

<400> SEQUENCE: 3

Met Asn Ile Gln Ile Leu Ala Phe Ile Ala Cys Val Leu Thr Gly Ala
1               5                   10                  15

Lys Gly Asp Lys Ile Cys Leu Gly His His Ala Val Ala Asn Gly Thr
            20                  25                  30

Lys Val Asn Thr Leu Thr Glu Lys Gly Ile Glu Val Val Asn Ala Thr
        35                  40                  45

Glu Thr Val Glu Thr Ala Asn Ile Lys Lys Ile Cys Thr Gln Gly Lys
    50                  55                  60
```

```
Arg Pro Thr Asp Leu Gly Gln Cys Gly Leu Leu Gly Thr Leu Ile Gly
 65                  70                  75                  80

Pro Pro Gln Cys Asp Gln Phe Leu Glu Phe Ser Ser Asp Leu Ile Ile
                 85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Arg Ser Gly Ile Gly Lys
        115                 120                 125

Glu Ser Met Gly Phe Thr Tyr Ser Gly Ile Arg Thr Asn Gly Ala Thr
    130                 135                 140

Ser Ala Cys Thr Arg Ser Gly Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
            180                 185                 190

His Ser Glu Ser Val Ser Glu Gln Thr Lys Leu Tyr Gly Ser Gly Asn
        195                 200                 205

Lys Leu Ile Lys Val Arg Ser Ser Lys Tyr Gln Gln Ser Phe Thr Pro
210                 215                 220

Asn Pro Gly Ala Arg Arg Ile Asp Phe His Trp Leu Leu Leu Asp Pro
225                 230                 235                 240

Asn Asp Thr Val Thr Phe Thr Phe Asn Gly Ala Phe Ile Ala Pro Asp
                245                 250                 255

Arg Ala Ser Phe Phe Arg Gly Glu Ser Ile Gly Val Gln Ser Asp Ala
            260                 265                 270

Pro Leu Asp Ser Ser Cys Gly Gly Asn Cys Phe His Asn Gly Gly Thr
        275                 280                 285

Ile Val Ser Ser Leu Pro Phe Gln Asn Ile Asn Pro Arg Thr Val Gly
    290                 295                 300

Lys Cys Pro Arg Tyr Val Lys Gln Lys Ser Leu Leu Leu Ala Thr Gly
305                 310                 315                 320

Met Arg Asn Val Pro Glu Lys Pro Lys Lys Arg Gly Leu Phe Gly Ala
                325                 330                 335

Ile Ala Gly Phe Ile Glu Asn Gly Trp Glu Gly Leu Ile Asn Gly Trp
            340                 345                 350

Tyr Gly Phe Arg His Gln Asn Ala Gln Gly Glu Gly Thr Ala Ala Asp
        355                 360                 365

Tyr Lys Ser Thr Gln Ser Ala Ile Asp Gln Ile Thr Gly Lys Leu Asn
    370                 375                 380

Arg Leu Ile Gly Lys Thr Asn Gln Gln Phe Glu Leu Ile Asn Asn Glu
385                 390                 395                 400

Phe Asn Glu Val Glu Gln Gln Ile Gly Asn Val Ile Asn Trp Thr Gln
                405                 410                 415

Asp Ala Met Thr Glu Val Trp Ser Tyr Asn Ala Glu Leu Leu Val Ala
            420                 425                 430

Met Glu Asn Gln His Thr Ile Asp Leu Thr Asp Ser Glu Met Ser Lys
        435                 440                 445

Leu Tyr Glu Arg Val Arg Lys Gln Leu Arg Glu Asn Ala Glu Glu Asp
    450                 455                 460

Gly Thr Gly Cys Phe Glu Ile Phe His Lys Cys Asp Asp His Cys Met
465                 470                 475                 480
```

-continued

```
Glu Ser Ile Arg Asn Asn Thr Tyr Asp His Thr Gln Tyr Arg Thr Glu
                485                 490                 495

Ser Leu Gln Asn Arg Ile Gln Ile Asp Pro Val Lys Leu Ser Gly Gly
            500                 505                 510

Tyr Lys Asp Ile Ile Leu Trp Phe Ser Phe Gly Ala Ser Cys Phe Leu
        515                 520                 525

Leu Leu Ala Ile Ala Met Gly Leu Val Phe Ile Cys Ile Lys Asn Gly
    530                 535                 540

Asn Met Gln Cys Thr Ile Cys Ile
545                 550

<210> SEQ ID NO 4
<211> LENGTH: 560
<212> TYPE: PRT
<213> ORGANISM: Influenza virus

<400> SEQUENCE: 4

Met Asn Thr Gln Ile Leu Ala Leu Ile Ala Tyr Met Leu Ile Gly Ala
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Val Asn Ile Lys Lys Ile Cys Thr Gln Gly Lys
    50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Asp Ala Asp Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Gly Ile Asp Lys
        115                 120                 125

Glu Ser Met Gly Phe Thr Tyr Ser Gly Ile Arg Thr Asn Gly Val Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
            180                 185                 190

His Ser Gly Ser Ala Thr Glu Gln Thr Lys Leu Tyr Gly Ser Gly Asn
        195                 200                 205

Lys Leu Ile Thr Val Gly Ser Ser Lys Tyr Gln Gln Ser Phe Thr Pro
    210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Arg Ala Ser Phe Phe Arg Gly Glu
            260                 265                 270

Ser Leu Gly Val Gln Ser Asp Val Pro Leu Asp Ser Gly Cys Glu Gly
        275                 280                 285

Asp Cys Phe His Ser Arg Gly Thr Ile Val Ser Ser Leu Pro Phe Gln
    290                 295                 300
```

```
Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Ser Glu Ile Glu Gln Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Arg Lys Gln
    450                 455                 460

Leu Arg Glu Asn Ala Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Thr Glu Ser Leu Gln Asn Arg Ile Gln Ile
            500                 505                 510

Asp Pro Val Lys Leu Ser Ser Gly Tyr Lys Asp Ile Ile Leu Trp Phe
        515                 520                 525

Ser Phe Gly Ala Ser Cys Phe Leu Leu Leu Ala Ile Ala Met Gly Leu
    530                 535                 540

Val Phe Ile Cys Ile Lys Asn Gly Asn Met Arg Cys Thr Ile Cys Ile
545                 550                 555                 560

<210> SEQ ID NO 5
<211> LENGTH: 560
<212> TYPE: PRT
<213> ORGANISM: Influenza virus

<400> SEQUENCE: 5

Met Asn Thr Gln Ile Leu Ala Leu Ile Ala Cys Met Leu Ile Gly Ala
1               5                   10                  15

Lys Gly Asp Lys Ile Cys Leu Gly His His Ala Val Ala Asn Gly Thr
                20                  25                  30

Lys Val Asn Thr Leu Thr Glu Arg Gly Ile Glu Val Val Asn Ala Thr
            35                  40                  45

Glu Thr Val Glu Thr Ala Asn Ile Lys Lys Ile Cys Thr Gln Gly Lys
        50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Asp Ala Asp Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Gly Ile Asp Lys
```

```
            115                 120                 125
Glu Ser Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
                180                 185                 190

His Ser Gly Ser Ala Thr Glu Gln Thr Lys Leu Tyr Gly Ser Gly Asn
            195                 200                 205

Lys Leu Ile Thr Val Gly Ser Ser Lys Tyr Gln Gln Ser Phe Thr Pro
210                 215                 220

Ser Pro Gly Ala Arg Pro Gln Val Asn Gly Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Gly
                260                 265                 270

Ser Leu Gly Val Gln Ser Asp Val Pro Leu Asp Ser Gly Cys Glu Gly
            275                 280                 285

Asp Cys Phe His Ser Gly Gly Thr Ile Val Ser Ser Leu Pro Phe Gln
            290                 295                 300

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Asn Glu Ile Glu Gln Gln Ile
                405                 410                 415

Gly Asn Val Ile Asn Trp Thr Arg Asp Ser Met Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asn Lys Leu Tyr Glu Arg Val Arg Lys Gln
            450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Thr Glu Ser Leu Gln Asn Arg Ile Gln Ile
                500                 505                 510

Asn Pro Val Lys Leu Ser Ser Gly Tyr Lys Asp Ile Ile Leu Trp Phe
                515                 520                 525

Ser Phe Gly Ala Ser Cys Phe Leu Leu Leu Ala Ile Ala Met Gly Leu
            530                 535                 540
```

```
Val Phe Ile Cys Ile Lys Asn Gly Asn Met Arg Cys Thr Ile Cys Ile
545                 550                 555                 560
```

<210> SEQ ID NO 6
<211> LENGTH: 568
<212> TYPE: PRT
<213> ORGANISM: Influenza virus

<400> SEQUENCE: 6

```
Met Glu Lys Ile Val Leu Leu Leu Ala Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Leu Asn Val Pro Glu Trp Ser Tyr Ile Val
                 85                  90                  95

Glu Lys Ile Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp Tyr Glu Ala Ser
130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Ile Arg Leu Tyr Gln
        195                 200                 205

Asn Pro Thr Thr Tyr Ile Ser Ile Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Ser Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Arg Lys Arg Gly Leu Phe Gly Ala Ile
            340                 345                 350

Ala Gly Phe Ile Glu Gly Gly Trp Gln Gly Met Val Asp Gly Trp Tyr
```

```
                355                 360                 365
Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asn Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Met Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Phe Leu Trp Met Cys Ser Asn Gly
545                 550                 555                 560

Ser Leu Gln Cys Arg Ile Cys Ile
                565

<210> SEQ ID NO 7
<211> LENGTH: 552
<212> TYPE: PRT
<213> ORGANISM: Influenza virus

<400> SEQUENCE: 7

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asn Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Ile Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Arg Ser Ser Phe Phe
    130                 135                 140

Arg Asn Val Val Trp Leu Ile Lys Lys Asp Asn Ala Tyr Pro Thr Ile
145                 150                 155                 160
```

```
Lys Arg Ser Tyr Asn Asn Thr Asn Gln Glu Asp Leu Leu Val Leu Trp
                165                 170                 175
Gly Ile His His Pro Asn Asp Ala Ala Glu Gln Thr Arg Leu Tyr Gln
            180                 185                 190
Asn Pro Thr Thr Tyr Ile Ser Val Gly Thr Ser Thr Leu Asn Gln Arg
        195                 200                 205
Leu Val Pro Lys Ile Ala Thr Arg Ser Lys Val Asn Gly Gln Ser Gly
210                 215                 220
Arg Met Glu Phe Phe Trp Thr Ile Leu Lys Pro Asn Asp Ala Ile Asn
225                 230                 235                 240
Phe Glu Ser Asn Gly Asn Phe Ile Ala Pro Glu Asn Ala Tyr Lys Ile
                245                 250                 255
Val Lys Lys Gly Asp Ser Thr Ile Met Lys Ser Glu Leu Glu Tyr Gly
            260                 265                 270
Asn Cys Asn Thr Lys Cys Gln Thr Pro Ile Gly Ala Ile Asn Ser Ser
        275                 280                 285
Met Pro Phe His Asn Ile His Pro Leu Thr Ile Gly Glu Cys Pro Lys
290                 295                 300
Tyr Val Lys Ser Asn Lys Leu Val Leu Ala Thr Gly Leu Arg Asn Ser
305                 310                 315                 320
Pro Gln Gly Glu Arg Arg Lys Lys Arg Gly Leu Phe Gly Ala Ile
                325                 330                 335
Ala Gly Phe Ile Glu Gly Gly Trp Gln Gly Met Val Asp Gly Trp Tyr
            340                 345                 350
Gly Tyr His His Ser Asn Glu Gln Gly Ser Gly Tyr Ala Ala Asp Lys
        355                 360                 365
Glu Ser Thr Gln Lys Ala Ile Asp Gly Val Thr Asn Lys Val Asn Ser
370                 375                 380
Ile Ile Asp Lys Met Asn Thr Gln Phe Glu Ala Val Gly Arg Glu Phe
385                 390                 395                 400
Asn Asn Leu Glu Arg Arg Ile Glu Asn Leu Asn Lys Lys Met Glu Asp
                405                 410                 415
Gly Phe Leu Asp Val Trp Thr Tyr Asn Ala Glu Leu Leu Val Leu Met
            420                 425                 430
Glu Asn Glu Arg Thr Leu Asp Phe His Asp Ser Asn Val Lys Asn Leu
        435                 440                 445
Tyr Asp Lys Ile Arg Leu Gln Leu Arg Asp Asn Ala Lys Glu Leu Gly
450                 455                 460
Asn Gly Cys Phe Glu Phe Tyr His Arg Cys Asp Asn Glu Cys Met Glu
465                 470                 475                 480
Ser Val Arg Asn Gly Thr Tyr Asp Tyr Pro Gln Tyr Ser Glu Glu Ala
                485                 490                 495
Arg Leu Lys Arg Glu Glu Ile Ser Gly Val Lys Leu Glu Ser Ile Gly
            500                 505                 510
Thr Tyr Gln Ile Leu Ser Ile Tyr Ser Thr Val Ala Ser Ser Leu Thr
        515                 520                 525
Leu Ala Ile Met Val Ala Gly Leu Ser Leu Trp Met Cys Ser Asn Gly
530                 535                 540
Ser Leu Gln Cys Arg Ile Cys Ile
545                 550

<210> SEQ ID NO 8
<211> LENGTH: 567
<212> TYPE: PRT
```

<213> ORGANISM: Influenza virus

<400> SEQUENCE: 8

```
Met Glu Lys Ile Val Leu Leu Leu

-continued

```
Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 9
<211> LENGTH: 563
<212> TYPE: PRT
<213> ORGANISM: Influenza virus

<400> SEQUENCE: 9

Met Glu Lys Ile Val Leu Leu Phe Ala Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Lys His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Thr Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205
```

```
Asn Pro Thr Thr Tyr Ile Ser Val Gly Thr Ser Thr Leu Asn Gln Arg
            210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys

<210> SEQ ID NO 10
<211> LENGTH: 552
<212> TYPE: PRT
<213> ORGANISM: Influenza virus

<400> SEQUENCE: 10

Asp Gln Ile Cys Ile Gly Tyr His Ala Asn Asn Ser Thr Glu Gln Val
1               5                   10                  15
```

```
Asp Thr Ile Met Glu Lys Asn Val Thr Val Thr His Ala Gln Asp Ile
             20                  25                  30

Leu Glu Lys Thr His Asn Gly Lys Leu Cys Asp Leu Asp Gly Val Lys
         35                  40                  45

Pro Leu Ile Leu Arg Asp Cys Ser Val Ala Gly Trp Leu Leu Gly Asn
 50                  55                  60

Pro Met Cys Asp Glu Phe Ile Asn Val Pro Glu Trp Ser Tyr Ile Val
 65                  70                  75                  80

Glu Lys Ala Asn Pro Thr Asn Asp Leu Cys Tyr Pro Gly Ser Phe Asn
                 85                  90                  95

Asp Tyr Glu Glu Leu Lys His Leu Leu Ser Arg Ile Asn His Phe Glu
                100                 105                 110

Lys Ile Gln Ile Ile Pro Lys Ser Ser Trp Ser Asp His Glu Ala Ser
            115                 120                 125

Ser Gly Val Ser Ser Ala Cys Pro Tyr Leu Gly Ser Pro Ser Phe Phe
130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Asn Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430
```

```
Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
            485                 490                 495

Arg Leu Lys Arg Glu Glu Ile Ser Gly Val Lys Leu Glu Ser Ile Gly
                500                 505                 510

Thr Tyr Gln Ile Leu Ser Ile Tyr Ser Thr Val Ala Ser Ser Leu Ala
            515                 520                 525

Leu Ala Ile Met Met Ala Gly Leu Ser Leu Trp Met Cys Ser Asn Gly
        530                 535                 540

Ser Leu Gln Cys Arg Ile Cys Ile
545                 550

<210> SEQ ID NO 11
<211> LENGTH: 566
<212> TYPE: PRT
<213> ORGANISM: Influenza virus

<400> SEQUENCE: 11

Met Lys Thr Ile Ile Ala Leu Ser Tyr Ile Leu Cys Leu Val Ser Ala
1               5                   10                  15

Gln Lys Phe Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Glu Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Arg Ser Arg Pro Arg Val Arg
225                 230                 235                 240

Asn Ile Pro Ser Arg Ile Ser Ile Tyr Trp Thr Ile Val Lys Pro Gly
                245                 250                 255
```

```
Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 12
<211> LENGTH: 566
<212> TYPE: PRT
<213> ORGANISM: Influenza virus

<400> SEQUENCE: 12

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
```

```
             50                  55                  60
Gly Glu Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Lys Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Lys Glu Lys Phe Asp Lys
                180                 185                 190

Leu Tyr Ile Trp Gly Val His His Pro Gly Thr Asp Asn Asp Gln Ile
                195                 200                 205

Phe Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Leu Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
                290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Thr Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Lys Thr Lys Lys Gln Leu Arg Glu Asn Ala Glu Asp Met Gly Asn
465                 470                 475                 480
```

```
Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 13
<211> LENGTH: 566
<212> TYPE: PRT
<213> ORGANISM: Influenza virus

<400> SEQUENCE: 13

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Lys
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
```

```
                    275                 280                 285
Pro Ile Gly Lys Cys Asn Ser Glu Cys Ile Thr Pro Asn Gly Ser Ile
            290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
                355                 360                 365
Phe Arg His Gln Asn Ser Glu Gly Ile Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
            450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
            530                 535                 540
Val Ala Leu Leu Gly Phe Ile Met Trp Ala Cys Gln Lys Gly Asn Ile
545                 550                 555                 560
Arg Cys Asn Ile Cys Ile
            565

<210> SEQ ID NO 14
<211> LENGTH: 566
<212> TYPE: PRT
<213> ORGANISM: Influenza virus

<400> SEQUENCE: 14

Met Lys Thr Ile Ile Ala Leu Ser Tyr Ile Leu Cys Leu Val Phe Ala
1               5                  10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
        35                  40                  45
Gln Ile Glu Val Thr Asn Ala Thr Glu Leu Val Gln Ser Ser Ser Thr
    50                  55                  60
Gly Glu Ile Cys Asp Ser Pro His Gln Ile Leu Asp Gly Glu Asn Cys
65                  70                  75                  80
```

-continued

```
Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
```

```
                    500             505             510
Asn Asn Arg Phe Gln Ile Lys Gly Val Glu Leu Lys Ser Gly Tyr Lys
            515             520             525

Asp Trp Ile Leu Trp Ile Ser Phe Ala Ile Ser Cys Phe Leu Leu Cys
            530             535             540

Val Ala Leu Leu Gly Phe Ile Met Trp Ala Cys Gln Lys Gly Asn Ile
545             550             555             560

Arg Cys Asn Ile Cys Ile
            565

<210> SEQ ID NO 15
<211> LENGTH: 565
<212> TYPE: PRT
<213> ORGANISM: Influenza virus

<400> SEQUENCE: 15

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr His Trp Thr Leu Leu Glu Pro Gly Asp Thr Ile
                245                 250                 255

Ile Phe Glu Ala Asn Gly Asn Leu Ile Ala Pro Arg Tyr Ala Phe Thr
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300
```

```
Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
            325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
                435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 16
<211> LENGTH: 565
<212> TYPE: PRT
<213> ORGANISM: Influenza virus

<400> SEQUENCE: 16

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Le

Ala Asp Tyr Glu Glu Leu Arg Glu Gln Leu Ser Ser Val Ser Ser Phe
    115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Thr Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

-continued

```
Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 17
<211> LENGTH: 565
<212> TYPE: PRT
<213> ORGANISM: Influenza virus
<220> FEATURE:
<221> NAME/KEY: VARIANT
<222> LOCATION: 158, 169, 238, 458, 500
<223> OTHER INFORMATION: Xaa = Any Amino Acid

<400> SEQUENCE: 17

Met Lys Val Lys Leu Val Leu Leu Cys Thr Phe Thr Ala Thr Tyr
  1               5                  10                  15

Ala Asp Thr Ile Cys Ile Gly Tyr His Ala Asn Asn Ser Thr Asp Thr
                 20                  25                  30

Val Asp Thr Val Leu Glu Lys Asn Val Thr Val Thr His Ser Val Asn
             35                  40                  45

Leu Leu Glu Asn Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ala Trp Pro Asn His Thr
130                 135                 140

Val Thr Gly Val Ser Ala Ser Cys Ser His Asn Gly Glu Xaa Ser Phe
145                 150                 155                 160

Tyr Arg Asn Leu Leu Trp Leu Thr Xaa Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Xaa Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
```

```
             305                 310                 315                 320
Lys Tyr Val Arg Ser Ala Lys Leu Arg Met Val Thr Gly Leu Arg Asn
             325                 330                 335

Ile Pro Ser Ile Gln Ser Arg Gly Leu Phe Gly Ala Ile Ala Gly Phe
             340                 345                 350

Ile Glu Gly Gly Trp Thr Gly Met Val Asp Gly Trp Tyr Gly Tyr His
             355                 360                 365

His Gln Asn Glu Gln Gly Ser Gly Tyr Ala Ala Asp Gln Lys Ser Thr
             370                 375                 380

Gln Asn Ala Ile Asn Gly Ile Thr Asn Lys Val Asn Ser Val Ile Glu
385              390                 395                 400

Lys Met Asn Thr Gln Phe Thr Ala Val Gly Lys Glu Phe Asn Lys Leu
                 405                 410                 415

Glu Arg Arg Met Glu Asn Leu Asn Lys Lys Val Asp Asp Gly Phe Ile
                 420                 425                 430

Asp Ile Trp Thr Tyr Asn Ala Glu Leu Leu Val Leu Leu Glu Asn Glu
             435                 440                 445

Arg Thr Leu Asp Phe His Asp Ser Asn Xaa Lys Asn Leu Tyr Glu Lys
             450                 455                 460

Val Lys Ser Gln Leu Lys Asn Asn Ala Lys Glu Ile Gly Asn Gly Cys
465              470                 475                 480

Phe Glu Phe Tyr His Lys Cys Asn Asp Glu Cys Met Glu Ser Val Lys
                 485                 490                 495

Asn Gly Thr Xaa Asp Tyr Pro Lys Tyr Ser Glu Glu Ser Lys Leu Asn
                 500                 505                 510

Arg Glu Lys Ile Asp Gly Val Lys Leu Glu Ser Met Gly Val Tyr Gln
                 515                 520                 525

Ile Leu Ala Ile Tyr Ser Thr Val Ala Ser Ser Leu Val Leu Leu Val
             530                 535                 540

Ser Leu Gly Ala Ile Ser Phe Trp Met Cys Ser Asn Gly Ser Leu Gln
545              550                 555                 560

Cys Arg Ile Cys Ile
             565

<210> SEQ ID NO 18
<211> LENGTH: 565
<212> TYPE: PRT
<213> ORGANISM: Influenza virus
<220> FEATURE:
<221> NAME/KEY: VARIANT
<222> LOCATION: 178, 410
<223> OTHER INFORMATION: Xaa = Any Amino Acid

<400> SEQUENCE: 18

Met Lys Val Lys Leu Leu Val Leu Leu Cys Thr Phe Thr Ala Thr Tyr
 1               5                  10                  15

Ala Asp Thr Ile Cys Ile Gly Tyr His Ala Asn Asn Ser Thr Asp Thr
                 20                  25                  30

Val Asp Thr Val Leu Glu Lys Asn Val Thr Val Thr His Ser Val Asn
             35                  40                  45

Leu Leu Glu Asn Asn His Asn Gly Lys Leu Cys Leu Leu Lys Gly Ile
         50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                 85                  90                  95
```

```
Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Met Phe Pro Lys Glu Gly Ser Trp Pro Asn His Thr
            130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Xaa Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
            195                 200                 205

His Thr Glu Asn Ala Tyr Val Ser Val Val Ser Ser His Tyr Ser Arg
            210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285

Asp Asn Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Xaa Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510
```

```
Arg Glu Lys Ile Asp Gly Val Lys Leu Glu Ser Met Gly Val Tyr Gln
            515                 520                 525
Ile Leu Ala Ile Tyr Ser Thr Val Ala Ser Ser Leu Val Leu Leu Val
        530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 19
<211> LENGTH: 565
<212> TYPE: PRT
<213> ORGANISM: Influenza virus

<400> SEQUENCE: 19

Met Lys Val Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Leu Leu Glu Asn Ser His Asn Gly Lys Leu Cys Leu Leu Lys Gly Ile
    50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Lys Glu Ser Trp Ser Tyr Ile
                85                  90                  95
Val Glu Lys Pro Asn Pro Glu Asn Gly Thr Cys Tyr Pro Gly His Phe
            100                 105                 110
Ala Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Asn His Thr
    130                 135                 140
Val Thr Gly Val Ser Ala Ser Cys Ser His Asn Gly Glu Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
            180                 185                 190
Trp Gly Val His His Pro Pro Asp Ile Gly Asp Gln Lys Thr Leu Tyr
        195                 200                 205
His Thr Glu Asn Ala Tyr Val Ser Val Val Ser Ser His Tyr Ser Arg
    210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Leu Ser Arg Gly Phe Gly Ser Gly Ile Ile Asn Ser Asn Ala Pro Met
        275                 280                 285
Asp Lys Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
```

```
Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 20
<211> LENGTH: 577
<212> TYPE: PRT
<213> ORGANISM: Influenza virus

<400> SEQUENCE: 20

Ala Lys Ala Gly Val Gln Ser Val Lys Met Glu Lys Ile Val Leu Leu
1               5                   10                  15

Phe Ala Ile Val Ser Leu Val Lys Ser Asp Gln Ile Cys Ile Gly Tyr
            20                  25                  30

His Ala Asn Asn Ser Thr Glu Gln Val Asp Thr Ile Met Glu Lys Asn
        35                  40                  45

Val Thr Val Thr His Ala Gln Asp Ile Leu Glu Lys Thr His Asn Gly
    50                  55                  60

Lys Leu Cys Asp Leu Asp Gly Val Lys Pro Leu Ile Leu Arg Asp Cys
65                  70                  75                  80

Ser Val Ala Gly Trp Leu Leu Gly Asn Pro Met Cys Asp Glu Phe Ile
                85                  90                  95

Asn Val Pro Glu Trp Ser Tyr Ile Val Glu Lys Ala Asn Pro Val Asn
            100                 105                 110

Asp Leu Cys Tyr Pro Gly Asp Phe Asn Asp Tyr Glu Glu Leu Lys His
```

```
              115                 120                 125
Leu Leu Ser Arg Ile Asn His Phe Glu Lys Ile Gln Ile Ile Pro Lys
            130                 135                 140
Ser Ser Trp Ser Ser His Glu Ala Ser Leu Gly Val Ser Ser Ala Cys
145                 150                 155                 160
Pro Tyr Gln Gly Lys Ser Ser Phe Phe Arg Asn Val Val Trp Leu Ile
                165                 170                 175
Lys Lys Asn Ser Thr Tyr Pro Thr Ile Lys Arg Ser Tyr Asn Asn Thr
            180                 185                 190
Asn Gln Glu Asp Leu Leu Val Leu Trp Gly Ile His His Pro Asn Asp
            195                 200                 205
Ala Ala Glu Gln Thr Lys Leu Tyr Gln Asn Pro Thr Thr Tyr Ile Ser
            210                 215                 220
Val Gly Thr Ser Thr Leu Asn Gln Arg Leu Val Pro Arg Ile Ala Thr
225                 230                 235                 240
Arg Ser Lys Val Asn Gly Gln Ser Gly Arg Met Glu Phe Phe Trp Thr
                245                 250                 255
Ile Leu Lys Pro Asn Asp Ala Ile Asn Phe Glu Ser Asn Gly Asn Phe
            260                 265                 270
Ile Ala Pro Glu Tyr Ala Tyr Lys Ile Val Lys Lys Gly Asp Ser Thr
            275                 280                 285
Ile Met Lys Ser Glu Leu Glu Tyr Gly Asn Cys Asn Thr Lys Cys Gln
            290                 295                 300
Thr Pro Met Gly Ala Ile Asn Ser Ser Met Pro Phe His Asn Ile His
305                 310                 315                 320
Pro Leu Thr Ile Gly Glu Cys Pro Lys Tyr Val Lys Ser Asn Arg Leu
                325                 330                 335
Val Leu Ala Thr Gly Leu Arg Asn Ser Pro Gln Arg Glu Arg Arg Arg
            340                 345                 350
Lys Lys Arg Gly Leu Phe Gly Ala Ile Ala Gly Phe Ile Glu Gly Gly
            355                 360                 365
Trp Gln Gly Met Val Asp Gly Trp Tyr Gly Tyr His His Ser Asn Glu
            370                 375                 380
Gln Gly Ser Gly Tyr Ala Ala Asp Lys Glu Ser Thr Gln Lys Ala Ile
385                 390                 395                 400
Asp Gly Val Thr Asn Lys Val Asn Ser Ile Ile Asp Lys Met Asn Thr
                405                 410                 415
Gln Phe Glu Ala Val Gly Arg Glu Phe Asn Asn Leu Glu Arg Arg Ile
            420                 425                 430
Glu Asn Leu Asn Lys Lys Met Glu Asp Gly Phe Leu Asp Val Trp Thr
            435                 440                 445
Tyr Asn Ala Glu Leu Leu Val Leu Met Glu Asn Glu Arg Thr Leu Asp
            450                 455                 460
Phe His Asp Ser Asn Val Lys Asn Leu Tyr Asp Lys Val Arg Leu Gln
465                 470                 475                 480
Leu Arg Asp Asn Ala Lys Glu Leu Gly Asn Gly Cys Phe Glu Phe Tyr
                485                 490                 495
His Lys Cys Asp Asn Glu Cys Met Glu Ser Val Arg Asn Gly Thr Tyr
            500                 505                 510
Asp Tyr Pro Gln Tyr Ser Glu Glu Ala Arg Leu Lys Arg Glu Glu Ile
            515                 520                 525
Ser Gly Val Lys Leu Glu Ser Ile Gly Ile Tyr Gln Ile Leu Ser Ile
            530                 535                 540
```

```
Tyr Ser Thr Val Ala Ser Ser Leu Ala Leu Ala Leu Met Val Ala Gly
545                 550                 555                 560

Leu Ser Leu Trp Met Cys Ser Asn Gly Ser Leu Gln Cys Arg Ile Cys
            565                 570                 575

Ile

<210> SEQ ID NO 21
<211> LENGTH: 566
<212> TYPE: PRT
<213> ORGANISM: Influenza virus

<400> SEQUENCE: 21

Met Lys Thr Ile Ile Ala Leu Ser Tyr Ile Leu Cys Leu Val Phe Ser
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
    35                  40                  45

Gln Ile Glu Val Thr Asn Ala Thr Glu Leu Val Gln Ser Ser Ser Thr
50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Ser Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Tyr Arg Pro Arg Val Arg
225                 230                 235                 240

Asp Ile Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335
```

-continued

Arg Asn Val Pro Glu Lys Gln Thr Arg Gly Ile Phe Gly Ala Ile Ala
        340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
        370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
        405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
        450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
        485                 490                 495

Ile Arg Asn Gly Thr Tyr Asp His Asp Val Tyr Arg Asp Glu Ala Leu
        500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 22
<211> LENGTH: 567
<212> TYPE: PRT
<213> ORGANISM: Influenza virus

<400> SEQUENCE: 22

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
        20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
        85                  90                  95

Glu Lys Ala Asn Pro Ala Asn Asp Leu Cys Tyr Pro Gly Asn Phe Asn
        100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser

```
            130                 135                 140
Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
                180                 185                 190

Gly Ile His His Ser Asn Asp Ala Ala Glu Gln Thr Lys Leu Tyr Gln
                195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Val Lys Ser Glu Val Glu Tyr Gly
                275                 280                 285

Asn Cys Asn Thr Lys Cys Gln Thr Pro Ile Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335

Pro Leu Arg Glu Arg Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
                370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
                435                 440                 445

Asn Glu Arg Thr Leu Asp Phe His Asp Ser Asn Val Lys Asn Leu Tyr
                450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
                515                 520                 525

Tyr Gln Ile Leu Ser Ile Tyr Ser Thr Val Ala Ser Ser Leu Ala Leu
                530                 535                 540

Ala Ile Met Val Ala Gly Leu Ser Leu Trp Met Cys Ser Asn Gly Ser
545                 550                 555                 560
```

Leu Gln Cys Arg Ile Cys Ile
                565

<210> SEQ ID NO 23
<211> LENGTH: 568
<212> TYPE: PRT
<213> ORGANISM: Influenza virus

<400> SEQUENCE: 23

Met Glu Lys Ile Val Leu Leu Leu Ala Ile Val Ser Leu Val Lys Ser
  1               5                  10                  15

Asp Gln Ile Cys Ile Gly Tyr His Ala Asn Asn Ser Thr Glu Gln Val
             20                  25                  30

Asp Thr Ile Met Glu Lys Asn Val Thr Val Thr His Ala Gln Asp Ile
         35                  40                  45

Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr

```
                    355                 360                 365
Gly Tyr His His Ser Asn Glu Gln Gly Ser Gly Tyr Ala Ala Asp Lys
            370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Ile Arg Asn Gly Thr Tyr Asn Tyr Pro Gln Tyr Ser Glu Glu Ala
            500                 505                 510
Arg Leu Lys Arg Glu Glu Ile Ser Gly Val Lys Leu Glu Ser Ile Gly
        515                 520                 525
Thr Tyr Gln Ile Leu Ser Ile Tyr Ser Thr Val Ala Ser Ser Leu Ala
    530                 535                 540
Leu Ala Ile Met Met Ala Gly Leu Ser Leu Trp Met Cys Ser Asn Gly
545                 550                 555                 560
Ser Leu Gln Cys Arg Ile Cys Ile
                565

<210> SEQ ID NO 24
<211> LENGTH: 560
<212> TYPE: PRT
<213> ORGANISM: Influenza virus

<400> SEQUENCE: 24

Met Glu Arg Ile Val Leu Leu Leu Ala Ile Val Ser Leu Val Lys Ser
1               5                   10                  15
Asp Gln Ile Cys Ile Gly Tyr His Ala Asn Asn Ser Thr Glu Gln Val
            20                  25                  30
Asp Thr Ile Met Glu Lys Asn Val Thr Val Thr His Ala Gln Asp Ile
        35                  40                  45
Leu Glu Lys Thr His Asn Gly Lys Leu Cys Asp Leu Asp Gly Val Lys
    50                  55                  60
Pro Leu Ile Leu Arg Asp Cys Ser Val Ala Gly Trp Leu Leu Gly Asn
65                  70                  75                  80
Pro Met Cys Asp Glu Phe Leu Asn Val Pro Glu Trp Ser Tyr Ile Val
                85                  90                  95
Glu Lys Ile Asn Pro Ala Asn Asp Leu Cys Tyr Pro Gly Asn Phe Asn
            100                 105                 110
Asp Tyr Glu Glu Leu Lys His Leu Leu Ser Arg Ile Asn His Phe Glu
        115                 120                 125
Arg Ile Gln Ile Ile Pro Lys Ser Ser Trp Ser Asp His Glu Ala Ser
    130                 135                 140
Ser Gly Val Ser Ser Ala Cys Pro Tyr Gln Gly Arg Ser Ser Phe Phe
145                 150                 155                 160
```

Arg Asn Val Val Trp Leu Ile Lys Lys Asn Asn Ala Tyr Pro Thr Ile
            165                 170                 175

Lys Arg Ser Tyr Asn Asn Thr Asn Gln Glu Asp Leu Leu Val Leu Trp
        180                 185                 190

Gly Ile His His Pro Asn Asp Ala Ala Glu Gln Thr Arg Leu Tyr Gln
    195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Asn
            260                 265                 270

Cys Gln Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

<210> SEQ ID NO 25
<211> LENGTH: 568
<212> TYPE: PRT

<213> ORGANISM: Influenza virus

<400> SEQUENCE: 25

```
Met Glu Lys Ile Val Leu Leu Phe Ala

-continued

```
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Arg Asn Gly Thr Tyr Asp Tyr Pro Gln Tyr Ser Glu Glu Ala
            500                 505                 510
Arg Leu Lys Arg Glu Glu Ile Ser Gly Val Lys Leu Glu Ser Ile Gly
        515                 520                 525
Ile Tyr Gln Ile Leu Ser Ile Tyr Ser Thr Val Ala Ser Ser Leu Ala
    530                 535                 540
Leu Ala Ile Met Val Ala Gly Leu Ser Leu Trp Met Cys Ser Asn Gly
545                 550                 555                 560
Ser Leu Gln Cys Arg Ile Cys Ile
                565

<210> SEQ ID NO 26
<211> LENGTH: 584
<212> TYPE: PRT
<213> ORGANISM: Influenza virus

<400> SEQUENCE: 26

Met Lys Ala Ile Ile Val Leu Leu Met Val Val Thr Ser Asn Ala Asp
  1               5                  10                  15
Arg Ile Cys Thr Gly Ile Thr Ser Ser Asn Ser Pro His Val Val Lys
                20                  25                  30
Thr Ala Thr Gln Gly Glu Val Asn Val Thr Gly Val Ile Pro Leu Thr
            35                  40                  45
Thr Thr Pro Thr Lys Ser Tyr Phe Ala Asn Leu Lys Gly Thr Lys Thr
        50                  55                  60
Arg Gly Lys Leu Cys Pro Asp Cys Leu Asn Cys Thr Asp Leu Asp Val
65                  70                  75                  80
Ala Leu Gly Arg Pro Met Cys Val Gly Thr Thr Pro Ser Ala Lys Ala
                85                  90                  95
Ser Ile Leu His Glu Val Arg Pro Val Thr Ser Gly Cys Phe Pro Ile
                100                 105                 110
Met His Asp Arg Thr Lys Ile Arg Gln Leu Ala Asn Leu Leu Arg Gly
            115                 120                 125
Tyr Glu Asn Ile Arg Leu Ser Thr Gln Asn Val Ile Asp Ala Glu Lys
        130                 135                 140
Ala Pro Gly Gly Pro Tyr Arg Leu Gly Thr Ser Gly Ser Cys Pro Asn
145                 150                 155                 160
Ala Thr Ser Lys Ser Gly Phe Phe Ala Thr Met Ala Trp Ala Val Pro
                165                 170                 175
Lys Asp Asn Asn Lys Asn Ala Thr Asn Pro Leu Thr Val Glu Val Pro
            180                 185                 190
Tyr Ile Cys Thr Glu Gly Glu Asp Gln Ile Thr Val Trp Gly Phe His
        195                 200                 205
```

```
Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
            245                 250                 255

Ser Gly Arg Ile Val Val Asp Tyr Met Met Gln Lys Pro Gly Lys Thr
        260                 265                 270

Gly Thr Ile Val Tyr Gln Arg Gly Val Leu Leu Pro Gln Lys Val Trp
    275                 280                 285

Cys Ala Ser Gly Arg Ser Lys Val Ile Lys Gly Ser Leu Pro Leu Ile
290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 27
<211> LENGTH: 565
<212> TYPE: PRT
<213> ORGANISM: Influenza virus
```

```
<400> SEQUENCE: 27

Met Lys Val Lys Leu Leu Val Leu Leu Cys Thr Phe Thr Ala Thr Tyr
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415
```

Glu Arg Arg Met Glu Asn Leu Asn Lys Lys Val Asp Gly Phe Ile
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 28
<211> LENGTH: 548
<212> TYPE: PRT
<213> ORGANISM: Influenza virus

<400> SEQUENCE: 28

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Glu Ile Cys Asp Ser Pro His Gln Ile Leu Asp Gly Glu Asn Cys
        50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asn Glu Ser Phe Asn Trp Thr
            115                 120                 125

Gly Val Thr Gln Asn Gly Thr Ser Ser Ala Cys Ile Arg Arg Ser Asn
        130                 135                 140

Asn Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Asn Asp Gln Ile
                180                 185                 190

Phe Pro Tyr Ala Gln Ala Ser Gly Arg Ile Thr Val Ser Thr Lys Arg
            195                 200                 205

Ser Gln Gln Thr Val Ile Pro Asn Ile Gly Ser Arg Pro Arg Val Arg

```
                210                 215                 220
Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Ile Gly Gln Ala Ala Asp Leu Lys
        355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Tyr Lys
            500                 505                 510

Asp Trp Ile Leu Trp Ile Ser Phe Ala Ile Ser Cys Phe Leu Leu Cys
        515                 520                 525

Val Ala Leu Leu Gly Phe Ile Met Trp Ala Cys Gln Lys Gly Asn Ile
    530                 535                 540

Arg Cys Asn Ile
545

<210> SEQ ID NO 29
<211> LENGTH: 584
<212> TYPE: PRT
<213> ORGANISM: Influenza virus

<400> SEQUENCE: 29

Met Lys Ala Ile Ile Val Leu Leu Met Val Val Thr Ser Asn Ala Asp
  1               5                  10                  15

Arg Ile Cys Thr Gly Ile Thr Ser Ser Asn Ser Pro His Val Val Lys
            20                  25                  30
```

```
Thr Ala Thr Gln Gly Glu Val Asn Val Thr Gly Val Ile Pro Leu Thr
            35                  40                  45
Thr Thr Pro Thr Lys Ser Tyr Phe Ala Asn Leu Lys Gly Thr Arg Thr
 50                  55                  60
Arg Gly Lys Leu Cys Pro Asp Cys Leu Asn Cys Thr Asp Leu Asp Val
 65                  70                  75                  80
Ala Leu Gly Arg Pro Met Cys Val Gly Thr Thr Pro Ser Ala Lys Ala
                 85                  90                  95
Ser Ile Leu His Glu Val Lys Pro Val Thr Ser Gly Cys Phe Pro Ile
            100                 105                 110
Met His Asp Arg Thr Lys Ile Arg Gln Leu Pro Asn Leu Leu Arg Gly
        115                 120                 125
Tyr Glu Asn Ile Arg Leu Ser Thr Gln Asn Val Ile Asp Ala Glu Lys
130                 135                 140
Ala Pro Gly Gly Pro Tyr Arg Leu Gly Thr Ser Gly Ser Cys Pro Asn
145                 150                 155                 160
Ala Thr Ser Lys Ser Gly Phe Phe Ala Thr Met Ala Trp Ala Val Pro
                165                 170                 175
Lys Asp Asn Asn Lys Asn Ala Thr Asn Pro Leu Thr Val Glu Val Pro
            180                 185                 190
Tyr Ile Cys Thr Glu Gly Glu Asp Gln Ile Thr Val Trp Gly Phe His
        195                 200                 205
Ser Asp Asp Lys Thr Gln Met Lys Asn Leu Tyr Gly Asp Ser Asn Pro
210                 215                 220
Gln Lys Phe Thr Ser Ala Asn Gly Val Thr Thr His Tyr Val Ser
225                 230                 235                 240
Gln Ile Gly Ser Phe Pro Asp Gln Thr Glu Asp Gly Gly Leu Pro Gln
                245                 250                 255
Ser Gly Arg Ile Val Val Asp Tyr Met Met Gln Lys Pro Gly Lys Thr
            260                 265                 270
Gly Thr Ile Val Tyr Gln Arg Gly Val Leu Leu Pro Gln Lys Val Trp
        275                 280                 285
Cys Ala Ser Gly Arg Ser Lys Val Ile Lys Gly Ser Leu Pro Leu Ile
290                 295                 300
Gly Glu Ala Asp Cys Leu His Glu Lys Tyr Gly Gly Leu Asn Lys Ser
305                 310                 315                 320
Lys Pro Tyr Tyr Thr Gly Glu His Ala Lys Ala Ile Gly Asn Cys Pro
                325                 330                 335
Ile Trp Val Lys Thr Pro Leu Lys Leu Ala Asn Gly Thr Lys Tyr Arg
            340                 345                 350
Pro Pro Ala Lys Leu Leu Lys Glu Arg Gly Phe Phe Gly Ala Ile Ala
        355                 360                 365
Gly Phe Leu Glu Gly Gly Trp Glu Gly Met Ile Ala Gly Trp His Gly
370                 375                 380
Tyr Thr Ser His Gly Ala His Gly Val Ala Val Ala Ala Asp Leu Lys
385                 390                 395                 400
Ser Thr Gln Glu Ala Ile Asn Lys Ile Thr Lys Asn Leu Asn Ser Leu
                405                 410                 415
Ser Glu Leu Glu Val Lys Asn Leu Gln Arg Leu Ser Gly Ala Met Asp
            420                 425                 430
Glu Leu His Asn Glu Ile Leu Glu Leu Asp Glu Lys Val Asp Asp Leu
        435                 440                 445
Arg Ala Asp Thr Ile Ser Ser Gln Ile Glu Leu Ala Val Leu Leu Ser
```

```
                 450                 455                 460
Asn Glu Gly Ile Ile Asn Ser Glu Asp Glu His Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
            515                 520                 525

Asp Ser Leu Asn Ile Thr Ala Ala Ser Leu Asn Asp Asp Gly Leu Asp
            530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 30
<211> LENGTH: 586
<212> TYPE: PRT
<213> ORGANISM: Influenza virus

<400> SEQUENCE: 30

Met Lys Ala Ile Ile Val Leu Leu Met Val Val Thr Ser Asn Ala Asp
1               5                   10                  15

Arg Ile Ile Cys Thr Gly Ile Thr Ser Ser Asn Ser Pro His Val Val
                20                  25                  30

Lys Thr Ala Thr Gln Gly Glu Val Asn Val Thr Gly Val Ile Pro Leu
            35                  40                  45

Thr Thr Thr Pro Thr Lys Ser His Phe Ala Asn Leu Lys Gly Thr Glu
        50                  55                  60

Thr Arg Gly Lys Leu Cys Pro Lys Cys Leu Asn Cys Thr Asp Leu Asp
65                  70                  75                  80

Val Ala Leu Gly Arg Pro Lys Cys Thr Gly Asn Ile Pro Ser Ala Arg
                85                  90                  95

Val Ser Ile Leu His Glu Val Arg Pro Val Thr Ser Gly Cys Phe Pro
            100                 105                 110

Ile Met His Asp Arg Thr Lys Ile Arg Gln Leu Pro Asn Leu Leu Arg
        115                 120                 125

Gly Tyr Glu His Ile Arg Leu Ser Thr His Asn Val Ile Asn Ala Glu
    130                 135                 140

Asn Ala Pro Gly Gly Pro Tyr Lys Ile Gly Thr Ser Gly Ser Cys Pro
145                 150                 155                 160

Asn Val Thr Asn Gly Asn Gly Phe Phe Ala Thr Met Ala Trp Ala Val
                165                 170                 175

Pro Lys Asn Asp Asn Asn Lys Thr Ala Thr Asn Ser Leu Thr Ile Glu
            180                 185                 190

Val Pro Tyr Ile Cys Thr Glu Gly Glu Asp Gln Ile Thr Val Trp Gly
        195                 200                 205

Phe His Ser Asp Asn Glu Thr Gln Met Ala Lys Leu Tyr Gly Asp Ser
    210                 215                 220

Lys Pro Gln Lys Phe Thr Ser Ser Ala Asn Gly Val Thr Thr His Tyr
225                 230                 235                 240
```

```
Val Ser Gln Ile Gly Gly Phe Pro Asn Gln Thr Glu Asp Gly Gly Leu
            245                 250                 255
Pro Gln Ser Gly Arg Ile Val Val Asp Tyr Met Val Gln Lys Ser Gly
        260                 265                 270
Lys Thr Gly Thr Ile Thr Tyr Gln Arg Gly Ile Leu Leu Pro Gln Lys
    275                 280                 285
Val Trp Cys Ala Ser Gly Arg Ser Lys Val Ile Lys Gly Ser Leu Pro
290                 295                 300
Leu Ile Gly Glu Ala Asp Cys Leu His Glu Lys Tyr Gly Gly Leu Asn
305                 310                 315                 320
Lys Ser Lys Pro Tyr Tyr Thr Gly Glu His Ala Lys Ala Ile Gly Asn
                325                 330                 335
Cys Pro Ile Trp Val Lys Thr Pro Leu Lys Leu Ala Asn Gly Thr Lys
            340                 345                 350
Tyr Arg Pro Pro Ala Lys Leu Leu Lys Glu Arg Gly Phe Phe Gly Ala
        355                 360                 365
Ile Ala Gly Phe Leu Glu Gly Gly Trp Glu Gly Met Ile Ala Gly Trp
    370                 375                 380
His Gly Tyr Thr Ser His Gly Ala His Gly Val Ala Val Ala Ala Asp
385                 390                 395                 400
Leu Lys Ser Thr Gln Glu Ala Ile Asn Lys Ile Thr Lys Asn Leu Asn
                405                 410                 415
Ser Leu Ser Glu Leu Glu Val Lys Asn Leu Gln Arg Leu Ser Gly Ala
            420                 425                 430
Met Asp Glu Leu His Asn Glu Ile Leu Glu Leu Asp Glu Lys Val Asp
        435                 440                 445
Asp Leu Arg Ala Asp Thr Ile Ser Ser Gln Ile Glu Leu Ala Val Leu
    450                 455                 460
Leu Ser Asn Glu Gly Ile Ile Asn Ser Glu Asp Glu His Leu Leu Ala
465                 470                 475                 480
Leu Glu Arg Lys Leu Lys Lys Met Leu Gly Pro Ser Ala Val Glu Ile
                485                 490                 495
Gly Asn Gly Cys Phe Glu Thr Lys His Lys Cys Asn Gln Thr Cys Leu
            500                 505                 510
Asp Arg Ile Ala Ala Gly Thr Phe Asp Ala Gly Glu Phe Ser Leu Pro
        515                 520                 525
Thr Phe Asp Ser Leu Asn Ile Thr Ala Ala Ser Leu Asn Asp Asp Gly
    530                 535                 540
Leu Asp Asn His Thr Ile Leu Leu Tyr Tyr Ser Thr Ala Ala Ser Ser
545                 550                 555                 560
Leu Ala Val Thr Leu Met Ile Ala Ile Phe Val Val Tyr Met Val Ser
                565                 570                 575
Arg Asp Asn Val Ser Cys Ser Ile Cys Leu
            580                 585

<210> SEQ ID NO 31
<211> LENGTH: 565
<212> TYPE: PRT
<213> ORGANISM: Influenza virus

<400> SEQUENCE: 31

Met Lys Ala Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
            20                  25                  30
```

```
Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
            130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
            195                 200                 205

His Thr Glu Asn Ala Tyr Val Ser Val Val Ser Ser His Tyr Ser Arg
        210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445
```

```
Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
            485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 32
<211> LENGTH: 565
<212> TYPE: PRT
<213> ORGANISM: Influenza virus

<400> SEQUENCE: 32

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
            85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
            165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Lys Glu Asn Ala Tyr Val Ser Val Val Ser Ser His Tyr Ser Arg
210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
            245                 250                 255
```

```
Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285

Asp Glu Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 33
<211> LENGTH: 566
<212> TYPE: PRT
<213> ORGANISM: Influenza virus

<400> SEQUENCE: 33

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
```

```
            50                  55                  60
Gly Gly Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
                115                 120                 125

Ala Ser Ser Gly Thr Leu Glu Phe Asn Asp Glu Ser Phe Asn Trp Thr
130                 135                 140

Gly Val Thr Gln Asn Gly Thr Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
                180                 185                 190

Leu Tyr Ile Trp Gly Val His His Pro Val Thr Asp Asn Asp Gln Ile
                195                 200                 205

Phe Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
                275                 280                 285

Pro Ile Gly Lys Cys Asn Ser Glu Cys Ile Thr Pro Asn Gly Ser Ile
                290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Ile Gly Gln Ala Ala Asp Leu Lys
                370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Arg Thr Lys Lys Gln Leu Arg Glu Asn Ala Glu Asp Met Gly Asn
465                 470                 475                 480
```

```
Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 34
<211> LENGTH: 566
<212> TYPE: PRT
<213> ORGANISM: Influenza virus

<400> SEQUENCE: 34

Met Lys Thr Ile Ile Ala Leu Ser Tyr Ile Leu Cys Leu Val Phe Ser
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65              70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Ala
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Ser Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Tyr Arg Pro Arg Val Arg
225                 230                 235                 240

Asp Ile Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
```

```
                275                 280                 285
Pro Ile Gly Lys Cys Asn Ser Glu Cys Ile Thr Pro Asn Gly Ser Ile
            290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
                355                 360                 365
Phe Arg His Gln Asn Ser Glu Gly Thr Gly Gln Ala Ala Asp Leu Lys
            370                 375                 380
Ser Thr Gln Ala Ala Ile Asn Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
            450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
            530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 35
<211> LENGTH: 569
<212> TYPE: PRT
<213> ORGANISM: Influenza virus

<400> SEQUENCE: 35

Ser Lys Ser Arg Gly Tyr Lys Met Asn Thr Gln Ile Leu Val Phe Ala
1               5                   10                  15
Leu Val Ala Ser Ile Pro Thr Asn Ala Asp Lys Ile Cys Leu Gly His
            20                  25                  30
His Ala Val Ser Asn Gly Thr Lys Val Asn Thr Leu Thr Glu Arg Gly
                35                  40                  45
Val Glu Val Val Asn Ala Thr Glu Thr Val Glu Arg Thr Asn Val Pro
            50                  55                  60
Arg Ile Cys Ser Lys Gly Lys Arg Thr Val Asp Leu Gly Gln Cys Gly
65                  70                  75                  80
```

Leu Leu Gly Thr Ile Thr Gly Pro Pro Gln Cys Asp Gln Phe Leu Glu
                85                  90                  95

Phe Ser Ala Asp Leu Ile Ile Glu Arg Arg Glu Gly Ser Asp Val Cys
            100                 105                 110

Tyr Pro Gly Lys Phe Val Asn Glu Glu Ala Leu Arg Gln Ile Leu Arg
        115                 120                 125

Glu Ser Gly Gly Ile Asp Lys Glu Thr Met Gly Phe Thr Tyr Ser Gly
    130                 135                 140

Ile Arg Thr Asn Gly Thr Thr Ser Ala Cys Arg Arg Ser Gly Ser Ser
145                 150                 155                 160

Phe Tyr Ala Glu Met Lys Trp Leu Leu Ser Asn Thr Asp Asn Ala Ala
                165                 170                 175

Phe Pro Gln Met Thr Lys Ser Tyr Lys Asn Thr Arg Lys Asp Pro Ala
            180                 185                 190

Leu Ile Ile Trp Gly Ile His His Ser Gly Ser Thr Thr Glu Gln Thr
        195                 200                 205

Lys Leu Tyr Gly Ser Gly Asn Lys Leu Ile Thr Val Gly Ser Ser Asn
    210                 215                 220

Tyr Gln Gln Ser Phe Val Pro Ser Pro Gly Ala Arg Pro Gln Val Asn
225                 230                 235                 240

Gly Gln Ser Gly Arg Ile Asp Phe His Trp Leu Ile Leu Asn Pro Asn
                245                 250                 255

Asp Thr Val Thr Phe Ser Phe Asn Gly Ala Phe Ile Ala Pro Asp Arg
            260                 265                 270

Ala Ser Phe Leu Arg Gly Lys Ser Met Gly Ile Gln Ser Glu Val Gln
        275                 280                 285

Val Asp Ala Asn Cys Glu Gly Asp Cys Tyr His Ser Gly Gly Thr Ile
    290                 295                 300

Ile Ser Asn Leu Pro Phe Gln Asn Ile Asn Ser Arg Ala Val Gly Lys
305                 310                 315                 320

Cys Pro Arg Tyr Val Lys Gln Glu Ser Leu Leu Leu Ala Thr Gly Met
                325                 330                 335

Lys Asn Val Pro Glu Ile Pro Lys Arg Arg Arg Arg Gly Leu Phe Gly
            340                 345                 350

Ala Ile Ala Gly Phe Ile Glu Asn Gly Trp Glu Gly Leu Ile Asp Gly
        355                 360                 365

Trp Tyr Gly Phe Arg His Gln Asn Ala Gln Gly Glu Gly Thr Ala Ala
    370                 375                 380

Asp Tyr Lys Ser Thr Gln Ser Ala Ile Asp Gln Ile Thr Gly Lys Leu
385                 390                 395                 400

Asn Arg Leu Ile Glu Lys Thr Asn Gln Gln Phe Glu Leu Ile Asp Asn
                405                 410                 415

Glu Phe Thr Glu Val Glu Arg Gln Ile Gly Asn Val Ile Asn Trp Thr
            420                 425                 430

Arg Asp Ser Met Thr Glu Val Trp Ser Tyr Asn Ala Glu Leu Leu Val
        435                 440                 445

Ala Met Glu Asn Gln His Thr Ile Asp Leu Ala Asp Ser Glu Met Asn
    450                 455                 460

Lys Leu Tyr Glu Arg Val Lys Arg Gln Leu Arg Glu Asn Ala Glu Glu
465                 470                 475                 480

Asp Gly Thr Gly Cys Phe Glu Ile Phe His Lys Cys Asp Asp Asp Cys
                485                 490                 495

Met Ala Ser Ile Arg Asn Asn Thr Tyr Asp His Ser Lys Tyr Arg Glu

```
                    500                 505                 510
Glu Ala Ile Gln Asn Arg Ile Gln Ile Asp Pro Val Lys Leu Ser Ser
                515                 520                 525

Gly Tyr Lys Asp Val Ile Leu Trp Phe Ser Phe Gly Ala Ser Cys Phe
530                 535                 540

Ile Leu Leu Ala Ile Ala Met Gly Leu Val Phe Ile Cys Val Lys Asn
545                 550                 555                 560

Gly Asn Met Arg Cys Thr Ile Cys Ile
                565

<210> SEQ ID NO 36
<211> LENGTH: 334
<212> TYPE: PRT
<213> ORGANISM: Clostridium thermocellum

<400> SEQUENCE: 36

Met Lys Asn Arg Val Ile Ser Leu Leu Met Ala Ser Leu Leu Leu Val
1               5                   10                  15

Leu Ser Val Ile Val Ala Pro Phe Tyr Lys Ala Glu Ala Ala Thr Val
                20                  25                  30

Val Asn Thr Pro Phe Val Ala Val Phe Ser Asn Phe Asp Ser Ser Gln
            35                  40                  45

Trp Glu Lys Ala Asp Trp Ala Asn Gly Ser Val Phe Asn Cys Val Trp
    50                  55                  60

Lys Pro Ser Gln Val Thr Phe Ser Asn Gly Lys Met Ile Leu Thr Leu
65                  70                  75                  80

Asp Arg Glu Tyr Gly Gly Ser Tyr Pro Tyr Lys Ser Gly Glu Tyr Arg
                85                  90                  95

Thr Lys Ser Phe Phe Gly Tyr Gly Tyr Tyr Glu Val Arg Met Lys Ala
                100                 105                 110

Ala Lys Asn Val Gly Ile Val Ser Ser Phe Phe Thr Tyr Thr Gly Pro
            115                 120                 125

Ser Asp Asn Asn Pro Trp Asp Glu Ile Asp Ile Glu Phe Leu Gly Lys
        130                 135                 140

Asp Thr Thr Lys Val Gln Phe Asn Trp Tyr Lys Asn Gly Val Gly Gly
145                 150                 155                 160

Asn Glu Tyr Leu His Asn Leu Gly Phe Asp Ala Ser Gln Asp Phe His
                165                 170                 175

Thr Tyr Gly Phe Glu Trp Arg Pro Asp Tyr Ile Asp Phe Tyr Val Asp
                180                 185                 190

Gly Lys Lys Val Tyr Arg Gly Thr Arg Asn Ile Pro Val Thr Pro Gly
        195                 200                 205

Lys Ile Met Met Asn Leu Trp Pro Gly Ile Gly Val Asp Glu Trp Leu
210                 215                 220

Gly Arg Tyr Asp Gly Arg Thr Pro Leu Gln Ala Glu Tyr Glu Tyr Val
225                 230                 235                 240

Lys Tyr Tyr Pro Asn Gly Val Pro Gln Asp Asn Pro Thr Pro Thr Pro
                245                 250                 255

Thr Ile Ala Pro Ser Thr Pro Thr Asn Pro Asn Leu Pro Leu Lys Gly
                260                 265                 270

Asp Val Asn Gly Asp Gly His Val Asn Ser Ser Asp Tyr Ser Leu Phe
            275                 280                 285

Lys Arg Tyr Leu Leu Arg Val Ile Asp Arg Phe Pro Val Gly Asp Gln
        290                 295                 300
```

```
Ser Val Ala Asp Val Asn Arg Asp Gly Arg Ile Asp Ser Thr Asp Leu
305                 310                 315                 320

Thr Met Leu Lys Arg Tyr Leu Ile Arg Ala Ile Pro Ser Leu
                325                 330
```

<210> SEQ ID NO 37
<211> LENGTH: 259
<212> TYPE: PRT
<213> ORGANISM: Brevibacillus brevis

<400> SEQUENCE: 37

```
Met Val Lys Ser Lys Tyr Leu Val Phe Ile Ser Val Phe Ser Leu Leu
1               5                   10                  15

Phe Gly Val Phe Val Gly Phe Ser His Gln Gly Val Lys Ala Glu
                20                  25                  30

Glu Glu Arg Pro Met Gly Thr Ala Phe Tyr Glu Ser Phe Asp Ala Phe
                35                  40                  45

Asp Asp Glu Arg Trp Ser Lys Ala Gly Val Trp Thr Asn Gly Gln Met
            50                  55                  60

Phe Asn Ala Thr Trp Tyr Pro Glu Gln Val Thr Ala Asp Gly Leu Met
65                  70                  75                  80

Arg Leu Thr Ile Ala Lys Lys Thr Thr Ser Ala Arg Asn Tyr Lys Ala
                85                  90                  95

Gly Glu Leu Arg Thr Asn Asp Phe Tyr His Tyr Gly Leu Phe Glu Val
                100                 105                 110

Ser Met Lys Pro Ala Lys Val Glu Gly Thr Val Ser Ser Phe Phe Thr
                115                 120                 125

Tyr Thr Gly Glu Trp Asp Trp Asp Gly Asp Pro Trp Asp Glu Ile Asp
130                 135                 140

Ile Glu Phe Leu Gly Lys Asp Thr Thr Arg Ile Gln Phe Asn Tyr Phe
145                 150                 155                 160

Thr Asn Gly Val Gly Gly Asn Glu Phe Tyr Tyr Asp Leu Gly Phe Asp
                165                 170                 175

Ala Ser Glu Ser Phe Asn Thr Tyr Ala Phe Glu Trp Arg Glu Asp Ser
                180                 185                 190

Ile Thr Trp Tyr Val Asn Gly Glu Ala Val His Thr Ala Thr Glu Asn
                195                 200                 205

Ile Pro Gln Thr Pro Gln Lys Ile Met Met Asn Leu Trp Pro Gly Val
                210                 215                 220

Gly Val Asp Gly Trp Thr Gly Val Phe Asp Gly Asp Asn Thr Pro Val
225                 230                 235                 240

Tyr Ser Tyr Tyr Asp Trp Val Arg Tyr Thr Pro Leu Gln Asn Tyr Gln
                245                 250                 255

Ile His Gln
```

<210> SEQ ID NO 38
<211> LENGTH: 349
<212> TYPE: PRT
<213> ORGANISM: Fibrobacter succinogenes

<400> SEQUENCE: 38

```
Met Asn Ile Lys Lys Thr Ala Val Lys Ser Ala Leu Ala Val Ala Ala
1               5                   10                  15

Ala Ala Ala Ala Leu Thr Thr Asn Val Ser Ala Lys Asp Phe Ser Gly
                20                  25                  30

Ala Glu Leu Tyr Thr Leu Glu Glu Val Gln Tyr Gly Lys Phe Glu Ala
```

```
              35                  40                  45
Arg Met Lys Met Ala Ala Ser Gly Thr Val Ser Ser Met Phe Leu
 50                  55                  60

Tyr Gln Asn Gly Ser Glu Ile Ala Asp Gly Arg Pro Trp Val Glu Val
 65                  70                  75                  80

Asp Ile Glu Val Leu Gly Lys Asn Pro Gly Ser Phe Gln Ser Asn Ile
                 85                  90                  95

Ile Thr Gly Lys Ala Gly Ala Gln Lys Thr Ser Glu Lys His His Ala
            100                 105                 110

Val Ser Pro Ala Ala Asp Gln Ala Phe His Thr Tyr Gly Leu Glu Trp
        115                 120                 125

Thr Pro Asn Tyr Val Arg Trp Thr Val Asp Gly Gln Glu Val Arg Lys
    130                 135                 140

Thr Glu Gly Gly Gln Val Ser Asn Leu Thr Gly Thr Gln Gly Leu Arg
145                 150                 155                 160

Phe Asn Leu Trp Ser Ser Glu Ser Ala Ala Trp Val Gly Gln Phe Asp
                165                 170                 175

Glu Ser Lys Leu Pro Leu Phe Gln Phe Ile Asn Trp Val Lys Val Tyr
            180                 185                 190

Lys Tyr Thr Pro Gly Gln Gly Glu Gly Gly Ser Asp Phe Thr Leu Asp
        195                 200                 205

Trp Thr Asp Asn Phe Asp Thr Phe Asp Gly Ser Arg Trp Gly Lys Gly
    210                 215                 220

Asp Trp Thr Phe Asp Gly Asn Arg Val Asp Leu Thr Asp Lys Asn Ile
225                 230                 235                 240

Tyr Ser Arg Asp Gly Met Leu Ile Leu Ala Leu Thr Arg Lys Gly Gln
                245                 250                 255

Glu Ser Phe Asn Gly Gln Val Pro Arg Asp Asp Glu Pro Ala Pro Gln
            260                 265                 270

Ser Ser Ser Ser Ala Pro Ala Ser Ser Ser Val Pro Ala Ser Ser
        275                 280                 285

Ser Ser Val Pro Ala Ser Ser Ser Ala Phe Val Pro Pro Ser Ser
    290                 295                 300

Ser Ser Ala Thr Asn Ala Ile His Gly Met Arg Thr Thr Pro Ala Val
305                 310                 315                 320

Ala Lys Glu His Arg Asn Leu Val Asn Ala Lys Gly Ala Lys Val Asn
                325                 330                 335

Pro Asn Gly His Lys Arg Tyr Arg Val Asn Phe Glu His
            340                 345

<210> SEQ ID NO 39
<211> LENGTH: 309
<212> TYPE: PRT
<213> ORGANISM: Streptomyces coelicolor

<400> SEQUENCE: 39

Met Val Asn Arg Arg Asp Leu Ile Lys Trp Ser Ala Val Ala Leu Gly
  1               5                  10                  15

Ala Gly Ala Gly Leu Ala Gly Pro Ala Pro Ala Ala His Ala Ala Asp
                 20                  25                  30

Leu Glu Trp Glu Gln Tyr Pro Val Pro Ala Ala Pro Gly Gly Asn Arg
            35                  40                  45

Ser Trp Gln Leu Leu Pro Ser His Ser Asp Asp Phe Asn Tyr Thr Gly
 50                  55                  60
```

```
Lys Pro Gln Thr Phe Arg Gly Arg Trp Leu Asp Gln His Lys Asp Gly
 65                  70                  75                  80

Trp Ser Gly Pro Ala Asn Ser Leu Tyr Ser Ala Arg His Ser Trp Val
                 85                  90                  95

Ala Asp Gly Asn Leu Ile Val Glu Gly Arg Arg Ala Pro Asp Gly Arg
            100                 105                 110

Val Tyr Cys Gly Tyr Val Thr Ser Arg Thr Pro Val Glu Tyr Pro Leu
        115                 120                 125

Tyr Thr Glu Val Leu Met Arg Val Ser Gly Leu Lys Leu Ser Ser Asn
    130                 135                 140

Phe Trp Leu Leu Ser Arg Asp Asp Val Asn Glu Ile Asp Val Ile Glu
145                 150                 155                 160

Cys Tyr Gly Asn Glu Ser Leu His Gly Lys His Met Asn Thr Ala Tyr
                165                 170                 175

His Ile Phe Gln Arg Asn Pro Phe Thr Glu Leu Ala Arg Ser Gln Lys
            180                 185                 190

Gly Tyr Phe Ala Asp Gly Ser Tyr Gly Tyr Asn Gly Thr Gly Gln
        195                 200                 205

Val Phe Gly Asp Gly Ala Gly Gln Pro Leu Leu Arg Asn Gly Phe His
    210                 215                 220

Arg Tyr Gly Val His Trp Ile Ser Ala Thr Glu Phe Asp Phe Tyr Phe
225                 230                 235                 240

Asn Gly Arg Leu Val Arg Arg Leu Asn Arg Ser Asn Asp Leu Arg Asp
                245                 250                 255

Pro Arg Ser Arg Phe Phe Asp Gln Pro Met His Leu Ile Leu Asn Thr
            260                 265                 270

Glu Ser His Gln Trp Arg Val Asp Arg Gly Ile Glu Pro Thr Asp Ala
        275                 280                 285

Glu Leu Ala Asp Pro Ser Ile Asn Asn Ile Tyr Tyr Arg Trp Val Arg
    290                 295                 300

Thr Tyr Gln Ala Val
305
```

<210> SEQ ID NO 40
<211> LENGTH: 682
<212> TYPE: PRT
<213> ORGANISM: Bacillus circulans

<400> SEQUENCE: 40

```
Met Lys Pro Ser His Phe Thr Glu Lys Arg Phe Met Lys Lys Val Leu
 1               5                  10                  15

Gly Leu Phe Leu Val Val Val Met Leu Ala Ser Val Gly Val Leu Pro
                20                  25                  30

Thr Ser Lys Val Gln Ala Ala Gly Thr Thr Val Thr Ser Met Glu Tyr
            35                  40                  45

Phe Ser Pro Ala Asp Gly Pro Val Ile Ser Lys Ser Gly Val Gly Lys
        50                  55                  60

Ala Ser Tyr Gly Phe Val Met Pro Lys Phe Asn Gly Gly Ser Ala Thr
 65                  70                  75                  80

Trp Asn Asp Val Tyr Ser Asp Val Gly Val Asn Val Lys Val Gly Asn
                 85                  90                  95

Asn Trp Val Asp Ile Asp Gln Ala Gly Gly Tyr Ile Tyr Asn Gln Asn
            100                 105                 110

Trp Gly His Trp Ser Asp Gly Gly Phe Asn Gly Tyr Trp Phe Thr Leu
        115                 120                 125
```

```
Ser Ala Thr Thr Glu Ile Gln Leu Tyr Ser Lys Ala Asn Gly Val Lys
        130                 135                 140

Leu Glu Tyr Gln Leu Val Phe Gln Asn Ile Asn Lys Thr Thr Ile Thr
145                 150                 155                 160

Ala Met Asn Pro Thr Gln Gly Pro Gln Ile Thr Ala Ser Phe Thr Gly
                165                 170                 175

Gly Ala Gly Phe Thr Tyr Pro Thr Phe Asn Asn Asp Ser Ala Val Thr
                180                 185                 190

Tyr Glu Ala Val Ala Asp Asp Leu Lys Val Tyr Val Lys Pro Val Asn
        195                 200                 205

Ser Ser Ser Trp Ile Asp Ile Asp Asn Asn Ala Ala Ser Gly Trp Ile
210                 215                 220

Tyr Asp His Asn Phe Gly Gln Phe Thr Asp Gly Gly Gly Tyr Trp
225                 230                 235                 240

Phe Asn Val Thr Glu Ser Ile Asn Val Lys Leu Glu Ser Lys Thr Ser
                245                 250                 255

Ser Ala Asn Leu Val Tyr Thr Ile Thr Phe Asn Glu Pro Thr Arg Asn
                260                 265                 270

Ser Tyr Val Ile Thr Pro Tyr Glu Gly Thr Thr Phe Thr Ala Asp Ala
                275                 280                 285

Asn Gly Ser Ile Gly Ile Pro Leu Pro Lys Ile Asp Gly Gly Ala Pro
290                 295                 300

Ile Ala Lys Glu Leu Gly Asn Phe Val Tyr Gln Ile Asn Ile Asn Gly
305                 310                 315                 320

Gln Trp Val Asp Leu Ser Asn Ser Ser Gln Ser Lys Phe Ala Tyr Ser
                325                 330                 335

Ala Asn Gly Tyr Asn Asn Met Ser Asp Ala Asn Gln Trp Gly Tyr Trp
                340                 345                 350

Ala Asp Tyr Ile Tyr Gly Leu Trp Phe Gln Pro Ile Gln Glu Asn Met
        355                 360                 365

Gln Ile Arg Ile Gly Tyr Pro Leu Asn Gly Gln Ala Gly Gly Asn Ile
        370                 375                 380

Gly Asn Asn Phe Val Asn Tyr Thr Phe Ile Gly Asn Pro Asn Ala Pro
385                 390                 395                 400

Arg Pro Asp Val Ser Asp Gln Glu Asp Ile Ser Ile Gly Thr Pro Thr
                405                 410                 415

Asp Pro Ala Ile Ala Gly Met Asn Leu Ile Trp Gln Asp Glu Phe Asn
                420                 425                 430

Gly Thr Thr Leu Asp Thr Ser Lys Trp Asn Tyr Glu Thr Gly Tyr Tyr
        435                 440                 445

Leu Asn Asn Asp Pro Ala Thr Trp Gly Trp Gly Asn Ala Glu Leu Gln
450                 455                 460

His Tyr Thr Asn Ser Thr Gln Asn Val Tyr Val Gln Asp Gly Lys Leu
465                 470                 475                 480

Asn Ile Lys Ala Met Asn Asp Ser Lys Ser Phe Pro Gln Asp Pro Asn
                485                 490                 495

Arg Tyr Ala Gln Tyr Ser Ser Gly Lys Ile Asn Thr Lys Asp Lys Leu
                500                 505                 510

Ser Leu Lys Tyr Gly Arg Val Asp Phe Arg Ala Lys Leu Pro Thr Gly
        515                 520                 525

Asp Gly Val Trp Pro Ala Leu Trp Met Leu Pro Lys Asp Ser Val Tyr
530                 535                 540
```

```
Gly Thr Trp Ala Ala Ser Gly Glu Ile Asp Val Met Glu Ala Arg Gly
545                 550                 555                 560

Arg Leu Pro Gly Ser Val Ser Gly Thr Ile His Phe Gly Gly Gln Trp
                565                 570                 575

Pro Val Asn Gln Ser Ser Gly Gly Asp Tyr His Phe Pro Glu Gly Gln
                580                 585                 590

Thr Phe Ala Asn Asp Tyr His Val Tyr Ser Val Val Trp Glu Glu Asp
            595                 600                 605

Asn Ile Lys Trp Tyr Val Asp Gly Lys Phe Phe Tyr Lys Val Thr Asn
            610                 615                 620

Gln Gln Trp Tyr Ser Thr Ala Ala Pro Asn Asn Pro Asn Ala Pro Phe
625                 630                 635                 640

Asp Glu Pro Phe Tyr Leu Ile Met Asn Leu Ala Val Gly Gly Asn Phe
                645                 650                 655

Asp Gly Gly Arg Thr Pro Asn Ala Ser Asp Ile Pro Ala Thr Met Gln
                660                 665                 670

Val Asp Tyr Val Arg Val Tyr Lys Glu Gln
                675                 680

<210> SEQ ID NO 41
<211> LENGTH: 243
<212> TYPE: PRT
<213> ORGANISM: Bacillus licheniformis

<400> SEQUENCE: 41

Met Ser Tyr Arg Val Lys Arg Met Leu Met Leu Leu Val Thr Gly Leu
1               5                   10                  15

Phe Leu Ser Leu Ser Thr Phe Ala Ala Ser Ala Ser Ala Gln Thr Gly
                20                  25                  30

Gly Ser Phe Tyr Glu Pro Phe Asn Asn Tyr Asn Thr Gly Leu Trp Gln
            35                  40                  45

Lys Ala Asp Gly Tyr Ser Asn Gly Asn Met Phe Asn Cys Thr Trp Arg
        50                  55                  60

Ala Asn Asn Val Ser Met Thr Ser Leu Gly Glu Met Arg Leu Ser Leu
65                  70                  75                  80

Thr Ser Pro Ser Tyr Asn Lys Phe Asp Cys Gly Glu Asn Arg Ser Val
                85                  90                  95

Gln Thr Tyr Gly Tyr Gly Leu Tyr Glu Val Asn Met Lys Pro Ala Lys
            100                 105                 110

Asn Val Gly Ile Val Ser Ser Phe Phe Thr Tyr Thr Gly Pro Thr Asp
        115                 120                 125

Gly Thr Pro Trp Asp Glu Ile Asp Ile Glu Phe Leu Gly Lys Asp Thr
    130                 135                 140

Thr Lys Val Gln Phe Asn Tyr Tyr Thr Asn Gly Val Gly Asn His Glu
145                 150                 155                 160

Lys Ile Val Asn Leu Gly Phe Asp Ala Ala Asn Ser Tyr His Thr Tyr
                165                 170                 175

Ala Phe Asp Trp Gln Pro Asn Ser Ile Lys Trp Tyr Val Asp Gly Gln
            180                 185                 190

Leu Lys His Thr Ala Thr Thr Gln Ile Pro Gln Thr Pro Gly Lys Ile
        195                 200                 205

Met Met Asn Leu Trp Asn Gly Ala Gly Val Asp Glu Trp Leu Gly Ser
    210                 215                 220

Tyr Asn Gly Val Thr Pro Leu Ser Arg Ser Leu His Trp Val Arg Tyr
225                 230                 235                 240
```

Thr Lys Arg

<210> SEQ ID NO 42
<211> LENGTH: 238
<212> TYPE: PRT
<213> ORGANISM: Paenibacillus polymyxa

<400> SEQUENCE: 42

Met Met Lys Lys Lys Ser Trp Phe Thr Leu Met Ile Thr Gly Val Ile
1               5                   10                  15

Ser Leu Phe Phe Ser Val Ser Ala Phe Ala Gly Asn Val Phe Trp Glu
                20                  25                  30

Pro Leu Ser Tyr Phe Asn Ser Ser Thr Trp Gln Lys Ala Asp Gly Tyr
            35                  40                  45

Ser Asn Gly Gln Met Phe Asn Cys Thr Trp Arg Ala Asn Asn Val Asn
50                  55                  60

Phe Thr Asn Asp Gly Lys Leu Lys Leu Ser Leu Thr Ser Pro Ala Asn
65                  70                  75                  80

Asn Lys Phe Asp Cys Gly Glu Tyr Arg Ser Thr Asn Asn Tyr Gly Tyr
                85                  90                  95

Gly Leu Tyr Glu Val Ser Met Lys Pro Ala Lys Asn Thr Gly Ile Val
            100                 105                 110

Ser Ser Phe Phe Thr Tyr Thr Gly Pro Ser His Gly Thr Gln Trp Asp
            115                 120                 125

Glu Ile Asp Ile Glu Phe Leu Gly Lys Asp Thr Thr Lys Val Gln Phe
130                 135                 140

Asn Tyr Tyr Thr Asn Gly Val Gly Gly His Glu Lys Ile Ile Asn Leu
145                 150                 155                 160

Gly Phe Asp Ala Ser Thr Ser Phe His Thr Tyr Ala Phe Asp Trp Gln
                165                 170                 175

Pro Gly Tyr Ile Lys Trp Tyr Val Asp Gly Val Leu Lys His Thr Ala
            180                 185                 190

Thr Thr Asn Ile Pro Ser Thr Pro Gly Lys Ile Met Met Asn Leu Trp
            195                 200                 205

Asn Gly Thr Gly Val Asp Ser Trp Leu Gly Ser Tyr Asn Gly Ala Asn
    210                 215                 220

Pro Leu Tyr Ala Glu Tyr Asp Trp Val Lys Tyr Thr Ser Asn
225                 230                 235

<210> SEQ ID NO 43
<211> LENGTH: 286
<212> TYPE: PRT
<213> ORGANISM: Rhodothermus marinus

<400> SEQUENCE: 43

Met Cys Thr Met Pro Leu Met Lys Leu Lys Lys Met Met Arg Arg Thr
1               5                   10                  15

Ala Phe Leu Leu Ser Val Leu Ile Gly Cys Ser Met Leu Gly Ser Asp
                20                  25                  30

Arg Ser Asp Lys Ala Pro His Trp Glu Leu Val Trp Ser Asp Glu Phe
            35                  40                  45

Asp Tyr Ser Gly Leu Pro Asp Pro Glu Lys Trp Asp Tyr Asp Val Gly
        50                  55                  60

Gly His Gly Trp Gly Asn Gln Glu Leu Gln Tyr Tyr Thr Arg Ala Arg
65                  70                  75                  80

```
Ile Glu Asn Ala Arg Val Gly Gly Val Leu Ile Glu Ala Arg
                85                  90                  95

His Glu Pro Tyr Glu Gly Arg Glu Tyr Thr Ser Ala Arg Leu Val Thr
            100                 105                 110

Arg Gly Lys Ala Ser Trp Thr Tyr Gly Arg Phe Glu Ile Arg Ala Arg
            115                 120                 125

Leu Pro Ser Gly Arg Gly Thr Trp Pro Ala Ile Trp Met Leu Pro Asp
            130                 135                 140

Arg Gln Thr Tyr Gly Ser Ala Tyr Trp Pro Asp Asn Gly Glu Ile Asp
145                 150                 155                 160

Ile Met Glu His Val Gly Phe Asn Pro Asp Val Val His Gly Thr Val
                165                 170                 175

His Thr Lys Ala Tyr Asn His Leu Leu Gly Thr Gln Arg Gly Gly Ser
            180                 185                 190

Ile Arg Val Pro Thr Ala Arg Thr Asp Phe His Val Tyr Ala Ile Glu
            195                 200                 205

Trp Thr Pro Glu Glu Ile Arg Trp Phe Val Asp Ser Leu Tyr Tyr
            210                 215                 220

Arg Phe Pro Asn Glu Arg Leu Thr Asp Pro Glu Ala Asp Trp Arg His
225                 230                 235                 240

Trp Pro Phe Asp Gln Pro Phe His Leu Ile Met Asn Ile Ala Val Gly
                245                 250                 255

Gly Ala Trp Gly Gly Gln Gln Gly Val Asp Pro Glu Ala Phe Pro Ala
            260                 265                 270

Gln Leu Val Val Asp Tyr Val Arg Val Tyr Arg Trp Val Glu
            275                 280                 285

<210> SEQ ID NO 44
<211> LENGTH: 473
<212> TYPE: PRT
<213> ORGANISM: Thermobispora bispora

<400> SEQUENCE: 44

Met Thr Glu Ser Ala Met Thr Ser Arg Ala Gly Arg Gly Arg Gly Ala
1               5                   10                  15

Asp Leu Val Ala Ala Val Val Gln Gly His Ala Ala Ser Asp Ala
            20                  25                  30

Ala Gly Asp Leu Ser Phe Pro Asp Gly Phe Ile Trp Gly Ala Ala Thr
            35                  40                  45

Ala Ala Tyr Gln Ile Glu Gly Ala Trp Arg Glu Asp Gly Arg Gly Leu
            50                  55                  60

Trp Asp Val Phe Ser His Thr Pro Gly Lys Val Ala Ser Gly His Thr
65                  70                  75                  80

Gly Asp Ile Ala Cys Asp His Tyr His Arg Tyr Ala Asp Asp Val Arg
                85                  90                  95

Leu Met Ala Gly Leu Gly Asp Arg Val Tyr Arg Phe Ser Val Ala Trp
            100                 105                 110

Pro Arg Ile Val Pro Asp Gly Ser Gly Pro Val Asn Pro Ala Gly Leu
            115                 120                 125

Asp Phe Tyr Asp Arg Leu Val Asp Glu Leu Leu Gly His Gly Ile Thr
            130                 135                 140

Pro Tyr Pro Thr Leu Tyr His Trp Asp Leu Pro Gln Thr Leu Glu Asp
145                 150                 155                 160

Arg Gly Gly Trp Ala Ala Arg Asp Thr Ala Tyr Arg Phe Ala Glu Tyr
                165                 170                 175
```

```
Ala Leu Ala Val His Arg Arg Leu Gly Asp Arg Val Arg Cys Trp Ile
            180                 185                 190
Thr Leu Asn Glu Pro Trp Val Ala Ala Phe Leu Ala Thr His Arg Gly
            195                 200                 205
Ala Pro Gly Ala Ala Asp Val Pro Arg Phe Arg Ala Val His His Leu
            210                 215                 220
Leu Leu Gly His Gly Leu Gly Leu Arg Leu Arg Ser Ala Gly Ala Gly
225                 230                 235                 240
Gln Leu Gly Leu Thr Leu Ser Leu Ser Pro Val Ile Glu Ala Arg Pro
                245                 250                 255
Gly Val Arg Gly Gly Arg Arg Val Asp Ala Leu Ala Asn Arg Gln
            260                 265                 270
Phe Leu Asp Pro Ala Leu Arg Gly Arg Tyr Pro Glu Glu Val Leu Lys
            275                 280                 285
Ile Met Ala Gly His Ala Arg Leu Gly His Pro Gly Arg Asp Leu Glu
            290                 295                 300
Thr Ile His Gln Pro Val Asp Leu Leu Gly Val Asn Tyr Tyr Ser His
305                 310                 315                 320
Val Arg Leu Ala Ala Glu Gly Glu Pro Ala Asn Arg Leu Pro Gly Ser
                325                 330                 335
Glu Gly Ile Arg Phe Glu Arg Pro Thr Ala Val Thr Ala Trp Pro Gly
            340                 345                 350
Asp Arg Pro Asp Gly Leu Arg Thr Leu Leu Leu Arg Leu Ser Arg Asp
            355                 360                 365
Tyr Pro Gly Val Gly Leu Ile Ile Thr Glu Asn Gly Ala Ala Phe Asp
            370                 375                 380
Asp Arg Ala Asp Gly Asp Arg Val His Asp Pro Glu Arg Ile Arg Tyr
385                 390                 395                 400
Leu Thr Ala Thr Leu Arg Ala Val His Asp Ala Ile Met Ala Gly Ala
                405                 410                 415
Asp Leu Arg Gly Tyr Phe Val Trp Ser Val Leu Asp Asn Phe Glu Trp
            420                 425                 430
Ala Tyr Gly Tyr His Lys Arg Gly Ile Val Tyr Val Asp Tyr Thr Thr
            435                 440                 445
Met Arg Arg Ile Pro Arg Glu Ser Ala Leu Trp Tyr Arg Asp Val Val
            450                 455                 460
Arg Arg Asn Gly Leu Arg Asn Gly Glu
465                 470

<210> SEQ ID NO 45
<211> LENGTH: 387
<212> TYPE: PRT
<213> ORGANISM: Clostridium stercorarium

<400> SEQUENCE: 45

Met Asn Lys Phe Leu Asn Lys Lys Trp Ser Leu Ile Leu Thr Met Gly
  1               5                  10                  15
Gly Ile Phe Leu Met Ala Thr Leu Ser Leu Ile Phe Ala Thr Gly Lys
            20                  25                  30
Lys Ala Phe Asn Asp Gln Thr Ser Ala Glu Asp Ile Pro Ser Leu Ala
            35                  40                  45
Glu Ala Phe Arg Asp Tyr Phe Pro Ile Gly Ala Ala Ile Glu Pro Gly
            50                  55                  60
Tyr Thr Thr Gly Gln Ile Ala Glu Leu Tyr Lys Lys His Val Asn Met
```

```
            65                  70                  75                  80
Leu Val Ala Glu Asn Ala Met Lys Pro Ala Ser Leu Gln Pro Thr Glu
                85                  90                  95

Gly Asn Phe Gln Trp Ala Asp Ala Asp Arg Ile Val Gln Phe Ala Lys
                100                 105                 110

Glu Asn Gly Met Glu Leu Arg Phe His Thr Leu Val Trp His Asn Gln
                115                 120                 125

Thr Pro Thr Gly Phe Ser Leu Asp Lys Glu Gly Lys Pro Met Val Glu
            130                 135                 140

Glu Thr Asp Pro Gln Lys Arg Glu Glu Asn Arg Lys Leu Leu Leu Gln
145                 150                 155                 160

Arg Leu Glu Asn Tyr Ile Arg Ala Val Val Leu Arg Tyr Lys Asp Asp
                165                 170                 175

Ile Lys Ser Trp Asp Val Val Asn Glu Val Ile Glu Pro Asn Asp Pro
                180                 185                 190

Gly Gly Met Arg Asn Ser Pro Trp Tyr Gln Ile Thr Gly Thr Glu Tyr
                195                 200                 205

Ile Glu Val Ala Phe Arg Ala Thr Arg Glu Ala Gly Gly Ser Asp Ile
            210                 215                 220

Lys Leu Tyr Ile Asn Asp Tyr Asn Thr Asp Asp Pro Val Lys Arg Asp
225                 230                 235                 240

Ile Leu Tyr Glu Leu Val Lys Asn Leu Leu Glu Lys Gly Val Pro Ile
                245                 250                 255

Asp Gly Val Gly His Gln Thr His Ile Asp Ile Tyr Asn Pro Pro Val
                260                 265                 270

Glu Arg Ile Ile Glu Ser Ile Lys Lys Phe Ala Gly Leu Gly Leu Asp
                275                 280                 285

Asn Ile Ile Thr Glu Leu Asp Met Ser Ile Tyr Ser Trp Asn Asp Arg
            290                 295                 300

Ser Asp Tyr Gly Asp Ser Ile Pro Asp Tyr Ile Leu Thr Leu Gln Ala
305                 310                 315                 320

Lys Arg Tyr Gln Glu Leu Phe Asp Ala Leu Lys Glu Asn Lys Asp Ile
                325                 330                 335

Val Ser Ala Val Val Phe Trp Gly Ile Ser Asp Lys Tyr Ser Trp Leu
                340                 345                 350

Asn Gly Phe Pro Val Lys Arg Thr Asn Ala Pro Leu Leu Phe Asp Arg
                355                 360                 365

Asn Phe Met Pro Lys Pro Ala Phe Trp Ala Ile Val Asp Pro Ser Arg
            370                 375                 380

Leu Arg Glu
385

<210> SEQ ID NO 46
<211> LENGTH: 755
<212> TYPE: PRT
<213> ORGANISM: Clostridium thermocellum

<400> SEQUENCE: 46

Met Ala Val Asp Ile Lys Lys Ile Ile Lys Gln Met Thr Leu Glu Glu
  1               5                  10                  15

Lys Ala Gly Leu Cys Ser Gly Leu Asp Phe Trp His Thr Lys Pro Val
                20                  25                  30

Glu Arg Leu Gly Ile Pro Ser Ile Met Met Thr Asp Gly Pro His Gly
            35                  40                  45
```

```
Leu Arg Lys Gln Arg Glu Asp Ala Glu Ile Ala Asp Ile Asn Asn Ser
    50                  55                  60

Val Pro Ala Thr Cys Phe Pro Ser Ala Ala Gly Leu Ala Cys Ser Trp
 65                  70                  75                  80

Asp Arg Glu Leu Val Glu Arg Val Gly Ala Ala Leu Gly Glu Cys
                 85                  90                  95

Gln Ala Glu Asn Val Ser Ile Leu Leu Gly Pro Gly Ala Asn Ile Lys
                100                 105                 110

Arg Ser Pro Leu Cys Gly Arg Asn Phe Glu Tyr Phe Ser Glu Asp Pro
            115                 120                 125

Tyr Leu Ser Ser Glu Leu Ala Ala Ser His Ile Lys Gly Val Gln Ser
    130                 135                 140

Gln Gly Val Gly Ala Cys Leu Lys His Phe Ala Ala Asn Asn Gln Glu
145                 150                 155                 160

His Arg Arg Met Thr Val Asp Thr Ile Val Asp Glu Arg Thr Leu Arg
                165                 170                 175

Glu Ile Tyr Phe Ala Ser Phe Glu Asn Ala Val Lys Lys Ala Arg Pro
            180                 185                 190

Trp Val Val Met Cys Ala Tyr Asn Lys Leu Asn Gly Glu Tyr Cys Ser
    195                 200                 205

Glu Asn Arg Tyr Leu Leu Thr Glu Val Leu Lys Asn Glu Trp Met His
210                 215                 220

Asp Gly Phe Val Val Ser Asp Trp Gly Ala Val Asn Asp Arg Val Ser
225                 230                 235                 240

Gly Leu Asp Ala Gly Leu Asp Leu Glu Met Pro Thr Ser His Gly Ile
                245                 250                 255

Thr Asp Lys Lys Ile Val Glu Ala Val Lys Ser Gly Lys Leu Ser Glu
            260                 265                 270

Asn Ile Leu Asn Arg Ala Val Glu Arg Ile Leu Lys Val Ile Phe Met
            275                 280                 285

Ala Leu Glu Asn Lys Lys Glu Asn Ala Gln Tyr Asp Lys Asp Ala His
    290                 295                 300

His Arg Leu Ala Arg Gln Ala Ala Ala Glu Ser Met Val Leu Leu Lys
305                 310                 315                 320

Asn Glu Asp Asp Val Leu Pro Leu Lys Lys Ser Gly Thr Ile Ala Leu
                325                 330                 335

Ile Gly Ala Phe Val Lys Lys Pro Arg Tyr Gln Gly Ser Gly Ser Ser
                340                 345                 350

His Ile Thr Pro Thr Arg Leu Asp Asp Ile Tyr Glu Glu Ile Lys Lys
            355                 360                 365

Ala Gly Gly Asp Lys Val Asn Leu Val Tyr Ser Glu Gly Tyr Arg Leu
    370                 375                 380

Glu Asn Asp Gly Ile Asp Glu Leu Ile Asn Glu Ala Lys Lys Ala
385                 390                 395                 400

Ala Ser Ser Ser Asp Val Ala Val Phe Ala Gly Leu Pro Asp Glu
                405                 410                 415

Tyr Glu Ser Glu Gly Phe Asp Arg Thr His Met Ser Ile Pro Glu Asn
                420                 425                 430

Gln Asn Arg Leu Ile Glu Ala Val Ala Glu Val Gln Ser Asn Ile Val
            435                 440                 445

Val Val Leu Leu Asn Gly Ser Pro Val Glu Met Pro Trp Ile Asp Lys
    450                 455                 460

Val Lys Ser Val Leu Glu Ala Tyr Leu Gly Gly Gln Ala Leu Gly Gly
```

```
                465                 470                 475                 480
Ala Leu Ala Asp Val Leu Phe Gly Glu Val Asn Pro Ser Gly Lys Leu
                        485                 490                 495

Ala Glu Thr Phe Pro Val Lys Leu Ser His Asn Pro Ser Tyr Leu Asn
                500                 505                 510

Phe Pro Gly Glu Asp Arg Val Glu Tyr Lys Glu Gly Leu Phe Val
            515                 520                 525

Gly Tyr Arg Tyr Tyr Asp Thr Lys Gly Ile Glu Pro Leu Phe Pro Phe
            530                 535                 540

Gly His Gly Leu Ser Tyr Thr Lys Phe Glu Tyr Ser Asp Ile Ser Val
545                 550                 555                 560

Asp Lys Lys Asp Val Ser Asp Asn Ser Ile Ile Asn Val Ser Val Lys
                565                 570                 575

Val Lys Asn Val Gly Lys Met Ala Gly Lys Glu Ile Val Gln Leu Tyr
            580                 585                 590

Val Lys Asp Val Lys Ser Ser Val Arg Arg Pro Glu Lys Glu Leu Lys
            595                 600                 605

Gly Phe Glu Lys Val Phe Leu Asn Pro Gly Glu Lys Thr Val Thr
            610                 615                 620

Phe Thr Leu Asp Lys Arg Ala Phe Ala Tyr Tyr Asn Thr Gln Ile Lys
625                 630                 635                 640

Asp Trp His Val Glu Ser Gly Glu Phe Leu Ile Leu Ile Gly Arg Ser
                645                 650                 655

Ser Arg Asp Ile Val Leu Lys Glu Ser Val Arg Val Asn Ser Thr Val
                660                 665                 670

Lys Ile Arg Lys Arg Phe Thr Val Asn Ser Ala Val Glu Asp Val Met
            675                 680                 685

Ser Asp Ser Ser Ala Ala Val Leu Gly Pro Val Leu Lys Glu Ile
            690                 695                 700

Thr Asp Ala Leu Gln Ile Asp Met Asp Asn Ala His Asp Met Met Ala
705                 710                 715                 720

Ala Asn Ile Lys Asn Met Pro Leu Arg Ser Leu Val Gly Tyr Ser Gln
                725                 730                 735

Gly Arg Leu Ser Glu Glu Met Leu Glu Glu Leu Val Asp Lys Ile Asn
            740                 745                 750

Asn Val Glu
        755

<210> SEQ ID NO 47
<211> LENGTH: 480
<212> TYPE: PRT
<213> ORGANISM: Thermotoga maritime

<400> SEQUENCE: 47

Met Pro Ser Val Lys Ile Gly Ile Gly Ala Gly Ser Ala Val Phe
1               5                   10                  15

Ser Leu Arg Leu Val Ser Asp Leu Cys Lys Thr Pro Gly Leu Ser Gly
                20                  25                  30

Ser Thr Val Thr Leu Met Asp Ile Asp Glu Glu Arg Leu Asp Ala Ile
            35                  40                  45

Leu Thr Ile Ala Lys Lys Tyr Val Glu Glu Val Gly Ala Asp Leu Lys
        50                  55                  60

Phe Glu Lys Thr Met Asn Leu Asp Asp Val Ile Ile Asp Ala Asp Phe
65                  70                  75                  80
```

```
Val Ile Asn Thr Ala Met Val Gly Gly His Thr Tyr Leu Glu Lys Val
                85                  90                  95

Arg Gln Ile Gly Glu Lys Tyr Gly Tyr Arg Gly Ile Asp Ala Gln
            100                 105                 110

Glu Phe Asn Met Val Ser Asp Tyr Tyr Thr Phe Ser Asn Tyr Asn Gln
            115                 120                 125

Leu Lys Tyr Phe Val Asp Ile Ala Arg Lys Ile Glu Lys Leu Ser Pro
            130                 135                 140

Lys Ala Trp Tyr Leu Gln Ala Ala Asn Pro Ile Phe Glu Gly Thr Thr
145                 150                 155                 160

Leu Val Thr Arg Thr Val Pro Ile Lys Ala Val Gly Phe Cys His Gly
                165                 170                 175

His Tyr Gly Val Met Glu Ile Val Glu Lys Leu Gly Leu Glu Glu Glu
            180                 185                 190

Lys Val Asp Trp Gln Val Ala Gly Val Asn His Gly Ile Trp Leu Asn
            195                 200                 205

Arg Phe Arg Tyr Asn Gly Gly Asn Ala Tyr Pro Leu Leu Asp Lys Trp
            210                 215                 220

Ile Glu Glu Lys Ser Lys Asp Trp Lys Pro Glu Asn Pro Phe Asn Asp
225                 230                 235                 240

Gln Leu Ser Pro Ala Ala Ile Asp Met Tyr Arg Phe Tyr Gly Val Met
                245                 250                 255

Pro Ile Gly Asp Thr Val Arg Asn Ser Ser Trp Arg Tyr His Arg Asp
            260                 265                 270

Leu Glu Thr Lys Lys Lys Trp Tyr Gly Glu Pro Trp Gly Gly Ala Asp
            275                 280                 285

Ser Glu Ile Gly Trp Lys Trp Tyr Gln Asp Thr Leu Gly Lys Val Thr
            290                 295                 300

Glu Ile Thr Lys Lys Val Ala Lys Phe Ile Lys Glu Asn Pro Ser Val
305                 310                 315                 320

Arg Leu Ser Asp Leu Gly Ser Val Leu Gly Lys Asp Leu Ser Glu Lys
                325                 330                 335

Gln Phe Val Leu Glu Val Glu Lys Ile Leu Asp Pro Glu Arg Lys Ser
            340                 345                 350

Gly Glu Gln His Ile Pro Phe Ile Asp Ala Leu Leu Asn Asp Asn Lys
            355                 360                 365

Ala Arg Phe Val Val Asn Ile Pro Asn Lys Gly Ile Ile His Gly Ile
            370                 375                 380

Asp Asp Asp Val Val Val Glu Val Pro Ala Leu Val Asp Lys Asn Gly
385                 390                 395                 400

Ile His Pro Glu Lys Ile Glu Pro Pro Leu Pro Asp Arg Val Val Lys
                405                 410                 415

Tyr Tyr Leu Arg Pro Arg Ile Met Arg Met Glu Met Ala Leu Glu Ala
            420                 425                 430

Phe Leu Thr Gly Asp Ile Arg Ile Ile Lys Glu Leu Tyr Arg Asp
            435                 440                 445

Pro Arg Thr Lys Ser Asp Glu Gln Val Glu Lys Val Ile Glu Glu Ile
            450                 455                 460

Leu Ala Leu Pro Glu Asn Glu Glu Met Arg Lys His Tyr Leu Lys Arg
465                 470                 475                 480

<210> SEQ ID NO 48
<211> LENGTH: 225
<212> TYPE: PRT
```

<213> ORGANISM: Thermomyces lanuginosus

<400> SEQUENCE: 48

Met Val Gly Phe Thr Pro Val Ala Leu Ala Ala Leu Ala Ala Thr Gly
1               5                   10                  15

Ala Leu Ala Phe Pro Ala Gly Asn Ala Thr Glu Leu Glu Lys Arg Gln
            20                  25                  30

Thr Thr Pro Asn Ser Glu Gly Trp His Asp Gly Tyr Tyr Tyr Ser Trp
        35                  40                  45

Trp Ser Asp Gly Gly Ala Gln Ala Thr Tyr Thr Asn Leu Glu Gly Gly
    50                  55                  60

Thr Tyr Glu Ile Ser Trp Gly Asp Gly Gly Asn Leu Val Gly Gly Lys
65                  70                  75                  80

Gly Trp Asn Pro Gly Leu Asn Ala Arg Ala Ile His Phe Glu Gly Val
                85                  90                  95

Tyr Gln Pro Asn Gly Asn Ser Tyr Leu Ala Val Tyr Gly Trp Thr Arg
            100                 105                 110

Asn Pro Leu Val Glu Tyr Tyr Ile Val Glu Asn Phe Gly Thr Tyr Asp
            115                 120                 125

Pro Ser Ser Gly Ala Thr Asp Leu Gly Thr Val Glu Cys Asp Gly Ser
        130                 135                 140

Ile Tyr Arg Leu Gly Lys Thr Thr Arg Val Asn Ala Pro Ser Ile Asp
145                 150                 155                 160

Gly Thr Gln Thr Phe Asp Gln Tyr Trp Ser Val Arg Gln Asp Lys Arg
                165                 170                 175

Thr Ser Gly Thr Val Gln Thr Gly Cys His Phe Asp Ala Trp Ala Arg
            180                 185                 190

Ala Gly Leu Asn Val Asn Gly Asp His Tyr Tyr Gln Ile Val Ala Thr
        195                 200                 205

Glu Gly Tyr Phe Ser Ser Gly Tyr Ala Arg Ile Thr Val Ala Asp Val
    210                 215                 220

Gly
225

<210> SEQ ID NO 49
<211> LENGTH: 562
<212> TYPE: PRT
<213> ORGANISM: Acidothermus cellulolyticus

<400> SEQUENCE: 49

Met Pro Arg Ala Leu Arg Arg Val Pro Gly Ser Arg Val Met Leu Arg
1               5                   10                  15

Val Gly Val Val Val Ala Val Leu Ala Leu Val Ala Leu Ala Leu Asn
            20                  25                  30

Leu Ala Val Pro Arg Pro Ala Arg Ala Ala Gly Gly Gly Tyr Trp His
        35                  40                  45

Thr Ser Gly Arg Glu Ile Leu Asp Ala Asn Asn Val Pro Val Arg Ile
    50                  55                  60

Ala Gly Ile Asn Trp Phe Gly Phe Glu Thr Cys Asn Tyr Val Val His
65                  70                  75                  80

Gly Leu Trp Ser Arg Asp Tyr Arg Ser Met Leu Asp Gln Ile Lys Ser
                85                  90                  95

Leu Gly Tyr Asn Thr Ile Arg Leu Pro Tyr Ser Asp Asp Ile Leu Lys
            100                 105                 110

Pro Gly Thr Met Pro Asn Ser Ile Asn Phe Tyr Gln Met Asn Gln Asp

```
            115                 120                 125
Leu Gln Gly Leu Thr Ser Leu Gln Val Met Asp Lys Ile Val Ala Tyr
130                 135                 140

Ala Gly Gln Ile Gly Leu Arg Ile Ile Leu Asp Arg His Arg Pro Asp
145                 150                 155                 160

Cys Ser Gly Gln Ser Ala Leu Trp Tyr Thr Ser Val Ser Glu Ala
                165                 170                 175

Thr Trp Ile Ser Asp Leu Gln Ala Leu Ala Gln Arg Tyr Lys Gly Asn
                180                 185                 190

Pro Thr Val Val Gly Phe Asp Leu His Asn Glu Pro His Asp Pro Ala
                195                 200                 205

Cys Trp Gly Cys Gly Asp Pro Ser Ile Asp Trp Arg Leu Ala Ala Glu
                210                 215                 220

Arg Ala Gly Asn Ala Val Leu Ser Val Asn Pro Asn Leu Leu Ile Phe
225                 230                 235                 240

Val Glu Gly Val Gln Ser Tyr Asn Gly Asp Ser Tyr Trp Trp Gly Gly
                245                 250                 255

Asn Leu Gln Gly Ala Gly Gln Tyr Pro Val Val Leu Asn Val Pro Asn
                260                 265                 270

Arg Leu Val Tyr Ser Ala His Asp Tyr Ala Thr Ser Val Tyr Pro Gln
                275                 280                 285

Thr Trp Phe Ser Asp Pro Thr Phe Pro Asn Asn Met Pro Gly Ile Trp
                290                 295                 300

Asn Lys Asn Trp Gly Tyr Leu Phe Asn Gln Asn Ile Ala Pro Val Trp
305                 310                 315                 320

Leu Gly Glu Phe Gly Thr Thr Leu Gln Ser Thr Thr Asp Gln Thr Trp
                325                 330                 335

Leu Lys Thr Leu Val Gln Tyr Leu Arg Pro Thr Ala Gln Tyr Gly Ala
                340                 345                 350

Asp Ser Phe Gln Trp Thr Phe Trp Ser Trp Asn Pro Asp Ser Gly Asp
                355                 360                 365

Thr Gly Gly Ile Leu Lys Asp Asp Trp Gln Thr Val Asp Thr Val Lys
370                 375                 380

Asp Gly Tyr Leu Ala Pro Ile Lys Ser Ser Ile Phe Asp Pro Val Gly
385                 390                 395                 400

Ala Ser Ala Ser Pro Ser Ser Gln Pro Ser Pro Ser Val Ser Pro Ser
                405                 410                 415

Pro Ser Pro Ser Pro Ser Ala Ser Arg Thr Pro Thr Pro Thr Pro Thr
                420                 425                 430

Pro Thr Ala Ser Pro Thr Pro Thr Leu Thr Pro Thr Ala Thr Pro Thr
                435                 440                 445

Pro Thr Ala Ser Pro Thr Pro Ser Pro Thr Ala Ala Ser Gly Ala Arg
                450                 455                 460

Cys Thr Ala Ser Tyr Gln Val Asn Ser Asp Trp Gly Asn Gly Phe Thr
465                 470                 475                 480

Val Thr Val Ala Val Thr Asn Ser Gly Ser Val Ala Thr Lys Thr Trp
                485                 490                 495

Thr Val Ser Trp Thr Phe Gly Gly Asn Gln Thr Ile Thr Asn Ser Trp
                500                 505                 510

Asn Ala Ala Val Thr Gln Asn Gly Gln Ser Val Thr Ala Arg Asn Met
                515                 520                 525

Ser Tyr Asn Asn Val Ile Gln Pro Gly Gln Asn Thr Thr Phe Gly Phe
                530                 535                 540
```

```
Gln Ala Ser Tyr Thr Gly Ser Asn Ala Pro Thr Val Ala Cys Ala
545                 550                 555                 560

Ala Ser

<210> SEQ ID NO 50
<211> LENGTH: 491
<212> TYPE: PRT
<213> ORGANISM: Sulfolobus acidocaldarius

<400> SEQUENCE: 50

Met Leu Ser Phe Pro Lys Gly Phe Lys Phe Gly Trp Ser Gln Ser Gly
  1               5                  10                  15

Phe Gln Ser Glu Met Gly Thr Pro Gly Ser Glu Asp Pro Asn Ser Asp
                20                  25                  30

Trp His Val Trp Val His Asp Arg Glu Asn Ile Val Ser Gln Val Val
            35                  40                  45

Ser Gly Asp Leu Pro Glu Asn Gly Pro Gly Tyr Trp Gly Asn Tyr Lys
 50                  55                  60

Arg Phe His Asp Glu Ala Glu Lys Ile Gly Leu Asn Ala Val Arg Ile
 65                  70                  75                  80

Asn Val Glu Trp Ser Arg Ile Phe Pro Arg Pro Leu Pro Lys Pro Glu
                85                  90                  95

Met Gln Thr Gly Thr Asp Lys Glu Asn Ser Pro Val Ile Ser Val Asp
            100                 105                 110

Leu Asn Glu Ser Lys Leu Arg Glu Met Asp Asn Tyr Ala Asn His Glu
        115                 120                 125

Ala Leu Ser His Tyr Arg Gln Ile Leu Glu Asp Leu Arg Asn Arg Gly
130                 135                 140

Phe His Ile Val Leu Asn Met Tyr His Trp Thr Leu Pro Ile Trp Leu
145                 150                 155                 160

His Asp Pro Ile Arg Val Arg Arg Gly Asp Phe Thr Gly Pro Thr Gly
                165                 170                 175

Trp Leu Asn Ser Arg Thr Val Tyr Glu Phe Ala Arg Phe Ser Ala Tyr
            180                 185                 190

Val Ala Trp Lys Leu Asp Asp Leu Ala Ser Glu Tyr Ala Thr Met Asn
        195                 200                 205

Glu Pro Asn Val Val Trp Gly Ala Gly Tyr Ala Phe Pro Arg Ala Gly
210                 215                 220

Phe Pro Pro Asn Tyr Leu Ser Phe Arg Leu Ser Glu Ile Ala Lys Trp
225                 230                 235                 240

Asn Ile Ile Gln Ala His Ala Arg Ala Tyr Asp Ala Ile Lys Ser Val
                245                 250                 255

Ser Lys Lys Ser Val Gly Ile Ile Tyr Ala Asn Thr Ser Tyr Tyr Pro
            260                 265                 270

Leu Arg Pro Gln Asp Asn Glu Ala Val Glu Ile Ala Glu Arg Leu Asn
        275                 280                 285

Arg Trp Ser Phe Phe Asp Ser Ile Ile Lys Gly Glu Ile Thr Ser Glu
290                 295                 300

Gly Gln Asn Val Arg Glu Asp Leu Arg Asn Arg Leu Asp Trp Ile Gly
305                 310                 315                 320

Val Asn Tyr Tyr Thr Arg Thr Val Val Thr Lys Ala Glu Ser Gly Tyr
                325                 330                 335

Leu Thr Leu Pro Gly Tyr Gly Asp Arg Cys Glu Arg Asn Ser Leu Ser
            340                 345                 350
```

```
Leu Ala Asn Leu Pro Thr Ser Asp Phe Gly Trp Glu Phe Pro Glu
        355                 360                 365

Gly Leu Tyr Asp Val Leu Leu Lys Tyr Trp Asn Arg Tyr Gly Leu Pro
    370                 375                 380

Leu Tyr Val Met Glu Asn Gly Ile Ala Asp Ala Asp Tyr Gln Arg
385                 390                 395                 400

Pro Tyr Tyr Leu Val Ser His Ile Tyr Gln Val His Arg Ala Leu Asn
                405                 410                 415

Glu Gly Val Asp Val Arg Gly Tyr Leu His Trp Ser Leu Ala Asp Asn
            420                 425                 430

Tyr Glu Trp Ser Ser Gly Phe Ser Met Arg Phe Gly Leu Leu Lys Val
        435                 440                 445

Asp Tyr Leu Thr Lys Arg Leu Tyr Trp Arg Pro Ser Ala Leu Val Tyr
    450                 455                 460

Arg Glu Ile Thr Arg Ser Asn Gly Ile Pro Glu Glu Leu Glu His Leu
465                 470                 475                 480

Asn Arg Val Pro Pro Ile Lys Pro Leu Arg His
                485                 490

<210> SEQ ID NO 51
<211> LENGTH: 510
<212> TYPE: PRT
<213> ORGANISM: Pyrococcus woesei

<400> SEQUENCE: 51

Met Phe Pro Glu Lys Phe Leu Trp Gly Val Ala Gln Ser Gly Phe Gln
1               5                   10                  15

Phe Glu Met Gly Asp Lys Leu Arg Arg Asn Ile Asp Thr Asn Thr Asp
            20                  25                  30

Trp Trp His Trp Val Arg Asp Lys Thr Asn Ile Glu Lys Gly Leu Val
        35                  40                  45

Ser Gly Asp Leu Pro Glu Glu Gly Ile Asn Asn Tyr Glu Leu Tyr Glu
    50                  55                  60

Lys Asp His Glu Ile Ala Arg Lys Leu Gly Leu Asn Ala Tyr Arg Ile
65                  70                  75                  80

Gly Ile Glu Trp Ser Arg Ile Phe Pro Trp Pro Thr Thr Phe Ile Asp
                85                  90                  95

Val Asp Tyr Ser Tyr Asn Glu Ser Tyr Asn Leu Ile Glu Asp Val Lys
                100                 105                 110

Ile Thr Lys Asp Thr Leu Glu Glu Leu Asp Glu Ile Ala Asn Lys Arg
            115                 120                 125

Glu Val Ala Tyr Tyr Arg Ser Val Ile Asn Ser Leu Arg Ser Lys Gly
        130                 135                 140

Phe Lys Val Ile Val Asn Leu Asn His Phe Thr Leu Pro Tyr Trp Leu
145                 150                 155                 160

His Asp Pro Ile Glu Ala Arg Glu Arg Ala Leu Thr Asn Lys Arg Asn
                165                 170                 175

Gly Trp Val Asn Pro Arg Thr Val Ile Glu Phe Ala Lys Tyr Ala Ala
            180                 185                 190

Tyr Ile Ala Tyr Lys Phe Gly Asp Ile Val Asp Met Trp Ser Thr Phe
        195                 200                 205

Asn Glu Pro Met Val Val Glu Leu Gly Tyr Leu Ala Pro Tyr Ser
    210                 215                 220

Gly Phe Pro Pro Gly Val Leu Asn Pro Glu Ala Ala Lys Leu Ala Ile
```

```
                225                 230                 235                 240
Leu His Met Ile Asn Ala His Ala Leu Ala Tyr Arg Gln Ile Lys Lys
                    245                 250                 255

Phe Asp Thr Glu Lys Ala Asp Lys Asp Ser Lys Glu Pro Ala Glu Val
                    260                 265                 270

Gly Ile Ile Tyr Asn Asn Ile Gly Val Ala Tyr Pro Lys Asp Pro Asn
                    275                 280                 285

Asp Ser Lys Asp Val Lys Ala Ala Glu Asn Asp Phe Phe His Ser
        290                 295                 300

Gly Leu Phe Phe Glu Ala Ile His Lys Gly Lys Leu Asn Ile Glu Phe
305                 310                 315                 320

Asp Gly Glu Thr Phe Ile Asp Ala Pro Tyr Leu Lys Gly Asn Asp Trp
                    325                 330                 335

Ile Gly Val Asn Tyr Tyr Thr Arg Glu Val Val Thr Tyr Gln Glu Pro
                    340                 345                 350

Met Phe Pro Ser Ile Pro Leu Ile Thr Phe Lys Gly Val Gln Gly Tyr
                    355                 360                 365

Gly Tyr Ala Cys Arg Pro Gly Thr Leu Ser Lys Asp Asp Arg Pro Val
        370                 375                 380

Ser Asp Ile Gly Trp Glu Leu Tyr Pro Glu Gly Met Tyr Asp Ser Ile
385                 390                 395                 400

Val Glu Ala His Lys Tyr Gly Val Pro Val Tyr Val Thr Glu Asn Gly
                    405                 410                 415

Ile Ala Asp Ser Lys Asp Ile Leu Arg Pro Tyr Tyr Ile Ala Ser His
                    420                 425                 430

Ile Lys Met Thr Glu Lys Ala Phe Glu Asp Gly Tyr Glu Val Lys Gly
                    435                 440                 445

Tyr Phe His Trp Ala Leu Thr Asp Asn Phe Glu Trp Ala Leu Gly Phe
            450                 455                 460

Arg Met Arg Phe Gly Leu Tyr Glu Val Asn Leu Ile Thr Lys Glu Arg
465                 470                 475                 480

Ile Pro Arg Glu Lys Ser Val Ser Ile Phe Arg Glu Ile Val Ala Asn
                    485                 490                 495

Asn Gly Val Thr Lys Lys Ile Glu Glu Leu Leu Arg Gly
                    500                 505                 510
```

<210> SEQ ID NO 52
<211> LENGTH: 562
<212> TYPE: PRT
<213> ORGANISM: Geobacillus thermoglucosidasius

<400> SEQUENCE: 52

```
Met Glu Arg Val Trp Trp Lys Glu Ala Val Tyr Gln Ile Tyr Pro
1               5                   10                  15

Arg Ser Phe Tyr Asp Ser Asn Gly Asp Gly Ile Gly Asp Ile Arg Gly
                20                  25                  30

Ile Ile Ala Lys Leu Asp Tyr Leu Lys Glu Leu Gly Val Asp Val Val
            35                  40                  45

Trp Leu Ser Pro Val Tyr Lys Ser Pro Asn Asp Asp Asn Gly Tyr Asp
50                  55                  60

Ile Ser Asp Tyr Arg Asp Ile Met Asp Glu Phe Gly Thr Met Ala Asp
65                  70                  75                  80

Trp Lys Thr Met Leu Glu Glu Met His Lys Arg Gly Ile Lys Leu Val
                85                  90                  95
```

```
Met Asp Leu Val Val Asn His Thr Ser Asp Glu His Pro Trp Phe Ile
            100                 105                 110

Glu Ser Arg Lys Ser Lys Asp Asn Pro Tyr Arg Asp Tyr Tyr Ile Trp
            115                 120                 125

Arg Pro Gly Lys Asn Gly Lys Glu Pro Asn Asn Trp Glu Ser Val Phe
        130                 135                 140

Ser Gly Ser Ala Trp Glu Tyr Asp Glu Met Thr Gly Glu Tyr Tyr Leu
145                 150                 155                 160

His Leu Phe Ser Lys Lys Gln Pro Asp Leu Asn Trp Glu Asn Pro Lys
                165                 170                 175

Val Arg Arg Glu Val Tyr Glu Met Met Lys Phe Trp Leu Asp Lys Gly
            180                 185                 190

Val Asp Gly Phe Arg Met Asp Val Ile Asn Met Ile Ser Lys Val Pro
        195                 200                 205

Glu Leu Pro Asp Gly Glu Pro Gln Ser Gly Lys Lys Tyr Ala Ser Gly
        210                 215                 220

Ser Arg Tyr Tyr Met Asn Gly Pro Arg Val His Glu Phe Leu Gln Glu
225                 230                 235                 240

Met Asn Arg Glu Val Leu Ser Lys Tyr Asp Ile Met Thr Val Gly Glu
            245                 250                 255

Thr Pro Gly Val Thr Pro Lys Glu Gly Ile Leu Tyr Thr Asp Pro Ser
        260                 265                 270

Arg Arg Glu Leu Asn Met Val Phe Gln Phe Glu His Met Asp Leu Asp
        275                 280                 285

Ser Gly Pro Gly Gly Lys Trp Asp Ile Arg Pro Trp Ser Leu Ala Asp
        290                 295                 300

Leu Lys Lys Thr Met Thr Lys Trp Gln Lys Glu Leu Glu Gly Lys Gly
305                 310                 315                 320

Trp Asn Ser Leu Tyr Leu Asn Asn His Asp Gln Pro Arg Ala Val Ser
                325                 330                 335

Arg Phe Gly Asp Asp Gly Lys Tyr Arg Val Glu Ser Ala Lys Met Leu
            340                 345                 350

Ala Thr Phe Leu His Met Met Gln Gly Thr Pro Tyr Ile Tyr Gln Gly
        355                 360                 365

Glu Glu Ile Gly Met Thr Asn Val Arg Phe Pro Ser Ile Glu Asp Tyr
        370                 375                 380

Arg Asp Ile Glu Thr Leu Asn Met Tyr Lys Glu Arg Val Glu Glu Tyr
385                 390                 395                 400

Gly Glu Asp Pro Gln Glu Val Met Glu Lys Ile Tyr Tyr Lys Gly Arg
            405                 410                 415

Asp Asn Ala Arg Thr Pro Met Gln Trp Asp Asp Ser Glu Asn Ala Gly
        420                 425                 430

Phe Thr Ala Gly Thr Pro Trp Ile Pro Val Asn Pro Asn Tyr Lys Glu
        435                 440                 445

Ile Asn Val Lys Ala Ala Leu Glu Asp Pro Asn Ser Val Phe His Tyr
450                 455                 460

Tyr Lys Lys Leu Ile Gln Leu Arg Lys Gln His Asp Ile Ile Val Tyr
465                 470                 475                 480

Gly Thr Tyr Asp Leu Ile Leu Glu Asp Asp Pro Tyr Ile Tyr Arg Tyr
                485                 490                 495

Thr Arg Thr Leu Gly Asn Glu Gln Leu Ile Val Ile Thr Asn Phe Ser
            500                 505                 510

Glu Lys Thr Pro Val Phe Arg Leu Pro Asp His Ile Ile Tyr Lys Thr
```

-continued

```
            515                 520                 525
Lys Glu Leu Leu Ile Ser Asn Tyr Asp Val Asp Glu Ala Glu Glu Leu
        530                 535                 540

Lys Glu Ile Arg Leu Arg Pro Trp Glu Ala Arg Val Tyr Lys Ile Arg
545                 550                 555                 560

Leu Pro

<210> SEQ ID NO 53
<211> LENGTH: 649
<212> TYPE: PRT
<213> ORGANISM: Pyrococcus furiosus

<400> SEQUENCE: 53

Met Gly Asp Lys Ile Asn Phe Ile Phe Gly Ile His Asn His Gln Pro
1               5                   10                  15

Leu Gly Asn Phe Gly Trp Val Phe Glu Glu Ala Tyr Glu Lys Cys Tyr
            20                  25                  30

Trp Pro Phe Leu Glu Thr Leu Glu Glu Tyr Pro Asn Met Lys Val Ala
        35                  40                  45

Ile His Thr Ser Gly Pro Leu Ile Glu Trp Leu Gln Asp Asn Arg Pro
    50                  55                  60

Glu Tyr Ile Asp Leu Leu Arg Ser Leu Val Lys Arg Gly Gln Val Glu
65                  70                  75                  80

Ile Val Val Ala Gly Phe Tyr Glu Pro Val Leu Ala Ser Ile Pro Lys
                85                  90                  95

Glu Asp Arg Ile Glu Gln Ile Arg Leu Met Lys Glu Trp Ala Lys Ser
            100                 105                 110

Ile Gly Phe Asp Ala Arg Gly Val Trp Leu Thr Glu Arg Val Trp Gln
        115                 120                 125

Pro Glu Leu Val Lys Thr Leu Lys Glu Ser Gly Ile Asp Tyr Val Ile
    130                 135                 140

Val Asp Asp Tyr His Phe Met Ser Ala Gly Leu Ser Lys Glu Glu Leu
145                 150                 155                 160

Tyr Trp Pro Tyr Tyr Thr Glu Asp Gly Gly Glu Val Ile Ala Val Phe
                165                 170                 175

Pro Ile Asp Glu Lys Leu Arg Tyr Leu Ile Pro Phe Arg Pro Val Asp
            180                 185                 190

Lys Val Leu Glu Tyr Leu His Ser Leu Ile Asp Gly Asp Glu Ser Lys
        195                 200                 205

Val Ala Val Phe His Asp Asp Gly Glu Lys Phe Gly Ile Trp Pro Gly
    210                 215                 220

Thr Tyr Glu Trp Val Tyr Glu Lys Gly Trp Leu Arg Glu Phe Phe Asp
225                 230                 235                 240

Arg Ile Ser Ser Asp Glu Lys Ile Asn Leu Met Leu Tyr Thr Glu Tyr
                245                 250                 255

Leu Glu Lys Tyr Lys Pro Arg Gly Leu Val Tyr Leu Pro Ile Ala Ser
            260                 265                 270

Tyr Phe Glu Met Ser Glu Trp Ser Leu Pro Ala Lys Gln Ala Arg Leu
        275                 280                 285

Phe Val Glu Phe Val Asn Glu Leu Lys Val Lys Gly Ile Phe Glu Lys
    290                 295                 300

Tyr Arg Val Phe Val Arg Gly Gly Ile Trp Lys Asn Phe Phe Tyr Lys
305                 310                 315                 320

Tyr Pro Glu Ser Asn Tyr Met His Lys Arg Met Leu Met Val Ser Lys
```

```
                      325                 330                 335
Leu Val Arg Asn Asn Pro Glu Ala Arg Lys Tyr Leu Arg Ala Gln
            340                 345                 350
Cys Asn Asp Ala Tyr Trp His Gly Leu Phe Gly Gly Val Tyr Leu Pro
            355                 360                 365
His Leu Arg Arg Ala Ile Trp Asn Asn Leu Ile Lys Ala Asn Ser Tyr
370                 375                 380
Val Ser Leu Gly Lys Val Ile Arg Asp Ile Asp Tyr Asp Gly Phe Glu
385                 390                 395                 400
Glu Val Leu Ile Glu Asn Asp Asn Phe Tyr Ala Val Phe Lys Pro Ser
                405                 410                 415
Tyr Gly Gly Ser Leu Val Glu Phe Ser Ser Lys Asn Arg Leu Val Asn
            420                 425                 430
Tyr Val Asp Val Leu Ala Arg Arg Trp Glu His Tyr His Gly Tyr Val
            435                 440                 445
Glu Ser Gln Phe Asp Gly Val Ala Ser Ile His Glu Leu Glu Lys Lys
            450                 455                 460
Ile Pro Asp Glu Ile Arg Lys Glu Val Ala Tyr Asp Lys Tyr Arg Arg
465                 470                 475                 480
Phe Met Leu Gln Asp His Val Val Pro Leu Gly Thr Thr Leu Glu Asp
                485                 490                 495
Phe Met Phe Ser Arg Gln Gln Glu Ile Gly Glu Phe Pro Arg Val Pro
                500                 505                 510
Tyr Ser Tyr Glu Leu Leu Asp Gly Gly Ile Arg Leu Lys Arg Glu His
            515                 520                 525
Leu Gly Ile Glu Val Glu Lys Thr Val Lys Leu Val Asn Asp Gly Phe
            530                 535                 540
Glu Val Glu Tyr Ile Val Asn Asn Lys Thr Gly Asn Pro Val Leu Phe
545                 550                 555                 560
Ala Val Glu Leu Asn Val Ala Val Gln Ser Ile Met Glu Ser Pro Gly
                565                 570                 575
Val Leu Arg Gly Lys Glu Ile Val Val Asp Asp Lys Tyr Ala Val Gly
            580                 585                 590
Lys Phe Ala Leu Lys Phe Glu Asp Glu Met Glu Val Trp Lys Tyr Pro
            595                 600                 605
Val Lys Thr Leu Ser Gln Ser Glu Ser Gly Trp Asp Leu Ile Gln Gln
            610                 615                 620
Gly Val Ser Tyr Ile Val Pro Ile Arg Leu Glu Asp Lys Ile Arg Phe
625                 630                 635                 640
Lys Leu Lys Phe Glu Glu Ala Ser Gly
                645

<210> SEQ ID NO 54
<211> LENGTH: 824
<212> TYPE: PRT
<213> ORGANISM: Bacillus sp.

<400> SEQUENCE: 54

Met Met Leu Arg Lys Lys Thr Lys Gln Leu Ile Ser Ser Ile Leu Ile
1               5                   10                  15
Leu Val Leu Leu Leu Ser Leu Phe Pro Ala Ala Leu Ala Ala Glu Gly
            20                  25                  30
Asn Thr Arg Glu Asp Asn Phe Lys His Leu Leu Gly Asn Asp Asn Val
        35                  40                  45
```

```
Lys Arg Pro Ser Glu Ala Gly Ala Leu Gln Leu Gln Glu Val Asp Gly
    50                  55                  60

Gln Met Thr Leu Val Asp Gln His Gly Glu Lys Ile Gln Leu Arg Gly
 65                  70                  75                  80

Met Ser Thr His Gly Leu Gln Trp Phe Pro Glu Ile Leu Asn Asp Asn
                 85                  90                  95

Ala Tyr Lys Ala Leu Ser Asn Asp Trp Asp Ser Asn Met Ile Arg Leu
            100                 105                 110

Ala Met Tyr Val Gly Glu Asn Gly Tyr Ala Thr Asn Pro Glu Leu Ile
            115                 120                 125

Lys Gln Arg Val Ile Asp Gly Ile Glu Leu Ala Ile Glu Asn Asp Met
130                 135                 140

Tyr Val Ile Val Asp Trp His Val His Ala Pro Gly Asp Pro Arg Asp
145                 150                 155                 160

Pro Val Tyr Ala Gly Ala Lys Asp Phe Phe Arg Glu Ile Ala Ala Leu
                165                 170                 175

Tyr Pro Asn Asn Pro His Ile Ile Tyr Glu Leu Ala Asn Glu Pro Ser
            180                 185                 190

Ser Asn Asn Asn Gly Gly Ala Gly Ile Pro Asn Asn Glu Glu Gly Trp
            195                 200                 205

Lys Ala Val Lys Glu Tyr Ala Asp Pro Ile Val Glu Met Leu Arg Lys
210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
                245                 250                 255

Thr Met Tyr Thr Val His Phe Tyr Thr Gly Ser His Ala Ala Ser Thr
            260                 265                 270

Glu Ser Tyr Pro Ser Glu Thr Pro Asn Ser Glu Arg Gly Asn Val Met
            275                 280                 285

Ser Asn Thr Arg Tyr Ala Leu Glu Asn Gly Val Ala Val Phe Ala Thr
            290                 295                 300

Glu Trp Gly Thr Ser Gln Ala Ser Gly Asp Gly Pro Tyr Phe Asp
305                 310                 315                 320

Glu Ala Asp Val Trp Ile Glu Phe Leu Asn Glu Asn Asn Ile Ser Trp
                325                 330                 335

Ala Asn Trp Ser Leu Thr Asn Lys Asn Glu Val Ser Gly Ala Phe Thr
            340                 345                 350

Pro Phe Glu Leu Gly Lys Ser Asn Ala Thr Asn Leu Asp Pro Gly Pro
            355                 360                 365

Asp His Val Trp Ala Pro Glu Glu Leu Ser Leu Ser Gly Glu Tyr Val
            370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
                405                 410                 415

Gly Val Asn Ser Asp Ser Pro Asn Lys Glu Leu Ile Ala Val Asp Asn
            420                 425                 430

Glu Asn Asn Thr Leu Lys Val Ser Gly Leu Asp Val Ser Asn Asp Val
            435                 440                 445

Ser Asp Gly Asn Phe Trp Ala Asn Ala Arg Leu Ser Ala Asn Gly Trp
450                 455                 460

Gly Lys Ser Val Asp Ile Leu Gly Ala Glu Lys Leu Thr Met Asp Val
```

```
            465                 470                 475                 480
    Ile Val Asp Glu Pro Thr Thr Val Ala Ile Ala Ala Ile Pro Gln Ser
                    485                 490                 495

Ser Lys Ser Gly Trp Ala Asn Pro Glu Arg Ala Val Arg Val Asn Ala
                    500                 505                 510

Glu Asp Phe Val Gln Gln Thr Asp Gly Lys Tyr Lys Ala Gly Leu Thr
                    515                 520                 525

Ile Thr Gly Glu Asp Ala Pro Asn Leu Lys Asn Ile Ala Phe His Glu
                    530                 535                 540

Glu Asp Asn Asn Met Asn Asn Ile Ile Leu Phe Val Gly Thr Asp Ala
    545                 550                 555                 560

Ala Asp Val Ile Tyr Leu Asp Asn Ile Lys Val Ile Gly Thr Glu Val
                    565                 570                 575

Glu Ile Pro Val Val His Asp Pro Lys Gly Glu Ala Val Leu Pro Ser
                    580                 585                 590

Val Phe Glu Asp Gly Thr Arg Gln Gly Trp Asp Trp Ala Gly Glu Ser
                    595                 600                 605

Gly Val Lys Thr Ala Leu Thr Ile Glu Glu Ala Asn Gly Ser Asn Ala
                    610                 615                 620

Leu Ser Trp Glu Phe Gly Tyr Pro Glu Val Lys Pro Ser Asp Asn Trp
    625                 630                 635                 640

Ala Thr Ala Pro Arg Leu Asp Phe Trp Lys Ser Asp Leu Val Arg Gly
                    645                 650                 655

Glu Asn Asp Tyr Val Ala Phe Asp Phe Tyr Leu Asp Pro Val Arg Ala
                    660                 665                 670

Thr Glu Gly Ala Met Asn Ile Asn Leu Val Phe Gln Pro Pro Thr Asn
                    675                 680                 685

Gly Tyr Trp Val Gln Ala Pro Lys Thr Tyr Thr Ile Asn Phe Asp Glu
                    690                 695                 700

Leu Glu Glu Ala Asn Gln Val Asn Gly Leu Tyr His Tyr Glu Val Lys
    705                 710                 715                 720

Ile Asn Val Arg Asp Ile Thr Asn Ile Gln Asp Asp Thr Leu Leu Arg
                    725                 730                 735

Asn Met Met Ile Ile Phe Ala Asp Val Glu Ser Asp Phe Ala Gly Arg
                    740                 745                 750

Val Phe Val Asp Asn Val Arg Phe Glu Gly Ala Ala Thr Thr Glu Pro
                    755                 760                 765

Val Glu Pro Glu Pro Val Asp Pro Gly Glu Glu Thr Pro Pro Val Asp
                    770                 775                 780

Glu Lys Glu Ala Lys Lys Glu Gln Lys Glu Ala Glu Lys Glu Glu Lys
    785                 790                 795                 800

Glu Ala Val Lys Glu Lys Lys Glu Ala Lys Glu Glu Lys Lys Ala
                    805                 810                 815

Val Lys Asn Glu Ala Lys Lys Lys
                    820

<210> SEQ ID NO 55
<211> LENGTH: 1059
<212> TYPE: PRT
<213> ORGANISM: Thermotoga maritima

<400> SEQUENCE: 55

Met Gln Val Arg Lys Arg Arg Gly Leu Leu Asp Val Ser Thr Ala Val
1               5                   10                  15
```

```
Leu Val Gly Ile Leu Ala Gly Phe Leu Gly Val Val Leu Ala Ala Ser
                20                  25                  30

Gly Val Leu Ser Phe Gly Lys Glu Ala Ser Ser Lys Gly Asp Ser Ser
            35                  40                  45

Leu Glu Thr Val Leu Ala Leu Ser Phe Glu Gly Thr Thr Glu Gly Val
        50                  55                  60

Val Pro Phe Gly Lys Asp Val Val Leu Thr Ala Ser Gln Asp Val Ala
 65                  70                  75                  80

Ala Asp Gly Glu Tyr Ser Leu Lys Val Glu Asn Arg Thr Ser Pro Trp
                85                  90                  95

Asp Gly Val Glu Ile Asp Leu Thr Gly Lys Val Lys Ser Gly Ala Asp
            100                 105                 110

Tyr Leu Leu Ser Phe Gln Val Tyr Gln Ser Ser Asp Ala Pro Gln Leu
        115                 120                 125

Phe Asn Val Val Ala Arg Thr Glu Asp Glu Lys Gly Glu Arg Tyr Asp
    130                 135                 140

Val Ile Leu Asp Lys Val Val Ser Asp His Trp Lys Glu Ile Leu
145                 150                 155                 160

Val Pro Phe Ser Pro Thr Phe Glu Gly Thr Pro Ala Lys Tyr Ser Leu
                165                 170                 175

Ile Ile Val Ala Ser Lys Asn Thr Asn Phe Asn Phe Tyr Leu Asp Lys
            180                 185                 190

Val Gln Val Leu Ala Pro Lys Glu Ser Gly Pro Lys Val Ile Tyr Glu
        195                 200                 205

Thr Ser Phe Glu Asn Gly Val Gly Asp Trp Gln Pro Arg Gly Asp Val
    210                 215                 220

Asn Ile Glu Ala Ser Ser Glu Val Ala His Ser Gly Lys Ser Ser Leu
225                 230                 235                 240

Phe Ile Ser Asn Arg Gln Lys Gly Trp Gln Gly Ala Gln Ile Asn Leu
                245                 250                 255

Lys Gly Ile Leu Lys Thr Gly Lys Thr Tyr Ala Phe Glu Ala Trp Val
            260                 265                 270

Tyr Gln Asn Ser Gly Gln Asp Gln Thr Ile Ile Met Thr Met Gln Arg
        275                 280                 285

Lys Tyr Ser Ser Asp Ala Ser Thr Gln Tyr Glu Trp Ile Lys Ser Ala
    290                 295                 300

Thr Val Pro Ser Gly Gln Trp Val Gln Leu Ser Gly Thr Tyr Thr Ile
305                 310                 315                 320

Pro Ala Gly Val Thr Val Glu Asp Leu Thr Leu Tyr Phe Glu Ser Gln
                325                 330                 335

Asn Pro Thr Leu Glu Phe Tyr Val Asp Asp Val Lys Ile Val Asp Thr
            340                 345                 350

Thr Ser Ala Glu Ile Lys Ile Glu Met Glu Pro Glu Lys Glu Ile Pro
        355                 360                 365

Ala Leu Lys Glu Val Leu Lys Asp Tyr Phe Lys Val Gly Val Ala Leu
    370                 375                 380

Pro Ser Lys Val Phe Leu Asn Pro Lys Asp Ile Glu Leu Ile Thr Lys
385                 390                 395                 400

His Phe Asn Ser Ile Thr Ala Glu Asn Glu Met Lys Pro Glu Ser Leu
                405                 410                 415

Leu Ala Gly Ile Glu Asn Gly Lys Leu Lys Phe Arg Phe Glu Thr Ala
            420                 425                 430

Asp Lys Tyr Ile Gln Phe Val Glu Glu Asn Gly Met Val Ile Arg Gly
```

```
                435                 440                 445
        His Thr Leu Val Trp His Asn Gln Thr Pro Asp Trp Phe Phe Lys Asp
        450                 455                 460

Glu Asn Gly Asn Leu Leu Ser Lys Glu Ala Met Thr Glu Arg Leu Lys
        465                 470                 475                 480

Glu Tyr Ile His Thr Val Gly His Phe Lys Gly Lys Val Tyr Ala
                        485                 490                 495

Trp Asp Val Val Asn Glu Ala Val Asp Pro Asn Gln Pro Asp Gly Leu
                        500                 505                 510

Arg Arg Ser Thr Trp Tyr Gln Ile Met Gly Pro Asp Tyr Ile Glu Leu
                        515                 520                 525

Ala Phe Lys Phe Ala Arg Glu Ala Asp Pro Asp Ala Lys Leu Phe Tyr
                        530                 535                 540

Asn Asp Tyr Asn Thr Phe Glu Pro Arg Lys Arg Asp Ile Ile Tyr Asn
        545                 550                 555                 560

Leu Val Lys Asp Leu Lys Glu Lys Gly Leu Ile Asp Gly Ile Gly Met
                        565                 570                 575

Gln Cys His Ile Ser Leu Ala Thr Asp Ile Lys Gln Ile Glu Glu Ala
                        580                 585                 590

Ile Lys Lys Phe Ser Thr Ile Pro Gly Ile Glu Ile His Ile Thr Glu
                        595                 600                 605

Leu Asp Met Ser Val Tyr Arg Asp Ser Ser Asn Tyr Pro Glu Ala
        610                 615                 620

Pro Arg Thr Ala Leu Ile Glu Gln Ala His Lys Met Met Gln Leu Phe
        625                 630                 635                 640

Glu Ile Phe Lys Lys Tyr Ser Asn Val Ile Thr Asn Val Thr Phe Trp
                        645                 650                 655

Gly Leu Lys Asp Asp Tyr Ser Trp Arg Ala Thr Arg Arg Asn Asp Trp
                        660                 665                 670

Pro Leu Ile Phe Asp Lys Asp His Gln Ala Lys Leu Ala Tyr Trp Ala
                        675                 680                 685

Ile Val Ala Pro Glu Val Leu Pro Pro Leu Pro Lys Glu Ser Arg Ile
        690                 695                 700

Ser Glu Gly Glu Ala Val Val Gly Met Met Asp Asp Ser Tyr Leu
        705                 710                 715                 720

Met Ser Lys Pro Ile Glu Ile Leu Asp Glu Glu Gly Asn Val Lys Ala
                        725                 730                 735

Thr Ile Arg Ala Val Trp Lys Asp Ser Thr Ile Tyr Ile Tyr Gly Glu
                        740                 745                 750

Val Gln Asp Lys Thr Lys Lys Pro Ala Glu Asp Gly Val Ala Ile Phe
                        755                 760                 765

Ile Asn Pro Asn Asn Glu Arg Thr Pro Tyr Leu Gln Pro Asp Asp Thr
        770                 775                 780

Tyr Ala Val Leu Trp Thr Asn Trp Lys Thr Glu Val Asn Arg Glu Asp
        785                 790                 795                 800

Val Gln Val Lys Lys Phe Val Gly Pro Gly Phe Arg Arg Tyr Ser Phe
                        805                 810                 815

Glu Met Ser Ile Thr Ile Pro Gly Val Glu Phe Lys Lys Asp Ser Tyr
                        820                 825                 830

Ile Gly Phe Asp Ala Ala Val Ile Asp Asp Gly Lys Trp Tyr Ser Trp
                        835                 840                 845

Ser Asp Thr Thr Asn Ser Gln Lys Thr Asn Thr Met Asn Tyr Gly Thr
        850                 855                 860
```

```
Leu Lys Leu Glu Gly Ile Met Val Ala Thr Ala Lys Tyr Gly Thr Pro
865                 870                 875                 880

Val Ile Asp Gly Glu Ile Asp Glu Ile Trp Asn Thr Thr Glu Glu Ile
            885                 890                 895

Glu Thr Lys Ala Val Ala Met Gly Ser Leu Asp Lys Asn Ala Thr Ala
                900                 905                 910

Lys Val Arg Val Leu Trp Asp Glu Asn Tyr Leu Tyr Val Leu Ala Ile
            915                 920                 925

Val Lys Asp Pro Val Leu Asn Lys Asp Asn Ser Asn Pro Trp Glu Gln
        930                 935                 940

Asp Ser Val Glu Ile Phe Ile Asp Glu Asn Asn His Lys Thr Gly Tyr
945                 950                 955                 960

Tyr Glu Asp Asp Asp Ala Gln Phe Arg Val Asn Tyr Met Asn Glu Gln
                965                 970                 975

Thr Phe Gly Thr Gly Gly Ser Pro Ala Arg Phe Lys Thr Ala Val Lys
            980                 985                 990

Leu Ile Glu Gly Gly Tyr Ile Val Glu Ala Ala Ile Lys Trp Lys Thr
        995                 1000                1005

Ile Lys Pro Thr Pro Asn Thr Val Ile Gly Phe Asn Ile Gln Val Asn
    1010                1015                1020

Asp Ala Asn Glu Lys Gly Gln Arg Val Gly Ile Ile Ser Trp Ser Asp
1025                1030                1035                1040

Pro Thr Asn Asn Ser Trp Arg Asp Pro Ser Lys Phe Gly Asn Leu Arg
                1045                1050                1055

Leu Ile Lys

<210> SEQ ID NO 56
<211> LENGTH: 512
<212> TYPE: PRT
<213> ORGANISM: Clostridium stercorarium

<400> SEQUENCE: 56

Met Lys Arg Lys Val Lys Lys Met Ala Ala Met Ala Thr Ser Ile Ile
1               5                   10                  15

Met Ala Ile Met Ile Ile Leu His Ser Ile Pro Val Leu Ala Gly Arg
                20                  25                  30

Ile Ile Tyr Asp Asn Glu Thr Gly Thr His Gly Gly Tyr Asp Tyr Glu
            35                  40                  45

Leu Trp Lys Asp Tyr Gly Asn Thr Ile Met Glu Leu Asn Asp Gly Gly
    50                  55                  60

Thr Phe Ser Cys Gln Trp Ser Asn Ile Gly Asn Ala Leu Phe Arg Lys
65                  70                  75                  80

Gly Arg Lys Phe Asn Ser Asp Lys Thr Tyr Gln Glu Leu Gly Asp Ile
                85                  90                  95

Val Val Glu Tyr Gly Cys Asp Tyr Asn Pro Asn Gly Asn Ser Tyr Leu
            100                 105                 110

Cys Val Tyr Gly Trp Thr Arg Asn Pro Leu Val Glu Tyr Tyr Ile Val
        115                 120                 125

Glu Ser Trp Gly Ser Trp Arg Pro Pro Gly Ala Thr Pro Lys Gly Thr
    130                 135                 140

Ile Thr Gln Trp Met Ala Gly Thr Tyr Glu Ile Tyr Glu Thr Thr Arg
145                 150                 155                 160

Val Asn Gln Pro Ser Ile Asp Gly Thr Ala Thr Phe Gln Gln Tyr Trp
                165                 170                 175
```

Ser Val Arg Thr Ser Lys Arg Thr Ser Gly Thr Ile Ser Val Thr Glu
                180                 185                 190

His Phe Lys Gln Trp Glu Arg Met Gly Met Arg Met Gly Lys Met Tyr
            195                 200                 205

Glu Val Ala Leu Thr Val Glu Gly Tyr Gln Ser Ser Gly Tyr Ala Asn
210                 215                 220

Val Tyr Lys Asn Glu Ile Arg Ile Gly Ala Asn Pro Thr Pro Ala Pro
225                 230                 235                 240

Ser Gln Ser Pro Ile Arg Arg Asp Ala Phe Ser Ile Ile Glu Ala Glu
                245                 250                 255

Glu Tyr Asn Ser Thr Asn Ser Ser Thr Leu Gln Val Ile Gly Thr Pro
            260                 265                 270

Asn Asn Gly Arg Gly Ile Gly Tyr Ile Glu Asn Gly Asn Thr Val Thr
        275                 280                 285

Tyr Ser Asn Ile Asp Phe Gly Ser Gly Ala Thr Gly Phe Ser Ala Thr
290                 295                 300

Val Ala Thr Glu Val Asn Thr Ser Ile Gln Ile Arg Ser Asp Ser Pro
305                 310                 315                 320

Thr Gly Thr Leu Leu Gly Thr Leu Tyr Val Ser Ser Thr Gly Ser Trp
                325                 330                 335

Asn Thr Tyr Gln Thr Val Ser Thr Asn Ile Ser Lys Ile Thr Gly Val
            340                 345                 350

His Asp Ile Val Leu Val Phe Ser Gly Pro Val Asn Val Asp Asn Phe
        355                 360                 365

Ile Phe Ser Arg Ser Ser Pro Val Pro Ala Pro Gly Asp Asn Thr Arg
370                 375                 380

Asp Ala Tyr Ser Ile Ile Gln Ala Glu Asp Tyr Asp Ser Ser Tyr Gly
385                 390                 395                 400

Pro Asn Leu Gln Ile Phe Ser Leu Pro Gly Gly Ser Ala Ile Gly
                405                 410                 415

Tyr Ile Glu Asn Gly Tyr Ser Thr Thr Tyr Lys Asn Ile Asp Phe Gly
            420                 425                 430

Asp Gly Ala Thr Ser Val Thr Ala Arg Val Ala Thr Gln Asn Ala Thr
        435                 440                 445

Thr Ile Gln Val Arg Leu Gly Ser Pro Ser Gly Thr Leu Leu Gly Thr
450                 455                 460

Ile Tyr Val Gly Ser Thr Gly Ser Phe Asp Thr Tyr Arg Asp Val Ser
465                 470                 475                 480

Ala Thr Ile Ser Asn Thr Ala Gly Val Lys Asp Ile Val Leu Val Phe
                485                 490                 495

Ser Gly Pro Val Asn Val Asp Trp Phe Val Phe Ser Lys Ser Gly Thr
            500                 505                 510

<210> SEQ ID NO 57
<211> LENGTH: 457
<212> TYPE: PRT
<213> ORGANISM: Solanum lycopersicum

<400> SEQUENCE: 57

Met Val Ile Gln Arg Asn Ser Ile Leu Leu Ile Ile Phe Ala
 1               5                  10                  15

Ser Ser Ile Ser Thr Cys Arg Ser Asn Val Ile Asp Asp Asn Leu Phe
                20                  25                  30

Lys Gln Val Tyr Asp Asn Ile Leu Glu Gln Glu Phe Ala His Asp Phe

-continued

```
            35                  40                  45
Gln Ala Tyr Leu Ser Tyr Leu Ser Lys Asn Ile Glu Ser Asn Asn Asn
            50                  55                  60

Ile Asp Lys Val Asp Lys Asn Gly Ile Lys Val Ile Asn Val Leu Ser
 65                  70                  75                  80

Phe Gly Ala Lys Gly Asp Gly Lys Thr Tyr Asp Asn Ile Ala Phe Glu
                 85                  90                  95

Gln Ala Trp Asn Glu Ala Cys Ser Ser Arg Thr Pro Val Gln Phe Val
                100                 105                 110

Val Pro Lys Asn Lys Asn Tyr Leu Leu Lys Gln Ile Thr Phe Ser Gly
                115                 120                 125

Pro Cys Arg Ser Ser Ile Ser Val Lys Ile Phe Gly Ser Leu Glu Ala
                130                 135                 140

Ser Ser Lys Ile Ser Asp Tyr Lys Asp Arg Arg Leu Trp Ile Ala Phe
145                 150                 155                 160

Asp Ser Val Gln Asn Leu Val Val Gly Gly Gly Thr Ile Asn Gly
                165                 170                 175

Asn Gly Gln Val Trp Pro Ser Ser Cys Lys Ile Asn Lys Ser Leu
                180                 185                 190

Pro Cys Arg Asp Ala Pro Thr Ala Leu Thr Phe Trp Asn Cys Lys Asn
                195                 200                 205

Leu Lys Val Asn Asn Leu Lys Ser Lys Asn Ala Gln Gln Ile His Ile
                210                 215                 220

Lys Phe Glu Ser Cys Thr Asn Val Val Ala Ser Asn Leu Met Ile Asn
225                 230                 235                 240

Ala Ser Ala Lys Ser Pro Asn Thr Asp Gly Val His Val Ser Asn Thr
                245                 250                 255

Gln Tyr Ile Gln Ile Ser Asp Thr Ile Ile Gly Thr Gly Asp Asp Cys
                260                 265                 270

Ile Ser Ile Val Ser Gly Ser Gln Asn Val Gln Ala Thr Asn Ile Thr
                275                 280                 285

Cys Gly Pro Gly His Gly Ile Ser Ile Gly Ser Leu Gly Ser Gly Asn
                290                 295                 300

Ser Glu Ala Tyr Val Ser Asn Val Thr Val Asn Glu Ala Lys Ile Ile
305                 310                 315                 320

Gly Ala Glu Asn Gly Val Arg Ile Lys Thr Trp Gln Gly Gly Ser Gly
                325                 330                 335

Gln Ala Ser Asn Ile Lys Phe Leu Asn Val Glu Met Gln Asp Val Lys
                340                 345                 350

Tyr Pro Ile Ile Ile Asp Gln Asn Tyr Cys Asp Arg Val Glu Pro Cys
                355                 360                 365

Ile Gln Gln Phe Ser Ala Val Gln Val Lys Asn Val Val Tyr Glu Asn
                370                 375                 380

Ile Lys Gly Thr Ser Ala Thr Lys Val Ala Ile Lys Phe Asp Cys Ser
385                 390                 395                 400

Thr Asn Phe Pro Cys Glu Gly Ile Ile Met Glu Asn Ile Asn Leu Val
                405                 410                 415

Gly Glu Ser Gly Lys Pro Ser Glu Ala Thr Cys Lys Asn Val His Phe
                420                 425                 430

Asn Asn Ala Glu His Val Thr Pro His Cys Thr Ser Leu Glu Ile Ser
                435                 440                 445

Glu Asp Glu Ala Leu Leu Tyr Asn Tyr
450                 455
```

-continued

```
<210> SEQ ID NO 58
<211> LENGTH: 649
<212> TYPE: PRT
<213> ORGANISM: Clostridium thermocellum

<400> SEQUENCE: 58

Met Ser Arg Met Thr Leu Lys Ser Ser Met Lys Lys Arg Val Leu Ser
1               5                   10                  15

Leu Leu Ile Ala Val Val Phe Leu Ser Leu Thr Gly Val Phe Pro Ser
            20                  25                  30

Gly Leu Ile Glu Thr Lys Val Ser Ala Ala Lys Ile Thr Glu Asn Tyr
        35                  40                  45

Gln Phe Asp Ser Arg Ile Arg Leu Asn Ser Ile Gly Phe Ile Pro Asn
    50                  55                  60

His Ser Lys Lys Ala Thr Ile Ala Ala Asn Cys Ser Thr Phe Tyr Val
65                  70                  75                  80

Val Lys Glu Asp Gly Thr Ile Val Tyr Thr Gly Thr Ala Thr Ser Met
                85                  90                  95

Phe Asp Asn Asp Thr Lys Glu Thr Val Tyr Ile Ala Asp Phe Ser Ser
            100                 105                 110

Val Asn Glu Glu Gly Thr Tyr Tyr Leu Ala Val Pro Gly Val Gly Lys
        115                 120                 125

Ser Val Asn Phe Lys Ile Ala Met Asn Val Tyr Glu Asp Ala Phe Lys
    130                 135                 140

Thr Ala Met Leu Gly Met Tyr Leu Leu Arg Cys Gly Thr Ser Val Ser
145                 150                 155                 160

Ala Thr Tyr Asn Gly Ile His Tyr Ser His Gly Pro Cys His Thr Asn
                165                 170                 175

Asp Ala Tyr Leu Asp Tyr Ile Asn Gly Gln His Thr Lys Lys Asp Ser
            180                 185                 190

Thr Lys Gly Trp His Asp Ala Gly Asp Tyr Asn Lys Tyr Val Val Asn
        195                 200                 205

Ala Gly Ile Thr Val Gly Ser Met Phe Leu Ala Trp Glu His Phe Lys
    210                 215                 220

Asp Gln Leu Glu Pro Val Ala Leu Glu Ile Pro Glu Lys Asn Asn Ser
225                 230                 235                 240

Ile Pro Asp Phe Leu Asp Glu Leu Lys Tyr Glu Ile Asp Trp Ile Leu
                245                 250                 255

Thr Met Gln Tyr Pro Asp Gly Ser Gly Arg Val Ala His Lys Val Ser
            260                 265                 270

Thr Arg Asn Phe Gly Gly Phe Ile Met Pro Glu Asn Glu His Asp Glu
        275                 280                 285

Arg Phe Phe Val Pro Trp Ser Ser Ala Ala Thr Ala Asp Phe Val Ala
    290                 295                 300

Met Thr Ala Met Ala Ala Arg Ile Phe Arg Pro Tyr Asp Pro Gln Tyr
305                 310                 315                 320

Ala Glu Lys Cys Ile Asn Ala Ala Lys Val Ser Tyr Glu Phe Leu Lys
                325                 330                 335

Asn Asn Pro Ala Asn Val Phe Ala Asn Gln Ser Gly Phe Ser Thr Gly
            340                 345                 350

Glu Tyr Ala Thr Val Ser Asp Ala Asp Asp Arg Leu Trp Ala Ala Ala
        355                 360                 365

Glu Met Trp Glu Thr Leu Gly Asp Glu Glu Tyr Leu Arg Asp Phe Glu
```

```
                    370                 375                 380
Asn Arg Ala Ala Gln Phe Ser Lys Lys Ile Glu Ala Asp Phe Asp Trp
385                 390                 395                 400

Asp Asn Val Ala Asn Leu Gly Met Phe Thr Tyr Leu Leu Ser Glu Arg
                405                 410                 415

Pro Gly Lys Asn Pro Ala Leu Val Gln Ser Ile Lys Asp Ser Leu Leu
            420                 425                 430

Ser Thr Ala Asp Ser Ile Val Arg Thr Ser Gln Asn His Gly Tyr Gly
        435                 440                 445

Arg Thr Leu Gly Thr Thr Tyr Tyr Trp Gly Cys Asn Gly Thr Val Val
    450                 455                 460

Arg Gln Thr Met Ile Leu Gln Val Ala Asn Lys Ile Ser Pro Asn Asn
465                 470                 475                 480

Asp Tyr Val Asn Ala Ala Leu Asp Ala Ile Ser His Val Phe Gly Arg
                485                 490                 495

Asn Tyr Tyr Asn Arg Ser Tyr Val Thr Gly Leu Gly Ile Asn Pro Pro
            500                 505                 510

Met Asn Pro His Asp Arg Arg Ser Gly Ala Asp Gly Ile Trp Glu Pro
        515                 520                 525

Trp Pro Gly Tyr Leu Val Gly Gly Trp Pro Gly Pro Lys Asp Trp
    530                 535                 540

Val Asp Ile Gln Asp Ser Tyr Gln Thr Asn Glu Ile Ala Ile Asn Trp
545                 550                 555                 560

Asn Ala Ala Leu Ile Tyr Ala Leu Ala Gly Phe Val Asn Tyr Asn Ser
                565                 570                 575

Pro Gln Asn Glu Val Leu Tyr Gly Asp Val Asn Asp Asp Gly Lys Val
            580                 585                 590

Asn Ser Thr Asp Leu Thr Leu Leu Lys Arg Tyr Val Leu Lys Ala Val
        595                 600                 605

Ser Thr Leu Pro Ser Ser Lys Ala Glu Lys Asn Ala Asp Val Asn Arg
    610                 615                 620

Asp Gly Arg Val Asn Ser Ser Asp Val Thr Ile Leu Ser Arg Tyr Leu
625                 630                 635                 640

Ile Arg Val Ile Glu Lys Leu Pro Ile
                645

<210> SEQ ID NO 59
<211> LENGTH: 203
<212> TYPE: PRT
<213> ORGANISM: Sulfolobus acidocaldarius

<400> SEQUENCE: 59

Met Leu Arg Ser Leu Val Leu Asn Glu Lys Leu Arg Ala Arg Val Leu
1               5                   10                  15

Glu Arg Ala Glu Glu Phe Leu Leu Asn Asn Lys Ala Asp Glu Glu Val
            20                  25                  30

Trp Phe Arg Glu Leu Val Leu Cys Ile Leu Thr Ser Asn Ser Ser Phe
        35                  40                  45

Ile Ser Ala Tyr Lys Ser Met Asn Tyr Ile Leu Asp Lys Ile Leu Tyr
    50                  55                  60

Met Asp Glu Lys Glu Ile Ser Ile Leu Gln Ser Gly Tyr Arg
65                  70                  75                  80

Phe Tyr Asn Leu Lys Ala Lys Tyr Leu Tyr Arg Ala Lys Asn Leu Tyr
                85                  90                  95
```

```
Gly Lys Val Lys Lys Thr Ile Lys Glu Ile Ala Asp Lys Asp Gln Met
            100                 105                 110

Gln Ala Arg Glu Phe Ile Ala Thr His Ile Tyr Gly Ile Gly Tyr Lys
            115                 120                 125

Glu Ala Ser His Phe Leu Arg Asn Val Gly Tyr Leu Asp Leu Ala Ile
            130                 135                 140

Ile Asp Arg His Ile Leu Arg Phe Ile Asn Asn Leu Gly Ile Pro Ile
145                 150                 155                 160

Lys Leu Lys Ser Lys Arg Glu Tyr Leu Leu Ala Glu Ser Leu Leu Arg
                165                 170                 175

Ser Ile Ala Asn Asn Leu Asn Val Gln Val Gly Leu Leu Asp Leu Phe
            180                 185                 190

Ile Phe Phe Lys Gln Thr Asn Thr Ile Val Lys
            195                 200

<210> SEQ ID NO 60
<211> LENGTH: 432
<212> TYPE: PRT
<213> ORGANISM: Thermotoga maritima

<400> SEQUENCE: 60

Met Phe Lys Pro Asn Tyr His Phe Phe Pro Ile Thr Gly Trp Met Asn
1               5                   10                  15

Asp Pro Asn Gly Leu Ile Phe Trp Lys Gly Lys Tyr His Met Phe Tyr
            20                  25                  30

Gln Tyr Asn Pro Arg Lys Pro Glu Trp Gly Asn Ile Cys Trp Gly His
            35                  40                  45

Ala Val Ser Asp Asp Leu Val His Trp Arg His Leu Pro Val Ala Leu
    50                  55                  60

Tyr Pro Asp Glu Thr His Gly Val Phe Ser Gly Ser Ala Val Glu
65                  70                  75                  80

Lys Asp Gly Lys Met Phe Leu Val Tyr Thr Tyr Tyr Arg Asp Pro Thr
                85                  90                  95

His Asn Lys Gly Glu Lys Glu Thr Gln Cys Val Ala Met Ser Glu Asn
            100                 105                 110

Gly Leu Asp Phe Val Lys Tyr Asp Gly Asn Pro Val Ile Ser Lys Pro
            115                 120                 125

Pro Glu Glu Gly Thr His Ala Phe Arg Asp Pro Lys Val Asn Arg Ser
            130                 135                 140

Asn Gly Glu Trp Arg Met Val Leu Gly Ser Gly Lys Asp Glu Lys Ile
145                 150                 155                 160

Gly Arg Val Leu Leu Tyr Thr Ser Asp Asp Leu Phe His Trp Lys Tyr
                165                 170                 175

Glu Gly Val Ile Phe Glu Asp Glu Thr Thr Lys Glu Ile Glu Cys Pro
            180                 185                 190

Asp Leu Val Arg Ile Gly Glu Lys Asp Ile Leu Ile Tyr Ser Ile Thr
            195                 200                 205

Ser Thr Asn Ser Val Leu Phe Ser Met Gly Glu Leu Lys Glu Gly Lys
    210                 215                 220

Leu Asn Val Glu Lys Arg Gly Leu Leu Asp His Gly Thr Asp Phe Tyr
225                 230                 235                 240

Ala Ala Gln Thr Phe Phe Gly Thr Asp Arg Val Val Ile Gly Trp
                245                 250                 255

Leu Gln Ser Trp Leu Arg Thr Gly Leu Tyr Pro Thr Lys Arg Glu Gly
            260                 265                 270
```

-continued

Trp Asn Gly Val Met Ser Leu Pro Arg Glu Leu Tyr Val Glu Asn Asn
            275                 280                 285

Glu Leu Lys Val Lys Pro Val Asp Glu Leu Leu Ala Leu Arg Lys Arg
    290                 295                 300

Lys Val Phe Glu Thr Ala Lys Ser Gly Thr Phe Leu Leu Asp Val Lys
305                 310                 315                 320

Glu Asn Ser Tyr Glu Ile Val Cys Glu Phe Ser Gly Glu Ile Glu Leu
                325                 330                 335

Arg Met Gly Asn Glu Ser Glu Val Val Ile Thr Lys Ser Arg Asp
                340                 345                 350

Glu Leu Ile Val Asp Thr Thr Arg Ser Gly Val Ser Gly Gly Glu Val
            355                 360                 365

Arg Lys Ser Thr Val Glu Asp Glu Ala Thr Asn Arg Ile Arg Ala Phe
    370                 375                 380

Leu Asp Ser Cys Ser Val Glu Phe Phe Asn Asp Ser Ile Ala Phe
385                 390                 395                 400

Ser Phe Arg Ile His Pro Glu Asn Val Tyr Asn Ile Leu Ser Val Lys
                405                 410                 415

Ser Asn Gln Val Lys Leu Glu Val Phe Glu Leu Glu Asn Ile Trp Leu
            420                 425                 430

<210> SEQ ID NO 61
<211> LENGTH: 1021
<212> TYPE: PRT
<213> ORGANISM: Rhodothermus marinus

<400> SEQUENCE: 61

Met Ala Gly Pro His Arg Ser Arg Ala Ala Gly Pro Pro Phe Ala
1               5                   10                  15

Val Asp Glu His Val Ala Leu Glu Met Val Ala Phe Arg Gly Glu Val
            20                  25                  30

Phe Ala Gly His Gly Leu Leu Ala Asp Gln Arg Leu Ile Ala His Thr
        35                  40                  45

Gly Arg Pro Ala Leu Asn Ala Gln Arg Ile Thr Gln Gln Lys Gln Arg
    50                  55                  60

Asp Gln Cys Arg Gly Gln Arg His Arg His Gln Gly Gly Arg Asn
65              70                  75                  80

Leu Arg Lys Ala His Arg Thr Phe His Glu His Gln Ser Thr Gln Asp
                85                  90                  95

Gln Ala His Asp Ala Pro His Gly Gln Gln Ala Lys Thr Gly His Glu
            100                 105                 110

Gly Leu Gly His Glu His Ala Gln Ala Gln His Gln Gln Gly Gln Ser
        115                 120                 125

Asn Val Val Asp Arg Gln Asp Gly Glu Pro Val Glu Ala Gln His Gln
    130                 135                 140

Lys Asp Gly Ala Gln Arg Ala Gly Asn Ala Pro Ala Gly Arg Val Glu
145                 150                 155                 160

Leu Glu Gln Gln Pro Val Glu Ala Gln His Gln Gln Glu Gly Asp
                165                 170                 175

Val Arg Ile Gly Lys Arg Arg Gln Asn Ala Phe Ala Pro Pro Ala Leu
            180                 185                 190

Asp His Val His Gly Gly Pro Gly Arg Leu Gln Arg His Gly Leu Ala
        195                 200                 205

Val Glu Arg His Val Pro Ala Val Gln Gln His Gln Gln Arg Val Gln

-continued

```
            210                 215                 220
Arg Gly Arg Gln Gln Ile Asp His Val Leu Gly His Gly Leu Pro Gly
225                 230                 235                 240

Arg Gln Arg Leu Ala Phe Arg Asp Gly Pro Arg Pro Val Gly Val
                245                 250                 255

Ala Ser Pro Val Leu Gly Gln Arg Pro Cys Pro Gly His Arg Ile Val
                260                 265                 270

Gln Asn Leu Phe Arg His Gly Ile Asp Pro Cys Arg Val Gly Arg Cys
            275                 280                 285

Arg Arg Ser Pro Ser Glu Leu His Gly Met Gly Cys Ala Asp Val Arg
290                 295                 300

Ala Arg Gly His Gly Arg His Met Arg Gly Gln Arg Asp Glu His Pro
305                 310                 315                 320

Gly Arg Gly Arg Pro Cys Ala Arg Arg His Val Asp Asp Arg
                325                 330                 335

Asp Arg Thr Pro Gln Glu Lys Leu Tyr Asp Val Ala Arg Gly Leu Asp
                340                 345                 350

Glu Pro Ala Arg Arg Val His Phe Asp Asp Glu Ala Asp Arg Ser Val
                355                 360                 365

Phe Arg Gly Leu Ala Gln Pro Ala Pro Asp Glu Pro Glu Gly Arg Arg
370                 375                 380

Arg Asp Arg Leu Val Leu Gln Arg Gln Ser Val Asn His Arg Arg Gly
385                 390                 395                 400

Arg Leu Ser Arg His Arg Gln His Gln Pro Gln Gln Arg Pro
                405                 410                 415

His Gly Asn Gln Ala Phe Leu Gly Lys Tyr Glu Lys Arg Arg Arg Lys
                420                 425                 430

Pro Thr Ala Cys Leu Lys Ser Leu Arg Arg Phe Pro Lys Asp Ala
                435                 440                 445

Pro Val Leu Tyr Phe Val Asn Gln Leu Glu Lys Thr Lys Arg Arg Met
                450                 455                 460

Thr Leu Leu Leu Val Trp Leu Ile Phe Thr Gly Val Ala Gly Glu Ile
465                 470                 475                 480

Arg Leu Glu Ala Glu Asp Gly Glu Leu Leu Gly Val Ala Val Asp Ser
                485                 490                 495

Thr Leu Thr Gly Tyr Ser Gly Arg Gly Tyr Val Thr Gly Phe Asp Ala
                500                 505                 510

Pro Glu Asp Ser Val Arg Phe Ser Phe Glu Ala Pro Arg Gly Val Tyr
                515                 520                 525

Arg Val Val Phe Gly Val Ser Phe Ser Arg Phe Ala Ser Tyr Ala
530                 535                 540

Leu Arg Val Asp Asp Trp His Gln Thr Gly Ser Leu Ile Lys Arg Gly
545                 550                 555                 560

Gly Gly Phe Phe Glu Ala Ser Ile Gly Glu Ile Trp Leu Asp Glu Gly
                565                 570                 575

Ala His Thr Met Ala Phe Gln Leu Met Asn Gly Ala Leu Asp Tyr Val
                580                 585                 590

Arg Leu Glu Pro Val Ser Tyr Gly Pro Pro Ala Arg Pro Pro Ala Gln
                595                 600                 605

Leu Ser Asp Ser Gln Ala Thr Ala Ser Ala Gln Ala Leu Phe Ala Phe
                610                 615                 620

Leu Leu Ser Glu Tyr Gly Arg His Ile Leu Ala Gly Gln Gln Gln Asn
625                 630                 635                 640
```

```
Pro Tyr Arg Arg Asp Phe Asp Ala Ile Asn Tyr Val Arg Asn Val Thr
            645                 650                 655

Gly Lys Glu Pro Ala Leu Val Ser Phe Asp Leu Ile Asp Tyr Ser Pro
            660                 665                 670

Thr Arg Glu Ala His Gly Val Val His Tyr Gln Thr Pro Glu Asp Trp
            675                 680                 685

Ile Ala Trp Ala Gly Arg Asp Gly Ile Val Ser Leu Met Trp His Trp
            690                 695                 700

Asn Ala Pro Thr Asp Leu Ile Glu Asp Pro Ser Gln Asp Cys Tyr Trp
705                 710                 715                 720

Trp Tyr Gly Phe Tyr Thr Arg Cys Thr Thr Phe Asp Val Ala Ala Ala
            725                 730                 735

Leu Ala Asp Thr Ser Ser Glu Arg Tyr Arg Leu Leu Leu Arg Asp Ile
            740                 745                 750

Asp Val Ile Ala Ala Gln Leu Gln Lys Phe Gln Gln Ala Asp Ile Pro
            755                 760                 765

Val Leu Trp Arg Pro Leu His Glu Ala Ala Gly Gly Trp Phe Trp Trp
770                 775                 780

Gly Ala Lys Gly Pro Glu Pro Phe Lys Gln Leu Trp Arg Leu Leu Tyr
785                 790                 795                 800

Glu Arg Leu Val His His Gly Leu His Asn Leu Ile Trp Val Tyr
            805                 810                 815

Thr His Glu Pro Gly Ala Ala Glu Trp Tyr Pro Gly Asp Ala Tyr Val
            820                 825                 830

Asp Ile Val Gly Arg Asp Val Tyr Ala Asp Asp Pro Ala Leu Met
            835                 840                 845

Arg Ser Asp Trp Asn Glu Leu Gln Thr Leu Phe Gly Gly Arg Lys Leu
850                 855                 860

Val Ala Leu Thr Glu Thr Gly Thr Leu Pro Asp Val Glu Val Ile Thr
865                 870                 875                 880

Asp Tyr Gly Ile Trp Trp Ser Trp Phe Ser Ile Trp Thr Asp Pro Phe
            885                 890                 895

Leu Arg Asp Val Asp Pro Asp Arg Leu Thr Arg Val Tyr His Ser Glu
            900                 905                 910

Arg Val Leu Thr Arg Asp Glu Leu Pro Asp Trp Arg Ser Tyr Val Leu
            915                 920                 925

His Ala Thr Thr Val Gln Pro Ala Gly Asp Leu Ala Leu Ala Val Tyr
930                 935                 940

Pro Asn Pro Gly Ala Gly Arg Leu His Val Glu Val Gly Leu Pro Val
945                 950                 955                 960

Ala Ala Pro Val Val Glu Val Phe Asn Leu Leu Gly Gln Arg Val
            965                 970                 975

Phe Gln Tyr Gln Ala Gly Met Gln Pro Ala Gly Leu Trp Arg Arg Ala
            980                 985                 990

Phe Glu Leu Ala Leu Ala Pro Gly Val Tyr Leu Val Gln Val Arg Ala
            995                 1000                1005

Gly Asn Leu Val Ala Arg Arg Trp Val Ser Val Arg
    1010                1015                1020

<210> SEQ ID NO 62
<211> LENGTH: 549
<212> TYPE: PRT
<213> ORGANISM: Geobacillus stearothermophilus
```

-continued

<400> SEQUENCE: 62

```
Met Leu Thr Phe His Arg Ile Ile Arg Lys Gly Trp Met Phe Leu Leu
 1               5                  10                  15
Ala Phe Leu Leu Thr Ala Leu Leu Phe Cys Pro Thr Gly Gln Pro Ala
             20                  25                  30
Lys Ala Ala Ala Pro Phe Asn Gly Thr Met Met Gln Tyr Phe Glu Trp
         35                  40                  45
Tyr Leu Pro Asp Asp Gly Thr Leu Trp Thr Lys Val Ala Asn Glu Ala
     50                  55                  60
Asn Asn Leu Ser Ser Leu Gly Ile Thr Ala Leu Trp Leu Pro Pro Ala
 65                  70                  75                  80
Tyr Lys Gly Thr Ser Arg Ser Asp Val Gly Tyr Gly Val Tyr Asp Leu
                 85                  90                  95
Tyr Asp Leu Gly Glu Phe Asn Gln Lys Gly Ala Val Arg Thr Lys Tyr
            100                 105                 110
Gly Thr Lys Ala Gln Tyr Leu Gln Ala Ile Gln Ala Ala His Ala Ala
        115                 120                 125
Gly Met Gln Val Tyr Ala Asp Val Val Phe Asp His Lys Gly Gly Ala
    130                 135                 140
Asp Gly Thr Glu Trp Val Asp Ala Val Glu Val Asn Pro Ser Asp Arg
145                 150                 155                 160
Asn Gln Glu Ile Ser Gly Thr Tyr Gln Ile Gln Ala Trp Thr Lys Phe
                165                 170                 175
Asp Phe Pro Gly Arg Gly Asn Thr Tyr Ser Ser Phe Lys Trp Arg Trp
            180                 185                 190
Tyr His Phe Asp Gly Val Asp Trp Asp Glu Ser Arg Lys Leu Ser Arg
        195                 200                 205
Ile Tyr Lys Phe Arg Gly Ile Gly Lys Ala Trp Asp Trp Glu Val Asp
    210                 215                 220
Thr Glu Asn Gly Asn Tyr Asp Tyr Leu Met Tyr Ala Asp Leu Asp Met
225                 230                 235                 240
Asp His Pro Glu Val Val Thr Glu Leu Lys Ser Trp Gly Lys Trp Tyr
                245                 250                 255
Val Asn Thr Thr Asn Ile Asp Gly Phe Arg Leu Asp Ala Val Lys His
            260                 265                 270
Ile Lys Phe Ser Phe Pro Asp Trp Leu Ser Asp Val Arg Ser Gln
    275                 280                 285
Thr Gly Lys Pro Leu Phe Thr Val Gly Glu Tyr Trp Ser Tyr Asp Ile
    290                 295                 300
Asn Lys Leu His Asn Tyr Ile Met Lys Thr Asn Gly Thr Met Ser Leu
305                 310                 315                 320
Phe Asp Ala Pro Leu His Asn Lys Phe Tyr Thr Ala Ser Lys Ser Gly
            325                 330                 335
Gly Thr Phe Asp Met Arg Thr Leu Met Thr Asn Thr Leu Met Lys Asp
        340                 345                 350
Gln Pro Thr Leu Ala Val Thr Phe Val Asp Asn His Asp Thr Glu Pro
    355                 360                 365
Gly Gln Ala Leu Gln Ser Trp Val Asp Pro Trp Phe Lys Pro Leu Ala
    370                 375                 380
Tyr Ala Phe Ile Leu Thr Arg Gln Glu Gly Tyr Pro Cys Val Phe Tyr
385                 390                 395                 400
Gly Asp Tyr Tyr Gly Ile Pro Gln Tyr Asn Ile Pro Ser Leu Lys Ser
                405                 410                 415
```

-continued

```
Lys Ile Asp Pro Leu Ile Ala Arg Arg Asp Tyr Ala Tyr Gly Thr
                420                 425                 430

Gln His Asp Tyr Leu Asp His Ser Asp Ile Ile Gly Trp Thr Arg Glu
            435                 440                 445

Gly Val Thr Glu Lys Pro Gly Ser Gly Leu Ala Ala Leu Ile Thr Asp
        450                 455                 460

Gly Pro Gly Ser Lys Trp Met Tyr Val Gly Lys Gln His Ala Gly
465                 470                 475                 480

Lys Val Phe Tyr Asp Leu Thr Gly Asn Arg Ser Asp Thr Val Thr Ile
                485                 490                 495

Asn Ser Asp Gly Trp Gly Glu Phe Lys Val Asn Gly Ser Val Ser
            500                 505                 510

Val Trp Val Pro Arg Lys Thr Thr Val Ser Thr Ile Ala Trp Ser Ile
        515                 520                 525

Thr Thr Arg Pro Trp Thr Asp Glu Phe Val Arg Trp Thr Glu Pro Arg
    530                 535                 540

Leu Val Ala Trp Pro
545

<210> SEQ ID NO 63
<211> LENGTH: 705
<212> TYPE: PRT
<213> ORGANISM: Geobacillus stearothermophilus

<400> SEQUENCE: 63

Met Pro Thr Asn Leu Phe Phe Asn Ala His His Ser Pro Val Gly Ala
  1               5                  10                  15

Phe Ala Ser Phe Thr Leu Gly Phe Pro Gly Lys Ser Gly Gly Leu Asp
                 20                  25                  30

Leu Glu Leu Ala Arg Pro Pro Arg Gln Asn Val Leu Ile Gly Val Glu
             35                  40                  45

Ser Leu His Glu Ser Gly Leu Tyr His Val Leu Pro Phe Leu Glu Thr
         50                  55                  60

Ala Glu Glu Asp Glu Ser Lys Arg Tyr Asp Ile Glu Asn Pro Asp Pro
 65                  70                  75                  80

Asn Pro Gln Lys Pro Asn Ile Leu Ile Pro Phe Ala Lys Glu Glu Ile
                 85                  90                  95

Gln Arg Glu Phe His Val Ala Thr Asp Thr Trp Lys Ala Gly Asp Leu
                100                 105                 110

Thr Phe Thr Ile Tyr Ser Pro Val Lys Ala Val Pro Asn Pro Glu Thr
            115                 120                 125

Ala Asp Glu Glu Glu Leu Lys Leu Ala Leu Val Pro Ala Val Ile Val
        130                 135                 140

Glu Met Thr Ile Asp Asn Thr Asn Gly Thr Arg Ala Arg Arg Ala Phe
145                 150                 155                 160

Phe Gly Phe Glu Gly Thr Asp Pro Tyr Thr Ser Met Arg Arg Ile Asp
                165                 170                 175

Asp Thr Cys Pro Gln Leu Arg Gly Val Gly Gln Gly Arg Ile Leu Ser
            180                 185                 190

Ile Val Ser Lys Asp Glu Gly Val Arg Ser Ala Leu His Phe Ser Met
        195                 200                 205

Glu Asp Ile Leu Thr Ala Gln Leu Glu Glu Asn Trp Thr Phe Gly Leu
    210                 215                 220

Gly Lys Val Gly Ala Leu Ile Val Asp Val Pro Ala Gly Glu Lys Lys
```

```
            225                 230                 235                 240
        Thr Tyr Gln Phe Ala Val Cys Phe Tyr Arg Gly Gly Tyr Val Thr Ala
                        245                 250                 255
        Gly Met Asp Ala Ser Tyr Phe Tyr Thr Arg Phe Phe Gln Asn Ile Glu
                        260                 265                 270
        Glu Val Gly Leu Tyr Ala Leu Glu Gln Ala Glu Val Leu Lys Glu Gln
                        275                 280                 285
        Ser Phe Arg Ser Asn Lys Leu Ile Glu Lys Glu Trp Leu Ser Asp Asp
                        290                 295                 300
        Gln Thr Phe Met Met Ala His Ala Ile Arg Ser Tyr Tyr Gly Asn Thr
        305                 310                 315                 320
        Gln Leu Leu Glu His Glu Gly Lys Pro Ile Trp Val Val Asn Glu Gly
                        325                 330                 335
        Glu Tyr Arg Met Met Asn Thr Phe Asp Leu Thr Val Asp Gln Leu Phe
                        340                 345                 350
        Phe Glu Leu Lys Leu Asn Pro Trp Thr Val Lys Asn Val Leu Asp Leu
                        355                 360                 365
        Tyr Val Glu Arg Tyr Ser Tyr Glu Asp Arg Val Arg Phe Pro Gly Glu
                        370                 375                 380
        Glu Thr Glu Tyr Pro Ser Gly Ile Ser Phe Thr His Asp Met Gly Val
        385                 390                 395                 400
        Ala Asn Thr Phe Ser Arg Pro His Tyr Ser Tyr Glu Leu Tyr Gly
                        405                 410                 415
        Ile Ser Gly Cys Phe Ser His Met Thr His Glu Gln Leu Val Asn Trp
                        420                 425                 430
        Val Leu Cys Ala Ala Val Tyr Ile Glu Gln Thr Lys Asp Trp Ala Trp
                        435                 440                 445
        Arg Asp Lys Arg Leu Ala Ile Leu Glu Gln Cys Leu Glu Ser Met Val
                        450                 455                 460
        Arg Arg Asp His Pro Asp Pro Glu Gln Arg Asn Gly Val Met Gly Leu
        465                 470                 475                 480
        Asp Ser Thr Arg Thr Met Gly Gly Ala Glu Ile Thr Thr Tyr Asp Ser
                        485                 490                 495
        Leu Asp Val Ser Leu Gly Gln Ala Arg Asn Asn Leu Tyr Leu Ala Gly
                        500                 505                 510
        Lys Cys Trp Ala Ala Tyr Val Ala Leu Glu Lys Leu Phe Arg Asp Val
                        515                 520                 525
        Gly Lys Glu Glu Leu Ala Ala Leu Ala Gly Glu Gln Ala Glu Lys Cys
                        530                 535                 540
        Ala Ala Thr Ile Val Ser His Val Thr Asp Asp Gly Tyr Ile Pro Ala
        545                 550                 555                 560
        Ile Met Gly Glu Gly Asn Asp Ser Lys Ile Ile Pro Ala Ile Glu Gly
                        565                 570                 575
        Leu Val Phe Pro Tyr Phe Thr Asn Cys His Glu Ala Leu Asp Glu Asn
                        580                 585                 590
        Gly Arg Phe Gly Ala Tyr Ile Gln Ala Leu Arg Asn His Leu Gln Tyr
                        595                 600                 605
        Val Leu Arg Glu Gly Ile Cys Leu Phe Pro Asp Gly Gly Trp Lys Ile
                        610                 615                 620
        Ser Ser Thr Ser Asn Asn Ser Trp Leu Ser Lys Ile Tyr Leu Cys Gln
        625                 630                 635                 640
        Phe Ile Ala Arg His Ile Leu Gly Trp Glu Trp Asp Glu Gln Gly Lys
                        645                 650                 655
```

Arg Ala Asp Ala Ala His Val Ala Trp Leu Thr His Pro Thr Leu Ser
            660                 665                 670

Ile Trp Ser Trp Ser Asp Gln Ile Ile Ala Gly Glu Ile Thr Gly Ser
        675                 680                 685

Lys Tyr Tyr Pro Arg Gly Val Thr Ser Ile Leu Trp Leu Glu Glu Gly
690                 695                 700

Glu
705

<210> SEQ ID NO 64
<211> LENGTH: 330
<212> TYPE: PRT
<213> ORGANISM: Geobacillus stearothermophilus

<400> SEQUENCE: 64

Met Cys Ser Ser Ile Pro Ser Leu Arg Glu Val Phe Ala Asn Asp Phe
1               5                   10                  15

Arg Ile Gly Ala Ala Val Asn Pro Val Thr Leu Glu Ala Gln Gln Ser
            20                  25                  30

Leu Leu Ile Arg His Val Asn Ser Leu Thr Ala Glu Asn His Met Lys
        35                  40                  45

Phe Glu His Leu Gln Pro Glu Glu Gly Arg Phe Thr Phe Asp Ile Ala
    50                  55                  60

Ile Lys Ser Ser Thr Ser Pro Phe Ser His Gly Val Arg Gly His
65                  70                  75                  80

Thr Leu Val Trp His Asn Gln Thr Pro Ser Trp Val Phe Gln Asp Ser
                85                  90                  95

Gln Gly His Phe Val Gly Arg Asp Val Leu Leu Glu Arg Met Lys Ser
            100                 105                 110

His Ile Ser Thr Val Val Gln Arg Tyr Lys Gly Lys Val Tyr Cys Trp
        115                 120                 125

Asp Val Ile Asn Glu Ala Val Ala Asp Glu Gly Ser Glu Trp Leu Arg
    130                 135                 140

Ser Ser Thr Trp Arg Gln Ile Ile Gly Asp Asp Phe Ile Gln Gln Ala
145                 150                 155                 160

Phe Leu Tyr Ala His Glu Ala Asp Pro Glu Ala Leu Leu Phe Tyr Asn
                165                 170                 175

Asp Tyr Asn Glu Cys Phe Pro Glu Lys Arg Glu Lys Ile Tyr Thr Leu
            180                 185                 190

Val Lys Ser Leu Arg Asp Lys Gly Ile Pro Ile His Gly Ile Gly Met
        195                 200                 205

Gln Ala His Trp Ser Leu Asn Arg Pro Thr Leu Asp Glu Ile Arg Ala
    210                 215                 220

Ala Ile Glu Arg Tyr Ala Ser Leu Gly Val Ile Leu His Ile Thr Glu
225                 230                 235                 240

Leu Asp Ile Ser Met Phe Glu Phe Asp Asp His Arg Lys Asp Leu Ala
                245                 250                 255

Ala Pro Thr Asn Glu Met Val Glu Arg Gln Ala Glu Arg Tyr Glu Gln
            260                 265                 270

Ile Phe Ser Leu Phe Lys Glu Tyr Arg Asp Val Ile Gln Asn Val Thr
        275                 280                 285

Phe Trp Gly Ile Ala Asp Asp His Thr Trp Leu Asp His Phe Pro Val
    290                 295                 300

Gln Gly Arg Lys Asn Trp Pro Leu Leu Phe Asp Glu Gln His Asn Pro

```
                305                 310                 315                 320
Lys Pro Ala Phe Trp Arg Val Val Asn Ile
                325                 330

<210> SEQ ID NO 65
<211> LENGTH: 407
<212> TYPE: PRT
<213> ORGANISM: Geobacillus stearothermophilus

<400> SEQUENCE: 65

Met Arg Asn Val Val Arg Lys Pro Leu Thr Ile Gly Leu Ala Leu Thr
  1               5                  10                  15

Leu Leu Leu Pro Met Gly Met Thr Ala Thr Ser Ala Lys Asn Ala Asp
                 20                  25                  30

Ser Tyr Ala Lys Lys Pro His Ile Ser Ala Leu Asn Ala Pro Gln Leu
             35                  40                  45

Asp Gln Arg Tyr Lys Asn Glu Phe Thr Ile Gly Ala Ala Val Glu Pro
         50                  55                  60

Tyr Gln Leu Gln Asn Glu Lys Asp Val Gln Met Leu Lys Arg His Phe
 65                  70                  75                  80

Asn Ser Ile Val Ala Glu Asn Val Met Lys Pro Ile Ser Ile Gln Pro
                 85                  90                  95

Glu Glu Gly Lys Phe Asn Phe Glu Gln Ala Asp Arg Ile Val Lys Phe
            100                 105                 110

Ala Lys Ala Asn Gly Met Asp Ile Arg Phe His Thr Leu Val Trp His
        115                 120                 125

Ser Gln Val Pro Gln Trp Phe Phe Leu Asp Lys Glu Gly Lys Pro Met
    130                 135                 140

Val Asn Glu Thr Asp Pro Val Lys Arg Glu Gln Asn Lys Gln Leu Leu
145                 150                 155                 160

Leu Lys Arg Leu Glu Thr His Ile Lys Thr Ile Val Glu Arg Tyr Lys
                165                 170                 175

Asp Asp Ile Lys Tyr Trp Asp Val Val Asn Glu Val Val Gly Asp Asp
            180                 185                 190

Gly Lys Leu Arg Asn Ser Pro Trp Tyr Gln Ile Ala Gly Ile Asp Tyr
        195                 200                 205

Ile Lys Val Ala Phe Gln Ala Ala Arg Lys Tyr Gly Gly Asp Asn Ile
    210                 215                 220

Lys Leu Tyr Met Asn Asp Tyr Asn Thr Glu Val Glu Pro Lys Arg Thr
225                 230                 235                 240

Ala Leu Tyr Asn Leu Val Lys Gln Leu Lys Glu Glu Gly Val Pro Ile
                245                 250                 255

Asp Gly Ile Gly His Gln Ser His Ile Gln Ile Gly Trp Pro Ser Glu
            260                 265                 270

Ala Glu Ile Glu Lys Thr Ile Asn Met Phe Ala Ala Leu Gly Leu Asp
        275                 280                 285

Asn Gln Ile Thr Glu Leu Asp Val Ser Met Tyr Gly Trp Pro Pro Arg
    290                 295                 300

Ala Tyr Pro Thr Tyr Asp Ala Ile Pro Lys Gln Lys Phe Leu Asp Gln
305                 310                 315                 320

Ala Ala Arg Tyr Asp Arg Leu Phe Lys Leu Tyr Glu Lys Leu Ser Asp
                325                 330                 335

Lys Ile Ser Asn Val Thr Phe Trp Gly Ile Ala Asp Asn His Thr Trp
            340                 345                 350
```

```
Leu Asp Ser Arg Ala Asp Val Tyr Tyr Asp Ala Asn Gly Asn Val Val
            355                 360                 365

Val Asp Pro Asn Ala Pro Tyr Ala Lys Val Glu Lys Gly Lys Gly Lys
370                 375                 380

Asp Ala Pro Phe Val Phe Gly Pro Asp Tyr Lys Val Lys Pro Ala Tyr
385                 390                 395                 400

Trp Ala Ile Ile Asp His Lys
                405

<210> SEQ ID NO 66
<211> LENGTH: 686
<212> TYPE: PRT
<213> ORGANISM: Dictyoglomus thermophilum

<400> SEQUENCE: 66

Met Thr Lys Ser Ile Tyr Phe Ser Leu Gly Ile His Asn His Gln Pro
  1               5                  10                  15

Val Gly Asn Phe Asp Phe Val Ile Glu Arg Ala Tyr Glu Met Ser Tyr
             20                  25                  30

Lys Pro Leu Ile Asn Phe Phe Lys His Pro Asp Phe Pro Ile Asn
         35                  40                  45

Val His Phe Ser Gly Phe Leu Leu Trp Leu Glu Lys Asn His Pro
 50                  55                  60

Glu Tyr Phe Glu Lys Leu Lys Ile Met Ala Glu Arg Gly Gln Ile Glu
 65                  70                  75                  80

Phe Val Ser Gly Gly Phe Tyr Glu Pro Ile Leu Pro Ile Ile Pro Asp
                 85                  90                  95

Lys Asp Lys Val Gln Gln Ile Lys Lys Leu Asn Lys Tyr Ile Tyr Asp
            100                 105                 110

Lys Phe Gly Gln Thr Pro Lys Gly Met Trp Leu Ala Glu Arg Val Trp
        115                 120                 125

Glu Pro His Leu Val Lys Tyr Ile Ala Glu Ala Gly Ile Glu Tyr Val
    130                 135                 140

Val Val Asp Asp Ala His Phe Phe Ser Val Gly Leu Lys Glu Glu Asp
145                 150                 155                 160

Leu Phe Gly Tyr Tyr Leu Met Glu Glu Gln Gly Tyr Lys Leu Ala Val
                165                 170                 175

Phe Pro Ile Ser Met Lys Leu Arg Tyr Leu Ile Pro Phe Ala Asp Pro
            180                 185                 190

Glu Glu Thr Ile Thr Tyr Leu Asp Lys Phe Ala Ser Glu Asp Lys Ser
        195                 200                 205

Lys Ile Ala Leu Leu Phe Asp Asp Gly Glu Lys Phe Gly Leu Trp Pro
    210                 215                 220

Asp Thr Tyr Arg Thr Val Tyr Glu Glu Gly Trp Leu Glu Thr Phe Val
225                 230                 235                 240

Ser Lys Ile Lys Glu Asn Phe Leu Leu Val Thr Pro Val Asn Leu Tyr
                245                 250                 255

Thr Tyr Met Gln Arg Val Lys Pro Lys Gly Arg Ile Tyr Leu Pro Thr
            260                 265                 270

Ala Ser Tyr Arg Glu Met Met Glu Trp Val Leu Phe Pro Glu Ala Gln
        275                 280                 285

Lys Glu Leu Glu Glu Leu Val Glu Lys Leu Thr Glu Asn Leu Trp
    290                 295                 300

Asp Lys Phe Ser Pro Tyr Val Lys Gly Gly Phe Trp Arg Asn Phe Leu
305                 310                 315                 320
```

Ala Lys Tyr Asp Glu Ser Asn His Met Gln Lys Lys Met Leu Tyr Val
            325                 330                 335

Trp Lys Lys Val Gln Asp Ser Pro Asn Glu Val Lys Glu Lys Ala
            340                 345                 350

Met Glu Glu Val Phe Gln Gly Gln Ala Asn Asp Ala Tyr Trp His Gly
            355                 360                 365

Ile Phe Gly Gly Leu Tyr Leu Pro His Leu Arg Thr Ala Ile Tyr Glu
        370                 375                 380

His Leu Ile Lys Ala Glu Asn Tyr Leu Glu Asn Ser Glu Ile Arg Phe
385                 390                 395                 400

Asn Ile Phe Asp Phe Asp Cys Asp Gly Asn Asp Glu Ile Ile Val Glu
                405                 410                 415

Ser Pro Phe Phe Asn Leu Tyr Leu Ser Pro Asn His Gly Gly Ser Val
            420                 425                 430

Leu Glu Trp Asp Phe Lys Thr Lys Ala Phe Asn Leu Thr Asn Val Leu
        435                 440                 445

Thr Arg Arg Lys Glu Ala Tyr His Ser Lys Leu Ser Tyr Val Thr Ser
    450                 455                 460

Glu Ala Gln Gly Lys Ser Ile His Glu Arg Trp Thr Ala Lys Glu Glu
465                 470                 475                 480

Gly Leu Glu Asn Ile Leu Phe Tyr Asp Asn His Arg Arg Val Ser Phe
                485                 490                 495

Thr Glu Lys Ile Phe Glu Ser Glu Pro Val Leu Glu Asp Leu Trp Lys
            500                 505                 510

Asp Ser Ser Arg Leu Glu Val Asp Ser Phe Tyr Glu Asn Tyr Asp Tyr
        515                 520                 525

Glu Ile Asn Lys Asp Glu Asn Lys Ile Arg Val Leu Phe Ser Gly Val
    530                 535                 540

Phe Arg Gly Phe Glu Leu Cys Lys Ser Tyr Ile Leu Tyr Lys Asp Lys
545                 550                 555                 560

Ser Phe Val Asp Val Val Tyr Glu Ile Lys Asn Val Ser Glu Thr Pro
                565                 570                 575

Ile Ser Leu Asn Phe Gly Trp Glu Ile Asn Leu Asn Phe Leu Ala Pro
            580                 585                 590

Asn His Pro Asp Tyr Tyr Phe Leu Ile Gly Asp Gln Lys Tyr Pro Leu
        595                 600                 605

Ser Ser Phe Gly Ile Glu Lys Val Asn Asn Trp Lys Ile Phe Ser Gly
    610                 615                 620

Ile Gly Ile Glu Leu Glu Cys Val Leu Asp Val Glu Ala Ser Leu Tyr
625                 630                 635                 640

Arg Tyr Pro Ile Glu Thr Val Ser Leu Ser Glu Glu Gly Phe Glu Arg
                645                 650                 655

Val Tyr Gln Gly Ser Ala Leu Ile His Phe Tyr Lys Val Asp Leu Pro
            660                 665                 670

Val Gly Ser Thr Trp Arg Thr Thr Ile Arg Phe Trp Val Lys
        675                 680                 685

<210> SEQ ID NO 67
<211> LENGTH: 1055
<212> TYPE: PRT
<213> ORGANISM: Thermotoga neapolitana

<400> SEQUENCE: 67

Met Arg Lys Lys Arg Arg Gly Phe Leu Asn Ala Ser Thr Ala Val Leu

```
                1               5                    10                   15
              Val Gly Ile Leu Ala Gly Phe Leu Gly Val Leu Ala Ala Thr Gly
                           20                   25                  30

Ala Leu Gly Phe Ala Val Arg Glu Ser Leu Leu Lys Gln Phe Leu
                           35                   40                  45

Phe Leu Ser Phe Glu Gly Asn Thr Asp Gly Ala Ser Pro Phe Gly Lys
                           50                   55                  60

Asp Val Val Thr Ala Ser Gln Asp Val Ala Ala Asp Gly Glu Tyr
              65                    70                  75                  80

Ser Leu Lys Val Glu Asn Arg Thr Ser Val Trp Asp Gly Val Glu Ile
                           85                   90                  95

Asp Leu Thr Gly Lys Val Asn Thr Gly Thr Asp Tyr Leu Leu Ser Phe
                           100                  105                 110

His Val Tyr Gln Thr Ser Asp Ser Pro Gln Leu Phe Ser Val Leu Ala
                           115                  120                 125

Arg Thr Glu Asp Glu Lys Gly Glu Arg Tyr Lys Ile Leu Ala Asp Lys
                           130                  135                 140

Val Val Pro Asn Tyr Trp Lys Glu Ile Leu Val Pro Phe Ser Pro
              145                  150                  155                 160

Thr Phe Glu Gly Thr Pro Ala Lys Phe Ser Leu Ile Ile Thr Ser Pro
                           165                  170                 175

Lys Lys Thr Asp Phe Val Phe Tyr Val Asp Asn Val Gln Val Leu Thr
                           180                  185                 190

Pro Lys Glu Ala Gly Pro Lys Val Val Tyr Glu Thr Ser Phe Glu Lys
                           195                  200                 205

Gly Ile Gly Asp Trp Gln Pro Arg Gly Ser Asp Val Lys Ile Ser Ile
                           210                  215                 220

Ser Pro Lys Val Ala His Ser Gly Lys Lys Ser Leu Phe Val Ser Asn
              225                  230                  235                 240

Arg Gln Lys Gly Trp His Gly Ala Gln Ile Ser Leu Lys Gly Ile Leu
                           245                  250                 255

Lys Thr Gly Lys Thr Tyr Ala Phe Glu Ala Trp Val Tyr Gln Glu Ser
                           260                  265                 270

Gly Gln Asp Gln Thr Ile Ile Met Thr Met Gln Arg Lys Tyr Ser Ser
                           275                  280                 285

Asp Ser Ser Thr Lys Tyr Glu Trp Ile Lys Ala Ala Thr Val Pro Ser
                           290                  295                 300

Gly Gln Trp Val Gln Leu Ser Gly Thr Tyr Thr Ile Pro Ala Gly Val
              305                  310                  315                 320

Thr Val Glu Asp Leu Thr Leu Tyr Phe Glu Ser Gln Asn Pro Thr Leu
                           325                  330                 335

Glu Phe Tyr Val Asp Asp Val Lys Val Asp Thr Thr Ser Ala Glu
                           340                  345                 350

Ile Lys Leu Glu Met Asn Pro Glu Glu Ile Pro Ala Leu Lys Asp
                           355                  360                 365

Val Leu Lys Asp Tyr Phe Arg Val Gly Val Ala Leu Pro Ser Lys Val
              370                  375                  380

Phe Ile Asn Gln Lys Asp Ile Ala Leu Ile Ser Lys His Ser Asn Ser
              385                  390                  395                 400

Ser Thr Ala Glu Asn Glu Met Lys Pro Asp Ser Leu Leu Ala Gly Ile
                           405                  410                 415

Glu Asn Gly Lys Leu Lys Phe Arg Phe Glu Thr Ala Asp Lys Tyr Ile
                           420                  425                 430
```

```
Glu Phe Ala Gln Gln Asn Gly Met Val Val Arg Gly His Thr Leu Val
        435                 440                 445

Trp His Asn Gln Thr Pro Glu Trp Phe Phe Lys Asp Glu Asn Gly Asn
    450                 455                 460

Leu Leu Ser Lys Glu Glu Met Thr Glu Arg Leu Arg Glu Tyr Ile His
465                 470                 475                 480

Thr Val Val Gly His Phe Lys Gly Lys Val Tyr Ala Trp Asp Val Val
                485                 490                 495

Asn Glu Ala Val Asp Pro Asn Gln Pro Asp Gly Leu Arg Arg Ser Thr
                500                 505                 510

Trp Tyr Gln Ile Met Gly Pro Asp Tyr Ile Glu Leu Ala Phe Lys Phe
        515                 520                 525

Ala Arg Glu Ala Asp Pro Asn Ala Lys Leu Phe Tyr Asn Asp Tyr Asn
    530                 535                 540

Thr Phe Glu Pro Lys Lys Arg Asp Ile Ile Tyr Asn Leu Val Lys Ser
545                 550                 555                 560

Leu Lys Glu Lys Gly Leu Ile Asp Gly Ile Gly Met Gln Cys His Ile
                565                 570                 575

Ser Leu Ala Thr Asp Ile Arg Gln Ile Glu Glu Ala Ile Lys Lys Phe
                580                 585                 590

Ser Thr Ile Pro Gly Ile Glu Ile His Ile Thr Glu Leu Asp Ile Ser
        595                 600                 605

Val Tyr Arg Asp Ser Thr Ser Asn Tyr Ser Glu Ala Pro Arg Thr Ala
    610                 615                 620

Leu Ile Glu Gln Ala His Lys Met Ala Gln Leu Phe Lys Ile Phe Lys
625                 630                 635                 640

Lys Tyr Ser Asn Val Ile Thr Asn Val Thr Phe Trp Gly Leu Lys Asp
                645                 650                 655

Asp Tyr Ser Trp Arg Ala Thr Arg Arg Asn Asp Trp Pro Leu Ile Phe
                660                 665                 670

Asp Lys Asp Tyr Gln Ala Lys Leu Ala Tyr Trp Ala Ile Val Ala Pro
        675                 680                 685

Glu Val Leu Pro Pro Leu Pro Lys Glu Ser Lys Ile Ser Glu Gly Glu
    690                 695                 700

Ala Val Val Val Gly Met Met Asp Asp Ser Tyr Met Met Ser Lys Pro
705                 710                 715                 720

Ile Glu Ile Tyr Asp Glu Gly Asn Val Lys Ala Thr Ile Arg Ala
                725                 730                 735

Ile Trp Lys Asp Ser Thr Ile Tyr Val Tyr Gly Glu Val Gln Asp Ala
                740                 745                 750

Thr Lys Lys Pro Ala Glu Asp Gly Val Ala Ile Phe Ile Asn Pro Asn
        755                 760                 765

Asn Glu Arg Thr Pro Tyr Leu Gln Pro Asp Asp Thr Tyr Val Val Leu
    770                 775                 780

Trp Thr Asn Trp Lys Ser Glu Val Asn Arg Glu Asp Val Glu Val Lys
785                 790                 795                 800

Lys Phe Val Gly Pro Gly Phe Arg Arg Tyr Ser Phe Glu Met Ser Ile
                805                 810                 815

Thr Ile Pro Gly Val Glu Phe Lys Lys Asp Ser Tyr Ile Gly Phe Asp
                820                 825                 830

Val Ala Val Ile Asp Asp Gly Lys Trp Tyr Ser Trp Ser Asp Thr Thr
        835                 840                 845
```

```
Asn Ser Gln Lys Thr Asn Thr Met Asn Tyr Gly Thr Leu Lys Leu Glu
    850                 855                 860

Gly Val Met Val Ala Thr Ala Lys Tyr Gly Thr Pro Val Ile Asp Gly
865                 870                 875                 880

Glu Ile Asp Asp Ile Trp Asn Thr Thr Glu Glu Ile Glu Thr Lys Ser
                885                 890                 895

Val Ala Met Gly Ser Leu Glu Lys Asn Ala Thr Ala Lys Val Arg Val
            900                 905                 910

Leu Trp Asp Glu Glu Asn Leu Tyr Val Leu Ala Ile Val Lys Asp Pro
        915                 920                 925

Val Leu Asn Lys Asp Asn Ser Asn Pro Trp Glu Gln Asp Ser Val Glu
930                 935                 940

Ile Phe Ile Asp Glu Asn Asn His Lys Thr Gly Tyr Tyr Glu Asp Asp
945                 950                 955                 960

Asp Ala Gln Phe Arg Val Asn Tyr Met Asn Glu Gln Ser Phe Gly Thr
                965                 970                 975

Gly Ala Ser Ala Ala Arg Phe Lys Thr Ala Val Lys Leu Ile Glu Gly
            980                 985                 990

Gly Tyr Ile Val Glu Ala Ala Ile Lys Trp Lys Thr Ile Lys Pro Ser
        995                 1000                1005

Pro Asn Thr Val Ile Gly Phe Asn Val Gln Val Asn Asp Ala Asn Glu
    1010                1015                1020

Lys Gly Gln Arg Val Gly Ile Ile Ser Trp Ser Asp Pro Thr Asn Asn
1025                1030                1035                1040

Ser Trp Arg Asp Pro Ser Lys Phe Gly Asn Leu Arg Leu Ile Lys
                1045                1050                1055

<210> SEQ ID NO 68
<211> LENGTH: 431
<212> TYPE: PRT
<213> ORGANISM: Thermus thermophilus

<400> SEQUENCE: 68

Met Asp Asp His Ala Glu Lys Phe Leu Trp Gly Val Ala Thr Ser Ala
1               5                   10                  15

Tyr Gln Ile Glu Gly Ala Thr Gln Glu Asp Gly Arg Gly Pro Ser Ile
            20                  25                  30

Trp Asp Ala Phe Ala Arg Arg Pro Gly Ala Ile Arg Asp Gly Ser Thr
        35                  40                  45

Gly Glu Pro Ala Cys Asp His Tyr Arg Arg Tyr Glu Glu Asp Ile Ala
50                  55                  60

Leu Met Gln Ser Leu Gly Val Arg Ala Tyr Arg Phe Ser Val Ala Trp
65                  70                  75                  80

Pro Arg Ile Leu Pro Glu Gly Arg Gly Ile Asn Pro Lys Gly Leu
                85                  90                  95

Ala Phe Tyr Asp Arg Leu Val Asp Arg Leu Leu Ala Ser Gly Ile Thr
            100                 105                 110

Pro Phe Leu Thr Leu Tyr His Trp Asp Leu Pro Leu Ala Leu Glu Glu
        115                 120                 125

Arg Gly Gly Trp Arg Ser Arg Glu Thr Ala Phe Ala Phe Ala Glu Tyr
    130                 135                 140

Ala Glu Ala Val Ala Arg Ala Leu Ala Asp Arg Val Pro Phe Phe Ala
145                 150                 155                 160

Thr Leu Asn Glu Pro Trp Cys Ser Ala Phe Leu Gly His Trp Thr Gly
                165                 170                 175
```

Glu His Ala Pro Gly Leu Arg Asn Leu Glu Ala Ala Leu Arg Ala Ala
              180                 185                 190

His His Leu Leu Leu Gly His Gly Leu Ala Val Glu Ala Leu Arg Ala
          195                 200                 205

Ala Gly Ala Arg Arg Val Gly Ile Val Leu Asn Phe Ala Pro Ala Tyr
    210                 215                 220

Gly Glu Asp Pro Glu Ala Val Asp Val Ala Asp Arg Tyr His Asn Arg
225                 230                 235                 240

Tyr Phe Leu Asp Pro Ile Leu Gly Lys Gly Tyr Pro Glu Ser Pro Phe
                245                 250                 255

Arg Asp Pro Pro Val Pro Ile Leu Ser Arg Asp Leu Glu Leu Val
            260                 265                 270

Ala Arg Pro Leu Asp Phe Leu Gly Val Asn Tyr Tyr Ala Pro Val Arg
        275                 280                 285

Val Ala Pro Gly Thr Gly Thr Leu Pro Val Arg Tyr Leu Pro Pro Glu
    290                 295                 300

Gly Pro Ala Thr Ala Met Gly Trp Glu Val Tyr Pro Glu Gly Leu His
305                 310                 315                 320

His Leu Leu Lys Arg Leu Gly Arg Glu Val Pro Trp Pro Leu Tyr Val
                325                 330                 335

Thr Glu Asn Gly Ala Ala Tyr Pro Asp Leu Trp Thr Gly Glu Ala Val
            340                 345                 350

Val Glu Asp Pro Glu Arg Val Ala Tyr Leu Glu Ala His Val Glu Ala
        355                 360                 365

Ala Leu Arg Ala Arg Glu Glu Gly Val Asp Leu Arg Gly Tyr Phe Val
    370                 375                 380

Trp Ser Leu Met Asp Asn Phe Glu Trp Ala Phe Gly Tyr Thr Arg Arg
385                 390                 395                 400

Phe Gly Leu Tyr Tyr Val Asp Phe Pro Ser Gln Arg Ile Pro Lys
                405                 410                 415

Arg Ser Ala Leu Trp Tyr Arg Glu Arg Ile Ala Arg Ala Gln Thr
            420                 425                 430

<210> SEQ ID NO 69
<211> LENGTH: 431
<212> TYPE: PRT
<213> ORGANISM: Thermus thermophilus

<400> SEQUENCE: 69

Met Thr Glu Asn Ala Glu Lys Phe Leu Trp Gly Val Ala Thr Ser Ala
1               5                   10                  15

Tyr Gln Ile Glu Gly Ala Thr Gln Glu Asp Gly Arg Gly Pro Ser Ile
                20                  25                  30

Trp Asp Ala Phe Ala Gln Arg Pro Gly Ala Ile Arg Asp Gly Ser Thr
            35                  40                  45

Gly Glu Pro Ala Cys Asp His Tyr Arg Tyr Glu Glu Asp Ile Ala
50                  55                  60

Leu Met Gln Ser Leu Gly Val Arg Ala Tyr Arg Phe Ser Val Ala Trp
65                  70                  75                  80

Pro Arg Ile Leu Pro Glu Gly Arg Gly Ile Asn Pro Lys Gly Leu
                85                  90                  95

Ala Phe Tyr Asp Arg Leu Val Asp Arg Leu Leu Ala Ser Gly Ile Thr
            100                 105                 110

Pro Phe Leu Thr Leu Tyr His Trp Asp Leu Pro Leu Ala Leu Glu Glu

```
                115                 120                 125
Arg Gly Gly Trp Arg Ser Arg Glu Thr Ala Phe Ala Phe Ala Glu Tyr
            130                 135                 140

Ala Glu Ala Val Ala Arg Ala Leu Ala Asp Arg Val Pro Phe Phe Ala
145                 150                 155                 160

Thr Leu Asn Glu Pro Trp Cys Ser Ala Phe Leu Gly His Trp Thr Gly
                165                 170                 175

Glu His Ala Pro Gly Leu Arg Asn Leu Glu Ala Leu Arg Ala Ala
            180                 185                 190

His His Leu Leu Leu Gly His Gly Leu Ala Val Glu Ala Leu Arg Ala
            195                 200                 205

Ala Gly Ala Arg Arg Val Gly Ile Val Leu Asn Phe Ala Pro Ala Tyr
            210                 215                 220

Gly Glu Asp Pro Glu Ala Val Asp Val Ala Asp Arg Tyr His Asn Arg
225                 230                 235                 240

Phe Phe Leu Asp Pro Ile Leu Gly Lys Gly Tyr Pro Glu Ser Pro Phe
                245                 250                 255

Arg Asp Pro Pro Val Pro Ile Leu Ser Arg Asp Leu Glu Leu Val
            260                 265                 270

Ala Arg Pro Leu Asp Phe Leu Gly Val Asn Tyr Tyr Ala Pro Val Arg
            275                 280                 285

Val Ala Pro Gly Thr Gly Thr Leu Pro Val Arg Tyr Leu Pro Pro Glu
            290                 295                 300

Gly Pro Ala Thr Ala Met Gly Trp Glu Val Tyr Pro Glu Gly Leu Tyr
305                 310                 315                 320

His Leu Leu Lys Arg Leu Gly Arg Glu Val Pro Trp Pro Leu Tyr Val
                325                 330                 335

Thr Glu Asn Gly Ala Ala Tyr Pro Asp Leu Trp Thr Gly Glu Ala Val
            340                 345                 350

Val Glu Asp Pro Glu Arg Val Ala Tyr Leu Glu Ala His Val Glu Ala
            355                 360                 365

Ala Leu Arg Ala Arg Glu Glu Gly Val Asp Leu Arg Gly Tyr Phe Val
            370                 375                 380

Trp Ser Leu Met Asp Asn Phe Glu Trp Ala Phe Gly Tyr Thr Arg Arg
385                 390                 395                 400

Phe Gly Leu Tyr Tyr Val Asp Phe Pro Ser Gln Arg Arg Ile Pro Lys
                405                 410                 415

Arg Ser Ala Leu Trp Tyr Arg Glu Arg Ile Ala Arg Ala Gln Thr
            420                 425                 430

<210> SEQ ID NO 70
<211> LENGTH: 280
<212> TYPE: PRT
<213> ORGANISM: Thermus filiformis

<400> SEQUENCE: 70

Met Ala Gln Val Gly Arg Gly Ala Ser Pro Leu Ser Arg Ala Arg Val
1               5                   10                  15

Pro Pro Leu Pro His Pro Leu Asp Gly Glu His Leu Pro His Asp Pro
            20                  25                  30

Ala Gly Gly Gly His Gly Lys Ala Ser Ser Gln Asp Ala Pro Val Gly
            35                  40                  45

Gln Leu Pro Gly His Leu Ala Arg Pro Ala Phe Phe His Tyr Leu Lys
        50                  55                  60
```

```
Asn Ser Phe Leu Val Cys Ser Leu Thr Thr Val Phe Ala Leu Ala Val
 65                  70                  75                  80

Ala Thr Phe Ala Gly Tyr Ala Leu Ala Arg Phe Arg Phe Pro Gly Ala
                 85                  90                  95

Glu Leu Phe Gly Gly Ser Val Leu Val Thr Gln Val Ile Pro Gly Ile
            100                 105                 110

Leu Phe Leu Ile Pro Ile Tyr Ile Met Tyr Ile Tyr Val Gln Asn Trp
        115                 120                 125

Val Arg Ser Ala Leu Gly Leu Glu Val Arg Leu Val Gly Ser Tyr Gly
130                 135                 140

Gly Leu Val Phe Thr Tyr Thr Ala Phe Phe Val Pro Leu Ser Ile Trp
145                 150                 155                 160

Ile Leu Arg Gly Phe Phe Ala Ser Ile Pro Lys Glu Leu Glu Glu Ala
                165                 170                 175

Ala Met Val Asp Gly Ala Thr Pro Phe Gln Ala Phe His Arg Val Ile
            180                 185                 190

Leu Pro Leu Ala Leu Pro Gly Leu Ala Ala Thr Ala Val Tyr Ile Phe
        195                 200                 205

Leu Thr Ala Trp Asp Glu Leu Leu Phe Ala Gln Val Leu Thr Thr Glu
210                 215                 220

Ala Thr Ala Thr Val Pro Val Gly Ile Arg Asn Phe Val Gly Asn Tyr
225                 230                 235                 240

Gln Asn Arg Tyr Asp Leu Val Met Ala Ala Thr Val Ala Thr Leu
                245                 250                 255

Pro Val Leu Val Leu Phe Phe Val Gln Arg Gln Leu Ile Gln Gly
        260                 265                 270

Leu Thr Ala Gly Ala Val Lys Gly
        275                 280

<210> SEQ ID NO 71
<211> LENGTH: 431
<212> TYPE: PRT
<213> ORGANISM: Thermosphaera aggregans

<400> SEQUENCE: 71

Met Ala Glu Asn Ala Glu Lys Phe Leu Trp Gly Val Ala Thr Ser Ala
  1               5                  10                  15

Tyr Gln Ile Glu Gly Ala Thr Gln Glu Asp Gly Arg Gly Pro Ser Ile
             20                  25                  30

Trp Asp Thr Phe Ala Arg Arg Pro Gly Ala Ile Arg Asp Gly Ser Thr
         35                  40                  45

Gly Glu Pro Ala Cys Asp His Tyr His Arg Tyr Glu Glu Asp Ile Ala
 50                  55                  60

Leu Met Gln Ser Leu Gly Val Gly Val Tyr Arg Phe Ser Val Ala Trp
 65                  70                  75                  80

Pro Arg Ile Leu Pro Glu Gly Arg Gly Arg Ile Asn Pro Lys Gly Leu
                 85                  90                  95

Ala Phe Tyr Asp Arg Leu Val Asp Arg Leu Leu Ala Ala Gly Ile Thr
            100                 105                 110

Pro Phe Leu Thr Leu Tyr His Trp Asp Leu Pro Gln Ala Leu Glu Asp
        115                 120                 125

Arg Gly Gly Trp Arg Ser Arg Glu Thr Ala Phe Ala Phe Ala Glu Tyr
130                 135                 140

Ala Glu Ala Val Ala Arg Ala Leu Ala Asp Arg Val Pro Phe Phe Ala
145                 150                 155                 160
```

Thr Leu Asn Glu Pro Trp Cys Ser Ala Phe Leu Gly His Trp Thr Gly
            165                 170                 175

Glu His Ala Pro Gly Leu Arg Asn Leu Glu Ala Ala Leu Arg Ala Ala
            180                 185                 190

His His Leu Leu Leu Gly His Gly Leu Ala Val Glu Ala Leu Arg Ala
            195                 200                 205

Ala Gly Ala Lys Arg Val Gly Ile Val Leu Asn Phe Ala Pro Val Tyr
            210                 215                 220

Gly Glu Asp Pro Glu Ala Val Asp Val Ala Asp Arg Tyr His Asn Arg
225                 230                 235                 240

Tyr Phe Leu Asp Pro Ile Leu Gly Arg Gly Tyr Pro Glu Ser Pro Phe
            245                 250                 255

Gln Asp Pro Pro Thr Pro Asn Leu Ser Arg Asp Leu Glu Leu Val
            260                 265                 270

Ala Arg Pro Leu Asp Phe Leu Gly Val Asn Tyr Tyr Ala Pro Val Arg
            275                 280                 285

Val Ala Pro Gly Thr Gly Pro Leu Pro Val Arg Tyr Leu Pro Pro Glu
            290                 295                 300

Gly Pro Val Thr Ala Met Gly Trp Glu Val Tyr Pro Glu Gly Leu Tyr
305                 310                 315                 320

His Leu Leu Lys Arg Leu Gly Arg Glu Val Pro Trp Pro Leu Tyr Ile
            325                 330                 335

Thr Glu Asn Gly Ala Ala Tyr Pro Asp Leu Trp Thr Gly Glu Ala Val
            340                 345                 350

Val Glu Asp Pro Glu Arg Val Ala Tyr Leu Glu Ala His Val Glu Ala
            355                 360                 365

Ala Leu Arg Ala Arg Glu Glu Gly Val Asp Leu Arg Gly Tyr Phe Val
            370                 375                 380

Trp Ser Leu Met Asp Asn Phe Glu Trp Ala Phe Gly Tyr Thr Arg Arg
385                 390                 395                 400

Phe Gly Leu Tyr Tyr Val Asp Phe Pro Ser Gln Arg Arg Ile Pro Lys
            405                 410                 415

Arg Ser Ala Leu Trp Tyr Arg Glu Arg Ile Ala Arg Ala Gln Leu
            420                 425                 430

<210> SEQ ID NO 72
<211> LENGTH: 481
<212> TYPE: PRT
<213> ORGANISM: Clostridium thermocellum

<400> SEQUENCE: 72

Met Lys Phe Pro Lys Asp Phe Met Ile Gly Tyr Ser Ser Ser Pro Phe
1               5                   10                  15

Gln Phe Glu Ala Gly Ile Pro Gly Ser Glu Asp Pro Asn Ser Asp Trp
            20                  25                  30

Trp Val Trp Val His Asp Pro Glu Asn Thr Ala Ala Gly Leu Val Ser
            35                  40                  45

Gly Asp Phe Pro Glu Asn Gly Pro Gly Tyr Trp Asn Leu Asn Gln Asn
        50                  55                  60

Asp His Asp Leu Ala Glu Lys Leu Gly Val Asn Thr Ile Arg Val Gly
65                  70                  75                  80

Val Glu Trp Ser Arg Ile Phe Pro Lys Pro Thr Phe Asn Val Lys Val
            85                  90                  95

Pro Val Glu Arg Asp Glu Asn Gly Ser Ile Val His Val Asp Val Asp

```
                100             105             110
Asp Lys Ala Val Glu Arg Leu Asp Glu Leu Ala Asn Lys Glu Ala Val
            115                 120                 125
Asn His Tyr Val Glu Met Tyr Lys Asp Trp Val Arg Gly Arg Lys
        130                 135                 140
Leu Ile Leu Asn Leu Tyr His Trp Pro Leu Pro Leu Trp Leu His Asn
145                 150                 155                 160
Pro Ile Met Val Arg Arg Met Gly Pro Asp Arg Ala Pro Ser Gly Trp
                165                 170                 175
Leu Asn Glu Glu Ser Val Val Glu Phe Ala Lys Tyr Ala Ala Tyr Ile
            180                 185                 190
Ala Trp Lys Met Gly Glu Leu Pro Val Met Trp Ser Thr Met Asn Glu
        195                 200                 205
Pro Asn Val Val Tyr Glu Gln Gly Tyr Met Phe Val Lys Gly Gly Phe
    210                 215                 220
Pro Pro Gly Tyr Leu Ser Leu Glu Ala Ala Asp Lys Ala Arg Arg Asn
225                 230                 235                 240
Met Ile Gln Ala His Ala Arg Ala Tyr Asp Asn Ile Lys Arg Phe Ser
                245                 250                 255
Lys Lys Pro Val Gly Leu Ile Tyr Ala Phe Gln Trp Phe Glu Leu Leu
            260                 265                 270
Glu Gly Pro Ala Glu Val Phe Asp Lys Phe Lys Ser Ser Lys Leu Tyr
        275                 280                 285
Tyr Phe Thr Asp Ile Val Ser Lys Gly Ser Ser Ile Ile Asn Val Glu
    290                 295                 300
Tyr Arg Arg Asp Leu Ala Asn Arg Leu Asp Trp Leu Gly Val Asn Tyr
305                 310                 315                 320
Tyr Ser Arg Leu Val Tyr Lys Ile Val Asp Asp Lys Pro Ile Ile Leu
                325                 330                 335
His Gly Tyr Gly Phe Leu Cys Thr Pro Gly Gly Ile Ser Pro Ala Glu
            340                 345                 350
Asn Pro Cys Ser Asp Phe Gly Trp Glu Val Tyr Pro Glu Gly Leu Tyr
        355                 360                 365
Leu Leu Leu Lys Glu Leu Tyr Asn Arg Tyr Gly Val Asp Leu Ile Val
    370                 375                 380
Thr Glu Asn Gly Val Ser Asp Ser Arg Asp Ala Leu Arg Pro Ala Tyr
385                 390                 395                 400
Leu Val Ser His Val Tyr Ser Val Trp Lys Ala Ala Asn Glu Gly Ile
                405                 410                 415
Pro Val Lys Gly Tyr Leu His Trp Ser Leu Thr Asp Asn Tyr Glu Trp
            420                 425                 430
Ala Gln Gly Phe Arg Gln Lys Phe Gly Leu Val Met Val Asp Phe Lys
        435                 440                 445
Thr Lys Lys Arg Tyr Leu Arg Pro Ser Ala Leu Val Phe Arg Glu Ile
    450                 455                 460
Ala Thr His Asn Gly Ile Pro Asp Glu Leu Gln His Leu Thr Leu Ile
465                 470                 475                 480
Gln

<210> SEQ ID NO 73
<211> LENGTH: 263
<212> TYPE: PRT
<213> ORGANISM: Artificial Sequence
<220> FEATURE:
```

<223> OTHER INFORMATION: synthetic polypeptide

<400> SEQUENCE: 73

```
Met Gly Phe Val Leu Phe Ser Gln Leu Pro Ser Phe Leu Leu Val Ser
1               5                   10                  15

Thr Leu Leu Phe Leu Val Ile Ser His Ser Cys Arg Ala Gln Asn
            20                  25                  30

Gly Gly Ser Tyr Pro Tyr Lys Ser Gly Glu Tyr Arg Thr Lys Ser Phe
        35                  40                  45

Phe Gly Tyr Gly Tyr Tyr Glu Val Arg Met Lys Ala Ala Lys Asn Val
    50                  55                  60

Gly Ile Val Ser Ser Phe Phe Thr Tyr Thr Gly Pro Ser Asp Asn Asn
65                  70                  75                  80

Pro Trp Asp Glu Ile Asp Ile Glu Phe Leu Gly Lys Asp Thr Thr Lys
                85                  90                  95

Val Gln Phe Asn Trp Tyr Lys Asn Gly Val Gly Gly Asn Glu Tyr Leu
            100                 105                 110

His Asn Leu Gly Phe Asp Ala Ser Gln Asp Phe His Thr Tyr Gly Phe
        115                 120                 125

Glu Trp Arg Pro Asp Tyr Ile Asp Phe Tyr Val Asp Gly Lys Lys Val
    130                 135                 140

Tyr Arg Gly Thr Arg Asn Ile Pro Val Thr Pro Gly Lys Ile Met Met
145                 150                 155                 160

Asn Leu Trp Pro Gly Ile Gly Val Asp Glu Trp Leu Gly Arg Tyr Asp
                165                 170                 175

Gly Arg Thr Pro Leu Gln Ala Glu Tyr Glu Tyr Val Lys Tyr Tyr Pro
            180                 185                 190

Asn Gly Arg Ser Lys Leu Val Val Asn Thr Pro Phe Val Ala Val Phe
        195                 200                 205

Ser Asn Phe Asp Ser Ser Gln Trp Glu Lys Ala Asp Trp Ala Asn Gly
    210                 215                 220

Ser Val Phe Asn Cys Val Trp Lys Pro Ser Gln Val Thr Phe Ser Asn
225                 230                 235                 240

Gly Lys Met Ile Leu Thr Leu Asp Arg Glu Tyr Val Asp His His
                245                 250                 255

His His His Lys Asp Glu Leu
            260
```

<210> SEQ ID NO 74
<211> LENGTH: 462
<212> TYPE: PRT
<213> ORGANISM: Mus musculus

<400> SEQUENCE: 74

```
Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Arg Tyr Asn
65                  70                  75                  80

Glu Lys Phe Arg Val Lys Ala Thr Leu Thr Ser Asp Lys Ser Ser Ser
```

```
            85              90                95
Thr Ala Tyr Met Glu Leu Ser Ser Leu Thr Ser Glu Asp Ser Ala Val
            100             105              110
Tyr Tyr Cys Ala Arg Arg Gly Leu Ile Thr Thr Pro Thr Leu Asp Tyr
            115             120              125
Trp Gly Gln Gly Thr Thr Leu Thr Val Ser Ser Ala Lys Thr Thr Pro
130             135              140
Pro Ser Val Tyr Pro Leu Ala Pro Gly Ser Ala Ala Gln Thr Asn Ser
145             150              155             160
Met Val Thr Leu Gly Cys Leu Val Lys Gly Tyr Phe Pro Glu Pro Val
                165              170             175
Thr Val Thr Trp Asn Ser Gly Ser Leu Ser Ser Gly Val His Thr Phe
                180              185             190
Pro Ala Val Leu Gln Ser Asp Leu Tyr Thr Leu Ser Ser Ser Val Thr
                195              200             205
Val Pro Ser Ser Thr Trp Pro Ser Glu Thr Val Thr Cys Asn Val Ala
210             215              220
His Pro Ala Ser Ser Thr Lys Val Asp Lys Lys Ile Val Pro Arg Asp
225             230              235             240
Cys Gly Cys Lys Pro Cys Ile Cys Thr Val Pro Glu Val Ser Ser Val
                245              250             255
Phe Ile Phe Pro Pro Lys Pro Lys Asp Val Leu Thr Ile Thr Leu Thr
                260              265             270
Pro Lys Val Thr Cys Val Val Val Asp Ile Ser Lys Asp Asp Pro Glu
                275              280             285
Val Gln Phe Ser Trp Val Asp Asp Val Glu Val His Thr Ala Gln Thr
                290              295             300
Gln Pro Arg Glu Glu Gln Phe Asn Ser Thr Phe Arg Ser Val Ser Glu
305             310              315             320
Leu Pro Ile Met His Gln Asp Trp Leu Asn Gly Lys Glu Phe Lys Cys
                325              330             335
Arg Val Asn Ser Ala Ala Phe Pro Ala Pro Ile Glu Lys Thr Ile Ser
                340              345             350
Lys Thr Lys Gly Arg Pro Lys Ala Pro Gln Val Tyr Thr Ile Pro Pro
                355              360             365
Pro Lys Glu Gln Met Ala Lys Asp Lys Val Ser Leu Thr Cys Met Ile
                370              375             380
Thr Asp Phe Phe Pro Glu Asp Ile Thr Val Glu Trp Gln Trp Asn Gly
385             390              395             400
Gln Pro Ala Glu Asn Tyr Lys Asn Thr Gln Pro Ile Met Asp Thr Asp
                405              410             415
Gly Ser Tyr Phe Val Tyr Ser Lys Leu Asn Val Gln Lys Ser Asn Trp
                420              425             430
Glu Ala Gly Asn Thr Phe Thr Cys Ser Val Leu His Glu Gly Leu His
                435              440             445
Asn His His Thr Glu Lys Ser Leu Ser His Ser Pro Gly Lys
450             455              460

<210> SEQ ID NO 75
<211> LENGTH: 234
<212> TYPE: PRT
<213> ORGANISM: Mus musculus

<400> SEQUENCE: 75
```

-continued

```
Met Met Ser Ser Ala Gln Phe Leu Gly Leu Leu Leu Cys Phe Gln
 1               5                  10                  15

Gly Thr Arg Cys Asp Ile Gln Met Thr Gln Thr Ser Ser Leu Ser
             20                  25                  30

Ala Ser Leu Gly Asp Arg Val Thr Ile Ser Cys Arg Ala Ser Gln Asp
         35                  40                  45

Ile Arg Asn Tyr Leu Asn Trp Tyr Gln Gln Lys Pro Asp Gly Thr Val
50                  55                  60

Lys Leu Leu Ile Tyr Tyr Thr Ser Arg Leu His Ser Gly Val Pro Ser
65                  70                  75                  80

Arg Phe Ser Asp Ser Gly Ser Gly Thr Asp Tyr Ser Leu Thr Ile Ser
             85                  90                  95

Asn Leu Glu Gln Glu Asp Leu Ala Thr Tyr Phe Cys Gln Gln Thr Tyr
         100                 105                 110

Thr Leu Pro Trp Thr Phe Gly Gly Gly Thr Lys Leu Glu Ile Lys Arg
     115                 120                 125

Ala Asp Ala Ala Pro Thr Val Ser Ile Phe Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
             165                 170                 175

Asn Gly Val Leu Asn Ser Trp Thr Asp Gln Asp Ser Lys Asp Ser Thr
         180                 185                 190

Tyr Ser Met Ser Ser Thr Leu Thr Leu Thr Lys Asp Glu Tyr Glu Arg
     195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 76
<211> LENGTH: 460
<212> TYPE: PRT
<213> ORGANISM: Mus musculus

<400> SEQUENCE: 76

Met Lys Leu Trp Leu Asn Trp Ile Phe Leu Val Thr Leu Leu Asn Asp
 1               5                  10                  15

Ile Gln Cys Glu Val Lys Leu Val Glu Ser Gly Gly Gly Leu Val Gln
             20                  25                  30

Pro Gly Gly Ser Leu Arg Leu Ser Cys Ala Thr Ser Gly Phe Thr Phe
         35                  40                  45

Ser Asp Tyr Tyr Met Ser Trp Val Arg Gln Ser Pro Gly Lys Ala Leu
50                  55                  60

Glu Trp Leu Gly Phe Thr Arg Ser Arg Val Leu Gly Tyr Thr Thr Asp
65                  70                  75                  80

Tyr Ser Ala Ser Val Lys Gly Arg Phe Thr Ile Ser Arg Asp Asn Ser
             85                  90                  95

Gln Ser Ile Leu Tyr Leu Gln Met Asn Ser Leu Arg Gly Glu Asp Ser
         100                 105                 110

Ala Thr Tyr Tyr Cys Ala Arg Asp Arg Pro Met Asp Tyr Trp Gly Gln
     115                 120                 125

Gly Thr Ser Val Thr Val Ser Ser Ala Lys Thr Thr Pro Pro Ser Val
130                 135                 140
```

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
            165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Val Thr Val Pro Ser
        195                 200                 205

Ser Thr Trp Pro Ser Glu Thr Val Thr Cys Asn Val Ala His Pro Ala
210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350

Lys Gly Arg Pro Lys Ala Pro Gln Val Tyr Thr Ile Pro Pro Pro Lys
        355                 360                 365

Glu Gln Met Ala Lys Asp Lys Val Ser Leu Thr Cys Met Ile Thr Asp
370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
            420                 425                 430

Gly Asn Thr Phe Thr Cys Ser Val Leu His Glu Gly Leu His Asn His
        435                 440                 445

His Thr Glu Lys Ser Leu Ser His Ser Pro Gly Lys
450                 455                 460

<210> SEQ ID NO 77
<211> LENGTH: 233
<212> TYPE: PRT
<213> ORGANISM: Mus musculus

<400> SEQUENCE: 77

Met Arg Pro Ser Ile Gln Phe Leu Gly Leu Leu Leu Phe Trp Leu His
1               5                   10                  15

Gly Gly Gln Cys Asp Ile Gln Met Thr Gln Ser Pro Ser Ser Leu Ser
            20                  25                  30

Ala Ser Leu Gly Gly Asn Val Thr Ile Thr Cys Lys Ala Ser Gln Asp
        35                  40                  45

Ile Asn Lys Tyr Ile Ala Trp Tyr Gln His Lys Pro Gly Lys Gly Pro

```
            50                  55                  60
Arg Leu Val Ile His Tyr Thr Ser Thr Leu Gln Pro Gly Ile Pro Ser
 65                  70                  75                  80

Arg Phe Ser Gly Ser Gly Ser Gly Thr Asp Tyr Ser Phe Ser Ile Ser
                 85                  90                  95

Asn Leu Glu Pro Glu Asp Ile Ala Thr Tyr Tyr Cys Leu Gln Tyr Asp
            100                 105                 110

Ile Leu Tyr Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
210                 215                 220

Val Lys Ser Phe Asn Arg Asn Glu Cys
225                 230

<210> SEQ ID NO 78
<211> LENGTH: 443
<212> TYPE: PRT
<213> ORGANISM: Mus musculus

<400> SEQUENCE: 78

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
             20                  25                  30

Val Met His Trp Val Lys Gln Lys Pro Gly Gln Gly Leu Glu Trp Ile
         35                  40                  45

Gly Tyr Ile Asn Pro Tyr Asn Asp Gly Thr Arg Tyr Asn Glu Lys Phe
     50                  55                  60

Arg Val Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Arg Gly Leu Ile Thr Thr Pro Thr Leu Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190
```

```
Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 79
<211> LENGTH: 214
<212> TYPE: PRT
<213> ORGANISM: Mus musculus

<400> SEQUENCE: 79

Asp Ile Gln Met Thr Gln Thr Ser Ser Ser Leu Ser Ala Ser Leu Gly
1               5                   10                  15

Asp Arg Val Thr Ile Ser Cys Arg Ala Ser Gln Asp Ile Arg Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Asp
        50                  55                  60

Ser Gly Ser Gly Thr Asp Tyr Ser Leu Thr Ile Ser Asn Leu Glu Gln
65              70                  75                  80

Glu Asp Leu Ala Thr Tyr Phe Cys Gln Gln Thr Tyr Thr Leu Pro Trp
                85                  90                  95
```

```
Thr Phe Gly Gly Gly Thr Lys Leu Glu Ile Lys Arg Ala Asp Ala Ala
                100                 105                 110
Pro Thr Val Ser Ile Phe Pro Pro Ser Glu Gln Leu Thr Ser Gly
        115                 120                 125
Gly Ala Ser Val Val Cys Phe Leu Asn Asn Phe Tyr Pro Lys Asp Ile
    130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 80
<211> LENGTH: 441
<212> TYPE: PRT
<213> ORGANISM: Mus musculus

<400> SEQUENCE: 80

Glu Val Lys Leu Val Glu Ser Gly Gly Gly Leu Val Gln Pro Gly Gly
1               5                   10                  15
Ser Leu Arg Leu Ser Cys Ala Thr Ser Gly Phe Thr Phe Ser Asp Tyr
            20                  25                  30
Tyr Met Ser Trp Val Arg Gln Ser Pro Gly Lys Ala Leu Glu Trp Leu
        35                  40                  45
Gly Phe Thr Arg Ser Arg Val Leu Gly Tyr Thr Thr Asp Tyr Ser Ala
    50                  55                  60
Ser Val Lys Gly Arg Phe Thr Ile Ser Arg Asp Asn Ser Gln Ser Ile
65                  70                  75                  80
Leu Tyr Leu Gln Met Asn Ser Leu Arg Gly Glu Asp Ser Ala Thr Tyr
                85                  90                  95
Tyr Cys Ala Arg Asp Arg Pro Met Asp Tyr Trp Gly Gln Gly Thr Ser
            100                 105                 110
Val Thr Val Ser Ser Ala Lys Thr Thr Pro Pro Ser Val Tyr Pro Leu
        115                 120                 125
Ala Pro Gly Ser Ala Ala Gln Thr Asn Ser Met Val Thr Leu Gly Cys
    130                 135                 140
Leu Val Lys Gly Tyr Phe Pro Glu Pro Val Thr Val Thr Trp Asn Ser
145                 150                 155                 160
Gly Ser Leu Ser Ser Gly Val His Thr Phe Pro Ala Val Leu Gln Ser
                165                 170                 175
Asp Leu Tyr Thr Leu Ser Ser Ser Val Thr Val Pro Ser Ser Thr Trp
            180                 185                 190
Pro Ser Glu Thr Val Thr Cys Asn Val Ala His Pro Ala Ser Ser Thr
        195                 200                 205
Lys Val Asp Lys Lys Ile Val Pro Arg Asp Cys Gly Cys Lys Pro Cys
    210                 215                 220
Ile Cys Thr Val Pro Glu Val Ser Ser Val Phe Ile Phe Pro Pro Lys
225                 230                 235                 240
Pro Lys Asp Val Leu Thr Ile Thr Leu Thr Pro Lys Val Thr Cys Val
                245                 250                 255
```

```
Val Val Asp Ile Ser Lys Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
                340                 345                 350

Ala Lys Asp Lys Val Ser Leu Thr Cys Met Ile Thr Asp Phe Phe Pro
            355                 360                 365

Glu Asp Ile Thr Val Glu Trp Gln Trp Asn Gly Gln Pro Ala Glu Asn
            370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
                420                 425                 430

Lys Ser Leu Ser His Ser Pro Gly Lys
                435                 440

<210> SEQ ID NO 81
<211> LENGTH: 213
<212> TYPE: PRT
<213> ORGANISM: Mus musculus

<400> SEQUENCE: 81

Asp Ile Gln Met Thr Gln Ser Pro Ser Ser Leu Ser Ala Ser Leu Gly
 1               5                  10                  15

Gly Asn Val Thr Ile Thr Cys Lys Ala Ser Gln Asp Ile Asn Lys Tyr
                20                  25                  30

Ile Ala Trp Tyr Gln His Lys Pro Gly Lys Pro Arg Leu Val Ile
            35                  40                  45

His Tyr Thr Ser Thr Leu Gln Pro Gly Ile Pro Ser Arg Phe Ser Gly
        50                  55                  60

Ser Gly Ser Gly Thr Asp Tyr Ser Phe Ser Ile Ser Asn Leu Glu Pro
65                  70                  75                  80

Glu Asp Ile Ala Thr Tyr Tyr Cys Leu Gln Tyr Asp Ile Leu Tyr Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160
```

-continued

```
Ser Trp Thr Asp Gln Asp Ser Lys Asp Ser Thr Tyr Ser Met Ser Ser
            165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```